US006991797B2

(12) United States Patent
Andersen et al.

(10) Patent No.: US 6,991,797 B2
(45) Date of Patent: Jan. 31, 2006

(54) M. TUBERCULOSIS ANTIGENS

(75) Inventors: Peter Andersen, Brønshøj (DK); Rikke Louise Vinther Skjøt, Hedehusene (DK)

(73) Assignee: Statens Serum Institut, Copenhagen S (DK)

( * ) Notice: Subject to any disclaimer, the term of this patent is extended or adjusted under 35 U.S.C. 154(b) by 1 day.

(21) Appl. No.: 09/804,980

(22) Filed: Mar. 13, 2001

(65) Prior Publication Data

US 2003/0147897 A1 Aug. 7, 2003

Related U.S. Application Data

(63) Continuation-in-part of application No. 09/791,171, filed on Feb. 20, 2001, which is a division of application No. 09/050,739, filed on Mar. 30, 1998, and a continuation-in-part of application No. 09/289,388, filed on Apr. 12, 1999, now abandoned, which is a continuation of application No. 08/465,640, filed on Jun. 5, 1995, now Pat. No. 5,955,077, which is a continuation-in-part of application No. PCT/DK94/00273, filed on Jul. 1, 1994, and a continuation-in-part of application No. 08/123,182, filed on Sep. 20, 1993, said application No. 09/804,980, is a continuation-in-part of application No. 09/246,191, filed on Dec. 30, 1998, and a continuation-in-part of application No. 09/050,739, filed on Mar. 30, 1998.

(60) Provisional application No. 60/070,488, filed on Jan. 5, 1998, and provisional application No. 60/044,624, filed on Apr. 18, 1997.

(30) Foreign Application Priority Data

| Jul. 2, 1993 | (DK) | ........................................ | 1993 00798 |
| Apr. 2, 1997 | (DK) | ........................................ | 1997 00376 |
| Nov. 10, 1997 | (DK) | ........................................ | 1997 01277 |

(51) Int. Cl.
*A61K 39/04* (2006.01)
*A61K 39/02* (2006.01)
*A61K 39/00* (2006.01)

(52) U.S. Cl. ................................ 424/248.1; 424/184.1; 424/185.1; 424/192.1; 424/234.1; 530/300; 530/350

(58) Field of Classification Search .............. 424/184.1, 424/185.1, 192.1, 234.1, 248.1; 530/300, 530/350

See application file for complete search history.

(56) References Cited

U.S. PATENT DOCUMENTS

| 4,683,578 | A | | 7/1987 | Betts et al. |
| 4,891,315 | A | | 1/1990 | Watson et al. |
| 4,952,395 | A | | 8/1990 | Shinnick et al. |
| 4,976,958 | A | | 12/1990 | Shinnick et al. |
| 5,026,546 | A | | 6/1991 | Hilgers et al. |
| 5,330,754 | A | | 7/1994 | Kapoor et al. |
| 5,559,011 | A | | 9/1996 | Kapoor et al. |
| 5,955,077 | A | * | 9/1999 | Andersen et al. ........ 424/184.1 |

FOREIGN PATENT DOCUMENTS

| DE | 195 40 250 | 2/1997 |
| EP | 0 729 250 | 8/1996 |
| EP | 0 734 132 | 9/1996 |
| EP | 0 869 649 | 10/1998 |
| WO | WO 92 14823 | 9/1992 |
| WO | WO 95/01441 | 1/1995 |
| WO | WO 96/37219 | 11/1996 |
| WO | WO 97/09428 | 3/1997 |
| WO | WO 97/09429 | 3/1997 |
| WO | 98/16645 | 4/1998 |
| WO | 98/16646 | 4/1998 |
| WO | WO 98 44119 | 10/1998 |
| WO | WO 98 53075 | 11/1998 |
| WO | WO 98 53076 | 11/1998 |

OTHER PUBLICATIONS

Borodovsky et al., Computers Chem., vol. 17, pp. 123–133.
Brown, EMBL Sequence database.
Harboe et al., Infect. Immun. vol. 64, pp. 16–22.
Von Heijne et al., J. Mol. Biol., vol. 173, pp. 243–251.
Hochstrasser et al., Annal Biochem., vol. 173, pp. 424–435.
Kohler et al., Nature, vol. 256, pp. 495–497.
Li et al., Infect. Immun., vol. 61, pp. 1730–1734.
Lindblad et al., Infect. Immun., vol. 65, pp. 623–629.
Mahairs et al., J. Bacteriol., vol. 178, pp. 1274–1282.
Nagai et al., Infect. Immun., vol. 59, pp. 372–382.
Oettinger et al., Infect. Immun., vol. 62, pp. 2058–2064.
Ohara et al., Scand. J. Immunol., vol. 41, pp. 433–442.
Pal et al., Infect. Immun., vol. 60, pp. 4781–4792.
Pearson et al., Proc. Natl. Acad. Sci., USA, vol. 85, pp. 2444–2448.
Ploug et al., Anal Biochem., vol. 181, pp. 33–39.
Porath et al., FEBS Lett., vol. 185, pp. 306–310.
Roberts et al., Immunol., vol. 85, pp. 502–508.
Rosenkrands et al., Infect. Immun., vol. 66, No. 6, pp. 2728–2735.
Andersen et al., J. Immunol. vol. 154, pp. 3359–3372.
Rosenkrands et al., EMBL: Y12820.
Sorensen et al., Infect. Immun., vol. 63, pp. 1710–1717.
Theisen et al., Clinical and Diagnostic Laboratory Immunology, vol. 2, pp. 30–34.
Valdes–Stauber et al., Appl. Environ. Microbiol., vol. 60, pp. 3809–3814.
Valdes–Stauber et al., Appl. Environ. Microbiol., vol. 62, No. 4, pp. 1283–1286.

(Continued)

*Primary Examiner*—Rodney P Swartz
(74) *Attorney, Agent, or Firm*—Frommer Lawrence & Haug; Thomas J. Kowalski

(57) ABSTRACT

The present invention is based on the identification and characterization of a number of novel *M. tuberculosis* derived proteins and protein fragments. The invention is directed to the polypeptides and immunologically active fragments thereof, the genes encoding them, immunological compositions such as vaccines and skin test reagents containing the polypeptides.

13 Claims, 15 Drawing Sheets

OTHER PUBLICATIONS

Figure 1:
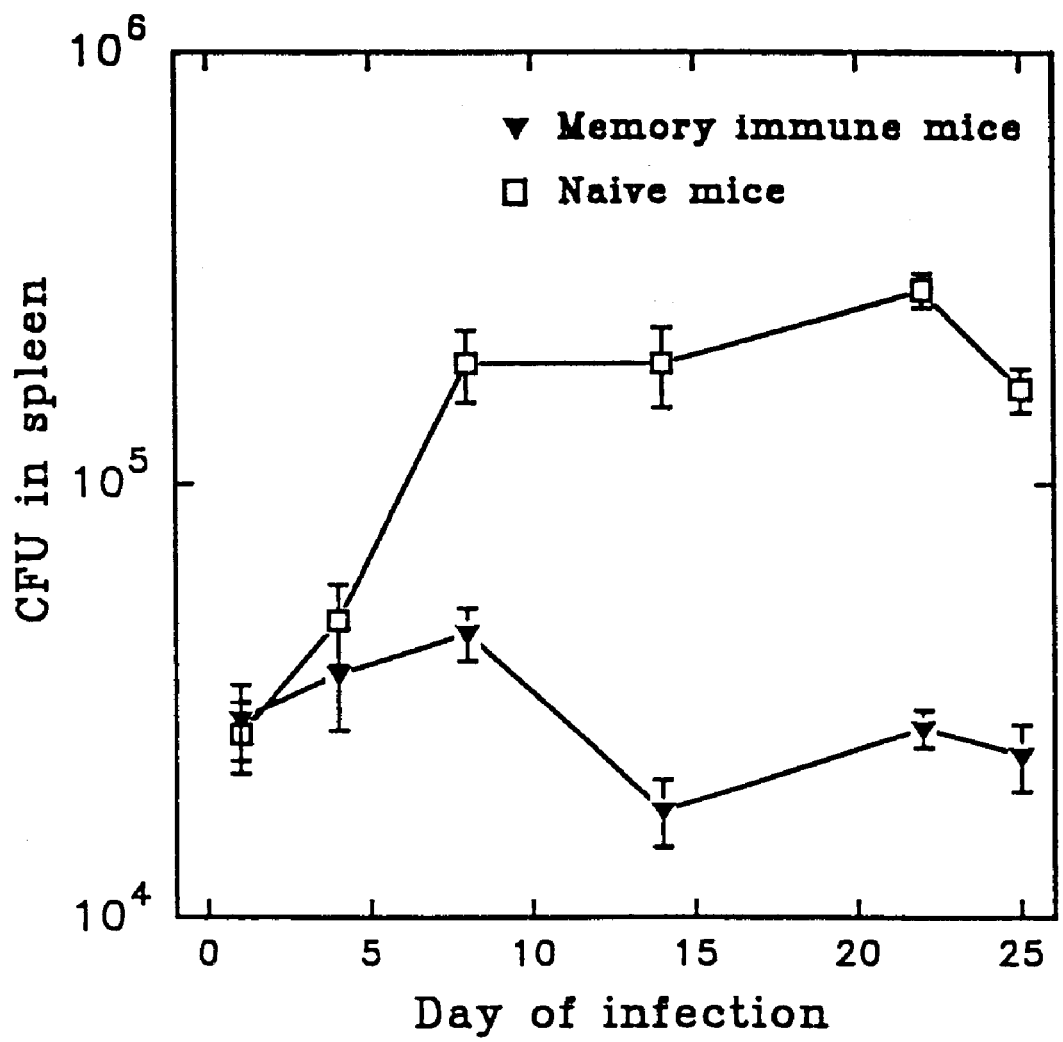

Williams, Science, 272:27.
Young et al., Proc. Natl. Acad. Sci. USA, vol. 82, pp. 2583–2587.
Crabtree et al., EMBL Sequence database.
Van Dyke et al., Gene, pp. 99–104.
Gosselin et al., J. Immunol., vol. 149, pp. 3477–3481.
XP002092185 EMBL Sequence.
Andersen et al., J. Immunol. Methods, vol. 161, pp. 29–39.
Andersen et al., Infect. Immun., vol. 60, pp. 2317–2323.
Rosenkrands et al., EMBL: 007812.
Wiegeshaus, E.H., et al. "Evaluation of the Protective Protency of New Tuberculosis Vaccines", Reviews of Infectious Diseases, vol. 11, supplement 2, pp. S484–S490, Mar. 1989.
Orme, I.M., "New Vaccines against Tuberculosis", Infectious Disease Clinic of North America, vol. 13, No. 1, pp. 169–185, Mar. 1999.
Andersen, Infect. Immun. vol. 62, pp. 2536–2544.
Barkholt et al., Anal. Biochem., vol. 177, pp. 318–322.
Scandinavian Journal of Immunology vol. 36, 1992 pp. 823–831 P. Andersen et al. 'Identification of immunodominant antigens during infection with *Mycobacterium tuberculosis*'.
Infection and Immunity vol. 61, No. 3, Mar. 1993, Washington US pp. 844–851 Peter Andersen et al. 'Specificity of a protective memory immune response against *Mycobacterium tuberculosis*'.
Infection and Immunity vol. 59, No. 4, Apr. 1991, Washington US pp. 1558–1563 Peter Andersen et al. 'T–cell proliferative response to antigens secreted by *Mycobacterium tuberculosis*' cited in the application.
Infection and Immunity vol. 60, No. 7, Jul. 1992, Washington US pp. 2880–2886 Kris Huygen et al. 'Spleen cell cytokine secretion in *Mycobacterium bovis* BCG–infected mice'.
Infection and Immunity vol. 59, No. 6, Jun. 1991, Washington US pp. 1905–1910 Peter Andersen et al. 'Proteins released from *Mycobacterium tuberculosis* during growth' cited in the application.
Infection and Immunity vol. 56, No. 12, Dec. 1988, Washington US pp. 3046–3051 Christiane Abou–Zeid et al. 'Characterization of fibronectin–binding antigens released by *Mycobacterium toberculosis* and *Mycobacterium bovis* BCG'.
Infection and Immunity vol. 57, No. 10, Oct. 1989, Washington US pp. 3123–3130 Martine Borremans et al. 'Cloning sequence determination, and expression of a 32–kilodalton–protein gene of *Mycobacterium tuberculosis*'.
Infection and Immunity vol. 62, No. 6, Jun. 1994, Washington US pp. 2536–2544 Peter Andersen 'Effective vaccination of mice against *Mycobacterium tuberculosis* infection with a soluble mixture of secreted mycobacterial proteins'.
Moriyama S et al.: "Digital Transmission of High Bit Rate Signals Using 16DAPSK–OFDM Modulation Scheme" IEEE Transactions on Broadcasting, Mar. 1998, vol. 44, No. 1, pp. 115–122, XP002105431.
Man et al. "Treatment of human muscle creatine kinase with glutaraldehyde preferentially increases the immunogenicity of the native conformation and permits production of high-affinity monoclonal antibodies which recognize two distinct surface epitopes", J, Oct. 1, 1989.
A.B. Andersen et al., MPB64 Possesses Tuberculosis–Complex'–Specific B– and T–Cell Epitopes, Scand J. Immunol 34, 365–372, 1991.

Anne Worsaee et al., Allergenic and Blastogenic Reactivity of Three Antigens from *Mycobacterium tuberculosis* in Sensitized Guinea Pigs, Infection and Immunity, Dec. 1987, p 2922–2927.
Yamaguchi Ryugi, et al. "Cloning and Characterization of the Gene for immunogenic Protein MPB64 of *Mycobacterium bovis* BCG" Infection and Immunity 57(1):283–288 (1989).
Wiker, H.G., et al., "A Family of Cross–Reacting Proteins Secreted by *Mycobacterium tuberculosis*", Scand J. Immunol. 36:307–319 (1992).
Leao, S.C., "Tuberculosis: New Strategies for the Development of Diagnostic Tests and Vaccines", Brazilian J. Med. Biol. Res. 26:827–833 (1993).
Oettiner, Thomas, et al., "Cloning and B–Cell–Epitope Mapping of MPT64 from *Mycobacterium tuberculosis* H37Rv", Infection and Immunity 62(5):2058–2064 (1994).
Boswell et al. Computational Molecular Biology, Oxford University Press, pp. 161–178, 1988.
Flesch and Kaufmann, Mycobacterial Growth Inhibition by Interferon–y–Activated Bone Marrow Macrophages and Differential . . . tuberculosis, The Journal of Immunology, vol. 138, No. 12, pp. 4408–4413, Jun. 15, 1987.
Lefford and McGregor, Immunological Memory in Tuberculosis, Cellular Immunology, vol. 14, pp. 417–428, 1974.
Orme, Characteristics and Specificity of Acquired Immunologic Memory to *Mycobacterium tuberculosis* Infection The Journal of Immunology, vol. 140, No. 10, pp. 3589–3593, May 15, 1988.
G.A.W. Rock, The Role of Activated Macrophages in protection and immunopathology in Tuberculosis, Research in Microbiology vol. 141, No. 2, Feb. 1990, pp. 253–256.
Sanger, Nicklen and Coulson, DNA Sequencing with Chain–Terminating Inhibitors, Proc. Natl. Acad. Sci USA, vol. 74, No. 12, pp. 5463–5467, Dec. 1977.
Andersen, P. et al., Jun. 1991, Proteins released from *Mycobacterium Tuberculosis* during growth, Infect. Immun. 59(6): 1905–1910.
Baldwin, S.L. et al., Jun. 1998, Evaluation of new vaccines in the mouse and guinea pig model of tuberculosis, Infect. Immun. 66(6):2951–2959.
Boesen, H. et al., Apr. 1995, Human T–cell responses to secreted antigen fractions of *Mycobacterium tuberculosis*, Infect. Immun. 63(4): 1491–1497.
Brandt et al., 1996, Key epitopes on the ESAT–6 antigen recognized in mice during the recall of protective immunity to *Mycobacterium tuberculosis*, J. Immunol. 157:3527–3533.
Brandt L. et al., Feb. 2000, ESAT–6 subunit vaccination against *Mycobacterium tuberculosis*, Infect. Immun. 68:791–795.
Cole, S.T. et al., Jun. 1998, Deciphering the biology of *Mycobacterium tuberculosis* from the complete genome sequence, Nature 393:537–544.
Horwitz et al., Feb. 1995, Protective immunity against tuberculosis induced by vaccination with major extracellular proteins of *Mycobacterium tuberculosis*, Proc. Natl. Acad. Sci. USA.92:1530–1534.
Olsen A.W. et al., Jun. 2000, Efficient protection against *Mycobacterium tuberculosis* by vaccination with a single subdominant epitope from the ESAT–6 antigen, Eur J. Immunol. 30(6):1724–1732.

Ravn, P. et al., Mar. 1999, Human T Cell responses to ESAT-6 antigen from *Mycobacterium tuberculosis*, J. Infect. Dis. 179:637–645.

Roche, P.W. et al. Dec. 1994, T–cell determinants and antibody binding sites on the major mycobacterial secretory protein MPB59 of *Mycobacterium bovis* , Infect. Immun.62(12):5319–5326.

Rosenkrands, I., et al., Identification and characterization of a 29–kilodalton protein from *Mycobacterium tuberculosis* culture filtrate recognized by mouse memory effector cells, Infect. Immun 66(6); 2728–2735.

Skjøt, R.L.V., et al., Jan. 2000, Comparative evaluation of low–molecular–mass proteinsfrom *Mycobacterium tuberculosis* identifies members of the ESAT-6 family as immunodominant T–cell antigens, Infect. Immun. 68(I):214–220.

Stryhn, A., et al., 1996, Peptide binding specificity of major histocompatibility complex class I resolved into an array of apparently independent subspecificites: quantitation by peptide libraries and improved preiction of binding, Eur. J. Immunol. 26:1911–1918.

Ulrichs, T. et al. , 1998, Differential T cell responses to *Mycobacterium tuberculosis* ESAT in tuberculosis patients and healthy donors, Eur. J. Immunol. 28:3949–3958.

P. Andersen et al., Identification of Immunodominant antigens during infection with *mycobacterium tuberculosis*, J. Immunol, 36, 823–831, 1992.

Peter Andersen et al., Proteins released from *Mycobacterium tuberculosis* during growth, Infection and Immunity, Jun. 1991, vol. 59, No. 6, P. 1905–1910.

Peter Andersen et al., Specificty of a protective memory immune response against *Mycobacterium tuberculosis*, Infection and Immunity, Mar. 1993, vol. 61, No. 3, p. 844–851.

Peter Andersen et al., T–cell proliferative response to antigens secreted by *Mycobacterium tuberculosis*, Infection and Immunity, Apr. 1991, vol. 59, No. 4, p. 1558–1563.

Kris Huygen et al., Spleen cell cytokine secretion in *Mycobacterium bovis* BCG–infected mice, infection and immunity, Jul. 1992, vol. 60, No. 7, p. 2880–2886.

Christiane Abou–Zeid et al., Characterization of fibronectin–binding antigens released by *Mycobacterium tuberculosis* and *Mycobacterium bovis* BCG, Infection and Immunity, Dec. 1988, vol. 56, No. 12, p. 3046–3051.

Martine Borremans et al., Cloning sequence determination, and expression of a 32– kilodalton–protein of gene *Mycobacterium tuberculosis*, Infection and Immunity , Oct. 1989, vol. 57, No. 10, p. 3123–3130.

Peter Andersen, Effective vaccination of mice against *Mycobacterium tuberculosis* infection with a soluble mixture of secreted mycobacterial proteins, Infection and Immunity, Jun. 1994, vol. 62, No. 6.

Nagai et al., Isolation and partial characterization of major protein antigens in the culture fluid of *Mycobacterium tuberculosis*, Infection and Immunity, Jan. 1991, vol. 59, No. 1, p. 372–382.

* cited by examiner

Physical map of recombinant lambda phages expressing products reactive with Mabs recognizing low M.W. components

```
  1  GGCCGCCGGT ACCTATGTGG CCGCCGATGC TGCGGNCGCG TCGACCTATA CCGGGTTCTG   60
               -35region                                  -10 region 61  ATCGAACCCT GCTGACCGAG AGGACTTGTG ATG TCG CAA ATC ATG TAC AAC TAC CCC GCG  120
                           Shine Delgarno              M   S   Q   I   M   Y   N   Y   P   A 121  ATG TTG GGT CAC GCC GGG GAT ATG GCC GGA TAT GCC ACG CTG ACG AGT TTG GGT GCC  180
      M   L   G   H   A   G   D   M   A   G   Y   A   T   L   T   S   L   G   A 181  GAG ATC GCC GTG GAG CAG GCG GCA CAG TTG CAG GCG AGT ACC GGT GGG ATC ACG  240
      E   I   A   V   E   Q   A   A   Q   L   Q   A   S   T   G   G   I   T 241  TAT CAG GGG TGG CAG GCA TGG AAC CAG GCC ATG GAA GAT TTG GTG CGC TAT CAT  300
      Y   Q   G   W   Q   A   W   N   Q   A   M   E   D   L   V   R   Y   H 301  GCG ATG TCC AGC ACC CAT GAA GCC ATG GCG ATG ATG GCC CGC GAC ACC GCC GAA  360
      A   M   S   S   T   H   E   A   M   A   M   M   A   R   D   T   A   E 361  GCC GCC AAA TGG GGC TAG                                              381
      A   A   K   W   G   *
```

Fig. 9

```
  1  GGGTAGCCCG ACCACGGCTG GGCAAAGATG TGCAGGCCGC CATCAAGGCG GTCAAGGCCG      60
        -35 region 61  GCGACGGCGT CATAAACCCG GACGGCACCT TGTTGGCGGG CCCCGCGGTG CTGACGCCCG     120
                -10 region 121  ACCAGTACAA CTCCCGGCTG GTG GCC GCC GAC CCG GAG TCC ACC GCG GCG            170
     Shine Delgarno       V   A   A   D   P   E   S   T   A   A 171  TTG CCC GAC GGC GCC GGG CTG GTC GTT CTG GAT GGC ACC GTC ACT GCC GAA CTC GAA GCC    230
      L   P   D   G   A   G   L   V   V   L   D   G   T   V   T   A   E   L   E   A 231  GAG GGC TGG GCC AAA GAT CGC ATC CGC GAA CTG CAA GAG CTG CGT AAG TCG ACC GGG CTG    290
      E   G   W   A   K   D   R   I   R   E   L   Q   E   L   R   K   S   T   G   L 291  GAC GTT TCC GAC CGC ATC CGG GTG GTG ATG TCG GTG CCT GCG GAA CGC GAA GAC TGG GCG    350
      D   V   S   D   R   I   R   V   V   M   S   V   P   A   E   R   E   D   W   A 351  CGC ACC CAT CGC GAC CTC ATT GCC GGA GAA ATC TTG GCT ACC GAC TTC GAA TTC GCC GAC    410
      R   T   H   R   D   L   I   A   G   E   I   L   A   T   D   F   E   F   A   D 411  CTC GCC GAT GGT GTG GCC ATC GGC GAC GGC GTG CGG GTA AGC ATC GAA AAG ACC TGA        467
      L   A   D   G   V   A   I   G   D   G   V   R   V   S   I   E   K   T   *
```

Fig. 10

```
  1 GAATTCGCCGGGTGCACACAGCCTTACACGACGGAGGTGGACACATGAAG   50
                                                    M  K
 51 GGTCGGTCGGCGCTGCTGCGGGCGCTCTGGATTGCCGCACTGTCATTCGG  100
     G  R  S  A  L  L  R  A  L  W  I  A  A  L  S  F  G
101 GTTGGGCGGTGTCGCGGTAGCCGCGGAACCCACCGCCAAGGCCGCCCCAT  150
     L  G  G  V  A  A  A  E  P  T  A  K  A  A  P
151 ACGAGAACCTGATGGTGCCGTCGCCCTCGATGGGCCGGGACATCCCGGTG  200
     Y  E  N  L  M  V  P  S  P  S  M  G  R  D  I  P  V
201 GCCTTCCTAGCCGGTGGGCCGCACGCGGTGTATCTGCTGGACGCCTTCAA  250
     A  F  L  A  G  G  P  H  A  V  Y  L  L  D  A  F  N
251 CGCCGGCCCGGATGTCAGTAACTGGGTCACCGCGGGTAACGCGATGAACA  300
     A  G  P  D  V  S  N  W  V  T  A  G  N  A  M  N
301 CGTTGGCGGGCAAGGGGATTTCGGTGGTGGCACCGGCCGGTGGTGCGTAC  350
     T  L  A  G  K  G  I  S  V  V  A  P  A  G  G  A  Y
351 AGCATGTACACCAACTGGGAGCAGGATGGCAGCAAGCAGTGGGACACCTT  400
     S  M  Y  T  N  W  E  Q  D  G  S  K  Q  W  D  T  F
401 CTTGTCCGCTGAGCTGCCCGACTGGCTGGCCGCTAACCGGGGCTTGGCCC  450
     L  S  A  E  L  P  D  W  L  A  A  N  R  G  L  A
451 CCGGTGGCCATGCGGCCGTTGGCGCCGCTCAGGGCGGTTACGGGGCGATG  500
     P  G  G  H  A  A  V  G  A  A  Q  G  G  Y  G  A  M
501 GCGCTGGCGGCCTTCCACCCCGACCGCTTCGGCTTCGCTGGCTCGATGTC  550
     A  L  A  A  F  H  P  D  R  F  G  F  A  G  S  M  S
551 GGGCTTTTTGTACCCGTCGAACACCACCACCAACGGTGCGATCGCGGCGG  600
     G  F  L  Y  P  S  N  T  T  T  N  G  A  I  A  A
601 GCATGCAGCAATTCGGCGGTGTGGACACCAACGGAATGTGGGGAGCACCA  650
     G  M  Q  Q  F  G  G  V  D  T  N  G  M  W  G  A  P
651 CAGCTGGGTCGGTGGAAGTGGCACGACCCGTGGGTGCATGCCAGCCTGCT  700
     Q  L  G  R  W  K  W  H  D  P  W  V  H  A  S  L  L
701 GGCGCAAAACAACACCCGGGTGTGGGTGTGGAGCCCGACCAACCCGGGAG  750
     A  Q  N  N  T  R  V  W  V  W  S  P  T  N  P  G
751 CCAGCGATCCCGCCGCCATGATCGGCCAAACCGCCGAGGCGATGGGTAAC  800
     A  S  D  P  A  A  M  I  G  Q  T  A  E  A  M  G  N
801 AGCCGCATGTTCTACAACCAGTATCGCAGCGTCGGCGGGCACAACGGACA  850
     S  R  M  F  Y  N  Q  Y  R  S  V  G  G  H  N  G  H
851 CTTCGACTTCCCAGCCAGCGGTGACAACGGCTGGGGCTCGTGGGCGCCCC  900
     F  D  F  P  A  S  G  D  N  G  W  G  S  W  A  P
901 AGCTGGGCGCTATGTCGGGCGATATCGTCGGTGCGATCCGCTAAGCGAAT  950
     Q  L  G  A  M  S  G  D  I  V  G  A  I  R
951 TC                                                  952
```

Fig. 11

```
TB10.4     MSQIMYNYPAMLGHAGDMAGYAGTLQSLGAEIAVEQAALQSAWQGDTGITYQAWQAQWNQAMEDLVRAYHAMSSTHEANTMAMMARDTAEAAKWGG
TB10.4-P1  MSQIMYNYPAMLGHAGDM
TB10.4-P2           MLGHAGDMAGYAGTLQ

```
TB10.3     MSQIMYNYPAMMAHAGDMAGYAGTLQSLGADIASEQAVLSSAWQGDTGITYQGWQTQWNQALEDLVRAYQSMSGTHESNTMAMLARDGAEAAKWGG
TB10.3-P1  MSQIMYNYPAMMAHAGDMAG
TB10.3-P2         MMAHAGDMAGYAGTLQSLGA
TB10.3-P3                 YAGTLQSLGADIASEQAVLS
TB10.3-P4                         DIASEQAVLSSAWQGDTGIT
TB10.3-P5                                 SAWQGDTGITYQGWQTQWNQ
TB10.3-P6                                         YQGWQTQWNQALEDLVRAYQ
TB10.3-P7                                                 ALEDLVRAYQSMSGTHESNT
TB10.3-P8                                                         SMSGTHESNTMAMLARDGAE
TB10.3-P9                                                                 MAMLARDGAEAAKWGG
```

Fig. 14

```
TB12.9      MSQSMYSYPAMTANVGDMAGYTGTTQSLGADIASERTAPSRACQGDLGMSHQDWQAQWNQAMEALARAYRRCRRALRQIGVLERPVGDSSDCGTIRVGSFRGRWLDPRHAGPATAADAGD
TB12.9-P1   MSQSMYSYPAMTANVGDMAG
TB12.9-P2        MTANVGDMAGYTGTTQSLGA
TB12.9-P3             YTGTTQSLGADIASERTAPS
TB12.9-P4                  DIASERTAPSRACQGDLGMS
TB12.9-P5                       RACQGDLGMSHQDWQAQWNQ
TB12.9-P6                            HQDWQAQWNQAMEALARAYR
TB12.9-P7                                 AMEALARAYRRCRRALRQIG
TB12.9-P8                                      RCRRALRQIGVLERPVGDSS
TB12.9-P9                                           VLERPVGDSSDCGTIRVGSF
TB12.9-P10                                               DCGTIRVGSFRGRWLDPRHA
TB12.9-P11                                                    RGRWLDPRHAGPATAADAGD
```

Fig. 15

M. TUBERCULOSIS ANTIGENS

RELATED APPLICATIONS

This application is a continuation-in-part of:

U.S. application Ser. No. 09/289,388 filed 12 Apr. 1999, now abandoned which is a continuation of U.S. application Ser. No. 08/465,640 filed 5 Jun. 1995, now U.S. Pat. No. 5,955,077, issued Sep. 21, 1999, which is a continuation-in-part of U.S. Ser. No. 08/123,182 filed 20 Sep. 1993, now abandoned, and a continuation-in-part of PCT/DK94/00273, filed Jul. 1, 1994, published as WO95/01441, and claiming priority from Danish application 0798/93, filed Jul. 2, 1993;

U.S. application Ser. No. 09/050,739 filed 30 Mar. 1998, which is claims priority from U.S. provisional application Ser. No. 60/044,624 filed 18 Apr. 1997;

Andersen et al., application Ser. No. 09/791,171, filed 20 Feb. 2001, as a divisional of U.S. application Ser. No. 09/050,739; and U.S. application Ser. No. 09/246,191, filed 30 Dec. 1998, which claims priority from U.S. provisional 60/070,488 filed 5 Jan. 1998.

Reference is also made to commonly-owned U.S. Pat. No. 6,120,776.

Each of these patents, patent applications and patent publications, as well as all documents cited in the text of this application, and references cited in the documents referred to in this application (including references cited in the aforementioned patents, patent applications and patent publications or during their prosecution) are hereby incorporated herein by reference.

FIELD OF INVENTION

The present application discloses new immunogenic polypeptides and new immunogenic compositions based on polypeptides derived from the short time culture filtrate of *M. tuberculosis*.

GENERAL BACKGROUND

Human tuberculosis caused by *Mycobacterium tuberculosis* (*M. tuberculosis*) is a severe global health problem, responsible for approx. 3 million deaths annually, according to the WHO. The worldwide incidence of new tuberculosis (TB) cases had been falling during the 1960s and 1970s but during recent years this trend has markedly changed in part due to the advent of AIDS and the appearance of multidrug resistant strains of *M. tuberculosis*.

The only vaccine presently available for clinical use is BCG, a vaccine whose efficacy remains a matter of controversy. BCG generally induces a high level of acquired resistance in animal models of TB, but several human trials in developing countries have failed to demonstrate significant protection. Notably, BCG is not approved by the FDA for use in the United States because BCG vaccination impairs the specificity of the Tuberculin skin test for diagnosis of TB infection.

This makes the development of a new and improved vaccine against TB an urgent matter, which has been given a very high priority by the WHO. Many attempts to define protective mycobacterial substances have been made, and different investigators have reported increased resistance after experimental vaccination. However, the demonstration of a specific long-term protective immune response with the potency of BCG has not yet been achieved.

Immunity to *M. tuberculosis* is characterized by some basic features; specifically sensitized T lymphocytes mediates protection, and the most important mediator molecule seems to be interferon gamma (IFN-γ).

*M. tuberculosis* holds, as well as secretes, several proteins of potential relevance for the generation of a new TB vaccine. For a number of years, a major effort has been put into the identification of new protective antigens for the development of a novel vaccine against TB. The search for candidate molecules has primarily focused on proteins released from dividing bacteria. Despite the characterization of a large number of such proteins only a few of these have been demonstrated to induce a protective immune response as subunit vaccines in animal models, most notably ESAT-6 and Ag85B (Brandt et al 2000 Infect. Imm. 68:2; 791–795).

In 1998 Cole et al published the complete genome sequence of *M. tuberculosis* and predicted the presence of approximately 4000 open reading frames (Cole et al 1998). Following the sequencing of the *M. tuberculosis* genome, nucleotide sequences comprising Rv0288, Rv3019c or Rv3017c are described in various databases and putative protein sequences for the above sequences are suggested, Rv3017c either comprising methionin or valine as the first amino acid (The Sanger Centre database (http://www.sanger.ac.uk/Projects/*M_tuberculosis*), Institut Pasteur database (http://genolist.pasteur.fr/TubercuList) and GenBank (http://www4.ncbi.nlm.nih.gov)). However important, this sequence information cannot be used to predict if the DNA is translated and expressed as proteins in vivo. More importantly, it is not possible on the basis of the sequences, to predict whether a given sequence will encode an immunogenic or an inactive protein. The only way to determine if a protein is recognized by the immune system during or after an infection with *M. tuberculosis* is to produce the given protein and test it in an appropriate assay as described herein.

Diagnosing *M. tuberculosis* infection in its earliest stage is important for effective treatment of the disease. Current diagnostic assays to determine *M. tuberculosis* infection are expensive and labour-intensive. In the industrialised part of the world the majority of patients exposed to *M. tuberculosis* receive chest x-rays and attempts are made to culture the bacterium in vitro from sputum samples. X-rays are insensitive as a diagnostic assay and can only identify infections in a very progressed stage. Culturing of *M. tuberculosis* is also not ideal as a diagnostic tool, since the bacteria grows poorly and slowly outside the body, which can produce false negative test results and take weeks before results are obtained. The standard tuberculin skin test is an inexpensive assay, used in third world countries, however it is far from ideal in detecting infection because it cannot distinguish *M. tuberculosis*-infected individuals from *M. bovis* BCG-vaccinated individuals and therefore cannot be used in areas of the world where patients receive or have received childhood vaccination with bacterial strains related to *M. tuberculosis,* e.g. a BCG vaccination.

Animal tuberculosis is caused by *Mycobacterium bovis,* which is closely related to *M. tuberculosis* and within the tuberculosis complex. *M. bovis* is an important pathogen that can infect a range of hosts, including cattle and humans. Tuberculosis in cattle is a major cause of economic loss and represents a significant cause of zoonotic infection. A number of strategies have been employed against bovine TB, but the approach has generally been based on government-organised programmes by which animals deemed positive to defined screening test are slaughtered. The most common test used in cattle is Delayed-type hypersensitivity with PPD as antigen, but alternative in vitro assays are also developed. However, investigations have shown the both the in vivo and the in vitro tests have a relative low specificity, and the detection of false-positive is a significant economic problem (Pollock et al 2000). There is therefore a great need for a more specific diagnostic reagent, which can be used either in vivo or in vitro to detect *M. bovis* infections in animals.

SUMMARY OF THE INVENTION

The present invention is related to preventing, treating and detecting infections caused by species of the tuberculosis complex (*M. tuberculosis, M.bovis, M. africanum*) by the use of a polypeptide comprising an immunogenic portion of one or more of the polypeptides TB10.3 (also named ORF7-1 or Rv3019c), TB10.4 (also named CFP7 or Rv0288) and TB12.9 (also named ORF7-2 or Rv3017c) (WO98/44119, WO99/24577 and Skjøt et al, 2000) or by a nucleotide sequence comprising a nucleotide sequence encoding an immunogenic portion of TB10.3, TB10.4 or TB12.9.

DETAILED DISCLOSURE

The present invention discloses a substantially pure polypeptide, which comprises an amino acid sequence selected from
(a) the group consisting of Rv0288 (SEQ ID NO: 2 and 195) and its homologues Rv3019c (SEQ ID NO: 199) and Rv3017c (SEQ ID NO: 197);
(b) an immunogenic portion, e.g. a T-cell epitope, of any one of the sequences in (a); and/or
(c) an amino acid sequence analogue having at least 70% sequence identity to any one of the sequences in (a) or (b) and at the same time being immunogenic.

Preferred immunogenic portions are the fragments TB10.3-P1, TB10.3-P2, TB10.3-P3, TB10.3-P4, TB10.3-P5, TB10.3-P6, TB10.3-P7, TB10.3-P8, TB10.3-P9, TB10.4-P1, TB10.4-P2, TB10.4-P3, TB10.4-P4, TB10.4-P5, TB10.4-P6, TB10.4-P7, TB10.4-P8, TB10.4-P9, TB12.9-P1, TB12.9-P2, TB12.9-P3, TB12.9-P4, TB12.9-P5, TB12.9-P6, TB12.9-P7, TB12.9-P8, TB12.9-P9, TB12.9-P10 and TB12.9-P11, which have immunological activity. They are recognized in an in vitro cellular assay determining the release of IFN-γ from lymphocytes withdrawn from an individual currently or previously infected with a virulent *mycobacterium*.

Further, the present invention discloses a vaccine, a pharmaceutical composition and a diagnostic reagent, all comprising an amino acid sequence selected from
(a) the group consisting of Rv0288 (SEQ ID NO: 2 and 195) and its homologues Rv3019c (SEQ ID NO: 199) or Rv3017c (SEQ ID NO: 197);
(b) an immunogenic portion, e.g. a T-cell epitope, of any one of the sequences in (a); and/or
(c) an amino acid sequence analogue having at least 70% sequence identity to any one of the sequences in (a) or (b) and at the same time being immunogenic.

DEFINITIONS

The word "polypeptide" in the present specification and claims should have its usual meaning. That is an amino acid chain of any length, including a full-length protein, oligopeptides, short peptides and fragments thereof, wherein the amino acid residues are linked by covalent peptide bonds.

The polypeptide may be chemically modified by being glycosylated, by being lipidated (e.g. by chemical lipidation with palmitoyloxy succinimide as described by Mowat et al. 1991 or with dodecanoyl chloride as described by Lustig et al. 1976), by comprising prosthetic groups, or by containing additional amino acids such as e.g. a his-tag or a signal peptide.

Each polypeptide may thus be characterised by comprising specific amino acid sequences and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". These are defined according to the following table. Amino acids in the same block in the second column and preferably in the same line in the third column may be substituted for each other. The amino acids in the third column are indicated in one-letter code.

| ALIPHATIC | Non-polar | GAP |
| --- | --- | --- |
| | | ILV |
| | Polar-uncharged | CSTM |
| | | NQ |
| | Polar-charged | DE |
| | | KR |
| AROMATIC | | HFWY |

A preferred polypeptide within the present invention is an immunogenic antigen from *M. tuberculosis*. Such antigen can for example be derived from *M. tuberculosis* and/or *M. tuberculosis* culture filtrate. Thus, a polypeptide comprising an immunogenic portion of one of the above antigens may consist entirely of the immunogenic portion, or may contain additional sequences. The additional sequences may be derived from the native *M. tuberculosis* antigen or be heterologous and such sequences may, but need not, be immunogenic.

Each polypeptide is encoded by a specific nucleic acid sequence. It will be understood that such sequences include analogues and variants hereof wherein such nucleic acid sequences have been modified by substitution, insertion, addition or deletion of one or more nucleic acids. Substitutions are preferably silent substitutions in the codon usage which will not lead to any change in the amino acid sequence, but may be introduced to enhance the expression of the protein.

In the present context the term "substantially pure polypeptide fragment" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is in "essentially pure form", i.e. that the polypeptide fragment is essentially free of any other antigen with which it is natively associated, i.e. free of any other antigen from bacteria belonging to the tuberculosis complex or a virulent *mycobacterium*. This can be accomplished by preparing the polypeptide fragment by means of recombinant methods in a non-mycobacterial host cell as will be described in detail below, or by synthesizing the polypeptide fragment by the well-known methods of solid or liquid phase peptide synthesis, e.g. by the method described by Merrifield or variations thereof.

By the term "virulent *mycobacterium*" is understood a bacterium capable of causing the tuberculosis disease in an animal or in a human being. Examples of virulent mycobacteria are *M. tuberculosis, M. africanum,* and *M. bovis*. Examples of relevant animals are cattle, possums, badgers and kangaroos.

By "a TB patient" is understood an individual with culture or microscopically proven infection with virulent mycobacteria, and/or an individual clinically diagnosed with TB and who is responsive to anti-TB chemotherapy. Culture, microscopy and clinical diagnosis of TB are well known by any person skilled in the art.

By the term "PPD-positive individual" is understood an individual with a positive Mantoux test or an individual where PPD induces a positive in vitro recall response determined by release of IFN-γ.

By the term "delayed type hypersensitivity reaction" (DTH) is understood a T-cell mediated inflammatory response elicited after the injection of a polypeptide into, or application to, the skin, said inflammatory response appearing 72–96 hours after the polypeptide injection or application.

By the term "IFN-γ" is understood interferon-gamma. The measurement of IFN-γ is used as an indication of an immunological response.

By the terms "nucleic acid fragment" and "nucleic acid sequence" are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length e.g. from 10 to 10000 nucleotides, depending on the use. When the nucleic acid molecule is for use as a pharmaceutical, e.g. in DNA therapy, or for use in a method for producing a polypeptide according to the invention, a molecule encoding at least one epitope is preferably used, having a length from about 18 to about 1000 nucleotides, the molecule being optionally inserted into a vector. When the nucleic acid molecule is used as a probe, as a primer or in antisense therapy, a molecule having a length of 10–100 is preferably used. According to the invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, 30 or 20 nucleotides (or nucleotide derivatives).

The term "stringent" when used in conjunction with nucleic acid hybridization conditions is as defined in the art, i.e. the hybridization is performed at a temperature not more than 15–20° C. under the melting point Tm, cf. Sambrook et al, 1989, pages 11.45–11.49. Preferably, the conditions are "highly stringent", i.e. 5–10° C. under the melting point Tm.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

The term "sequence identity" indicates a quantitative measure of the degree of homology between two amino acid sequences of equal length or between two nucleotide sequences of equal length. If the two sequences to be compared are not of equal length, they must be aligned to best possible fit possible with the insertion of gaps or alternatively, truncation at the ends of the protein sequences. The sequence identity can be calculated as $(N_{ref}-N_{dif})100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$). Sequence identity can alternatively be calculated by the BLAST program e.g. the BLASTP program (Pearson W. R and D. J. Lipman (1988) PNAS USA 85:2444–2448)(www.ncbi.nlm.nih.gov/cgi-bin/Blast). In one aspect of the invention, alignment is performed with the sequence alignment method ClustalW with default parameters as described by Thompson J., et al 1994, available at http://www2.ebi.ac.uk/clustalw/.

A preferred minimum percentage of sequence identity is at least 70%, such as at least 75%, at least 80%, such as at least 85%, at least 90%, at least 91%, at least 92%, at least 93%, at least 94%, at least 95%, at least 96%, at least 97%, at least 98%, at least 99%, such as at least 99.5%.

In a preferred embodiment of the invention, the polypeptide comprises an immunogenic portion of the polypeptide, such as an epitope for a B-cell or T-cell. The immunogenic portion of a polypeptide is a part of the polypeptide, which elicits an immune response in an animal or a human being, and/or in a biological sample determined by any of the biological assays described herein. The immunogenic portion of a polypeptide may be a T-cell epitope or a B-cell epitope. Immunogenic portions can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence (Ravn et al 1999).

In order to identify relevant T-cell epitopes which are recognised during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-γ assay described herein. Another method utilises overlapping oligopeptides for the detection of MHC class II epitopes, preferably synthetic, having a length of e.g. 20 amino acid residues derived from the polypeptide. These peptides can be tested in biological assays (e.g. the IFN-γ assay as described herein) and some of these will give a positive response (and thereby be immunogenic) as evidence for the presence of a T cell epitope in the peptide. For the detection of MHC class I epitopes it is possible to predict peptides that will bind (Stryhn et al 1996) and hereafter produce these peptides synthetically and test them in relevant biological assays e.g. the IFN-γ assay as described herein. The peptides preferably having a length of e.g. 8 to 11 amino acid residues derived from the polypeptide. B-cell epitopes can be determined by analysing the B cell recognition to overlapping peptides covering the polypeptide of interest as e.g. described in Harboe et al 1998.

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, such as at least 30 amino acid residues. Hence, in important embodiments of the inventive method, it is preferred that the polypeptide fragment has a length of at most 50 amino acid residues, such as at most 40, 35, 30, 25, e.g. at most 20 amino acid residues. It is expected that the peptides having a length of between 10 and 20 amino acid residues will prove to be most efficient as MHC class II epitopes and therefore especially preferred lengths of the polypeptide fragment used in the method according to the invention are 18, such as 15, 14, 13, 12 and even 11 amino acid residues. It is expected that the peptides having a length of between 7 and 12 amino acid residues will prove to be most efficient as MHC class I epitopes and therefore especially other lengths of the polypeptide fragment used in the method according to the invention are 11, such as 10, 9, 8 and even 7 amino acid residues.

Immunogenic portions of polypeptides may be recognised by a broad part (high frequency) or by a minor part (low frequency) of the genetically heterogenic human population. In addition some immunogenic portions induce high immunological responses (dominant), whereas others induce lower, but still significant, responses (subdominant). High frequency><low frequency can be related to the immunogenic portion binding to widely distributed MHC molecules (HLA type) or even by multiple MHC molecules (Kilgus et al. 1991, Sinigaglia et al 1988).

In the context of providing candidate molecules for a new vaccine against tuberculosis, the subdominant epitopes are however as relevant as are the dominant epitopes since it has been show (Olsen et al 2000) that such epitopes can induce protection regardless of being subdominant.

A common feature of the polypeptides of the invention is their capability to induce an immunological response as illustrated in the examples. It is understood that a variant of a polypeptide of the invention produced by substitution, insertion, addition or deletion is also immunogenic as determined by at least one of the assays described herein.

An immune individual is defined as a person or an animal, which has cleared or controlled an infection with virulent mycobacteria or has received a vaccination with *M.bovis* BCG.

An immunogenic polypeptide is defined as a polypeptide that induces an immune response in a biological sample or an individual currently or previously infected with a virulent *mycobacterium*. The immune response may be monitored by one of the following methods:

An in vitro cellular response is determined by release of a relevant cytokine such as IFN-γ from lymphocytes withdrawn from an animal or human being currently or previously infected with virulent mycobacteria, or by detection of proliferation of these T cells, the induction being performed by the addition of the polypeptide or the immunogenic portion to a suspension comprising from $1 \times 10^5$ cells to $3 \times 10^5$ cells per well. The cells are isolated from either the blood, the spleen, the liver or the lung and the addition of the polypeptide or the immunogenic portion resulting in a concentration of not more than 20 µg per ml suspension and the stimulation being performed from two to five days. For monitoring cell proliferation the cells are pulsed with radioactive labeled Thymidine and after 16–22 hours of incubation detecting the proliferation by liquid scintillation counting, a positive response being a response more than background plus two standard derivations. The release of IFN-γ can be determined by the ELISA method, which is well known to a person skilled in the art, a positive response being a response more than background plus two standard derivations. Other cytokines than IFN-γ could be relevant when monitoring the immunological response to the polypeptide, such as IL-12, TNF-α, IL-4, IL-5, IL-10, IL-6, TGF-β. Another and more sensitive method for determining the presence of a cytokine (e.g. IFN-γ) is the ELISPOT method where the cells isolated from either the blood, the spleen, the liver or the lung are diluted to a concentration of preferably 1 to $4 \times 10^6$ cells/ml and incubated for 18–22 hrs in the presence of the polypeptide or the immunogenic portion resulting in a concentration of not more than 20 µg per ml. The cell suspensions are hereafter diluted to 1 to $2 \times 10^6$/ml and transferred to Maxisorp plates coated with anti-IFN-γ and incubated for preferably 4 to 16 hours. The IFN-γ producing cells are determined by the use of labelled secondary anti-IFN-γ antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or a person infected with *M. tuberculosis* where the T cell lines have been driven with either live mycobacteria, extracts from the bacterial cell or culture filtrate for 10 to 20 days with the addition of IL-2. The induction is performed by addition of not more than 20 µg polypeptide per ml suspension to the T cell lines containing from $1 \times 10^5$ cells to $3 \times 10^5$ cells per well and incubation being performed from two to six days. The induction of IFN-γ or release of another relevant cytokine is detected by ELISA. The stimulation of T cells can also be monitored by detecting cell proliferation using radioactively labeled Thymidine as described above. For both assays a positive response is a response more than background plus two standard derivations.

An in vivo cellular response which may be determined as a positive DTH response after intradermal injection or local application patch of at most 100 µg of the polypeptide or the immunogenic portion to an individual who is clinically or subclinically infected with a virulent *Mycobacterium*, a positive response having a diameter of at least 5 mm 72–96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the OD e.g.

by ELISA where a positive response is a response of more than background plus two standard derivations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of a virulent *Mycobacterium*. Readout for induced protection could be decrease of the bacterial load in target organs compared to non-vaccinated animals, prolonged survival times compared to non-vaccinated animals and diminished weight loss compared to non-vaccinated animals.

In general, *M. tuberculosis* antigens, and DNA sequences encoding such antigens, may be prepared using any one of a variety of procedures. They may be purified as native proteins from the *M. tuberculosis* cell or culture filtrate by procedures such as those described above. Immunogenic antigens may also be produced recombinantly using a DNA sequence encoding the antigen, which has been inserted into an expression vector and expressed in an appropriate host. Examples of host cells are *E. coli*. The polypeptides or immunogenic portion hereof can also be produced synthetically if having fewer than about 100 amino acids, generally fewer than 50 amino acids, and may be generated using techniques well known to those ordinarily skilled in the art, such as commercially available solid-phase techniques where amino acids are sequentially added to a growing amino acid chain.

In the construction and preparation of plasmid DNA encoding the polypeptide as defined for DNA vaccination a host strain such as *E. coli* can be used. Plasmid DNA can then be prepared from overnight cultures of the host strain carrying the plasmid of interest and purified using e.g. the Qiagen Giga-Plasmid column kit (Qiagen, Santa Clarita, Calif., USA) including an endotoxin removal step. It is essential that plasmid DNA used for DNA vaccination is endotoxin free.

The immunogenic polypeptides may also be produced as fusion proteins, by which methods superior characteristics of the polypeptide of the invention can be achieved. For instance, fusion partners that facilitate export of the polypeptide when produced recombinantly, fusion partners that facilitate purification of the polypeptide, and fusion partners which enhance the immunogenicity of the polypeptide fragment of the invention are all interesting possibilities. Therefore, the invention also pertains to a fusion polypeptide comprising at least one polypeptide or immunogenic portion defined above and at least one fusion partner. The fusion partner can, in order to enhance immunogenicity, be another polypeptide derived from *M. tuberculosis*, such as of a polypeptide fragment derived from a bacterium belonging to the tuberculosis complex, such as ESAT-6, TB10.4, CFP10, RD1-ORF5, RD1-ORF2, Rv1036, MPB64, MPT64, Ag85A, Ag85B (MPT59), MPB59, Ag85C, 19 kDa lipoprotein, MPT32 and alpha-crystallin, or at least one T-cell epitope of any of the above mentioned antigens ((Skjøt et al, 2000; Danish Patent application PA 2000 00666; Danish Patent application PA 1999 01020; U.S. patent application Ser. No. 09/0505,739; Rosenkrands et al, 1998; Nagai et al, 1991). The invention also pertains to a fusion polypeptide comprising mutual fusions of two or more of the polypeptides (or immunogenic portions thereof) of the invention.

Other fusion partners, which could enhance the immunogenicity of the product, are lymphokines such as IFN-γ, IL-2 and IL-12. In order to facilitate expression and/or purification, the fusion partner can e.g. be a bacterial fimbrial protein, e.g. the pilus components pilin and papA; protein A; the ZZ-peptide (ZZ-fusions are marketed by Pharmacia in Sweden); the maltose binding protein; gluthatione S-transferase; β-galactosidase; or poly-histidine. Fusion proteins can be produced recombinantly in a host cell, which could be *E. coli*, and it is a possibility to induce a linker region between the different fusion partners.

Other interesting fusion partners are polypeptides, which are lipidated so that the immunogenic polypeptide is presented in a suitable manner to the immune system. This effect is e.g. known from vaccines based on the *Borrelia burgdorferi* OspA polypeptide as described in e.g. WO 96/40718 A or vaccines based on the *Pseudomonas aeruginosa* Oprl lipoprotein (Cote-Sierra J, et al, 1998). Another possibility is N-terminal fusion of a known signal sequence and an N-terminal cystein to the immunogenic polypeptide. Such a fusion results in lipidation of the immunogenic polypeptide at the N-terminal cystein, when produced in a suitable production host.

Another part of the invention pertains to a vaccine composition comprising a polypeptide (or at least one immunogenic portion thereof) or fusion polypeptide according to the invention. In order to ensure optimum performance of such a vaccine composition it is preferred that it comprises an immunologically and pharmaceutically acceptable carrier, vehicle or adjuvant.

An effective vaccine, wherein a polypeptide of the invention is recognized by the animal, will in an animal model be able to decrease bacterial load in target organs, prolong survival times and/or diminish weight loss after challenge with a virulent *Mycobacterium*, compared to non-vaccinated animals.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyldioctadecylammonium bromide (DDA), Quil A, poly I:C, aluminium hydroxide, Freund's incomplete adjuvant, IFN-γ, IL-2, IL-12, monophosphoryl lipid A (MPL), Treholose Dimycolate (TDM), Trehalose Dibehenate and muramyl dipeptide (MDP).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-γ inducers such as poly I:C in combination with the above-mentioned adjuvants.

Another interesting possibility for achieving adjuvant effect is to employ the technique described in Gosselin et al., 1992 (which is hereby incorporated by reference herein). In brief, a relevant antigen such as an antigen of the present invention can be conjugated to an antibody (or antigen binding antibody fragment) against the Fcγ receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10–95% of active ingredient, preferably 25–70%.

In many instances, it will be necessary to have multiple administrations of the vaccine. Especially, vaccines can be administered to prevent an infection with virulent mycobacteria and/or to treat established mycobacterial infection. When administered to prevent an infection, the vaccine is given prophylactically, before definitive clinical signs or symptoms of an infection are present.

Due to genetic variation, different individuals may react with immune responses of varying strength to the same polypeptide. Therefore, the vaccine according to the invention may comprise several different polypeptides in order to increase the immune response. The vaccine may comprise two or more polypeptides or immunogenic portions, where all of the polypeptides are as defined above, or some but not all of the peptides may be derived from virulent mycobacteria. In the latter example, the polypeptides not necessarily fulfilling the criteria set forth above for polypeptides may either act due to their own immunogenicity or merely act as adjuvants.

The vaccine may comprise 1–20, such as 2–20 or even 3–20 different polypeptides or fusion polypeptides, such as 3–10 different polypeptides or fusion polypeptides.

The invention also pertains to a method for immunising an animal, including a human being, against TB caused by virulent mycobacteria, comprising administering to the animal the polypeptide of the invention, or a vaccine composition of the invention as described above, or a living vaccine described above.

The invention also pertains to a method for producing an immunologic composition according to the invention, the method comprising preparing, synthesising or isolating a polypeptide according to the invention, and solubilizing or dispersing the polypeptide in a medium for a vaccine, and optionally adding other *M. tuberculosis* antigens and/or a carrier, vehicle and/or adjuvant substance.

The nucleic acid fragments of the invention may be used for effecting in vivo expression of antigens, ie. the nucleic acid fragments may be used in so-called DNA vaccines as reviewed in Ulmer et al., 1993, which is included by reference.

Hence, the invention also relates to a vaccine comprising a nucleic acid fragment according to the invention, the vaccine effecting in vivo expression of antigen by an animal, including a human being, to whom the vaccine has been administered, the amount of expressed antigen being effective to confer substantially increased resistance to infections caused by virulent mycobacteria in an animal, including a human being.

The efficacy of such a DNA vaccine can possibly be enhanced by administering the gene encoding the expression product together with a DNA fragment encoding a polypeptide which has the capability of modulating an immune response.

One possibility for effectively activating a cellular immune response for a vaccine can be achieved by expressing the relevant antigen in a vaccine in a non-pathogenic microorganism or virus. Well-known examples of such microorganisms are *Mycobacterium bovis* BCG, *Salmonella* and *Pseudomona* and examples of viruses are Vaccinia Virus and Adenovirus.

Therefore, another important aspect of the present invention is an improvement of the living BCG vaccine presently available, wherein one or more copies of a DNA sequence encoding one or more polypeptide as defined above has been incorporated into the genome of the micro-organism in a manner allowing the micro-organism to express and secrete the polypeptide. The incorporation of more than one copy of a nucleotide sequence of the invention is contemplated to enhance the immune response Another possibility is to integrate the DNA encoding the polypeptide according to the invention in an attenuated virus such as the vaccinia virus or Adenovirus (Rolph et al 1997). The recombinant vaccinia virus is able to replicate within the cytoplasma of the infected host cell and the polypeptide of interest can therefore induce an immune response, which is envisioned to induce protection against TB.

The invention also relates to the use of a polypeptide or nucleic acid of the invention for use as a therapeutic vaccine, which concept has been described in the literature exemplified by D. Lowry (1999, Nature 400: 269–71). Antigens with therapeutic properties may be identified based on their ability to diminish the severity of *M. tuberculosis* infection in experimental animals or prevent reactivation of previous infection, when administered as a vaccine. The composition used for therapeutic vaccines can be prepared as described above for vaccines.

The invention also relates to a method of diagnosing TB caused by a virulent *mycobacterium* in an animal, including a human being, comprising intradermally injecting, in the animal, a polypeptide according to the invention, a positive skin response at the location of injection being indicative of the animal having TB, and a negative skin response at the location of injection being indicative of the animal not having TB.

When diagnosis of previous or ongoing infection with virulent mycobacteria is the aim, a blood sample comprising mononuclear cells (i.e. T-lymphocytes) from a patient could be contacted with a sample of one or more polypeptides of the invention. This contacting can be performed in vitro and a positive reaction could e.g. be proliferation of the T-cells or release of cytokines such as IFN-γ into the extracellular phase. It is also conceivable to contact a serum sample from a subject with a polypeptide of the invention, the demonstration of a binding between antibodies in the serum sample and the polypeptide being indicative of previous or ongoing infection.

The invention therefore also relates to an in vitro method for diagnosing ongoing or previous sensitisation in an animal or a human being with a virulent *mycobacterium,* the method comprising providing a blood sample from the animal or human being, and contacting the sample from the animal with the polypeptide of the invention, a significant release into the extracellular phase of at least one cytokine by mononuclear cells in the blood sample being indicative of the animal being sensitised. A positive response is a response more than release from a blood sample derived from a patient without the TB diagnosis plus two standard derivations. The invention also relates to an in vitro method for diagnosing ongoing or previous sensitisation in an animal or a human being with a virulent *mycobacterium,* the method comprising providing a blood sample from the animal or human being, and contacting the sample from the animal with the polypeptide of the invention demonstrating the presence of antibodies recognizing the polypeptide of the invention in the serum sample.

The immunogenic composition used for diagnosing may comprise 1–20, such as 2–20 or even 3–20 different polypeptides or fusion polypeptides, such as 3–10 different polypeptides or fusion polypeptides.

The nucleic acid probes encoding the polypeptide of the invention can be used in a variety of diagnostic assays for detecting the presence of pathogenic organisms in a given sample. A method of determining the presence of mycobacterial nucleic acids in an animal, including a human being, or in a sample, comprising administering a nucleic acid fragment of the invention to the animal or incubating the sample with the nucleic acid fragment of the invention or a nucleic acid fragment complementary thereto, and detecting the presence of hybridised nucleic acids resulting from the incubation (by using the hybridisation assays which are well-known in the art), is also included in the invention. Such a method of diagnosing TB might involve the use of a composition comprising at least a part of a nucleotide sequence as defined above and detecting the presence of nucleotide sequences in a sample from the animal or human being to be tested which hybridise with the nucleic acid fragment (or a complementary fragment) by the use of PCR technique.

A monoclonal or polyclonal antibody, which is specifically reacting with a polypeptide of the invention in an immuno assay, or a specific binding fragment of said antibody, is also a part of the invention. The antibodies can be produced by methods known to the person skilled in the art. Polyclonal antibodies can be raised in a mammal, for example, by one or more injections of a polypeptide according to the present invention and, if desired, an adjuvant. The monoclonal antibodies according to the present invention may, for example, be produced by the hybridoma method first described by Köhler and Milstein (1975), or may be produced by recombinant DNA methods such as described in U.S. Pat. No. 4,816,567. The monoclonal antibodies may also be isolated from phage libraries generated using the techniques described in McCafferty et al (1990), for example. Methods for producing antibodies are described in the literature, e.g. in U.S. Pat. No. 6,136,958.

A sample of a potentially infected organ may be contacted with such an antibody recognizing a polypeptide of the invention. The demonstration of the reaction by means of methods well known in the art between the sample and the antibody will be indicative of an ongoing infection. It is of course also a possibility to demonstrate the presence of anti-mycobacterial antibodies in serum by contacting a serum sample from a subject with at least one of the polypeptide fragments of the invention and using well-known methods for visualising the reaction between the antibody and antigen.

In diagnostics, an antibody, a nucleic acid fragment and/or a polypeptide of the invention can be used either alone, or as a constituent in a composition. Such compositions are known in the art, and comprise compositions in which the antibody, the nucleic acid fragment or the polypeptide of the invention is coupled, preferably covalently, to at least one other molecule, e.g. a label (e.g. radioactive or fluorescent) or a carrier molecule.

Concordance list

| | Synonyms CFP7, TB10.4, PV-2 binding protein | DNA SEQ ID NO 1 and 194 | Protein SEQ ID NO 2 and 195 |
|---|---|---|---|
| Rv0288 | | | |
| Rv3017c | ORF7-2, TB12.9 | 196 | 197 |
| Rv3019c | ORF7-1, TB10.3 | 198 | 199 |
| TB10.3-P1 | | 200 | 201 |
| TB10.3-P2 | | 202 | 203 |
| TB10.3-P3 | | 204 | 205 |
| TB10.3-P4 | | 206 | 207 |
| TB10.3-P5 | | 208 | 209 |
| TB10.3-P6 | | 210 | 211 |
| TB10.3-P7 | | 212 | 213 |
| TB10.3-P8 | | 214 | 215 |
| TB10.3-P9 | | 216 | 217 |
| TB10.4-P1 | | 218 | 219 |
| TB10.4-P2 | | 220 | 221 |
| TB10.4-P3 | | 222 | 223 |
| TB10.4-P4 | | 224 | 225 |
| TB10.4-P5 | | 226 | 227 |
| TB10.4-P6 | | 228 | 229 |
| TB10.4-P7 | | 230 | 231 |
| TB10.4-P8 | | 232 | 233 |
| TB10.4-P9 | | 234 | 235 |
| TB12.9-P1 | | 236 | 237 |
| TB12.9-P2 | | 238 | 239 |
| TB12.9-P3 | | 240 | 241 |
| TB12.9-P4 | | 242 | 243 |
| TB12.9-P5 | | 244 | 245 |
| TB12.9-P6 | | 246 | 247 |
| TB12.9-P7 | | 248 | 249 |
| TB12.9-P8 | | 250 | 251 |
| TB12.9-P9 | | 252 | 253 |
| TB12.9-P10 | | 254 | 255 |
| TB12.9-P11 | | 256 | 257 |

LEGENDS TO FIGURES

FIG. 1: Course of infection with *M. tuberculosis* in naive and memory immune mice.

C57Bl/6j mice were infected with 2.5×10⁵ viable units of M. tuberculosis and the growth of the organisms in the spleen was investigated for a period of 25 days. The count of the CFU indicated represent the means of 4–5 mice.

Figure 2:
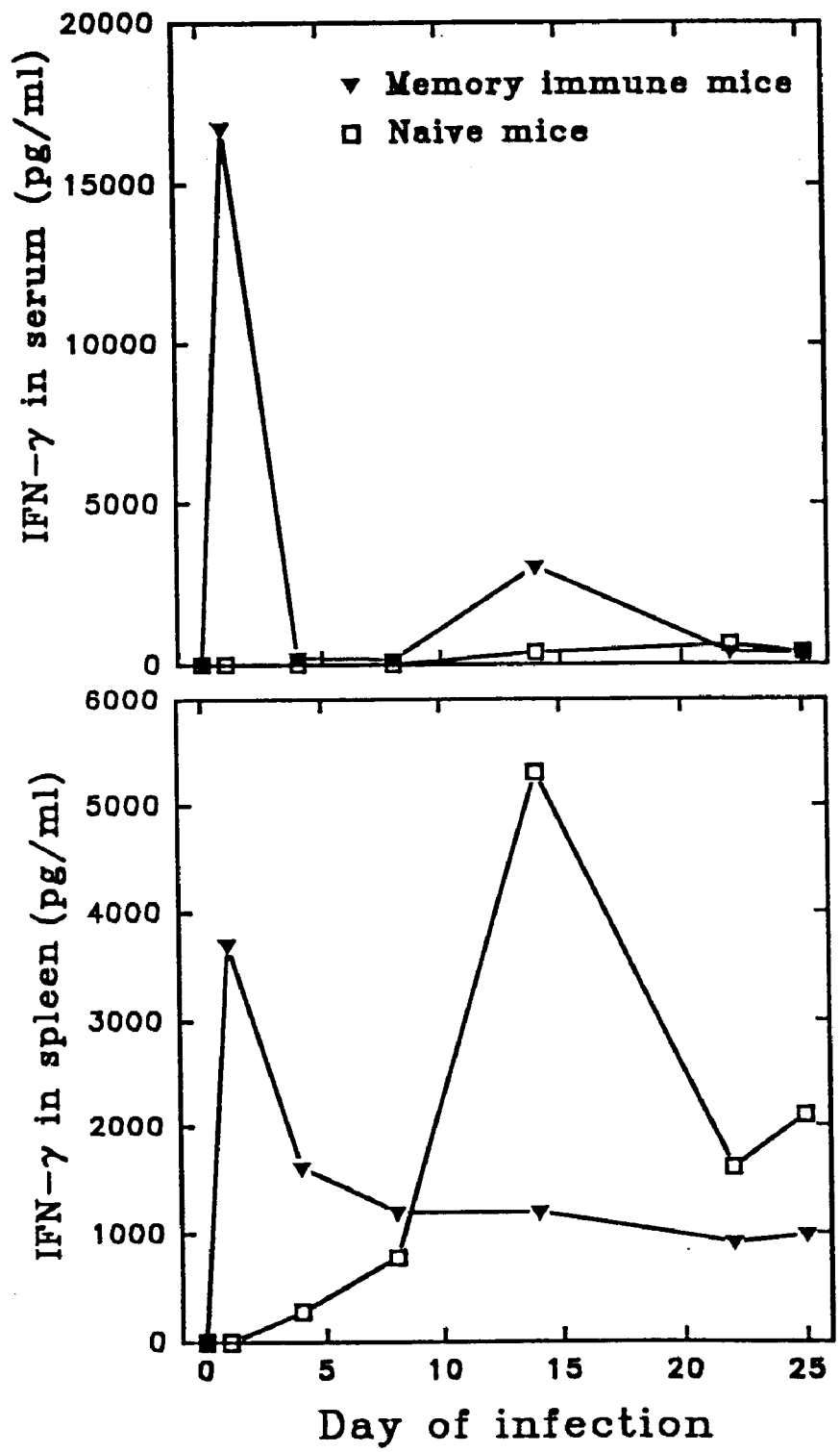

FIG. 2: In vivo IFN-γ production during tuberculosis infection.

Memory immune or naive mice were infected with 2.5×10⁵ colony forming units of M. tuberculosis i.v. and the level of IFN-γ was monitored in the spleen or serum of animals during the course of infection.

Figure 3:
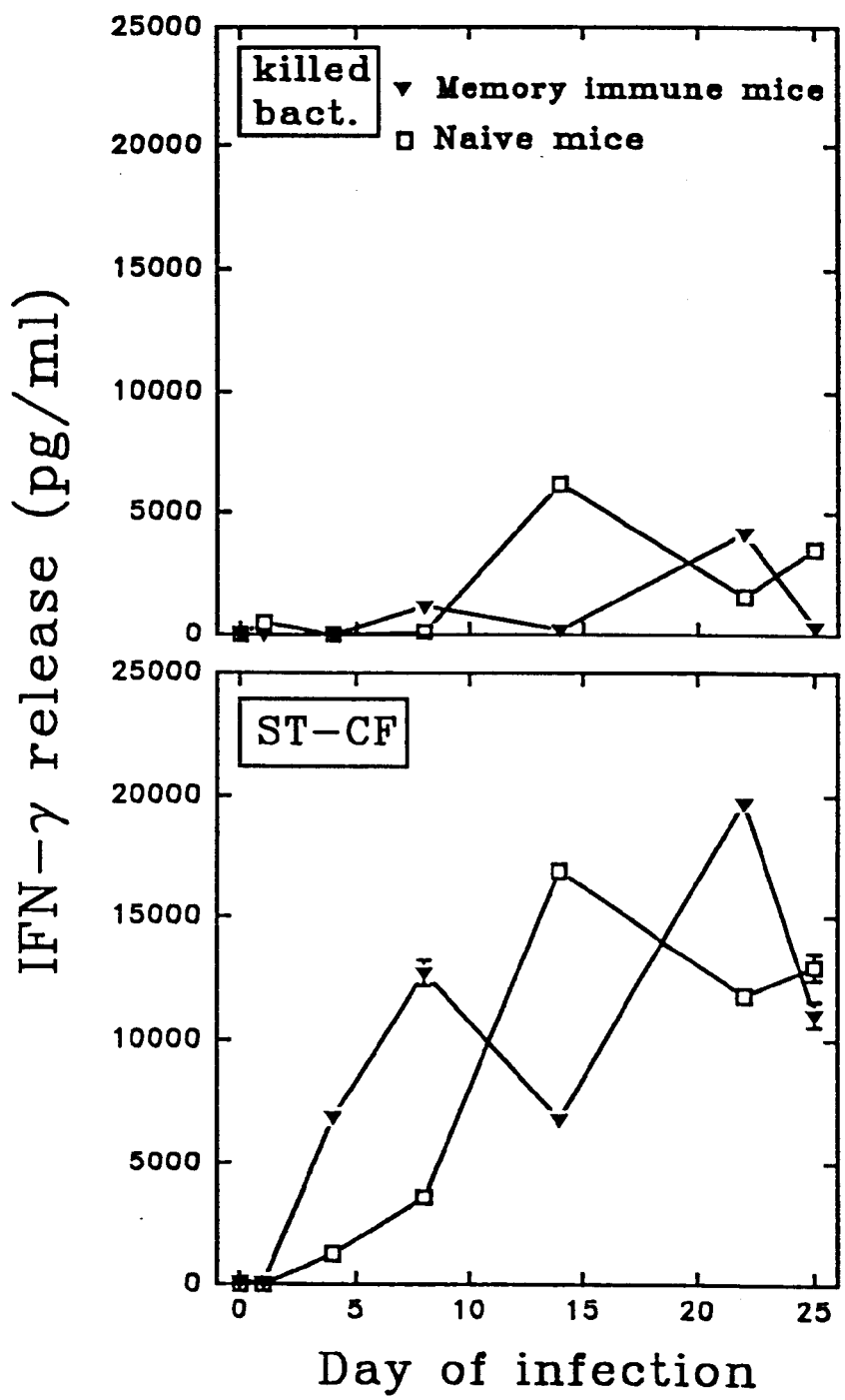

FIG. 3: In vitro response of spleen lymphocytes from infected mice.

Memory immune or naive mice were sacrificed at different time points during the course of infection, and spleen lymphocytes were stimulated in vitro with ST-CF or killed bacilli. Cell culture supernatants were tested for the presence of IFN-γ.

Figure 4:
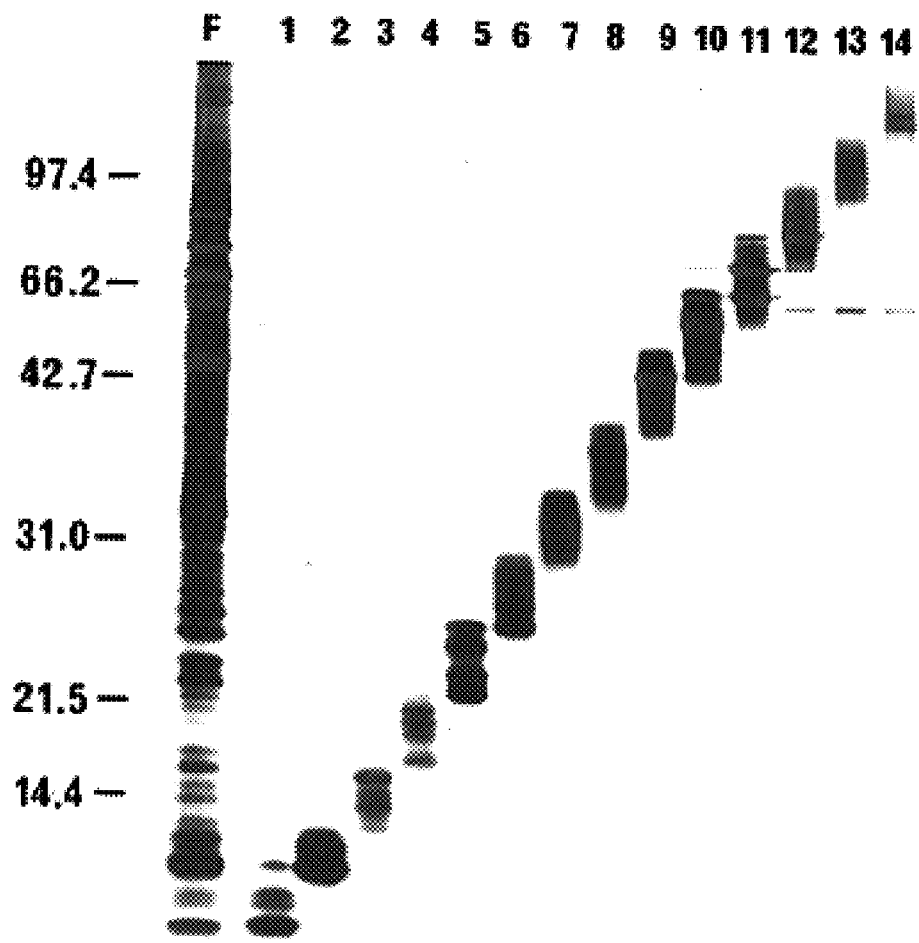

FIG. 4: Short-term culture-filtrate fractions.

ST-CF was divided into 14 fractions by the multi-elution technique and the fractions were analyzed by SDS-PAGE and Silver-staining. Lane F: ST-CF Lane 1–15: fractions 1–15.

Figure 5:
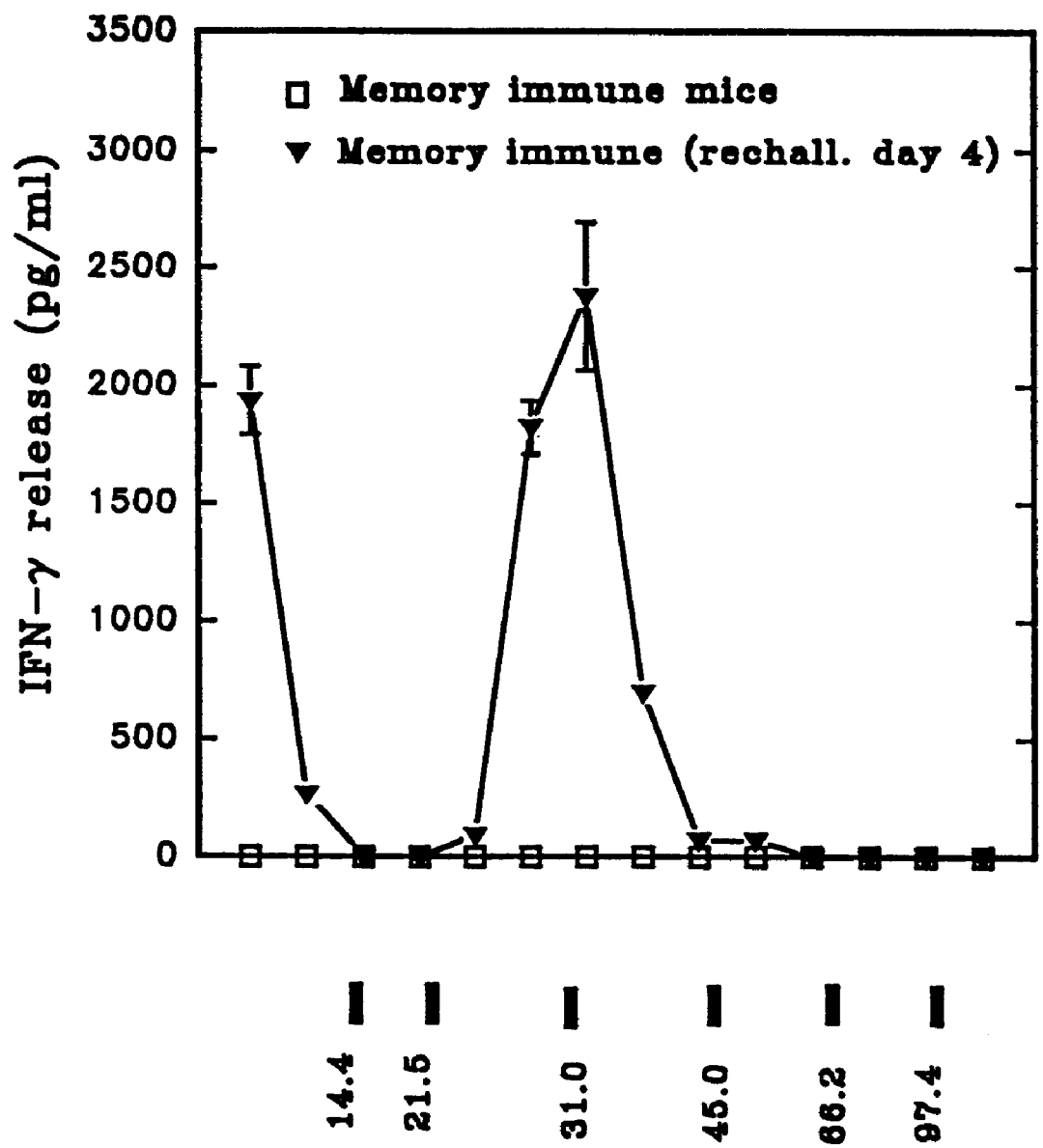

FIG. 5: T-cell reactivation during a secondary infection.

IFN-γ release by spleen lymphocytes isolated either directly from memory immune mice or four days after the mice had received a secondary infection. The lymphocytes were stimulated in vitro with ST-CF fractions and the supernatants harvested for quantification of IFN-γ. The migration of molecular mass markers (as shown in FIG. 4) are indicated at the bottom.

Figure 6:
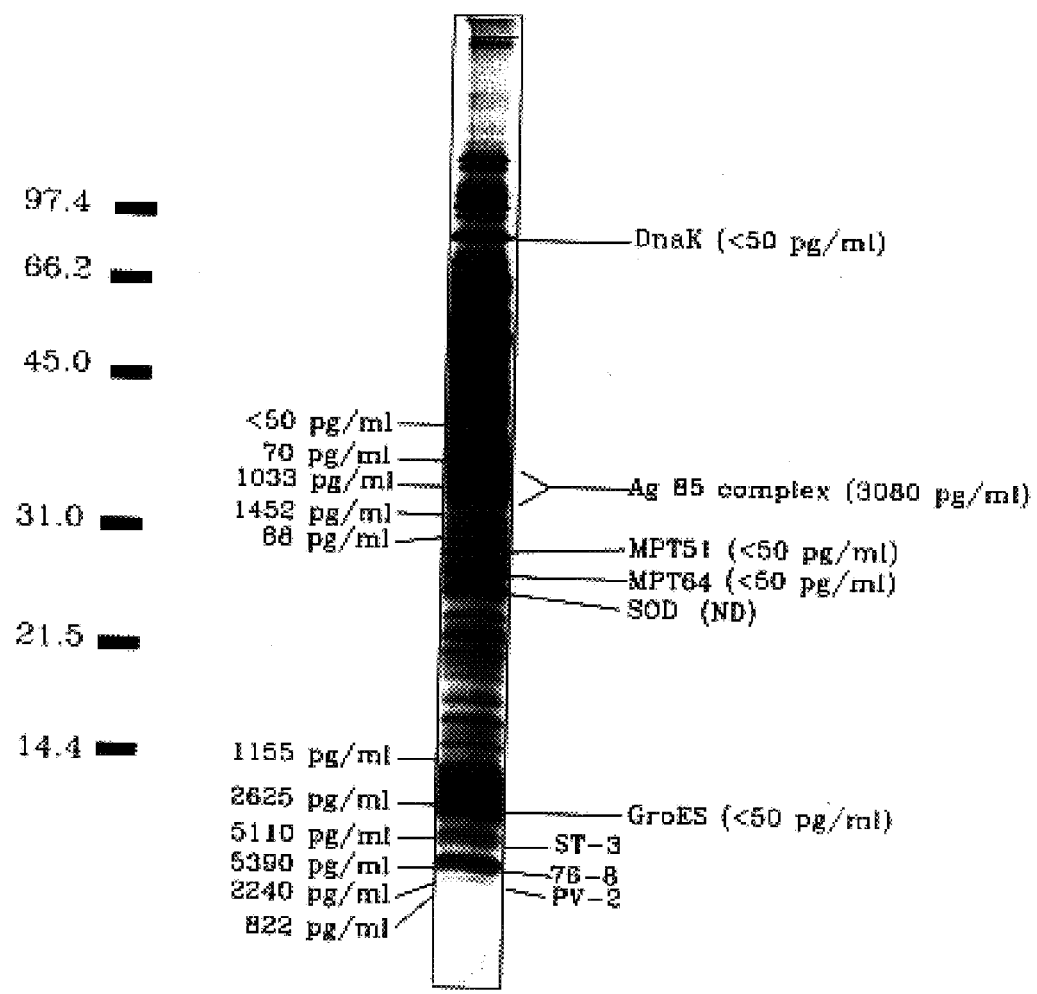

FIG. 6: Precise mapping of IFN-γ release in response to single secreted antigens.

A panel of narrow fractions within the stimulatory regions 4–14 and 26–34 enabled the precise mapping of proteins capable of inducing IFN-γ in microcultures containing lymphocytes from memory immune mice at day 4 of rechallenge.

On the left hand side: IFN-γ release by single secreted antigens.

On the right hand side: The localization of and IFN-γ induction by defined secreted antigens of M. tuberculosis. ST-3, 76-8 and PV-2 are the designation of three mAbs which defines secreted antigens of molecular mass 5–8 kDa.

Figure 7:
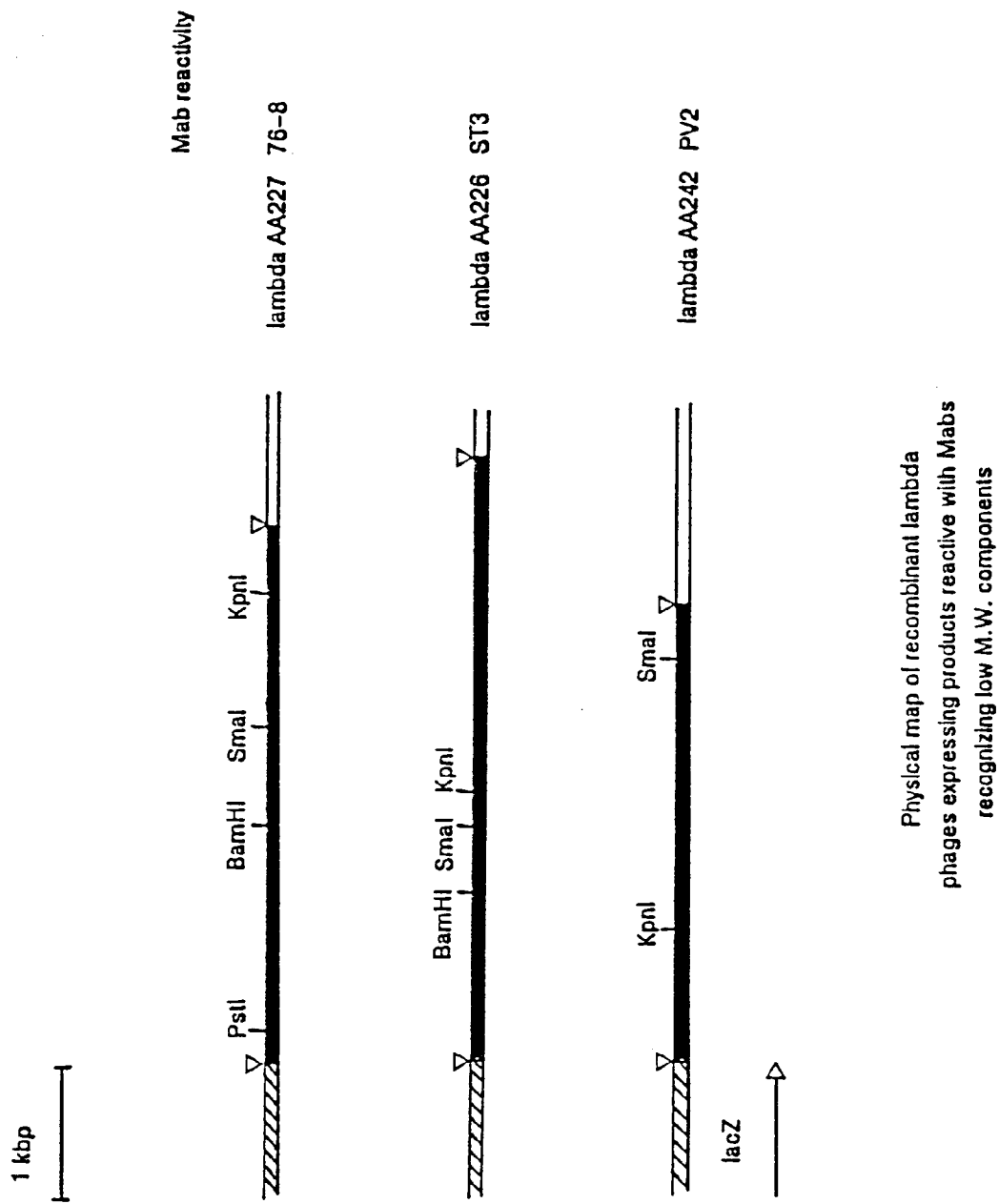

FIG. 7: Physical map of recombinant lambda phages expressing products reactive with Mabs recognizing low MW components.

Cross-hatched bar; lacZ, solid bar; M. tuberculosis DNA, open bar; lambdagt11 DNA (right arm), open triangles indicate EcoRI cleavage sites originating from the lambdagt11 vector. The direction of translation and transcription of the gene products fused to beta-galactosidase is indicated by an arrow.

Figure 8:
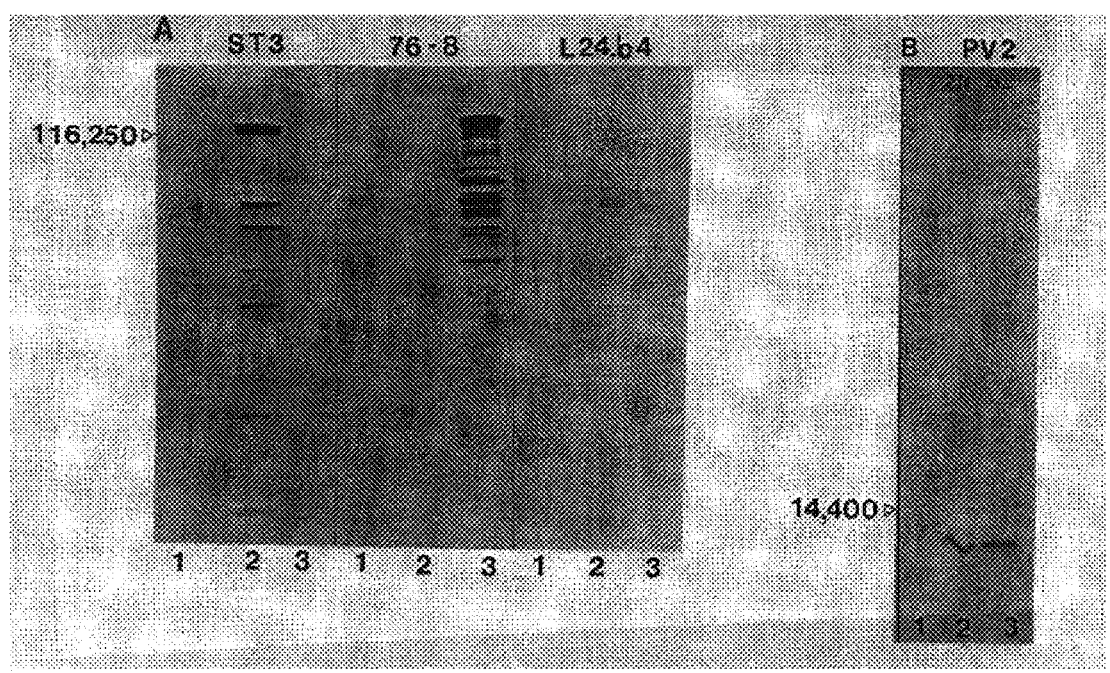

FIG. 8: Western blot analyses demonstrating recombinant expression of low molecular weight components.

Lysates of E. coli Y1089 lysogenized with lambda AA226, lambda AA227 or lambda were analyzed in Western blot experiments after PAGE (A: 10%, B: 10 to 20% gradient).

Panel A: lanes 1: lambda gt11, lanes 2: lambda AA226, lanes 3: lambda AA227.

Panel B: lane 1: lambda gt11, lanes 2 and 3: lambda AA242 and AA230 (identical clones).

The monoclonal antibodies are indicated on top of each panel. L24,c24 is an anti-MPT64 reactive monoclonal antibody.

FIG. 9: Nucleotide sequence (SEQ ID NO: 1) of cfp7. The deduced amino acid sequence (SEQ ID NO: 2) of CFP7 is given in conventional one-letter code below the nucleotide sequence. The putative ribosome-binding site is written in underlined italics as are the putative −10 and −35 regions. Nucleotides written in bold are those encoding CFP7.

FIG. 10. Nucleotide sequence (SEQ ID NO: 3) of cfp9. The deduced amino acid sequence (SEQ ID NO: 4) of CFP9 is given in conventional one-letter code below the nucleotide sequence. The putative ribosome-binding site Shine Delgarno sequence is written in underlined italics as are the putative −10 and −35 regions. Nucleotides in bold writing are those encoding CFP9. The nucleotide sequence obtained from the lambda 226 phage is double underlined.

FIG. 11: Nucleotide sequence of mpt51. The deduced amino acid sequence of MPT51 is given in a one-letter code below the nucleotide sequence. The signal is indicated in italics. The putative potential ribosome-binding site is underlined. The nucleotide difference and amino acid difference compared to the nucleotide sequence of MPB51 (Ohara et al., 1995) are underlined at position 780. The nucleotides given in italics are not present in M. tuberculosis H37Rv.

Figure 12:
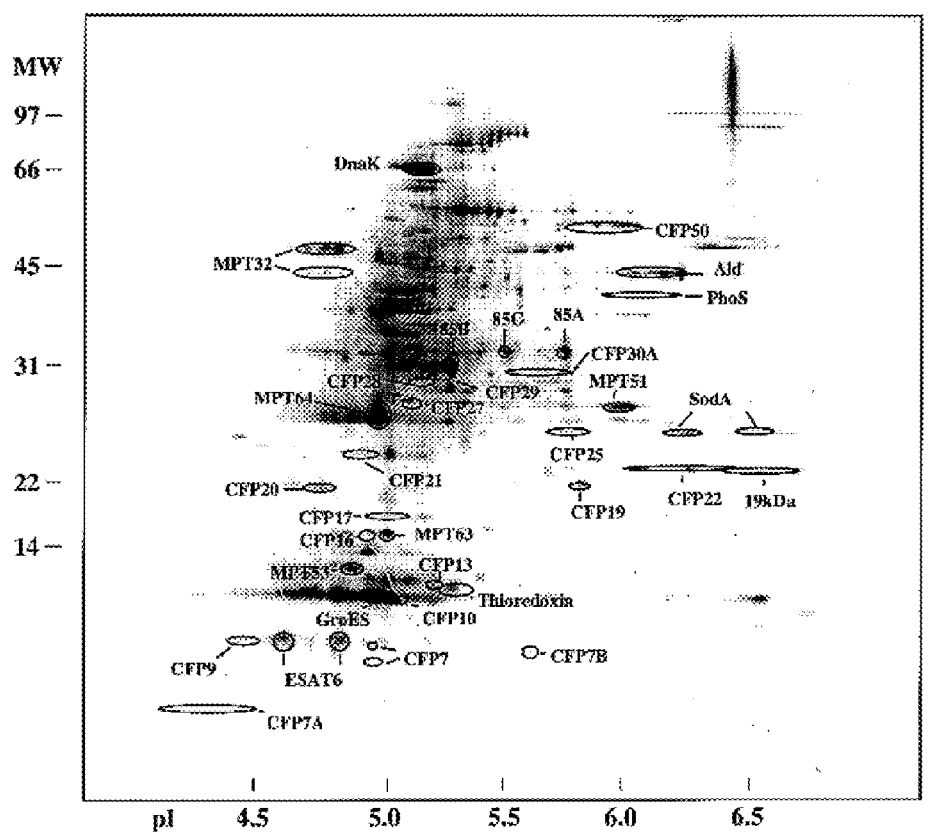

FIG. 12: the position of the purified antigens in the 2DE system have been determined and mapped in a reference gel. The newly purified antigens are encircled and the position of well-known proteins are also indicated.

FIG. 13 Indication of the TB10.4 immunogenic portions in alignment to the full sequence of TB10.4.

FIG. 14 Indication of the TB10.3 immunogenic portions in alignment to the full sequence of TB10.3. Underlined amino acids are different from the TB10.4 peptide.

FIG. 15 Indication of the TB12.9 immunogenic portions in alignment to the full sequence of TB12.9. Underlined amino acids are different from the TB10.4 peptide.

PREABLE TO EXAMPLES

It is an established fact that long-term immunological memory resides after termination of a tuberculous infection (Orme, I. M. 1988., Lefford, M. J. et al. 1974.). This memory immunity efficiently protects the host against a secondary infection with M. tuberculosis later in life. When an immune host mounts a protective immune response, the specific T-cells responsible for the early recognition of the infected macrophage, stimulates a powerful bactericidal activity through their production of IFN-γ (Rook, G. A. W. 1990., Flesch, I. et al. 1987.). Protective antigens, which are to be incorporated in a future sub-unit vaccine, have in the examples below been sought among the molecular targets of the effector cells responsible for the recall of a protective immune response. This has resulted in the identification of immunodominant antigenic targets for T-cells during the first phase of a protective immune response.

Example 1

Isolation of T-cell Stimulating Low Molecular Weight ST-CF Antigens

Bacteria. M. tuberculosis H37Rv (ATCC 27294) was grown at 37° C. on Löwenstein-Jensen medium or in suspension in modified Sauton medium. BCG Copenhagen was obtained as a freeze dried vaccine and were rehydrated with diluted sauton followed by a brief sonication to ensure a disperse suspension.

Production of short-term culture filtrate (ST-CF). ST-CF was produced as described previously (Andersen et al., 1991b). Briefly M. tuberculosis (4×10⁶ CFU/ml) were incubated in Sauton medium and grown on an orbital shaker for 7 days. The bacteria were removed by filtration and the culture supernatants were passed through sterile filters (0.2 µm) and concentrated on an Amicon YM 3 membrane (Amicon, Danvers, Mass.).

Fractionation of ST-CF by the multi-elution technique. ST-CF (5 mg) was separated in 10–20% SDS-PAGE overnight (11 cm vide centerwell, 0.75 mm gel). After the termination of the electrophoretic run the gel was trimmed for excess gel, and preequilibrated in 3 changes of 2 mM phosphate buffer for 40 min. The multi-elution was performed as described previously (Andersen and Heron, 1993b). Briefly, gels were transferred to the Multi-Eluter™ (KEM-EN-TECH) and electroeluted (40 V) into 2 mM phosphate buffer for 20 min. The polypeptide fractions were aspirated and adjusted to isotonia with concentrated PBS. All fractions were stabilized with 0.5% mice serum and were kept frozen at −80° C. until use.

Lymphocyte cultures. Lymphocytes were obtained by preparing single-cell suspensions from spleens as described in Andersen et al., 1991a. Briefly, ST-CF or antigenic fractions were added to microcultures containing $2 \times 10^5$ lymphocyte in a volume of 200 µl Rpmi 1640 supplemented with $5 \times 10^5$ M 2-mercaptoethanol, penicillin, streptomycin, 1 mM glutamine and 0.5% (vol/vol) fresh mouse serum.

ST-CF was used in the concentration 4 µg/ml while ST-CF fractions were used in 1 µg/ml.

Cellular proliferation was investigated by pulsing the cultures (1 µCi [$^3$H] thymidine/well) after 48 h of incubation, further incubating the plates for 22 hours and finally harvesting and processing the plates for liquid scintillation counting (Lkb, Beta counter). Culture supernatants were harvested from parallel cultures after 48 hours incubation and used for lymphokine analyses.

Lymphokine analyses. The amount of INF-γ present in culture supernatants and in homogenised organs was quantified by an IFN-γ ELISA kit (Holland Biotechnology, Leiden, the Netherlands). Values below 10 pg were considered negative.

A group of efficiently protected mice was generated by infecting 8–12 weeks old female C57Bl/6j mice bred at Statens Seruminstitut, Copenhagen, Denmark, with $2.5 \times 10^3$ *M. tuberculosis* i.v. After 30 days of infection the mice were subjected to 60 days of antibiotic treatment with isoniazid and were then left for 200–240 days to ensure the establishment of resting long-term memory immunity. The mice were then reinfected with $2.5 \times 10^5$ *M. tuberculosis* i.v. and the course of infection was compared with that of a corresponding naive group of mice (FIG. 1).

As seen in FIG. 1, *M. tuberculosis* grow rapidly in the spleens of naive mice whereas the infection is controlled within the first few days in memory immune mice. This finding emphasizes that early immunological events occurring during the first days determines the outcome of infection.

Gamma interferon (IFN-γ) is a lymphokine which is involved directly in protective immunity against *M. tuberculosis* (Rook G. A. W., 1990, Flesch I. and Kaufmann S., 1987). To monitor the onset of a protective immune response, the content of IFN-γ in spleen homogenates (4% w/v in PBS) and in serum samples was investigated during the course of infection (FIG. 2). Memory immune mice were found to respond immediately (<24 h) by a marked production of IFN-γ detectable both in spleen and in serum. Naive mice, in contrast, had a 14 days delay before any significant production was evident, a period during which infection rapidly progressed. Immune mice were characterized by an accelerated release of IFN-γ and to determine the molecular targets of this immunological response, spleen lymphocytes were obtained from animals at different time points during the course of infection. The lymphocytes were stimulated in vitro with either bacteria, killed with glutaraldehyde and washed with PBS or short-term culture-filtrate (ST-CF) which is a complex mixture of proteins secreted by *M. tuberculosis* during growth (Andersen, P. et al. 1991.) (FIG. 3). The memory immune mice were found to be characterized by an accelerated generation of IFN-γ producing T-cells responding to ST-CF whereas killed bacteria in contrast were found to elicit only a marginal response at a very late stage of infection.

To map the molecular targets of protective T-cells among the multiple secreted proteins present in ST-CF a screening of ST-CF was performed using the multi-elution technique (Andersen and Heron, 1993). This technique divides complex protein mixtures separated in SDS-PAGE into narrow fractions in a physiological buffer (FIG. 4). These fractions were used to stimulate spleen lymphocytes in vitro and the release of IFN-γ was monitored (FIG. 5). The response of long-term memory immune mice (the mice were left for 200–240 days to ensure immunological rest) was compared to the response generated after 4 days of rechallenge infection. This comparison enable the mapping of targets for memory effector T-cells triggered to release IFN-γ during the first phase of a protective immune response. Using this approach it was demonstrated that the targets for these protective T-cells were secreted proteins or fragments of proteins of apparent molecular mass 6–10 and 26–34 kDa (FIG. 5).

To precisely map single molecules within the stimulatory regions the induction of IFN-γ by a panel of narrow overlapping fractions was investigated. This enabled the identification of a 6–8 kDa protein fraction with exceedingly stimulatory capacity (5100–5400 pg IFN-γ units/ml) (FIG. 6). The 6-kDa protein band yielding the highest release of IFN-γ (5390 pg/ml) was recognized by the mAb HYB76-8, whereas the adjacent protein bands were recognized by the mAbs ST-3 and PV-2.

Example 2

Cloning of Genes Expressing Low Mass Culture Filtrate Antigens

In example 1 it was demonstrated that antigens in the low molecular mass fraction are recognized strongly by cells isolated from memory immune mice. Monoclonal antibodies (mAbs) to these antigens were therefore generated by immunizing with the low mass fraction in RIBI adjuvant (first and second immunization) followed by two injections with the fractions in aluminium hydroxide. Fusion and cloning of the reactive cell lines were done according to standard procedures (Kohler and Milstein 1975). The procedure resulted in the provision of two mAbs: ST-3 directed to a 9 kDa culture filtrate antigen (CFP9) and PV-2 directed to a 7 kDa antigen (CFP7), when the molecular weight is estimated from migration of the antigens in an SDS-PAGE.

In order to identify the antigens binding to the Mab's, the following experiments were carried out:

The recombinant λgt11 *M. tuberculosis* DNA library constructed by R. Young (Young, R. A. et al. 1985) and obtained through the World Health Organization IMMTUB programme (WHO.0032.wibr) was screened for phages expressing gene products which would bind the monoclonal antibodies ST-3 and PV-2.

Approximately $1 \times 10^5$ pfu of the gene library (containing approximately 25% recombinant phages) were plated on *Eschericia coli* Y1090 (DlacU169, proA$^+$, Dlon, araD139, supF, trpC22::tn10[pMC9] ATCC#37197) in soft agar and incubated for 2.5 hours at 42° C.

The plates were overlaid with sheets of nitrocellulose saturated with isopropyl-β-D-thiogalactopyranoside and incubation was continued for 2.5 hours at 37° C. The nitrocellulose was removed and incubated with samples of the monoclonal antibodies in PBS with Tween 20 added to a final concentration of 0.05%. Bound monoclonal antibodies were visualized by horseradish peroxidase-conjugated rabbit anti-mouse immunoglobulins (P260, Dako, Glostrup, DK) and a staining reaction involving 5,5',3,3'-tetramethylbenzidine and $H_2O_2$.

Positive plaques were recloned and the phages originating from a single plaque were used to lysogenize E. coli Y1089 (DlacU169, proA$^+$, Dlon, araD139, strA, hfl150 [chr::tn10] [pMC9] ATCC nr. 37196). The resultant lysogenic strains were used to propagate phage particles for DNA extraction. These lysogenic E. coli strains have been named:

AA242 (expressing PV-2 reactive polypeptide CFP7) which has been deposited 28 Jun. 1993 with the collection of Deutsche Sammlung von Mikroorganismen und Zellkulturen GmbH (DSM) under the accession number DSM 8379 and in accordance with the provisions of the Budapest Treaty.

A physical map of the recombinant phages is shown in FIG. 7 and the expression of the recombinant gene products is shown in FIG. 8.

The PV-2 binding protein appears to be expressed in an unfused version.

Sequencing of the Nucleotide Sequence Encoding the PV-2 Binding Protein

In order to obtain the nucleotide sequence of the gene encoding the pv-2 binding protein, the approximately 3 kb *M. tuberculosis* derived EcoRI-EcoRI fragment from AA242 was subcloned in the EcoRI site in the pBluescriptSK+ (Stratagene) and used to transform *E. coli* XL-1Blue (Stratagene).

The complete DNA sequence of the gene was obtained by the dideoxy chain termination method adapted for supercoiled DNA by use of the Sequenase DNA sequencing kit version 1.0 (United States Biochemical Corp., Cleveland, Ohio) and by cycle sequencing using the Dye Terminator system in combination with an automated gel reader (model 373A; Applied Biosystems) according to the instructions provided. The DNA sequence is shown in SEQ ID NO: 1 (CFP7) as well as in FIG. 9. Both strands of the DNA were sequenced.

CFP7

An open reading frame (ORF) encoding a sequence of 96 amino acid residues was identified from an ATG start codon at position 91–93 extending to a TAG stop codon at position 379–381. The deduced amino acid sequence is shown in SEQ ID NO: 2 (and in FIG. 9 where conventional one-letter amino acid codes are used).

CFP7 appear to be expressed in *E. coli* as an unfused version. The nucleotide sequence at position 78–84 is expected to be the Shine Delgarno sequence and the sequences from position 47–50 and 14–19 are expected to be the −10 and −35 regions, respectively:

Subcloning CFP7 in Expression Vectors

The ORF encoding CFP7 was PCR cloned into the pMST24 (Theisen et al., 1995) expression vector pRVN01.

The PCR amplification was carried out in a thermal reactor (Rapid cycler, Idaho Technology, Idaho) by mixing 10 ng plasmid DNA with the mastermix (0.5 μM of each oligonucleotide primer, 0.25 μM BSA (Stratagene), low salt buffer (20 mM Tris-HCl, pH 8.8, 10 mM KCl, 10 mM $(NH_4)_2SO_4$, 2 mM $MgSO_4$ and 0.1% Triton X-100) (Stratagene), 0.25 mM of each deoxynucleoside triphosphate and 0.5 U Taq Plus Long DNA polymerase (Stratagene)). Final volume was 10 μl (all concentrations given are concentrations in the final volume). Predenaturation was carried out at 94° C. for 30 s. 30 cycles of the following was performed; Denaturation at 94° C. for 30 s, annealing at 55° C. for 30 s and elongation at 72° C. for 1 min.

The oligonucleotide primers were synthesised automatically on a DNA synthesizer (Applied Biosystems, Forster City, Calif., ABI-391, PCR-mode), deblocked, and purified by ethanol precipitation.

The cfp7oligonucleotides (TABLE 1) were synthesised on the basis of the nucleotide sequence from the CFP7 sequence (FIG. 9). The oligonucleotides were engineered to include an SmaI restriction enzyme site at the 5' end and a BamHI restriction enzyme site at the 3' end for directed subcloning.

CFP7

By the use of PCR a SmaI site was engineered immediately 5' of the first codon of the ORF of 291 bp, encoding the cfp7 gene, so that only the coding region would be expressed, and a BamHI site was incorporated right after the stop codon at the 3' end. The 291 bp PCR fragment was cleaved by SmaI and BamHI, purified from an agarose gel and subcloned into the SmaI-BamHI sites of the pMST24 expression vector. Vector DNA containing the gene fusion was used to transform the *E. coli* XL1-Blue (pRVN01).

Purification of Recombinant CFP7

The ORF was fused N-terminally to the $(His)_6$-tag (cf. EP-A-0 282 242). Recombinant antigen was prepared as follows: Briefly, a single colony of *E. coli* harbouring either the pRVN01 or the pRVN02 plasmid, was inoculated into Luria-Bertani broth containing 100 μg/ml ampicillin and 12.5 μg/ml tetracycline and grown at 37° C. to $OD_{600\ nm}$=0.5. IPTG (isopropyl-β-D-thiogalactoside) was then added to a final concentration of 2 mM (expression was regulated either by the strong IPTG inducible $P_{tac}$ or the T5 promoter) and growth was continued for further 2 hours. The cells were harvested by centrifugation at 4,200×g at 4° C. for 8 min. The pelleted bacteria were stored overnight at −20° C. The pellet was resuspended in BC 40/100 buffer (20 mM Tris-HCl pH 7.9, 20% glycerol, 100 mM KCl, 40 mM Imidazole) and cells were broken by sonication (5 times for 30 s with intervals of 30 s) at 4° C. followed by centrifugation at 12,000×g for 30 min at 4° C., the supernatant (crude extract) was used for purification of the recombinant antigens.

The Histidine fusion protein (His-rCFP7) was purified from the crude extract by affinity chromatography on a $Ni^{2+}$-NTA column from QIAGEN with a volume of 100 ml. His-rCFP7 binds to $Ni^{2+}$. After extensive washes of the column in BC 40/100 buffer, the fusion protein was eluted with a BC 1000/100 buffer containing 100 mM imidazole, 20 mM Tris pH 7.9, 20% glycerol and 1 M KCl. subsequently, the purified products were dialysed extensively against 10 mM Tris pH 8.0. His-rCFP7 was then separated from contaminants by fast protein liquid chromatography (FPLC) over an anion-exchange column (Mono Q, Pharmacia, Sweden) in 10 mM Tris pH 8.0 with a linear gradient of NaCl from 0 to 1 M. Aliquots of the fractions were analyzed by 10%–20% gradient sodium dodecyl sulphate polyacrylamide gel electrophoresis (SDS-PAGE). Fractions containing purified His-rCFP7 was pooled.

TABLE 1

Sequence of the cfp7 oligonucleotides[a].

| Orientation and oligonucleotide | Sequences (5' → 3') | | Position[b] (nucleotide) |
|---|---|---|---|
| Sense pvR3 | <u>GCAACACCCGGG</u>ATGTCGCAAATCATG | (SEQ ID NO: 43) | 91–105 (SEQ ID NO: 1) |
| Antisense pvF4 | <u>CTACTAAGCTTGGATCCC</u>TAGCCG-CCCCATTTGGCGG | (SEQ ID NO: 45) | 381–362 (SEQ ID NO: 1) |

[a]The cfp7 oligonucleotides were based on the nucleotide sequence shown in FIG. 9 (SEQ ID NO: 1).
Nucleotides underlined are not contained in the nucleotide sequence of cfp7.
[b]The positions referred to are of the non-underlined part of the primers and correspond to the nucleotide sequence shown in FIG. 9 and FIG. 10, respectively.

Example 3
Identification of Antigens which are not Expressed in BCG Strains.

In an effort to control the treat of TB, attenuated *bacillus Calmette-Guérin* (BCG) has been used as a live attenuated vaccine. BCG is an attenuated derivative of a virulent *Mycobacterium bovis*. The original BCG from the Pasteur Institute in Paris, France was developed from 1908 to 1921 by 231 passages in liquid culture and has never been shown to revert to virulence in animals, indicating that the attenuating mutation(s) in BCG are stable deletions and/or multiple mutations which do not readily revert. While physiological differences between BCG and *M. tuberculosis* and *M. bovis* has been noted, the attenuating mutations which arose during serial passage of the original BCG strain has been unknown until recently. The first mutations described are the loss of the gene encoding MPB64 in some BCG strains (Li et al., 1993, Oettinger and Andersen, 1994) and the gene encoding ESAT-6 in all BCG strain tested (Harboe et al., 1996), later 3 large deletions in BCG have been identified (Mahairas et al., 1996). The region named RD1 includes the gene encoding ESAT-6 and an other (RD2) the gene encoding MPT64. Both antigens have been shown to have diagnostic potential and ESAT-6 has been shown to have properties as a vaccine candidate (cf. PCT/DK94/00273 and PCT/DK94/00270). In order to find new *M. tuberculosis* specific diagnostic antigens as well as antigens for a new vaccine against TB, the RD1 region (17.499 bp) of *M. tuberculosis* H37Rv has been analyzed for Open Reading Frames (ORF). ORFs with a minimum length of 96 bp have been predicted using the algorithm described by Borodovsky and McIninch (1993), in total 27 ORFs have been predicted, 20 of these have possible diagnostic and/or vaccine potential, as they are deleted from all known BCG strains. The predicted ORFs include ESAT-6 (RD1-ORF7) and CFP10 (RD1-ORF6) described previously (Sørensen et al., 1995), as a positive control for the ability of the algorithm. In the present is described the potential of 7 of the predicted antigens for diagnosis of TB as well as potential as candidates for a new vaccine against TB.

Seven open reading frames (ORF) from the 17,499 kb RD1 region (Accession no. U34848) with possible diagnostic and vaccine potential have been identified and cloned.

Identification of the ORF's rd1-orf2, rd1-orf3, rd1-orf4, rd1-orf5, rd1-orf8, rd1-orf9a, and rd1-orf9b.

The nucleotide sequence of rd1-orf2 from *M. tuberculosis* H37Rv is set forth in SEQ ID NO: 71. The deduced amino acid sequence of RD1-ORF2 is set forth in SEQ ID NO: 72.

The nucleotide sequence of rd1-orf3 from *M. tuberculosis* H37Rv is set forth in SEQ ID NO: 87. The deduced amino acid sequence of RD1-ORF2 is set forth in SEQ ID NO: 88.

The nucleotide sequence of rd1-orf4 from *M. tuberculosis* H37Rv is set forth in SEQ ID NO: 89. The deduced amino acid sequence of RD1-ORF2 is set forth in SEQ ID NO: 90.

The nucleotide sequence of rd1-orf5 from *M. tuberculosis* H37Rv is set forth in SEQ ID NO: 91. The deduced amino acid sequence of RD1-ORF2 is set forth in SEQ ID NO: 92.

The nucleotide sequence of rd1-orf8 from *M. tuberculosis* H37Rv is set forth in SEQ ID NO: 67. The deduced amino acid sequence of RD1-ORF2 is set forth in SEQ ID NO: 68.

The nucleotide sequence of rd1-orf9a from *M. tuberculosis* H37Rv is set forth in SEQ ID NO: 93. The deduced amino acid sequence of RD1-ORF2 is set forth in SEQ ID NO: 94.

The nucleotide sequence of rd1-orf9b from *M. tuberculosis* H37Rv is set forth in SEQ ID NO: 69. The deduced amino acid sequence of RD1-ORF2 is set forth in SEQ ID NO: 70.

The DNA sequence rd1-orf2 (SEQ ID NO: 71) contained an open reading frame starting with an ATG codon at position 889–891 and ending with a termination codon (TAA) at position 2662–2664 (position numbers referring to the location in RD1). The deduced amino acid sequence (SEQ ID NO: 72) contains 591 residues corresponding to a molecular weight of 64,525.

The DNA sequence rd1-orf3 (SEQ ID NO: 87) contained an open reading frame starting with an ATG codon at position 2807–2809 and ending with a termination codon (TAA) at position 3101–3103 (position numbers referring to the location in RD1). The deduced amino acid sequence (SEQ ID NO: 88) contains 98 residues corresponding to a molecular weight of 9,799.

The DNA sequence rd1-orf4 (SEQ ID NO: 89) contained an open reading frame starting with a GTG codon at position 4014–4012 and ending with a termination codon (TAG) at position 3597–3595 (position numbers referring to the location in RD1). The deduced amino acid sequence (SEQ ID NO: 90) contains 139 residues corresponding to a molecular weight of 14,210.

The DNA sequence rd1-odf5 (SEQ ID NO: 91) contained an open reading frame starting with a GTG codon at position 3128–3130 and ending with a termination codon (TGA) at position 4241–4243 (position numbers referring to the location in RD1). The deduced amino acid sequence (SEQ ID NO: 92) contains 371 residues corresponding to a molecular weight of 37,647.

The DNA sequence rd1-orf8 (SEQ ID NO: 67) contained an open reading frame starting with a GTG codon at position 5502–5500 and ending with a termination codon (TAG) at position 5084–5082 (position numbers referring to the location in RD1), and the deduced amino acid sequence (SEQ ID NO: 68) contains 139 residues with a molecular weight of 11,737.

The DNA sequence rd1-orf9a (SEQ ID NO: 93) contained an open reading frame starting with a GTG codon at position 6146–6148 and ending with a termination codon (TAA) at position 7070–7072 (position numbers referring to the location in RD1). The deduced amino acid sequence (SEQ ID NO: 94) contains 308 residues corresponding to a molecular weight of 33,453.

The DNA sequence rd1-orf9b (SEQ ID NO: 69) contained an open reading frame starting with an ATG codon at position 5072–5074 and ending with a termination codon (TAA) at position 7070–7072 (position numbers referring to the location in RD1). The deduced amino acid sequence (SEQ ID NO: 70) contains 666 residues corresponding to a molecular weight of 70,650.

Cloning of the ORF's rd1-orf2, rd1-orf3, rd1-orf4, rd1-orf5, rd1-orf8, rd1-orf9a, and rd1-orf9b.

The ORF's rd1-orf2, rd1-orf3, rd1-orf4, rd1-orf5, rd1-orf8, rd1-orf9a and rd1-orf9b were PCR cloned in the pMST24 (Theisen et al., 1995) (rd1-orf3) or the pQE32 (QIAGEN) (rd1-orf2, rd1-orf4, rd1-orf5, rd1-orf8, rd1-odf9a and rd1-orf9b) expression vector. Preparation of oligonucleotides and PCR amplification of the rd1-orf encoding genes, was carried out as described in example 2. Chromosomal DNA from *M. tuberculosis* H37Rv was used as template in the PCR reactions. Oligonucleotides were synthesized on the basis of the nucleotide sequence from the RD1 region (Accession no. U34848). The oligonucleotide primers were engineered to include an restriction enzyme site at the 5' end and at the 3' end by which a later subcloning was possible. Primers are listed in TABLE 2.

rd1-orf2. A BamHI site was engineered immediately 5' of the first codon of rd1-orf2, and a HindIII site was incorporated right after the stop codon at the 3' end. The gene rd1-orf2 was subcloned in pQE32, giving pTO96.

rd1-orf3. A SmaI site was engineered immediately 5' of the first codon of rd1-orf3, and a NcoI site was incorporated right after the stop codon at the 3' end. The gene rd1-orf3 was subcloned in pMST24, giving pTO87.

rd1-orf4. A BamHI site was engineered immediately 5' of the first codon of rd1-orf4, and a HindIII site was incorporated right after the stop codon at the 3' end. The gene rd1-orf4 was subcloned in pQE32, giving pTO89.

rd1-orf5. A BamHI site was engineered immediately 5' of the first codon of rd1-orf5, and a HindIII site was incorporated right after the stop codon at the 3' end. The gene rd1-orf5 was subcloned in pQE32, giving pTO88.

rd1-orf8. A BamHI site was engineered immediately 5' of the first codon of rd1-orf8, and a NcoI site was incorporated right after the stop codon at the 3' end. The gene rd1-orf8 was subcloned in pMST24, giving pTO98.

rd1-orf9a. A BamHI site was engineered immediately 5' of the first codon of rd1-orf9a, and a HindIII site was incorporated right after the stop codon at the 3' end. The gene rd1-orf9a was subcloned in pQE32, giving pTO91.

rd1-orf9b. A ScaI site was engineered immediately 5' of the first codon of rd1-orf9b, and a Hind III site was incorporated right after the stop codon at the 3' end. The gene rd1-orf9b was subcloned in pQE32, giving pTO90.

The PCR fragments were digested with the suitable restriction enzymes, purified from an agarose gel and cloned into either pMST24 or pQE-32. The seven constructs were used to transform the *E. coli* XL1-Blue. Endpoints of the gene fusions were determined by the dideoxy chain termination method. Both strands of the DNA were sequenced.

Purification of Recombinant RD1-ORF2, RD1-ORF3, RD1-ORF4, RD1-ORF5, RD1-ORF8, RD1-ORF9a and RD1-ORF9b.

The rRD1-ORFs were fused N-terminally to the $(His)_6$-tag. Recombinant antigen was prepared as described in example 2 (with the exception that pTO91 was expressed at 30° C. and not at 37° C.), using a single colony of *E. coli* harbouring either the pTO87, pTO88, pTO89, pTO90, pTO91, pTO96 or pTO98 for inoculation. Purification of recombinant antigen by $Ni^{2+}$ affinity chromatography was also carried out as described in example 2. Fractions containing purified His-rRD1-ORF2, His-rRD1-ORF3 His-rRD1-ORF4, His-rRD1-ORF5, His-rRD1-ORF8, His-rRD1-ORF9a or His-rRD1-ORF9b were pooled. The His-rRD1-ORF's were extensively dialysed against 10 mM Tris/HCl, pH 8.5, 3 M urea followed by an additional purification step performed on an anion exchange column (Mono Q) using fast protein liquid chromatography (FPLC) (Pharmacia, Uppsala, Sweden). The purification was carried out in 10 mM Tris/HCl, pH 8.5, 3 M urea and protein was eluted by a linear gradient of NaCl from 0 to 1 M. Fractions containing the His-rRD1-ORF's were pooled and subsequently dialysed extensively against 25 mM Hepes, pH 8.0 before use.

TABLE 2

Sequence of the rd1-orf's oligonucleotides[a].

| Orientation and oligonucleotide | Sequences (5' → 3') | Position (nt) |
| --- | --- | --- |
| Sense | | |
| RD1-ORF2f | CTGGGGATCCGCATGACTGCTGAACCG | 886–903 |
| RD1-ORF3f | CTTCCCGGGATGGAAAAAATGTCAC | 2807–2822 |
| RD1-ORF4f | GTAGGATCCTAGGAGACATCAGCGGC | 4028–4015 |
| RD1-ORF5f | CTGGGGATCCGCGTGATCACCAT-GCTGTGG | 3028–3045 |
| RD1-ORF8f | CTCGGATCCTGTGGGTGCAGGTCCGGC GATGGGC | 5502–5479 |
| RD1-ORF9af | GTGATGTGAGCTCAGGTGAAGAA-GGTGAAG | 6144–6160 |

TABLE 2-continued

Sequence of the rd1-orf's oligonucleotides[a].

| Orientation and oligonucleotide | Sequences (5' → 3') | Position (nt) |
|---|---|---|
| RD1-ORF9bf | GTGATGTGAGCTCCTATGGCGGCCGAC-TACGAC | 5072–5089 |
| Antisense | | |
| RD1-ORF2r | TGCAAGCTTTTAACCGGCGCTTGGGGTGC | 2664–2644 |
| RD1-ORF3r | GATGCCATGGTTAGGCGAAGACGC-CGGC | 3103–3086 |
| RD1-ORF4r | CGATCTAAGCTTGGCAATGGAGGTCTA | 3582–3597 |
| RD1-ORF5r | TGCAAGCTTTCACCAGTCGTCCT-CTTCGTC | 4243–4223 |
| RD1-ORF8r | CTCCCATGGCTACGACAAGCTCTTC-CGGCCGC | 5083–5105 |
| RD1-ORF9a/br | CGATCTAAGCTTTCAACGACGTCCAGCC | 7073–7056 |

[a]The oligonucleotides were constructed from the Accession number U34484 nucleotide sequence (Mahairas et al., 1996).
Nucleotides (nt) underlined are not contained in the nucleotide sequence of RD1-ORF's.
The positions correspond to the nucleotide sequence of Accession number U34484.

The nucleotide sequences of rd1-orf2, rd1-orf3, rd1-orf4, rd1-orf5, rd1-orf8, rd1-orf9a, and rd1-orf9b from *M. tuberculosis* H37Rv are set forth in SEQ ID NO: 71, 87, 89, 91, 67, 93, and 69, respectively. The deduced amino acid sequences of rd1-orf2, rd1-orf3, rd1-orf4 rd1-orf5, rd1-orf8, rd1-orf9a, and rd1-orf9b are set forth in SEQ ID NO: 72, 88, 90, 92, 68, 94, and 70, respectively.

Example 4

Cloning of the Genes Expressing 17–30 kDa Antigens from ST-CF

Isolation of CFP17, CFP20, CFP21, CFP22, CFP25, and CFP28

ST-CF was precipitated with ammonium sulphate at 80% saturation. The precipitated proteins were removed by centrifugation and after resuspension washed with 8 M urea. CHAPS and glycerol were added to a final concentration of 0.5% (w/v) and 5% (v/v) respectively and the protein solution was applied to a Rotofor isoelectrical Cell (BioRad). The Rotofor Cell had been equilibrated with an 8 M urea buffer containing 0.5% (w/v) CHAPS, 5% (v/v) glycerol, 3% (v/v) Biolyt 3/5 and 1% (v/v) Biolyt 4/6 (BioRad). Isoelectric focusing was performed in a pH gradient from 3–6. The fractions were analyzed on silver-stained 10–20% SDS-PAGE. Fractions with similar band patterns were pooled and washed three times with PBS on a Centriprep concentrator (Amicon) with a 3 kDa cut off membrane to a final volume of 1–3 ml. An equal volume of SDS containing sample buffer was added and the protein solution boiled for 5 min before further separation on a Prep Cell (BioRad) in a matrix of 16% polyacrylamide under an electrical gradient. Fractions containing pure proteins with an molecular mass from 17–30 kDa were collected.

Isolation of CFP29

Anti-CFP29, reacting with CFP29 was generated by immunization of BALB/c mice with crushed gel pieces in RIBI adjuvant (first and second immunization) or aluminium hydroxide (third immunization and boosting) with two week intervals. SDS-PAGE gel pieces containing 2–5 μg of CFP29 were used for each immunization. Mice were boosted with antigen 3 days before removal of the spleen. Generation of a monoclonal cell line producing antibodies against CFP29 was obtained essentially as described by Köhler and Milstein (1975). Screening of supernatants from growing clones was carried out by immunoblotting of nitrocellulose strips containing ST-CF separated by SDS-PAGE. Each strip contained approximately 50 μg of ST-CF. The antibody class of anti-CFP29 was identified as IgM by the mouse monoclonal antibody isotyping kit, RPN29 (Amersham) according to the manufacturer's instructions.

CFP29 was purified by the following method: ST-CF was concentrated 10 fold by ultrafiltration, and ammonium sulphate precipitation in the 45 to 55% saturation range was performed. The pellet was redissolved in 50 mM sodium phosphate, 1.5 M ammonium sulphate, pH 8.5, and subjected to thiophilic adsorption chromatography (Porath et al., 1985) on an Affi-T gel column (Kem-En-Tec). Protein was eluted by a linear 1.5 to 0 M gradient of ammonium sulphate and fractions collected in the range 0.44 to 0.31 M ammonium sulphate were identified as CFP29 containing fractions in Western blot experiments with mAb Anti-CFP29. These fractions were pooled and anion exchange chromatography was performed on a Mono Q HR 5/5 column connected to an FPLC system (Pharmacia). The column was equilibrated with 10 mM Tris-HCl, pH 8.5 and the elution was performed with a linear gradient from 0 to 500 mM NaCl. From 400 to 500 mM sodium chloride, rather pure CFP29 was eluted. As a final purification step the Mono Q fractions containing CFP29 were loaded on a 12.5% SDS-PAGE gel and pure CFP29 was obtained by the multi-elution technique (Andersen and Heron, 1993).

N-terminal Sequencing and Amino Acid Analysis

CFP17, CFP20, CFP21, CFP22, CFP25, and CFP28 were washed with water on a Centricon concentrator (Amicon) with cutoff at 10 kDa and then applied to a ProSpin concentrator (Applied Biosystems) where the proteins were collected on a PVDF membrane. The membrane was washed 5 times with 20% methanol before sequencing on a Procise sequencer (Applied Biosystems).

CFP29 containing fractions were blotted to PVDF membrane after tricine SDS-PAGE (Ploug et al., 1989). The relevant bands were excised and subjected to amino acid analysis (Barkholt and Jensen, 1989) and N-terminal sequence analysis on a Procise sequencer (Applied Biosystems).

The following N-terminal sequences were obtained:

```
                                        (SEQ ID NO: 17)
For CFP17:   A/S E L D A P A Q A G T E X A V (SEQ ID NO: 18)
For CFP20:   A Q I T L R G N A I N T V G E (SEQ ID NO: 19)
For CFP21:   D P X S D I A V V F A R G T H (SEQ ID NO: 20)
For CFP22:   T N S P L A T A T A T L H T N (SEQ ID NO: 21)
For CFP25:   A X P D A E V V F A R G R F E (SEQ ID NO: 22)
For CFP28:   X I/V Q K S L E L I V/T V/F T A D/Q E (SEQ ID NO: 23)
For CFP29:   M N N L Y R D L A P V T E A A W A E I
```

"X" denotes an amino acid which could not be determined by the sequencing method used, whereas a "/" between two amino acids denotes that the sequencing method could not determine which of the two amino acids is the one actually present.

Cloning the Gene Encoding CFP29

The N-terminal sequence of CFP29 was used for a homology search in the EMBL database using the TFASTA program of the Genetics Computer Group sequence analysis software package. The search identified a protein, Linocin M18, from *Brevibacterium linens* that shares 74% identity with the 19 N-terminal amino acids of CFP29.

Based on this identity between the N-terminal sequence of CFP29 and the sequence of the Linocin M18 protein from *Brevibacterium linens,* a set of degenerated primers were constructed for PCR cloning of the *M. tuberculosis* gene encoding CFP29. PCR reactions were containing 10 ng of *M. tuberculosis* chromosomal DNA in 1× low salt Taq+ buffer from Stratagene supplemented with 250 μM of each of the four nucleotides (Boehringer Mannheim), 0.5 mg/ml BSA (IgG technology), 1% DMSO (Merck), 5 pmoles of each primer and 0.5 unit Tag+ DNA polymerase (Stratagene) in 10 μl reaction volume. Reactions were initially heated to 94° C. for 25 sec. and run for 30 cycles of the program; 94° C. for 15 sec., 55° C. for 15 sec. and 72° C. for 90 sec, using thermocycler equipment from Idaho Technology.

An approx. 300 bp fragment was obtained using primers with the sequences:

```
                                        (SEQ ID NO: 24)
  1:   5'-CCCGGCTCGAGAACCTSTACCGCGACCTSGCSCC (SEQ ID NO: 25)
  2:   5'-GGGCCGGATCCGASGCSGCGTCCTTSACSGGYTGCCA
```

—where S=G/C and Y=T/C

The fragment was excised from a 1% agarose gel, purified by Spin-X spinn columns (Costar), cloned into pBluescript SK II+-T vector (Stratagene) and finally sequenced with the Sequenase kit from United States Biochemical.

The first 150 bp of this sequence was used for a homology search using the Blast program of the Sanger *Mycobacterium tuberculosis* database:

(http//www.sanger.ac.uk/projects/*M-tuberculosis*/blast_server).

This program identified a *Mycobacterium tuberculosis* sequence on cosmid cy444 in the database that is nearly 100% identical to the 150 bp sequence of the CFP29 protein. The sequence is contained within a 795 bp open reading frame of which the 5' end translates into a sequence that is 100% identical to the N-terminally sequenced 19 amino acids of the purified CFP29 protein.

Finally, the 795 bp open reading frame was PCR cloned under the same PCR conditions as described above using the primers:

```
                                        (SEQ ID NO: 26)
  3:      5'-GGAAGCCCCATATGAACAATCTCTACCG (SEQ ID NO: 27)
  4:      5'-CGCGCTCAGCCCTTAGTGACTGAGCGCGACCG
```

The resulting DNA fragments were purified from agarose gels as described above sequenced with primer 3 and 4 in addition to the following primers:

```
5:  5'-GGACGTTCAAGCGACACATCGCCG-3'    (SEQ ID NO: 115)

6:  5'-CAGCACGAACGCGCCGTCGATGGC-3'    (SEQ ID NO: 116)
```

Three independent cloned were sequenced. All three clones were in 100% agreement with the sequence on cosmid cy444.

All other DNA manipulations were done according to Maniatis et al. (1989).

All enzymes other than Taq polymerase were from New England Biolabs.

Homology Searches in the Sanger Database

For CFP17, CFP20, CFP21, CFP22, CFP25, and CFP28 the N-terminal amino acid sequence from each of the proteins were used for a homology search using the blast program of the Sanger *Mycobacterium tuberculosis* database:

http://www.sanger.ac.uk/pathogens/TB-blast-server.html.

For CFP29 the first 150 bp of the DNA sequence was used for the search. Furthermore, the EMBL database was searched for proteins with homology to CFP29.

Thereby, the following information were obtained:

CFP17

Of the 14 determined amino acids in CFP17 a 93% identical sequence was found with MTCY1A11.16c. The difference between the two sequences is in the first amino acid: It is an A or an S in the N-terminal determined sequenced and a S in MTCY1A11. From the N-terminal sequencing it was not possible to determine amino acid number 13.

Within the open reading frame the translated protein is 162 amino acids long. The N-terminal of the protein purified from culture filtrate starts at amino acid 31 in agreement with the presence of a signal sequence that has been cleaved off. This gives a length of the mature protein of 132 amino acids, which corresponds to a theoretical molecular mass of 13833 Da and a theoretical pI of 4.4. The observed mass in SDS-PAGE is 17 kDa.

CFP20

A sequence 100% identical to the 15 determined amino acids of CFP20 was found on the translated cosmid cscy09F9. A stop codon is found at amino acid 166 from the amino acid M at position 1. This gives a predicted length of 165 amino acids, which corresponds to a theoretical molecular mass of 16897 Da and a pI of 4.2. The observed molecular weight in a SDS-PAGE is 20 kDa.

Searching the GenEMBL database using the TFASTA algorithm (Pearson and Lipman, 1988) revealed a number of proteins with homology to the predicted 164 amino acids long translated protein.

The highest homology, 51.5% identity in a 163 amino acid overlap, was found to a Haemophilus influenza Rd toxR reg. (HIHI0751).

CFP21

A sequence 100% identical to the 14 determined amino acids of CFP21 was found at MTCY39. From the N-terminal sequencing it was not possible to determine amino acid number 3; this amino acid is a C in MTCY39. The amino acid C can not be detected on a Sequencer which is probably the explanation of this difference.

Within the open reading frame the translated protein is 217 amino acids long. The N-terminally determined sequence from the protein purified from culture filtrate starts at amino acid 33 in agreement with the presence of a signal sequence that has been cleaved off. This gives a length of the mature protein of 185 amino acids, which corresponds to a theoretical molecular weigh at 18657 Da, and a theoretical pI at 4.6. The observed weight in a SDS-PAGE is 21 kDa.

In a 193 amino acids overlap the protein has 32.6% identity to a cutinase precursor with a length of 209 amino acids (CUTI_ALTBR P41744).

A comparison of the 14 N-terminal determined amino acids with the translated region (RD2) deleted in *M. bovis* BCG revealed a 100% identical sequence (mb3484) (Mahairas et al. (1996)).

CFP22

A sequence 100% identical to the 15 determined amino acids of CFP22 was found at MTCY10H4. Within the open reading frame the translated protein is 182 amino acids long. The N-terminal sequence of the protein purified from culture filtrate starts at amino acid 8 and therefore the length of the protein occurring in *M. tuberculosis* culture filtrate is 175 amino acids.

This gives a theoretical molecular weigh at 18517 Da and a pI at 6.8. The observed weight in a SDS-PAGE is 22 kDa.

In an 182 amino acids overlap the translated protein has 90.1% identity with E235739; a peptidyl-prolyl cis-trans isomerase.

CFP25

A sequence 93% identical to the 15 determined amino acids was found on the cosmid MTCY339.08c. The one amino acid that differs between the two sequences is a C in MTCY339.08c and a X from the N-terminal sequence data. On a Sequencer a C can not be detected which is a probable explanation for this difference.

The N-terminally determined sequence from the protein purified from culture filtrate begins at amino acid 33 in agreement with the presence of a signal sequence that has been cleaved off. This gives a length of the mature protein of 187 amino acids, which corresponds to a theoretical molecular weigh at 19665 Da, and a theoretical pI at 4.9. The observed weight in a SDS-PAGE is 25 kDa.

In a 217 amino acids overlap the protein has 42.9% identity to CFP21 (MTCY39.35).

CFP28

No homology was found when using the 10 determined amino acid residues 2–8, 11, 12, and 14 of SEQ ID NO: 22 in the database search.

CFP29

Sanger database searching: A sequence nearly 100% identical to the 150 bp sequence of the CFP29 protein was found on cosmid cy444. The sequence is contained within a 795 bp open reading frame of which the 5' end translates into a sequence that is 100% identical to the N-terminally sequenced 19 amino acids of the purified CFP29 protein. The open reading frame encodes a 265 amino acid protein.

The amino acid analysis performed on the purified protein further confirmed the identity of CFP29 with the protein encoded in open reading frame on cosmid 444.

EMBL database searching: The open reading frame encodes a 265 amino acid protein that is 58% identical and 74% similar to the Linocin M18 protein (61% identity on DNA level). This is a 28.6 kDa protein with bacteriocin activity (Valdés-Stauber and Scherer, 1994; Valdés-Stauber and Scherer, 1996). The two proteins have the same length (except for 1 amino acid) and share the same theoretical physicochemical properties. We therefore suggest that CFP29 is a mycobacterial homolog to the *Brevibacterium linens* Linocin M18 protein.

The amino acid sequences of the purified antigens as picked from the Sanger database are shown in the following list. The amino acids determined by N-terminal sequencing are marked with bold.

```
CFP17:
  1  MTDMNPDIEK DQTSDEVTVE TTSVFRADFL SELDAPAQAG TESAVSGVEG    (SEQ ID NO: 6)

51  LPPGSALLVV KRGPNAGSRF LLDQAITSAG RHPDSDIFLD DVTVSRRHAE

101  FRLENNEFNV VDVGSLNGTY VNREPVDSAV LANGDEVQIG KFRLVFLTGP

151  KQGEDDGSTG GP

CFP20:
  1  MAQITLRGNA INTVGELPAV GSPAPAFTLT GGDLGVISSD QFRGKSVLLN    (SEQ ID NO: 8)

51  IFPSVDTPVC ATSVRTFDER AAASGATVLC VSKDLPFAQK RFCGAEGTEN

101  VMPASAFRDS FGEDYGVTIA DGPMAGLLAR AIVVIGADGN VAYTELVPEI

151  AQEPNYEAAL AALGA

CFP21:
  1  MTPRSLVRIV GVVVATTLAL VSAPAGGRAA HADPCSDIAV              (SEQ ID NO: 10)
```

```
 41  VFARGTHQAS GLGDVGEAFV DSLTSQVGGR SIGVYAVNYP ASDDYRASAS

91  NGSDDASAHI QRTVASCPNT RIVLGGYSQG ATVIDLSTSA MPPAVADHVA

141  AVALFGEPSS GFSSMLWGGG SLPTIGPLYS SKTINLCAPD DPICTGGGNI

191  MAHVSYVQSG MTSQAATFAA NRLDHAG

CFP22:
  1  MADCDSVTNS PLATATATLH TNRGDIKIAL FGNHAPKTVA NFVGLAQGTK  (SEQ ID NO: 12)

51  DYSTQNASGG PSGPFYDGAV FHRVIQGFMI QGGDPTGTGR GGPGYKFADE

101  FHPELQFDKP YLLAMANAGP GTNGSQFFIT VGKTPHLNRR HTIFGEVIDA

151  ESQRVVEAIS KTATDGNDRP TDPVVIESIT IS

CFP25:
  1  MGAAAAMLAA VLLLTPITVP AGYPGAVAPA TAACPDAEVV FARGRFEPPG  (SEQ ID NO: 14)

51  IGTVGNAFVS ALRSKVNKNV GVYAVKYPAD NQIDVGANDM SAHIQSMANS

101  CPNTRLVPGG YSLGAAVTDV VLAVPTQMWG FTNPLPPGSD EHIAAVALFG

151  NGSQWVGPIT NFSPAYNDRT IELCHGDDPV CHPADPNTWE ANWPQHLAGA

201  YVSSGMVNQA ADFVAGKLQ

CFP29:
  1  MNNLYRDLAP VTEAAWAEIE LEAARTFKRH IAGRRVVDVS DPGGPVTAAV  (SEQ ID NO: 16)

51  STGRLIDVKA PTNGVIAHLR ASKPLVRLRV PFTLSRNEID DVERGSKDSD

101  WEPVKEAAKK LAFVEDRTIF EGYSAASIEG IRSASSNPAL TLPEDPREIP

151  DVISQALSEL RLAGVDGPYS VLLSADVYTK VSETSDHGYP IREHLNRLVD

201  GDIIWAPAID GAFVLTTRGG DFDLQLGTDV AIGYASHDTD TVRLYLQETL

251  TFLCYTAEAS VALSH
```

For all six proteins the molecular weights predicted from the sequences are in agreement with the molecular weights observed on SDS-PAGE.

Cloning of the Genes Encoding CFP17, CFP20, CFP21, CFP22 and CFP25.

The genes encoding CFP17, CFP20, CFP21, CFP22 and CFP25 were all cloned into the expression vector pMCT6, by PCR amplification with gene specific primers, for recombinant expression in E. coli of the proteins.

PCR reactions contained 10 ng of M. tuberculosis chromosomal DNA in 1× low salt Taq+ buffer from Stratagene supplemented with 250 mM of each of the four nucleotides (Boehringer Mannheim), 0.5 mg/ml BSA (IgG technology), 1% DMSO (Merck), 5 pmoles of each primer and 0.5 unit Taq+ DNA polymerase (Stratagene) in 10 μl reaction volume. Reactions were initially heated to 94° C. for 25 sec. and run for 30 cycles according to the following program; 94° C. for 10 sec., 55° C. for 10 sec. and 72° C. for 90 sec, using thermocycler equipment from Idaho Technology.

The DNA fragments were subsequently run on 1% agarose gels, the bands were excised and purified by Spin-X spin columns (Costar) and cloned into pBluescript SK II+-T vector (Stratagene). Plasmid DNA was thereafter prepared from clones harbouring the desired fragments, digested with suitable restriction enzymes and subcloned into the expression vector pMCT6 in frame with 8 histidine residues which are added to the N-terminal of the expressed proteins. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

For cloning of the individual antigens, the following gene specific primers were used:

CFP17: Primers used for cloning of cfp17:

```
OPBR-51:
ACAGATCTGTGACGGACATGAACCCG         (SEQ ID NO: 117)

OPBR-52:
TTTTCCATGGTCACGGGCCCCCGGTACT       (SEQ ID NO: 118)
```

OPBR-51 and OPBR-52 create BglII and NcoI sites, respectively, used for the cloning in pMCT6.

CFP20: Primers used for cloning of cfp20:

```
OPBR-53:
ACAGATCTGTGCCCATGGCACAGATA         (SEQ ID NO: 119)

OPBR-54:
TTTAAGCTTCTAGGCGCCCAGCGCGGC        (SEQ ID NO: 120)
```

OPBR-53 and OPBR-54 create BglII and HinDIII sites, respectively, used for the cloning in pMCT6.

CFP21: Primers used for cloning of cfp21:

```
OPBR-55:
ACAGATCTGCGCATGCGGATCCGTGT         (SEQ ID NO: 121)

OPBR-56:
TTTTCCATGGTCATCCGGCGTGATCGAG       (SEQ ID NO: 122)
```

OPBR-55 and OPBR-56 create BglII and NcoI sites, respectively, used for the cloning in pMCT6.

CFP22: Primers used for cloning of cfp22:

```
OPBR-57:
ACAGATCTGTAATGGCAGACTGTGAT        (SEQ ID NO: 123)
OPBR-58:
TTTTCCATGGTCAGGAGATGGTGATCGA      (SEQ ID NO: 124)
```

OPBR-57 and OPBR-58 create BglII and NcoI sites, respectively, used for the cloning in pMCT6.

CFP25: Primers used for cloning of cfp25:

```
OPBR-59:
ACAGATCTGCCGGCTACCCCGGTGCC        (SEQ ID NO: 125)

OPBR-60:
TTTTCGATGGCTATTGCAGCTTTCCGGC      (SEQ ID NO: 126)
```

OPBR-59 and OPBR-60 create BglII and NcoI sites, respectively, used for the cloning in pMCT6.

Expression/Purification of Recombinant CFP17, CFP20, CFP21, CFP22 and CFP25 Proteins.

Expression and metal affinity purification of recombinant proteins was undertaken essentially as described by the manufacturers. For each protein, 1 l LB-media containing 100 µg/ml ampicillin, was inoculated with 10 ml of an overnight culture of XL1-Blue cells harbouring recombinant pMCT6 plasmids. Cultures were shaken at 37° C. until they reached a density of $OD_{600}$=0.4–0.6. IPTG was hereafter added to a final concentration of 1 mM and the cultures were further incubated 4–16 hours. Cells were harvested, resuspended in 1× sonication buffer+8 M urea and sonicated 5×30 sec. with 30 sec. pausing between the pulses. After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at 280 nm. Fractions containing recombinant protein were pooled and dialysed against 3 M urea in 10 mM Tris-HCl, pH 8.5. The dialysed protein was further purified by FPLC (Pharmacia, Sweden) using a 6 ml Resource-Q column, eluted with a linear 0–1 M gradient of NaCl. Fractions were analyzed by SDS-PAGE and protein concentrations were estimated at $OD_{280}$. Fractions containing protein were pooled and dialysed against 25 mM Hepes buffer, pH 8.5.

Finally the protein concentration and the LPS content were determined by the BCA (Pierce, Holland) and LAL (Endosafe, Charleston, USA) tests, respectively.

Example 5

Identification of CFP7A, CFP8A, CFP8B, CFP16, CFP19, CFP19B, CFP22A, CFP23A, CFP23B, CFP25A, CFP27, CFP30A, CWP32 and CFP50.

Identification of CFP16 and CFP19B.

ST-CF was precipitated with ammonium sulphate at 80% saturation. The precipitated proteins were removed by centrifugation and after resuspension washed with 8 M urea. CHAPS and glycerol were added to a final concentration of 0.5% (w/v) and 5% (v/v) respectively and the protein solution was applied to a Rotofor isoelectrical Cell (BioRad). The Rotofor Cell had been equilibrated with a 8M urea buffer containing 0.5% (w/v) CHAPS, 5% (v/v) glycerol, 3% (v/v) Biolyt 3/5 and 1% (v/v) Biolyt 4/6 (BioRad). Isoelectric focusing was performed in a pH gradient from 3–6. The fractions were analyzed on silverstained 10–20% SDS-PAGE. Fractions with similar band patterns were pooled and washed three times with PBS on a Centriprep concentrator (Amicon) with a 3 kDa cut off membrane to a final volume of 1–3 ml. An equal volume of SDS containing sample buffer was added and the protein solution boiled for 5 min before further separation on a Prep Cell (BioRad) in a matrix of 16% polyacrylamide under an electrical gradient. Fractions containing well separated bands in SDS-PAGE were selected for N-terminal sequencing after transfer to PVDF membrane.

Isolation of CFP8A, CFP8B, CFP19, CFP23A, and CFP23B.

ST-CF was precipitated with ammonium sulphate at 80% saturation and redissolved in PBS, pH 7.4, and dialysed 3 times against 25 mM Piperazin-HCl, pH 5.5, and subjected to chromatofocusing on a matrix of PBE 94 (Pharmacia) in a column connected to an FPLC system (Pharmacia). The column was equilibrated with 25 mM Piperazin-HCl, pH 5.5, and the elution was performed with 10% PB74-HCl, pH 4.0 (Pharmacia). Fractions with similar band patterns were pooled and washed three times with PBS on a Centriprep concentrator (Amicon) with a 3 kDa cut off membrane to a final volume of 1–3 ml and separated on a Prepcell as described above.

Identification of CFP22A

ST-CF was concentrated approximately 10 fold by ultrafiltration and proteins were precipitated at 80% saturation, redissolved in PBS, pH 7.4, and dialysed 3 times against PBS, pH 7.4. 5.1 ml of the dialysed ST-CF was treated with RNase (0.2 mg/ml, QUIAGEN) and DNase (0.2 mg/ml, Boehringer Mannheim) for 6 h and placed on top of 6.4 ml of 48% (w/v) sucrose in PBS, pH 7.4, in Sorvall tubes (Ultracrimp 03987, DuPont Medical Products) and ultracentrifuged for 20 h at 257,300×$g_{max}$, 10° C. The pellet was redissolved in 200 µl of 25 mM Tris-192 mM glycine, 0.1% SDS, pH 8.3.

Identification of CFP7A, CFP25A, CFP27, CFP30A and CFP50

For CFP27, CFP30A and CFP50 ST-CF was concentrated approximately 10 fold by ultrafiltration and ammonium sulphate precipitation in the 45 to 55% saturation range was performed. Proteins were redissolved in 50 mM sodium phosphate, 1.5 M ammonium sulphate, pH 8.5, and subjected to thiophilic adsorption chromatography on an Affi-T gel column (Kem-En-Tec). Proteins were eluted by a 1.5 to 0 M decreasing gradient of ammonium sulphate. Fractions with similar band patterns in SDS-PAGE were pooled and anion exchange chromatography. was performed on a Mono Q HR 5/5 column connected to an FPLC system (Pharmacia). The column was equilibrated with 10 mM Tris-HCl, pH 8.5, and the elution was performed with a gradient of NaCl from 0 to 1 M. Fractions containing well separated bands in SDS-PAGE were selected.

CFP7A and CFP25A were obtained as described above except for the following modification: ST-CF was concentrated approximately 10 fold by ultrafiltration and proteins were precipitated at 80% saturation, redissolved in PBS, pH 7.4, and dialysed 3 times against PBS, pH 7.4. Ammonium sulphate was added to a concentration of 1.5 M, and ST-CF proteins were loaded on an Affi T-gel column. Elution from the Affi T-gel column and anion exchange were performed as described above.

Isolation of CWP32

Heat treated H37Rv was subfractionated into subcellular fractions as described in Sørensen et al 1995. The Cell wall fraction was resuspended in 8 M urea, 0.2% (w/v) N-octyl β-$_D$ glucopyranoside (Sigma) and 5% (v/v) glycerol and the protein solution was applied to a Rotofor isoelectrical Cell (BioRad) which was equilibrated with the same buffer. Isoelectric focusing was performed in a pH gradient from 3–6. The fractions were analyzed by SDS-PAGE and fractions containing well separated bands were polled and subjected to N-terminal sequencing after transfer to PVDF membrane.

N-Terminal Sequencing

Fractions containing CFP7A, CFP8A, CFP8B, CFP16, CFP19, CFP19B, CFP22A, CFP23A, CFP23B, CFP27, CFP30A, CWP32, and CFP50A were blotted to PVDF membrane after Tricine SDS-PAGE (Ploug et al, 1989). The relevant bands were excised and subjected to N-terminal amino acid sequence analysis on a Procise 494 sequencer (Applied Biosystems). The fraction containing CFP25A was blotted to PVDF membrane after 2-DE PAGE (isoelectric focusing in the first dimension and Tricin SDS-PAGE in the second dimension). The relevant spot was excised and sequenced as described above.

The following N-terminal sequences were obtained:

Query: 1 AEDVRAEIVASVLEVVVNEGDQIDKGDV-
VVLLESMYMEIPVLAEAAGTVS 50 AED-
VRAEIVASVLEVVVNEGDQIDKGDVVVLLESM
MEIPVLAEAAGTVS Sbjct: 257679 AEDVRAEIVASVLEVVVNEGDQIDKGD-
VVVLLESMKMEIPVLAEAAGTVS 257530

(SEQ ID NOs: 127, 128, and 129)

The identity is found within an open reading frame of 71 amino acids length corresponding to a theoretical MW of CFP7A of 7305.9 Da and a pI of 3.762. The observed molecular weight in an SDS-PAGE gel is 7 kDa.

CFP8A: A sequence 80% identical to the 15 N-terminal amino acids was found on contig TB_1884. The N-terminally determined sequence from the protein purified from culture filtrate starts at amino acid 32. This gives a length of the mature protein of 98 amino acids corresponding to a theoretical MW of 9700 Da and a pI of 3.72 This is in good agreement with the observed MW on SDS-PAGE at approximately 8 kDa. The full length protein has a theoretical MW of 12989 Da and a pI of 4.38.

```
CFP7A:   AEDVRAEIVA SVLEVVVNEG DQIDKGDVVV    (SEQ ID NO: 81)
         LLESMYMEIP VLAEAAGTVS

CFP8A:   DPVDDAFIAKLNTAG                     (SEQ ID NO: 73)

CFP8B:   DPVDAIINLDNYGX                      (SEQ ID NO: 74)

CFP16:   AKLSTDELLDAFKEM                     (SEQ ID NO: 79)

CFP19:   TTSPDPYAALPKLPS                     (SEQ ID NO: 82)

CFP19B:  DPAXAPDVPTAAQLT                     (SEQ ID NO: 80)

CFP22A:  TEYEGPKTKF HALMQ                    (SEQ ID NO: 83)

CFP23A:  VIQ/AGMVT/GHIHXVAG                  (SEQ ID NO: 76)

CFP23B:  AEMKXFKNAIVQEID                     (SEQ ID NO: 75)

CFP25A:  AIEVSVLRVF TDSDG                    (SEQ ID NO: 78)

CWP32:   TNIVVLIKQVPDTWS                     (SEQ ID NO: 77)

CFP27:   TTIVALKYPG GVVMA                    (SEQ ID NO: 84)

CFP30A:  SEPYFISPEX AMRE                     (SEQ ID NO: 85)

CFP50:   THYDVVVLGA GPGGY                    (SEQ ID NO: 86)
```

N-Terminal Homology Searching in the Sanger Database and Identification of the Corresponding Genes.

The N-terminal amino acid sequence from each of the proteins was used for a homology search using the blast program of the Sanger *Mycobacterium tuberculosis* database:

http://www.sanger.ac.uk/projects/*m-tuberculosis*/TB-blast-server.

For CFP23B, CFP23A, and CFP19B no similarities were found in the Sanger database. This could be due to the fact that only approximately 70% of the *M. tuberculosis* genome had been sequenced when the searches were performed. The genes encoding these proteins could be contained in the remaining 30% of the genome for which no sequence data is yet available.

For CFP7A, CFP8A, CFP8B, CFP16, CFP19, CFP19B, CFP22A, CFP25A, CFP27, CFP30A, CWP32, and CFP50, the following information was obtained:

CFP7A: Of the 50 determined amino acids in CFP7A a 98% identical sequence was found in cosmid csCY07D1 (contig 256):
Score=226 (100.4 bits), Expect=1.4e-24, P=1.4e-24
Identities=49/50 (98%), Positives=49/50 (98%), Frame=−1

CFP8B: A sequence 71% identical to the 14 N-terminal amino acids was found on contig TB_653. However, careful re-evaluation of the original N-terminal sequence data confirmed the identification of the protein. The N-terminally determined sequence from the protein purified from culture filtrate starts at amino acid 29. This gives a length of the mature protein of 82 amino acids corresponding to a theoretical MW of 8337 Da and a pI of 4.23. This is in good agreement with the observed MW on SDS-PAGE at approximately 8 kDa. Analysis of the amino acid sequence predicts the presence of a signal peptide which has been cleaved of the mature protein found in culture filtrate.

CFP16: The 15 aa N-terminal sequence was found to be 100% identical to a sequence found on cosmid MTCY20H1.

The identity is found within an open reading frame of 130 amino acids length corresponding to a theoretical MW of CFP16 of 13440.4 Da and a pI of 4.59. The observed molecular weight in an SDS-PAGE gel is 16 kDa.

CFP19: The 15 aa N-terminal sequence was found to be 100% identical to a sequence found on cosmid MTCY270.

The identity is found within an open reading frame of 176 amino acids length corresponding to a theoretical MW of CFP19 of 18633.9 Da and a pI of 5.41. The observed molecular weight in an SDS-PAGE gel is 19 kDa.

CFP22A: The 15 aa N-terminal sequence was found to be 100% identical to a sequence found on cosmid MTCY1A6.

The identity is found within an open reading frame of 181 amino acids length corresponding to a theoretical MW of CFP22A of 20441.9 Da and a pI of 4.73. The observed molecular weight in an SDS-PAGE gel is 22 kDa.

CFP25A: The 15 aa N-terminal sequence was found to be 100% identical to a sequence found on contig 255.

The identity is found within an open reading frame of 228 amino acids length corresponding to a theoretical MW of CFP25A of 24574.3 Da and a pI of 4.95. The observed molecular weight in an SDS-PAGE gel is 25 kDa.

CFP27: The 15 aa N-terminal sequence was found to be 100% identical to a sequence found on cosmid MTCY261.

The identity is found within an open reading frame of 291 amino acids length. The N-terminally determined sequence from the protein purified from culture filtrate starts at amino acid 58. This gives a length of the mature protein of 233 amino acids, which corresponds to a theoretical molecular weigh at 24422.4 Da, and a theoretical pI at 4.64. The observed weight in an SDS-PAGE gel is 27 kDa.

CFP30A: Of the 13 determined amino acids in CFP30A, a 100% identical sequence was found on cosmid MTCY261.

The identity is found within an open reading frame of 248 amino acids length corresponding to a theoretical MW of CFP30A of 26881.0 Da and a pI of 5.41. The observed molecular weight in an SDS-PAGE gel is 30 kDa.

CWP32: The 15 amino acid N-terminal sequence was found to be 100% identical to a sequence found on contig 281. The identity was found within an open reading frame of 266 amino acids length, corresponding to a theoretical MW of CWP32 of 28083 Da and a pI of 4.563. The observed molecular weight in an SDS-PAGE gel is 32 kDa.

CFP50: The 15 aa N-terminal sequence was found to be 100% identical to a sequence found in MTVO38.06. The identity is found within an open reading frame of 464 amino acids length corresponding to a theoretical MW of CFP50 of 49244 Da and a pI of 5.66. The observed molecular weight in an SDS-PAGE gel is 50 kDa.

Use of Homology Searching in the EMBL Database for Identification of CFP19A and CFP23.

Homology searching in the EMBL database (using the GCG package of the Biobase, Århus-DK) with the amino acid sequences of two earlier identified highly immunoreactive ST-CF proteins, using the TFASTA algorithm, revealed that these proteins (CFP21 and CFP25, EXAMPLE 3) belong to a family of fungal cutinase homologs. Among the most homologous sequences were also two *Mycobacterium tuberculosis* sequences found on cosmid MTCY13E12. The first, MTCY13E12.04 has 46% and 50% identity to CFP25 and CFP21 respectively. The second, MTCY13E12.05, has also 46% and 50% identity to CFP25 and CFP21. The two proteins share 62.5% aa identity in a 184 residues overlap. On the basis of the high homology to the strong T-cell antigens CFP21 and CFP25, respectively, it is believed that CFP19A and CFP23 are possible new T-cell antigens.

The first reading frame encodes a 254 amino acid protein of which the first 26 aa constitute a putative leader peptide that strongly indicates an extracellular location of the protein. The mature protein is thus 228 aa in length corresponding to a theoretical MW of 23149.0 Da and a Pi of 5.80. The protein is named CFP23.

The second reading frame encodes an 231 aa protein of which the first 44 aa constitute a putative leader peptide that strongly indicates an extracellular location of the protein. The mature protein is thus 187 aa in length corresponding to a theoretical MW of 19020.3 Da and a Pi of 7.03. The protein is named CFP19A.

The presence of putative leader peptides in both proteins (and thereby their presence in the ST-CF) is confirmed by theoretical sequence analysis using the signalP program at the Expasy molecular Biology server
  (http://expasy.hcuge.ch/www/tools.html).

Searching for Homologies to CFP7A, CFP16, CFP19, CFP19A, CFP19B, CFP22A, CFP23, CFP25A, CFP27, CFP30A, CWP32 and CFP50 in the EMBL Database.

The amino acid sequences derived from the translated genes of the individual antigens were used for homology searching in the EMBL and Genbank databases using the TFASTA algorithm, in order to find homologous proteins and to address eventual functional roles of the antigens.

CFP7A: CFP7A has 44% identity and 70% similarity to hypothetical *Methanococcus jannaschii* protein (*M. jannaschii* from base 1162199-1175341), as well as 43% and 38% identity and 68 and 64% similarity to the C-terminal part of *B. stearothermophilus* pyruvate carboxylase and *Streptococcus mutans* biotin carboxyl carrier protein.

CFP7A contains a consensus sequence EAMKM for a biotin binding site motif which in this case was slightly modified (ESMKM in amino acid residues 34 to 38). By incubation with alkaline phosphatase conjugated streptavidin after SDS-PAGE and transfer to nitrocellulose it was demonstrated that native CFP7A was biotinylated.

CFP16: RpIL gene, 130 aa. Identical to the *M. bovis* 50s ribosomal protein L7/L12 (acc. No P37381).

CFP19: CFP19 has 47% identity and 55% similarity to *E. coli* pectinesterase homolog (ybhC gene) in a 150 aa overlap.

CFP19A: CFP19A has between 38% and 45% identity to several cutinases from different fungal sp.

In addition CFP19A has 46% identity and 61% similarity to CFP25 as well as 50% identity and 64% similarity to CFP21 (both proteins are earlier isolated from the ST-CF).

CFP19B: No apparent homology

CFP22A: No apparent homology

CFP23: CFP23 has between 38% and 46% identity to several cutinases from different fungal sp.

In addition CFP23 has 46% identity and 61% similarity to CFP25 as well as 50% identity and 63% similarity to CFP21 (both proteins are earlier isolated from the ST-CF).

CFP25A: CFP25A has 95% identity in a 241 aa overlap to a putative *M. tuberculosis* thymidylate synthase (450 aa accession No p28176).

CFP27: CFP27 has 81% identity to a hypothetical *M. leprae* protein and 64% identity and 78% similarity to *Rhodococcus* sp. *proteasome* beta-type subunit 2 (prcB(2) gene).

CFP30A: CFP30A has 67% identity to *Rhodococcus proteasome* alfa-type 1 subunit.

CWP32: The CWP32 N-terminal sequence is 100% identical to the *Mycobacterium leprae* sequence MLCB637.03.

CFP50: The CFP50 N-terminal sequence is 100% identical to a putative lipoamide dehydrogenase from *M. leprae* (Accession 415183)

Cloning of the Genes Encoding CFP7A, CFP8A, CFP8B, CFP16, CFP19, CFP19A, CFP22A, CFP23, CFP25A, CFP27, CFP30A, CWP32, and CFP50.

The genes encoding CFP7A, CFP8A, CFP8B, CFP16, CFP19, CFP19A, CFP22A, CFP23, CFP25A, CFP27, CFP30A, CWP32 and CFP50 were all cloned into the expression vector pMCT6, by PCR amplification with gene specific primers, for recombinant expression in *E. coli* of the proteins.

PCR reactions contained 10 ng of M. tuberculosis chromosomal DNA in 1× low salt Taq+ buffer from Stratagene supplemented with 250 mM of each of the four nucleotides (Boehringer Mannheim), 0.5 mg/ml BSA (IgG technology), 1% DMSO (Merck), 5 pmoles of each primer and 0.5 unit Taq+ DNA polymerase (Stratagene) in 10 ml reaction volume. Reactions were initially heated to 94° C. for 25 sec. and run for 30 cycles of the program; 94° C. for 10 sec., 55° C. for 10 sec. and 72° C. for 90 sec, using thermocycler equipment from Idaho Technology.

The DNA fragments were subsequently run on 1% agarose gels, the bands were excised and purified by Spin-X spin columns (Costar) and cloned into pBluescript SK II+-T vector (Stratagene). Plasmid DNA was hereafter prepared from clones harbouring the desired fragments, digested with suitable restriction enzymes and subcloned into the expression vector pMCT6 in frame with 8 histidines which are added to the N-terminal of the expressed proteins. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

For cloning of the individual antigens, the following gene specific primers were used:

CFP7A: Primers used for cloning of cfp7A:

```
OPBR-79:
AAGAGTAGATCTATGATGGCCGAGGATGTTCGCG    (SEQ ID NO: 95)

OPBR-80:
CGGCGACGACGGATCCTACCGCGTCGG           (SEQ ID NO: 96)
```

OPBR-79 and OPBR-80 create BglII and BamHI sites, respectively, used for the cloning in pMCT6.

CFP8A: Primers used for cloning of cfp8A:

```
                                         (SEQ ID NO: 154)
CFP8A-F:  CTGAGATCTATGAACCTACGGCGCC
                                         (SEQ ID NO: 155)
CFP8A-R:  CTCCCATGGTACCCTAGGACCCGGGCAGCCCCGGC
```

CFP8A-F and CFP8A-R create BglII and NcoI sites, respectively, used for the cloning in pMCT6.

CFP8B: Primers used for cloning of cfp8B:

```
CFP8B-F:
CTGAGATCTATGAGGCTGTCGTTGACCGC         (SEQ ID NO: 156)

CFP8B-R:
CTCCCCGGGCTTAATAGTTGTTGCAGGAGC        (SEQ ID NO: 157)
```

CFP8B-F and CFP8B-R create BglII and SmaI sites, respectively, used for the cloning in pMCT6.

CFP16: Primers used for cloning of cfp16:

```
                                  (SEQ ID NOs: 111 and 130)
OPBR-104:  CCGGGAGATCTATGGCAAAGCTCTCCACCGACG (SEQ ID NOs: 112 and 131)
OPBR-105:  CGCTGGGCAGAGCTACTTGACGGTGACGGTGG
```

OPBR-104 and OPBR-105 create BglII and NcoI sites, respectively, used for the cloning in pMCT6.

CFP19: Primers used for cloning of cfp19:

```
OPBR-96:
GAGGAAGATCTATGACAACTTCACCCGACCCG      (SEQ ID NO: 107)

OPBR-97:
CATGAAGCCATGGCCCGCAGGCTGCATG          (SEQ ID NO: 108)
```

OPBR-96 and OPBR-97 create BglII and NcoI sites, respectively, used for the cloning in pMCT6.

CFP19A: Primers used for cloning of cfp19A:

```
OPBR-88:
CCCCCCAGATCTGCACCACCGGCATCGGCGGGC     (SEQ ID NO: 99)

OPBR-89:
GCGGCGGATCCGTTGCTTAGCCGG              (SEQ ID NO: 100)
```

OPBR-88 and OPBR-89 create BglII and BamHI sites, respectively, used for the cloning in pMCT6.

CFP22A: Primers used for cloning of cfp22A:

```
OPBR-90:
CCGGCTGAGATCTATGACAGAATACGAAGGGC      (SEQ ID NO: 101)

OPBR-91:
CCCCGCCAGGGAACTAGAGGCGGC              (SEQ ID NO: 102)
```

OPBR-90 and OPBR-91 create BglII and NcoI sites, respectively, used for the cloning in pMCT6.

CFP23: Primers used for cloning of cfp23:

```
OPBR-86:
CCTTGGGAGATCTTTGGACCCCGGTTGC          (SEQ ID NO: 97)

OPBR-87:
GACGAGATCTTATGGGCTTACTGAC             (SEQ ID NO: 98)
```

OPBR-86 and OPBR-87 both create a BglII site used for the cloning in pMCT6.

CFP25A: Primers used for cloning of cfp25A:

```
                                         (SEQ ID NO: 113)
OPBR-106:  GGCCCAGATCTATGGCCATTGAGGTTTCGGTGTTGC
                                         (SEQ ID NO: 114)
OPBR-107:  CGCCGTGTTGCATGGCAGCGCTGAGC
```

OPBR-106 and OPBR-107 create BglII and NcoI sites, respectively, used for the cloning in pMCT6.

CFP27: Primers used for cloning of cfp27:

```
                                         (SEQ ID NO: 103)
OPBR-92:  CTGCCGAGATCTACCACCATTGTCGCGCTGAAATACCC
                                         (SEQ ID NO: 104)
OPBR-93:  CGCCATGGCCTTACGCGCCAACTCG
```

OPBR-92 and OPBR-93 create BglII and NcoI sites, respectively, used for the cloning in pMCT6.

CFP30A: Primers used for cloning of cfp30A:

```
OPBR-94:
GGCGGAGATCTGTGAGTTTTCCGTATTTCATC      (SEQ ID NO: 105)

OPBR-95:
CGCGTCGAGCCATGGTTAGGCGCAG             (SEQ ID NO: 106)
```

OPBR-94 and OPBR-95 create BglII and NcoI sites, respectively, used for the cloning in pMCT6.

CWP32: Primers used for cloning of cwp32:

```
CWP32-F:
GCTTAGATCTATGATTTTCTGGGCAACCAGGTA    (SEQ ID NO: 158)

CWP32-R:
GCTTCCATGGGCGAGGCACAGGCGTGGGAA       (SEQ ID NO: 159)
```

CWP32-F and CWP32-R create BglII and NcoI sites, respectively, used for the cloning in pMCT6.

CFP50: Primers used for cloning of cfp50:

```
OPBR-100:
GGCCGAGATCTGTGACCCACTATGACGTCGTCG    (SEQ ID NO: 109)

OPBR-101:
GGCGCCCATGGTCAGAAATTGATCATGTGGCCAA   (SEQ ID NO: 110)
```

OPBR-100 and OPBR-101 create BglII and NcoI sites, respectively, used for the cloning in pMCT6.

Expression/Purification of Recombinant CFP7A, CFP8A, CFP8B, CFP16, CFP19, CFP19A, CFP22A, CFP23, CFP25A, CFP27, CFP30A, CWP32, and CFP50 Proteins.

Expression and metal affinity purification of recombinant proteins was undertaken essentially as described by the manufacturers. For each protein, 1 l LB-media containing 100 μg/ml ampicillin, was inoculated with 10 ml of an overnight culture of XL1-Blue cells harbouring recombinant pMCT6 plasmids. Cultures were shaken at 37° C. until they reached a density of $OD_{600}$=0.4–0.6. IPTG was hereafter added to a final concentration of 1 mM and the cultures were further incubated 4–16 hours. Cells were harvested, resuspended in 1× sonication buffer+8 M urea and sonicated 5×30 sec. with 30 sec. pausing between the pulses.

After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at 280 nm. Fractions containing recombinant protein were pooled and dialysed against 3 M urea in 10 mM Tris-HCl, pH 8.5. The dialysed protein was further purified by FPLC (Pharmacia, Sweden) using a 6 ml Resource-Q column, eluted with a linear 0–1 M gradient of NaCl. Fractions were analyzed by SDS-PAGE and protein concentrations were estimated at $OD_{280}$. Fractions containing protein were pooled and dialysed against 25 mM Hepes buffer, pH 8.5.

Finally the protein concentration and the LPS content were determined by the BCA (Pierce, Holland) and LAL (Endosafe, Charleston, USA) tests, respectively.

Example 6

Identification of CFP7B, CFP10A, CFP11 and CFP30B.

Isolation of CFP7B

ST-CF was precipitated with ammonium sulphate at 80% saturation and redissolved in PBS, pH 7.4, and dialyzed 3 times against 25 mM Piperazin-HCl, pH 5.5, and subjected to cromatofocusing on a matrix of PBE 94 (Pharmacia) in a column connected to an FPLC system (Pharmacia). The column was equilibrated with 25 mM Piperazin-HCl, pH 5.5, and the elution was performed with 10% PB74-HCl, pH 4.0 (Pharmacia). Fractions with similar band patterns were pooled and washed three times with PBS on a Centriprep concentrator (Amicon) with a 3 kDa cut off membrane to a final volume of 1–3 ml. An equal volume of SDS containing sample buffer was added and the protein solution boiled for 5 min before further separation on a Multi-Eluter (BioRad) in a matrix of 10–20% polyacrylamid (Andersen, P. & Heron, I., 1993). The fraction containing a well separated band below 10 kDa was selected for N-terminal sequencing after transfer to a PVDF membrane.

Isolation of CFP11

ST-CF was precipitated with ammonium sulphate at 80% saturation. The precipitated proteins were removed by centrifugation and after resuspension washed with 8 M urea. CHAPS and glycerol were added to a final concentration of 0.5% (w/v) and 5% (v/v) respectively and the protein solution was applied to a Rotofor isoelectrical Cell (BioRad). The Rotofor Cell had been equilibrated with an 8M urea buffer containing 0.5% (w/v) CHAPS, 5% (v/v) glycerol, 3% (v/v) Biolyt 3/5 and 1% (v/v) Biolyt 4/6 (BioRad). Isoelectric focusing was performed in a pH gradient from 3–6. The fractions were analyzed on silver-stained 10–20% SDS-PAGE. The fractions in the pH gradient 5.5 to 6 were pooled and washed three times with PBS on a Centriprep concentrator (Amicon) with a 3 kDa cut off membrane to a final volume of 1 ml. 300 mg of the protein preparation was separated on a 10–20% Tricine SDS-PAGE (Ploug et al 1989) and transferred to a PVDF membrane and Coomassie stained. The lowest band occurring on the membrane was excised and submitted for N-terminal sequencing.

Isolation of CFP10A and CFP30B

ST-CF was concentrated approximately 10-fold by ultra-filtration and ammonium sulphate precipitation at 80% saturation. Proteins were redissolved in 50 mM sodium phosphate, 1.5 M ammonium sulphate, pH 8.5, and subjected to thiophilic adsorption chromatography on an Affi-T gel column (Kem-En-Tec). Proteins were eluted by a 1.5 to 0 M decreasing gradient of ammonium sulphate. Fractions with similar band patterns in SDS-PAGE were pooled and anion exchange chromatography was performed on a Mono Q HR 5/5 column connected to an FPLC system (Pharmacia). The column was equilibrated with 10 mM Tris-HCl, pH 8.5, and the elution was performed with a gradient of NaCl from 0 to 1 M. Fractions containing well separated bands in SDS-PAGE were selected.

Fractions containing CFP10A and CFP30B were blotted to PVDF membrane after 2-DE PAGE (Ploug et al, 1989). The relevant spots were excised and subjected to N-terminal amino acid sequence analysis.

N-Terminal Sequencing

N-terminal amino acid sequence analysis was performed on a Procise 494 sequencer (applied Biosystems).

The following N-terminal sequences were obtained:

```
CFP7B:    PQGTVKWFNAEKGFG    (SEQ ID NO: 168)

CFP10A:   NVTVSIPTILRPXXX    (SEQ ID NO: 169)

CFP11:    TRFMTDPHAMRDMAG    (SEQ ID NO: 170)

CFP30B:   PKRSEYRQGTPNWVD    (SEQ ID NO: 171)
```

"X" denotes an amino acid which could not be determined by the sequencing method used.

N-Terminal Homology Searching in the Sanger Database and Identification of the Corresponding Genes.

The N-terminal amino acid sequence from each of the proteins was used for a homology search using the blast program of the Sanger *Mycobacterium tuberculosis* genome database:

http//www.sanger.ac.uk/projects/*m-tuberculosis*/TB-blast-server.

For CFP11 a sequence 100% identical to 15 N-terminal amino acids was found on contig TB_1314. The identity was found within an open reading frame of 98 amino acids length corresponding to a theoretical MW of 10977 Da and a pI of 5.14.

Amino acid number one can also be an Ala (insted of a Thr) as this sequence was also obtained (results not shown), and a 100% identical sequence to this N-terminal is found on contig TB_671 and on locus MTCI364.09.

For CFP7B a sequence 100% identical to 15 N-terminal amino acids was found on contig TB_2044 and on locus MTY15C10.04 with EMBL accession number: z95436. The identity was found within an open reading frame of 67 amino acids length corresponding to a theoretical MW of 7240 Da and a pI of 5.18.

For CFP10A a sequence 100% identical to 12 N-terminal amino acids was found on contig TB_752 and on locus CY130.20 with EMBL accession number: Q10646 and Z73902. The identity was found within an open reading frame of 93 amino acids length corresponding to a theoretical MW of 9557 Da and a pI of 4.78.

For CFP30B a sequence 100% identical to 15 N-terminal amino acids was found on contig TB_335. The identity was found within an open reading frame of 261 amino acids length corresponding to a theoretical MW of 27345 Da and a pI of 4.24.

The amino acid sequences of the purified antigens as picked from the Sanger database are shown in the following list.

Cloning of the Genes Encoding CFP7B, CFP10A, CFP11, and CFP30B.

PCR reactions contained 10 ng of *M. tuberculosis* chromosomal DNA in 1× low salt Taq+ buffer from Stratagene supplemented with 250 mM of each of the four nucleotides (Boehringer Mannheim), 0.5 mg/ml BSA (IgG technology), 1% DMSO (Merck), 5 pmoles of each primer and 0.5 unit Taq+ DNA polymerase (Stratagene) in 10 ml reaction volume. Reactions were initially heated to 94° C. for 25 sec. and run for 30 cycles of the program; 94° C. for 10 sec., 55° C. for 10 sec. and 72° C. for 90 sec., using thermocycler equipment from Idaho Technology.

The DNA fragments were subsequently run on 1% agarose gels, the bands were excised and purified by Spin-X spin columns (Costar) and cloned into pBluscript SK II+-T vector (Stratagene). Plasmid DNA was hereafter prepared from clones harbouring the desired fragments, digested with suitable restriction enzymes and subcloned into the expression vector pMCT6 in frame with 8 histidines which are added to the N-terminal of the expressed proteins. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

For cloning of the individual antigens, the following gene specific primers were used:

CFP7B: Primers used for cloning of cfp7B:

```
CFP7B-F:
CTGAGATCTAGAATGCCACAGGGAACTGTG     (SEQ ID NO: 160)

CFP7B-R:
TCTCCCGGGGGTAACTCAGAGCGAGCGGAC     (SEQ ID NO: 161)
```

CFP7B-F and CFP7B-R create BglII and SmaI sites, respectively, used for the cloning in pMCT6.

```
CFP7B
    1           MPQGTVKWFN AEKGFGFIAP EDGSADVFVH YTEIQGTGFR TLEENQKVEF  (SEQ ID NO: 147)

51           EIGHSPKGPQ ATGVRSL

CFP10A
    1           MNVTVSIPTI LRPHTGGQKS VSASGDTLGA VISDLEANYS GISERLMDPS  (SEQ ID NO: 141)

51           SPGKLHRFVN IYVNDEDVRF SGGLATAIAD GDSVTILPAV AGG

CFP11 protein
sequence
    1           MATRFMTDPH AMRDMAGRFE VHAQTVEDEA RRMWASAQNI SGAGWSGMAE  (SEQ ID NO: 143)

51           ATSLDTMAQM NQAFRNIVNM LHGVRDGLVR DANNYEQQEQ ASQQILSS

CFP30B
    1           MPKRSEYRQG TPNWVDLQTT DQSAAKKFYT SLFGWGYDDN PVPGGGGVYS  (SEQ ID NO: 145)

51           MATLNGEAVA AIAPMPPGAP EGMPPIWNTY IAVDDVDAVV DKVVPGGGQV

101           MMPAFDIGDA GRMSFITDPT GAAVGLWQAN RHIGATLVNE TGTLIWNELL

151           TDKPDLALAF YEAVVGLTHS SMEIAAGQNY RVLKAGDAEV GGCMEPPMPG

201           VPNHWHVYFA VDDADATAAK AAAAGGQVIA EPADIPSVGR FAVLSDPQGA

251           IFSVLKPAPQ Q
```

CFP10A: Primers used for cloning of cfp10A:

```
CFP10A-F:
CTGAGATCTATGAACGTCACCGTATCC    (SEQ ID NO: 162)

CFP10A-R:
TCTCCCGGGGCTCACCCACCGGCCACG    (SEQ ID NO: 163)
```

CFP10A-F and CFP10A-R create BglII and SmaI sites, respectively, used for the cloning in pMCT6.

CFP11: Primers used for cloning of cfp11:

```
CFP11-F:
CTGAGATCTATGGCAACACGTTTTATGACG    (SEQ ID NO: 164)

CFP11-R:
CTCCCCGGGTTAGGTGCTGAGGATCTGCTH   (SEQ ID NO: 165)
```

CFP11-F and CFP11-R create BglII and SmaI sites, respectively, used for the cloning in pMCT6.

CFP30B: Primers used for cloning of cfp30B:

```
CFP30B-F:
CTGAAGATCTATGCCCAAGAGAAGCGAATAC    (SEQ ID NO: 166)
CFP30B-R:
CGGCAGCTGCTAGCATTCTCCGAATCTGCCG    (SEQ ID NO: 167)
```

CFP30B-F and CFP30B-R create BglII and PvuII sites, respectively, used for the cloning in pMCT6.

Expression/Purification of Recombinant CFP7B, CFP10A, CFP11 and CFP30B Protein.

Expression and metal affinity purification of recombinant protein was undertaken essentially as described by the manufacturers. 1 l LB-media containing 100 μg/ml ampicillin, was inoculated with 10 ml of an overnight culture of XL1-Blue cells harbouring recombinant pMCT6 plasmid. The culture was shaken at 37° C. until it reached a density of $OD_{600}$=0.5. IPTG was hereafter added to a final concentration of 1 mM and the culture was further incubated 4 hours. Cells were harvested, resuspended in 1× sonication buffer+8 M urea and sonicated 5×30 sec. with 30 sec. pausing between the pulses.

After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at 280 nm. Fractions containing recombinant protein were pooled and dialysed against 3 M urea in 10 mM Tris-HCl, pH 8.5. The dialysed protein was further purified by FPLC (Pharmacia, Sweden) using a 6 ml Resource-Q column, eluted with a linear 0–1 M gradient of NaCl. Fractions were analysed by SDS-PAGE and protein concentrations were estimated at $OD_{280}$. Fractions containing protein were pooled and dialysed against 25 mM Hepes buffer, pH 8.5.

Finally the protein concentration and the LPS content was determined by the BCA (Pierce, Holland) and LAL (Endosafe, Charleston, USA) tests, respectively.

Example 7

Using Homology Searching for Identification of ORF11-1, ORF11-2, ORF11-3 and ORF11-4.

A search of the *Mycobacterium tuberculosis* Sanger sequence database with the amino acid sequences of CFP11, a previously identified ST-CF protein, identified 4 new very homologous proteins. All 4 proteins were at least 96% homologous to CFP11.

On the basis of the strong homology to CFP11, it is belived that ORF11-1, ORF11-2, ORF11-3 and ORF11-4 are potential new T-cell antigens.

The first open reading frame, MTCY10G2.11, homologous to CFP11, encodes a protein of 98 amino acids corresponding to a theoretical molecular mass of 10994 Da and a pI of 5.14. The protein was named ORF11-1.

The second open reading frame, MTC1364.09, homologous to CFP11, encodes a protein of 98 amino acids corresponding to a theoretical molecular mass of 10964 Da and a pI of 5.14. The protein was named ORF11-2.

The third open reading frame, MTV049.14, has an in frame stop codon. Because of the very conserved DNA sequence in this position amongst the 4 open reading frames it is however suggested that this is due to a sequence mistake.

The "T" in position 175 of the DNA sequence is therefor suggested to be a "C" as in the four other ORF's. The Q in position 59 in the amino acid sequence would have been a "stop" if the T in position 175 in the DNA sequence had not been substituted.

The open reading frame encodes a protein of 98 amino acids corresponding to a theoretical molecular mass of 10994 Da and a pI of 5.14. The protein was named ORF11-3.

The fourth open reading frame, MTCY15C10.32, homologous to CFP11, encodes a protein of 98 amino acids corresponding to a theoretical molecular mass of 11024 Da and a pI of 5.14. The protein was named ORF11-4.

Using Homology Searching for Identification of ORF7-1 and ORF7-2.

A search of the *Mycobacterium tuberculosis* Sanger sequence database with the amino acid sequences of a previously identified immunoreactive ST-CF protein, CFP7, identified 2 new very homologous proteins. The protein ORF7-1 (MTV012.33) was 84% identical to CFP7, with a primary structure of the same size as CFP7, and the protein ORF7-2 (MTV012.31) was 68% identical to CFP7 in a 69 amino acid overlap.

On the basis of the strong homology to the potent human T-cell antigen CFP7, ORF7-1 and ORF7-2 are belived to be potential new T-cell antigens.

The first open reading frame homologous to CFP7, encodes a protein of 96 amino acids corresponding to a theoretical molecular mass of 10313 Da and a pI of 4.186. The protein was named ORF7-1.

The second open reading frame homologous to CFP7, encodes a protein of 120 amino acids corresponding to a theoretical molecular mass of 12923.00 Da and a pI of 7.889. The protein was named ORF7-2.

Cloning of the Homologous orf7-1 and orf7-2.

Since ORF7-1 and ORF7-2 are nearly identical to CFP7 it was nessesary to use the flanking DNA regions in the cloning procedure, to ensure the cloning of the correct ORF. Two PCR reactions were carried out with two different primer sets. PCR reaction 1 was carried out using *M. tuberculosis* chromosomal DNA and a primerset corresponding to the flanking DNA. PCR reaction 2 was carried out directly on the first PCR product using ORF specific primers which introduced restriction sites for use in the later cloning procedure. The sequences of the primers used are given below;
Orf7-1:
Primers used for the initial PCR reaction (1) using *M. tuberculosis* chromosomal DNA as template;

(SEQ ID NO: 186)
Sence:     MTV012.33-R1: 5'-GGAATGAAAAGGGGTTTGTG-3'

(SEQ ID NO:187)
Antisence: MTV012.33-F1: 5'-GACCACGCCCGCGCCGTGTG-3'

Primers used for the second round of PCR (2) using PCR product 1 as template;
Sence:     MTV012.33-R2:     5'-GCAACACCCGGGATGTCGCAGATTATG-3' (SEQ ID NO: 188)
(introduces a SmaI upstream of the orf7-1 start codon)
Antisence: MTV012.33-F2:     5'-CTAAGCTTGGATCCCTAGCCGCCCCACTTG-3' ((SEQ ID NO: 189)
(introduces a BamHI downstream of the orf7-1 stop codon).
Orf7-2:
Primers used for the initial PCR reaction (1) using *M. tuberculosis* chromosomal DNA as template;
Sence:     MTV012.31-R1: 5'-GAATATTTGAAAGGGATTCGTG-3' (SEQ ID NO: 190)
Antisence: MTV012.31-F1:     5'-CTACTAAGCTTGGATCCTTAGTCTCCGGCG-3' (SEQ ID NO: 191)
(introduces a BamHI downstream of the orf7-2 stop codon)
Primers used for the second round of PCR (2) using PCR product 1 as template;
Sence:     MTV012.31-R2:     5'-GCAACACCCGGGGTGTCGCAGAGTATG-3' (SEQ ID NO: 192)
(introduces a SmaI upstream of the orf7-2 start codon)
Antisence: MTV012.31-F1:     5'-CTACTAAGCTTGGATCCTTAGTCTCCGGCG-3' (SEQ ID NO: 193)
(introduces a BamHI downstream of the orf7-2 stop codon)

The genes encoding ORF7-1 and ORF7-2 were cloned into the expression vector pMST24, by PCR amplification with gene specific primers, for recombinant expression in *E. coli* of the proteins.

The first PCR reactions contained either 10 ng of *M. tuberculosis* chromosomal DNA (PCR reaction 1) or 10 ng PCR product 1 (PCR reaction 2) in 1× low salt Taq+ buffer from Stratagene supplemented with 250 mM of each of the four nucleotides (Boehringer Mannheim), 0.5 mg/ml BSA (IgG technology), 1% DMSO (Merck), 5 pmoles of each primer and 0.5 unit Taq+ DNA polymerase (Stratagene) in 10 ml reaction volume. Reactions were initially heated to 94° C. for 25 sec. and run for 30 cycles of the program; 94° C. for 10 sec., 55° C. for 10 sec., and 72° C. for 90 sec, using thermocycler equipment from Idaho Technology.

The DNA fragments were subsequently run on 1% agarose gels, the bands were excised and purified by Spin-X spin columns (Costar) and cloned into pBluscript SK II+-T vector (Stratagene). Plasmid DNA was hereafter prepared from clones harbouring the desired fragments, digested with suitable restriction enzymes and subcloned into the expression vector pMST24 in frame with 6 histidines which are added to the N-terminal of the expressed proteins. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

Expression/purification of recombinant ORF7-1 and ORF7-2 protein.

Expression and metal affinity purification of recombinant protein was undertaken essentially as described by the manufacturers. 1 1 LB-media containing 100 µg/ml ampicillin, was inoculated with 10 ml of an overnight culture of XL1-Blue cells harbouring recombinant pMCT6 plasmid. The culture was shaken at 37° C. until it reached a density of OD600=0.5. IPTG was hereafter added to a final concentration of 1 mM and the culture was further incubated 2 hours. Cells were harvested, resuspended in 1× sonication buffer+8 M urea and sonicated 5×30 sec. with 30 sec. pausing between the pulses.

After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system. Fractions containing recombinant protein were pooled and dialysed against 3 M urea in 10 mM Tris-HCl, pH 8.5. The dialysed protein was further purified by FPLC (Pharmacia, Sweden) using a 6 ml Resource-Q column, eluted with a linear 0–1 M gradient of NaCl. Fractions were analysed by SDS-PAGE. Fractions containing protein were pooled and dialysed against 25 mM Hepes buffer, pH 8.5. Finally the protein concentration and the LPS content was determined by the BCA (Pierce, Holland) and LAL (Endosafe, Charleston, USA) tests, respectively.

Example 8
Cloning of the Gene Expressing CFP26 (MPT51)
Synthesis and Design of Probes Oligonucleotide primers were synthesized automatically on a DNA synthesizer (Applied Biosystems, Forster City, Calif., ABI-391, PCR-mode) deblocked and purified by ethanol precipitation.

Three oligonucleotides were synthesized (TABLE 3) on the basis of the nucleotide sequence from mpb51 described by Ohara et al. (1995). The oligonucleotides were engineered to include an EcoRI restriction enzyme site at the 5' end and at the 3' end by which a later subcloning was possible.

Additional four oligonucleotides were synthesized on the basis of the nucleotide sequence from MPT51 (FIG. 5 and SEQ ID NO: 41). The four combinations of the primers were used for the PCR studies.

DNA Cloning and PCR Technology

Standard procedures were used for the preparation and handling of DNA (Sambrook et al., 1989). The gene mpt51 was cloned from *M. tuberculosis* H37Rv chromosomal DNA by the use of the polymerase chain reactions (PCR) technology as described previously (Oettinger and Andersen, 1994). The PCR product was cloned in the pBluescriptSK+ (Stratagene).

Cloning of mPt51

The gene, the signal sequence and the Shine Delgarno region of MPT51 was cloned by use of the PCR technology as two fragments of 952 bp and 815 bp in pBluescript SK+, designated pTO52 and pTO53.

DNA Sequencing

The nucleotide sequence of the cloned 952 bp *M. tuberculosis* H37Rv PCR fragment, pTO52, containing the Shine Dalgarno sequence, the signal peptide sequence and the structural gene of MPT51, and the nucleotide sequence of the cloned 815 bp PCR fragment containing the structural gene of MPT51, pTO53, were determined by the dideoxy chain termination method adapted for supercoiled DNA by use of the Sequenase DNA sequencing kit version 1.0 (United States Biochemical Corp., Cleveland, Ohio) and by cycle sequencing using the Dye Terminator system in combination with an automated gel reader (model 373A; Applied Biosystems) according to the instructions provided. Both strands of the DNA were sequenced.

The nucleotide sequences of pTO52 and pTO53 and the deduced amino acid sequence are shown in FIG. 5. The DNA sequence contained an open reading frame starting with a ATG codon at position 45–47 and ending with a termination codon (TAA) at position 942–944. The nucleotide sequence of the first 33 codons was expected to encode the signal sequence. On the basis of the known N-terminal amino acid sequence (Ala-Pro-Tyr-Glu-Asn) of the purified MPT51 (Nagai et al., 1991) and the features of the signal peptide, it is presumed that the signal peptidase recognition sequence (Ala-X-Ala) (von Heijne, 1984) is located in front of the N-terminal region of the mature protein at position 144. Therefore, a structural gene encoding MPT51, mpt51, derived from *M. tuberculosis* H37Rv was found to be located at position 144–945 of the sequence shown in FIG. 11. The nucleotide sequence of mpt51 differed with one nucleotide compared to the nucleotide sequence of MPB51 described by Ohara et al. (1995) (FIG. 11). In mpt51 at position 780 was found a substitution of a guanine to an adenine. From the deduced amino acid sequence this change occurs at a first position of the codon giving a amino acid change from alanine to threonine. Thus it is concluded, that mpt51 consists of 801 bp and that the deduced amino acid sequence contains 266 residues with a molecular weight of 27,842, and MPT51 show 99.8% identity to MPB51.

Subcloning of mpt51

An EcoRI site was engineered immediately 5' of the first codon of mpt51 so that only the coding region of the gene encoding MPT51 would be expressed, and an EcoRI site was incorporated right after the stop codon at the 3' end.

DNA of the recombinant plasmid pTO53 was cleaved at the EcoRI sites. The 815 bp fragment was purified from an agarose gel and subcloned into the EcoRI site of the pMAL-cR1 expression vector (New England Biolabs), pTO54. Vector DNA containing the gene fusion was used to transform the *E. coli* XL1-Blue by the standard procedures for DNA manipulation.

The endpoints of the gene fusion were determined by the dideoxy chain termination method as described under section DNA sequencing. Both strands of the DNA were sequenced.

Preparation and Purification of rMPT51

Recombinant antigen was prepared in accordance with instructions provided by New England Biolabs. Briefly, single colonies of *E. coli* harbouring the pTO54 plasmid were inoculated into Luria-Bertani broth containing 50 μg/ml ampicillin and 12.5 μg/ml tetracycline and grown at 37° C. to $2\times10^8$ cells/ml. Isopropyl-β-D-thiogalactoside (IPTG) was then added to a final concentration of 0.3 mM and growth was continued for further 2 hours. The pelleted bacteria were stored overnight at −20° C. in new column buffer (20 mM Tris/HCl, pH 7.4, 200 mM NaCl, 1 mM EDTA, 1 mM dithiothreitol (DTT)) and thawed at 4° C. followed by incubation with 1 mg/ml lysozyme on ice for 30 min and sonication (20 times for 10 sec with intervals of 20 sec). After centrifugation at 9,000×g for 30 min at 4° C., the maltose binding protein-MPT51 fusion protein (MBP-rMPT51) was purified from the crude extract by affinity chromatography on amylose resin column. MBP-rMPT51 binds to amylose. After extensive washes of the column, the fusion protein was eluted with 10 mM maltose. Aliquots of the fractions were analyzed on 10% SDS-PAGE. Fractions containing the fusion protein of interest were pooled and was dialysed extensively against physiological saline.

Protein concentration was determined by the BCA method supplied by Pierce (Pierce Chemical Company, Rockford, Ill.).

TABLE 3

Sequence of the mpt 51 oligonucleotides[a].

| Orientation and oligonucleotide[a] | Sequences (5' → 3') | | Position[b] (nucleotide) | |
|---|---|---|---|---|
| Sense | | | | |
| MPT51-1 | CTCGAATTCGCCGGGTGCACACAG | (SEQ ID NO: 28) | 6–21 | (SEQ ID NO: 41) |
| MPT51-3 | CTCGAATTCGCCCCATACGAGAAC | (SEQ ID NO: 29) | 143–158 | (SEQ ID NO: 41) |
| MPT51-5 | GTGTATCTGCTGGAC | (SEQ ID NO: 30) | 228–242 | (SEQ ID NO: 41) |
| MPT51-7 | CCGACTGGCTGGCCG | (SEQ ID NO: 31) | 418–432 | (SEQ ID NO: 41) |
| Antisense | | | | |
| MPT51-2 | GAGGAATTCGCTTAGCGGATCGCA | (SEQ ID NO: 32) | 946–932 | (SEQ ID NO: 41) |

TABLE 3-continued Sequence of the mpt 51 oligonucleotides[a].

| Orientation and oligonucleotide[a] | Sequences (5' → 3') | Position[b] (nucleotide) |
|---|---|---|
| MPT51-4 | CCCACATTCCGTTGG (SEQ ID NO: 33) | 642–628 (SEQ ID NO: 41) |
| MPT51-6 | GTCCAGCAGATACAC (SEQ ID NO: 34) | 242–228 (SEQ ID NO: 41) |

[a]The oligonucleotides MPT51-1 and MPT51-2 were constructed from the MPB51 nucleotide sequence (Ohara et al., 1995). The other oligonucleotides constructions were based on the nucleotide sequence obtained from mpt51 reported in this work. Nucleotides (nt) underlined are not contained in the nucleotide sequence of MPB/T51.
[b]The positions referred to are of the non-underlined parts of the primers and correspond to the nucleotide sequence shown in SEQ ID NO: 41.

Cloning of mpt51 in the Expression Vector pMST24.

A PCR fragment was produced from pTO52 using the primer combination MPT51-F and MPT51-R (TABLE 4). A BamHI site was engineered immediately 5' of the first codon of mpt51 so that only the coding region of the gene encoding MPT51 would be expressed, and an NcoI site was incorporated right after the stop codon at the 3' end.

The PCR product was cleaved at the BamHI and the NcoI site. The 811 bp fragment was purified from an agarose gel and subcloned into the BamHI and the NcoI site of the pMST24 expression vector, pTO86. Vector DNA containing the gene fusion was used to transform the E. coli XL1-Blue by the standard procedures for DNA manipulation.

The nucleotide sequence of complete gene fusion was determined by the dideoxy chain termination method as described under section DNA sequencing. Both strands of the DNA were sequenced.

Preparation and Purification of rMPT51.

Recombinant antigen was prepared from single colonies of E. coli harbouring the pTO86 plasmid inoculated into Luria-Bertani broth containing 50 μg/ml ampicillin and 12.5 μg/ml tetracycline and grown at 37° C. to 2×10⁸ cells/ml. Isopropyl-β-D-thiogalactoside (IPTG) was then added to a final concentration of 1 mM and growth was continued for further 2 hours. The pelleted bacteria were resuspended in BC 100/20 buffer (100 mM KCl, 20 mM Imidazole, 20 mM Tris/HCl, pH 7.9, 20% glycerol). Cells were broken by sonication (20 times for 10 sec with intervals of 20 sec). After centrifugation at 9,000×g for 30 min. at 4° C. the insoluble matter was resuspended in BC 100/20 buffer with 8 M urea followed by sonication and centrifugation as above. The 6× His tag-MPT51 fusion protein (His-rMPT51) was purified by affinity chromatography on Ni-NTA resin column (Qiagen, Hilden, Germany). His-rMPT51 binds to Ni-NTA. After extensive washes of the column, the fusion protein was eluted with BC 100/40 buffer (100 mM KCl, 40 mM Imidazole, 20 mM Tris/HCl, pH 7.9, 20% glycerol) with 8 M urea and BC 1000/40 buffer (1000 mM KCl, 40 mM Imidazole, 20 mM Tris/HCl, pH 7.9, 20% glycerol) with 8 M urea. His-rMPT51 was extensive dialysed against 10 mM Tris/HCl, pH 8.5, 3 M urea followed by purification using fast protein liquid chromatography (FPLC) (Pharmacia, Uppsala, Sweden), over an anion exchange column (Mono Q) using 10 mM Tris/HCl, pH 8.5, 3 M urea with a 0–1 M NaCl linear gradient. Fractions containing rMPT51 were pooled and subsequently dialysed extensively against 25 mM Hepes, pH 8.0 before use.

Protein concentration was determined by the BCA method supplied by Pierce (Pierce Chemical Company, Rockford, Ill.).

The lipopolysaccharide (LPS) content was determined by the limulus amoebocyte lysate test (LAL) to be less than 0.004 ng/μg rMPT51, and this concentration had no influence on cellular activity.

TABLE 4

Sequence of the mpt 51 oligonucleotides.

| Orientation and oligonucleotide | Sequences (5' → 3') | Position (nt) |
|---|---|---|
| Sense | | |
| MPT51-F | CTCGGATCCTGCCCCATACGAGAA-CCTG | 139–156 |
| Antisense | | |
| MPT51-R | CTCCCATGGTTAGCGGATCGCACCG | 939–924 |

Example 9

Mapping of the Purified Antigens in a 2DE System.

In order to characterize the purified antigens they were mapped in a 2-dimensional electrophoresis (2DE) reference system. This consists of a silver stained gel containing ST-CF proteins separated by isoelectrical focusing followed by a separation according to size in a polyacrylamide gel electrophoresis. The 2DE was performed according to Hochstrasser et al. (1988). 85 μg of ST-CF was applied to the isoelectrical focusing tubes where BioRad ampholytes BioLyt 4–6 (2 parts) and BioLyt 5–7 (3 parts) were included. The first dimension was performed in acrylamide/piperazin diacrylamide tube gels in the presence of urea, the detergent CHAPS and the reducing agent DTT at 400 V for 18 hours and 800 V for 2 hours. The second dimension 10–20% SDS-PAGE was performed at 100 V for 18 hours and silver stained. The identification of CFP7, CFP7A, CFP7B, CFP8A, CFP8B, CFP9, CFP11, CFP16, CFP17, CFP19, CFP20, CFP21, CFP22, CFP25, CFP27, CFP28, CFP29, CFP30A, CFP50, and MPT51 in the 2DE reference gel were done by comparing the spot pattern of the purified antigen with ST-CF with and without the purified antigen. By the assistance of an analytical 2DE software system (Phoretix International, UK) the spots have been identified in FIG. 12. The position of MPT51 and CFP29 were confirmed by a Western blot of the 2DE gel using the Mab's anti-CFP29 and HBT 4.

Example 10

Biological Activity of the Purified Antigens.

IFN-γ Induction in the Mouse Model of TB Infection

The recognition of the purified antigens in the mouse model of memory immunity to TB (described in example 1)

was investigated. The results shown in TABLE 5 are representative for three experiments.

A very high IFN-γ response was induced by two of the antigens CFP17 and CFP21 at almost the same high level as ST-CF.

TABLE 5

IFN-γ release from splenic memory effector cells from C57BL/6J mice isolated after reinfection with *M. tuberculosis* after stimulation with native antigens.

| Antigen[a] | IFN-γ (pg/ml)[b] |
|---|---|
| ST-CF | 12564 |
| CFP7 | ND[d] |
| CFP9 | ND |
| CFP17 | 9251 |
| CFP20 | 2388 |
| CFP21 | 10732 |
| CFP22 + CFP25[c] | 5342 |
| CFP26 (MPT51) | ND |
| CFP28 | 2818 |
| CFP29 | 3700 |

The data is derived from a representative experiment out of three.
[a]ST-CF was tested in a concentration of 5 μg/ml and the individual antigens in a concentration of 2 μg/ml.
[b]Four days after rechallenge a pool of cells from three mice were tested. The results are expressed as mean of duplicate values and the difference between duplicate cultures are <15% of mean. The IFN-γ release of cultures incubated without antigen was 390 pg/ml.
[c]A pool of CFP22 and CFP25 was tested.
[d]ND, not determined.

Skin Test Reaction in TB Infected Guinea Pigs

The skin test activity of the purified proteins was tested in *M. tuberculosis* infected guinea pigs.

1 group of guinea pigs was infected via an ear vein with $1 \times 10^4$ CFU of *M. tuberculosis* H37Rv in 0.2 ml PBS. After 4 weeks skin tests were performed and 24 hours after injection erythema diameter was measured.

As seen in TABLES 6 and 6a all of the antigens induced a significant Delayed Type Hypersensitivity (DTH) reaction.

TABLE 6

DTH erythema diameter in guinea pigs infected with $1 \times 10^4$ CFU of *M. tuberculosis*, after stimulation with native antigens.

| Antigen[a] | Skin reaction (mm)[b] |
|---|---|
| Control | 2.00 |
| PPD[c] | 15.40 (0.53) |
| CFP7 | ND[e] |
| CFP9 | ND |
| CFP17 | 11.25 (0.84) |
| CFP20 | 8.88 (0.13) |
| CFP21 | 12.44 (0.79) |
| CFP22 + CFP25[d] | 9.19 (3.10) |
| CFP26 (MPT51) | ND |
| CFP28 | 2.90 (1.28) |
| CFP29 | 6.63 (0.88) |

The values presented are the mean of erythema diameter of four animals and the SEM's are indicated in the brackets. For PPD and CFP29 the values are mean of erythema diameter of ten animals.
[a]The antigens were tested in a concentration of 0.1 μg except for CFP29 which was tested in a concentration of 0.8 μg.
[b]The skin reactions are measured in mm erythema 24 h after intradermal injection.
[c]10 TU of PPD was used.
[d]A pool of CFP22 and CFP25 was tested.
[e]ND, not determined.

Together these analyses indicate that most of the antigens identified were highly biologically active and recognized during TB infection in different animal models.

TABLE 6A

DTH erythema diameter of recombinant antigens in outbred guinea pigs infected with $1 \times 10^4$ CFU of *M. Tuberculosis*.

| Antigen[a] | Skin reaction (mm)[b] |
|---|---|
| Control | 2.9 (0.3) |
| PPD[c] | 14.5 (1.0) |
| CFP 7a | 13.6 (1.4) |
| CFP 17 | 6.8 (1.9) |
| CFP 20 | 6.4 (1.4) |
| CFP 21 | 5.3 (0.7) |
| CFP 25 | 10.8 (0.8) |
| CFP 29 | 7.4 (2.2) |
| MPT 51 | 4.9 (1.1) |

The values presented are the mean of erythema diameter of four animals and the SEM's are indicated in the brackets. For Control, PPD, and CFP 20 the values are mean of erythema diameter of eight animals.
[a]The antigens were tested in a concentration of 1.0 μg.
[b]The skin test reactions are measured in mm erythema 24 h after intradermal infection.
[c]10 TU of PPD was used.

TABLE 6B

DTH erythema diameter in guinea pigs i.v. infected with $1 \times 10^4$ CFU *M. tuberculosis*, after stimulation with 10 μg antigen.

| Antigen | Mean (mm) | SEM |
|---|---|---|
| PBS | 3.25 | 0.48 |
| PPD (2TU) | 10.88 | 1 |
| nCFP7B | 7.0 | 0.46 |
| nCFP19 | 6.5 | 0.74 |

The values presented are the mean of erythema diameter of four animals.

The results in Table 6B indicates biological activity of nCFP7B and nCFP19.

Biological Activity of the Purified Recombinant Antigens.

Interferon-γ Induction in the Mouse Model of TB Infection.

Primary infections. 8 to 12 weeks old female C57BL/6j ($H-2^b$), CBA/J($H-2^k$), DBA.2($H-2^d$) and A.SW($H-2^s$) mice (Bomholtegaard, Ry) were given intravenous infections via the lateral tail vein with an inoculum of $5 \times 10^4$ *M. tuberculosis* suspended in PBS in a vol. of 0.1 ml. 14 days postinfection the animals were sacrificed and spleen cells were isolated and tested for the recognition of recombinant antigen.

As seen in TABLE 7 the recombinant antigens rCFP7A, rCFP17, rCFP21, rCFP25, and rCFP29 were all recognized in at least two strains of mice at a level comparable to ST-CF. rMPT51 and rCFP7 were only recognized in one or two strains respectively, at a level corresponding to no more than ⅓ of the response detected after ST-CF stimulation. Neither of the antigens rCFP20 and rCFP22 were recognized by any of the four mouse strains.

As shown in TABLE 7A, the recombinant antigens rCFP27, RD1-ORF2, rCFP10A, rCFP19, and rCFP25A were all recognized in at least two strains of mice at a level comparable to ST-CF, whereas rCFP23, and rCFP30B only were recognized in one strain at this level. rCFP30A, RD1-ORF5, rCFP16 gave rise to an IFN-γ release in two mice strains at a level corresponding to ⅔ of the response after stimulation with ST-CF. RD1-ORF3 was recognized in two strains at a level of ⅓ of ST-CF.

The native CFP7B was recognized in two strains at a level of ⅓ of the response seen after stimulation with ST-CF.

Memory responses. 8–12 weeks old female C57BL/6j(H-$2^b$) mice (Bomholtegaard, Ry) were given intravenous infections via the lateral tail vein with an inoculum of $5 \times 10^4$ *M. tuberculosis* suspended in PBS in a vol. of 0.1 ml. After 1 month of infection the mice were treated with isoniazid (Merck and Co., Rahway, N.J.) and rifabutin (Farmatalia Carlo Erba, Milano, Italy) in the drinking water, for two months. The mice were rested for 4–6 months before being used in experiments. For the study of the recall of memory immunity, animals were infected with an inoculum of $1 \times 10^6$ bacteria i.v. and sacrificed at day 4 postinfection. Spleen cells were isolated and tested for the recognition of recombinant antigen.

As seen from TABLE 8, IFN-γ release after stimulation with rCFP17, rCFP21 and rCFP25 was at the same level as seen from spleen cells stimulated with ST-CF. Stimulation with rCFP7, rCFP7A and rCFP29 all resulted in an IFN-γ no higher than ⅓ of the response seen with ST-CF. rCFP22 was not recognized by IFN-γ producing cells. None of the antigens stimulated IFN-γ release in naive mice. Additionally non of the antigens were toxic to the cell cultures.

As shown in TABLE 8A, IFN-γ release after stimulation with RD1-ORF2 and rCFP19 was at the same level as seen from spleen cells stimulated with ST-CF. Stimulation with rCFP10A and rCFP30A gave rise to an IFN-γ release of ⅔ of the response after stimulation with ST-CF, whereas rCFP27, RD1-ORF5, rCFP23, rCFP25A and rCFP30B all resulted in an IFN-γ release no higher than ⅓ of the response seen with ST-CF. RD1-ORF3 and rCFP16 were not recognized by IFN-γ producing memory cells.

TABLE 7

T cell responses in primary TB infection.

| Name | c57BL/6J(H2$^b$) | DBA.2(H2$^d$) | CBA/J(H2$^k$) | A.SW(H2$^s$) |
|---|---|---|---|---|
| rCFP7 | + | + | − | − |
| rCFP7A | +++ | +++ | +++ | + |
| rCFP17 | +++ | + | +++ | + |
| rCFP20 | − | − | − | − |
| rCFP21 | +++ | +++ | +++ | + |
| rCFP22 | − | − | − | − |
| rCFP25 | +++ | ++ | +++ | + |
| rCFP29 | +++ | +++ | +++ | ++ |
| rMPT51 | + | − | − | − |

Mouse IFN-γ release 14 days after primary infection with *M. tuberculosis*.
−: no response;
+: ⅓ of ST-CF;
++: ⅔ of ST-CF;
+++: level of ST-CF.

TABLE 7A

T cell responses in primary TB infection.

| Name | C57Bl/6j (H2$^b$) | DBA.2 (H2$^d$) | CBA/J (H2$^k$) | A.SW (H2$^s$) |
|---|---|---|---|---|
| rCFP27 | ++ | ++ | +++ | +++ |
| rCFP30A | − | + | ++ | ++ |
| RD1-ORF2 | +++ | +++ | +++ | ++ |
| RD1-ORF3 | − | − | + | + |
| RD1-ORF5 | + | + | ++ | ++ |
| rCFP10A | +++ | n.d. | +++ | n.d. |
| rCFP16 | ++ | n.d. | ++ | n.d. |
| rCFP19 | +++ | n.d. | +++ | n.d. |
| rCFP23 | ++ | n.d. | +++ | n.d. |
| rCFP25A | +++ | n.d. | +++ | n.d. |
| rCFP30B | + | n.d. | +++ | n.d. |
| CFP7B(native) | + | n.d. | + | n.d. |

Mouse IFN-γ release 14 days after primary infection with *M. tuberculosis*.
−: no response;
+: ⅓ of ST-CF;
++: ⅔ of ST-CF;
+++: level of ST-CF.
n.d. = not determined.

TABLE 8

T cell responses in memory immune animals.

| Name | Memory response |
|---|---|
| rCFP7 | + |
| rCFP7A | ++ |
| rCFP17 | +++ |
| rCFP21 | +++ |
| rCFP22 | − |
| rCFP29 | + |
| rCFP25 | +++ |
| rMPT51 | + |

Mouse IFN-γ release during recall of memory immunity to *M. tuberculosis*.
−: no response;
+: ⅓ of ST-CF;
++: ⅔ of ST-CF;
+++: level of ST-CF.

TABLE 8A

T cell responses in memory immune animals.

| Name | Memory response |
|---|---|
| rCFP27 | + |
| rCFP30A | ++ |
| RD1-ORF2 | +++ |
| RD1-ORF3 | − |
| RD1-ORF5 | + |
| rCFP10A | ++ |
| rCFP16 | − |
| rCFP19 | +++ |
| rCFP23 | + |
| rCFP25A | + |
| rCFP30B | + |

Mouse IFN-γ release during recall of memory immunity to *M. tuberculosis*.
−: no response;
+: ⅓ of ST-CF;
++: ⅔ of ST-CF;
+++: level of ST-CF.

Interferon-γ Induction in Human TB Patients and BCG Vaccinated People.

Human donors: PBMC were obtained from healthy BCG vaccinated donors with no known exposure to patients with TB and from patients with culture or microscopy proven infection with *Mycobacterium tuberculosis*. Blood samples were drawn from the TB patients 1–4 months after diagnosis.

Lymphocyte preparations and cell culture: PBMC were freshly isolated by gradient centrifugation of heparinized blood on Lymphoprep (Nycomed, Oslo, Norway). The cells were resuspended in complete medium: RPMI 1640 (Gibco, Grand Island, N.Y.) supplemented with 40 μg/ml streptomycin, 40 U/ml penicillin, and 0.04 mM/ml glutamine, (all from Gibco Laboratories, Paisley, Scotland) and 10% normal human ABO serum (NHS) from the local blood bank. The number and the viability of the cells were determined by trypan blue staining. Cultures were established with $2.5 \times 10^5$ PBMC in 200 μl in microtitre plates (Nunc, Roskilde, Denmark) and stimulated with no antigen, ST-CF, PPD (2.5 μg/ml); rCFP7, rCFP7A, rCFP17, rCFP20, rCFP21, rCFP22, rCFP25, rCFP26, rCFP29, in a final concentration of 5 μg/ml. Phytohaemagglutinin, 1 μg/ml (PHA, Difco laboratories, Detroit, Mich. was used as a positive control. Supernatants for the detection of cytokines were harvested after 5 days of culture, pooled and stored at −80° C. until use.

Cytokine analysis: Interferon-γ (IFN-γ) was measured with a standard ELISA technique using a commercially available pair of mAb's from Endogen and used according to the instructions for use. Recombinant IFN-γ (Gibco laboratories) was used as a standard. The detection level for the assay was 50 pg/ml. The variation between the duplicate wells did not exceed 10% of the mean. Responses of 9 individual donors are shown in TABLE 9.

A seen in TABLE 9 high levels of IFN-γ release are obtained after stimulation with several of the recombinant antigens. rCFP7a and rCFP17 gives rise to responses comparable to STCF in almost all donors. rCFP7 seems to be most strongly recognized by BCG vaccinated healthy donors. rCFP21, rCFP25, rCFP26, and rCFP29 gives rise to a mixed picture with intermediate responses in each group, whereas low responses are obtained by rCFP20 and rCFP22.

As is seen from Table 9A RD1-ORF2 and RD1-ORF5 give rise to IFN-γ responses close to the level of ST-CF. Between 60% and 90% of the donors show high IFN-γ responses (>1000 pg/ml). rCFP30A gives rise to a mixed response with 40–50% high responders, whilst low responses are obtained with RD1-ORF3.

TABLE 9

Results from the stimulation of human blood cells from 5 healthy BCG vaccinated and 4 Tb patients with recombinant antigen. ST-CF, PPD and PHA are shown for comparison. Results are given in pg IFN-γ/ml.

Controls, Healthy, BCG vaccinated, no known TB exposure

| donor: | no ag | PHA | PPD | STCF | CFP7 | CFP17 | CFP7A | CFP20 | CFP21 | CFP22 | CFP25 |
|---|---|---|---|---|---|---|---|---|---|---|---|
| 1 | 6 | 9564 | 6774 | 3966 | 7034 | 69 | 1799 | 58 | 152 | 73 | 182 |
| 2 | 48 | 12486 | 6603 | 8067 | 3146 | 10044 | 5267 | 29 | 6149 | 51 | 1937 |
| 3 | 190 | 11929 | 10000 | 8299 | 8015 | 11563 | 8641 | 437 | 3194 | 669 | 2531 |
| 4 | 10 | 21029 | 4106 | 3537 | 1323 | 1939 | 5211 | 1 | 284 | 1 | 1344 |
| 5 | 1 | 18750 | 14209 | 13027 | 17725 | 8038 | 19002 | 1 | 3008 | 1 | 2103 |

TB patients, 1–4 month after diagnosis

| | no ag | PHA | PPD | STCF | CFP7 | CFP17 | CFP7A | CFP20 | CFP21 | CFP22 | CFP25 |
|---|---|---|---|---|---|---|---|---|---|---|---|
| 6 | 9 | 8973 | 5096 | 6145 | 852 | 4250 | 4019 | 284 | 1131 | 48 | 2400 |
| 7 | 1 | 12413 | 6281 | 3393 | 168 | 6375 | 4505 | 11 | 4335 | 16 | 3082 |
| 8 | 4 | 11915 | 7671 | 7375 | 104 | 2753 | 3356 | 119 | 407 | 437 | 2069 |
| 9 | 32 | 22130 | 16417 | 17213 | 8450 | 9783 | 16319 | 91 | 5957 | 67 | 10043 |

TABLE 9A

Results from the stimulation of human blood cells from 10 healthy BCG vaccinated or non vaccinated ST-CF responsive healthy donors and 10 Tb patients with recombinant antigen are shown. ST-CF, PPD and PHA are included for comparison. Results are given in pg IFN-γ/ml and negative values below 300 pg/ml are shown as "<". nd = not done.

| Donor | no ag | PHA | PPD | STCF | RD1-ORF2 | RD1-ORF3 | RD1-ORF5 | rCFP30A |
|---|---|---|---|---|---|---|---|---|
| Controls, Healthy BCG vaccinated, or non vaccinated ST-CF positive | | | | | | | | |
| 10 | < | nd | 3500 | 4200 | 1250 | < | 690 | nd |
| 11 | < | nd | 5890 | 4040 | 5650 | 880 | 9030 | nd |
| 12 | < | nd | 6480 | 3330 | 2310 | < | 3320 | nd |
| 13 | < | nd | 7440 | 4570 | 920 | < | 1230 | nd |
| 14 | < | 8310 | nd | 2990 | 1870 | < | 4880 | < |
| 15 | < | 10820 | nd | 4160 | 5690 | < | 810 | 3380 |
| 16 | < | 8710 | nd | 5690 | 1630 | < | 5600 | < |
| 17 | < | 7020 | 4480 | 5340 | 2030 | nd | 670 | < |
| 18 | < | 8370 | 6250 | 4780 | 3850 | nd | 370 | 1730 |
| 19 | < | 8520 | 1600 | 310 | 5110 | nd | 2330 | 1800 |
| Tb patients, 1–4 month after diagnosis | | | | | | | | |
| 20 | < | nd | 10670 | 12680 | 2020 | < | 9670 | nd |
| 21 | < | nd | 3010 | 1420 | 850 | < | 350 | nd |
| 22 | < | nd | 8450 | 7850 | 430 | < | 1950 | nd |
| 23 | < | 10060 | nd | 3730 | < | < | 350 | < |
| 24 | < | 10830 | nd | 6180 | 2090 | < | 320 | 730 |
| 25 | < | 9000 | nd | 3200 | 4760 | < | 4960 | 2820 |
| 26 | < | 10740 | nd | 7650 | 4710 | < | 1170 | 2280 |
| 27 | < | 7550 | 6430 | 6220 | 2030 | nd | 3390 | 3069 |
| 28 | < | 8090 | 5790 | 4850 | 1100 | nd | 2095 | 550 |
| 29 | < | 7790 | 4800 | 4260 | 2800 | nd | 1210 | 420 |

Example 11

The recombinant antigens were tested individually as subunit vaccines in mice. Eleven groups of 6–8 weeks old, female C57BI/6j mice (Bomholtegård, Denmark) were immunized subcutaneously at the base of the tail with vaccines of the following composition:

Group 1: 10 µg CFP7
Group 2: 10 µg CFP17
Group 3: 10 µg CFP21
Group 4: 10 µg CFP22
Group 5: 10 µg CFP25
Group 6: 10 µg CFP29
Group 7: 10 µg MPT51
Group 8: 50 µg ST-CF
Group 9: Adjuvant control group
Group 10: BCG $2.5 \times 10^5$/ml, 0.2 ml
Group 11: Control group: Untreated All the subunit vaccines were given with DDA as adjuvant. The animals were vaccinated with a volume of 0.2 ml. Two weeks after the first injection and three weeks after the second injection group 1–9 were boosted a little further up the back. One week after the last injection the mice were bled and the blood cells were isolated. The immune response induced was monitored by release of IFN-γ into the culture supernatant when stimulated in vitro with the homologous protein.

6 weeks after the last immunization the mice were aerosol challenged with $5 \times 10^6$ viable *Mycobacterium tuberculosis*/ml. After 6 weeks of infection the mice were killed and the number of viable bacteria in lung and spleen of infected mice was determined by plating serial 3-fold dilutions of organ homogenates on 7H11 plates. Colonies were counted after 2–3 weeks of incubation. The protective efficacy is expressed as the difference between $\log_{10}$ values of the geometric mean of counts obtained from five mice of the relevant group and the geometric mean of counts obtained from five mouse of the relevant control group.

The results from the experiments are presented in the following table.

Immunogenicity and protective efficacy in mice, of ST-CF and 7 subunit vaccines

| Subunit Vaccine | Immunogenicity | Protective efficacy |
|---|---|---|
| ST-CF | +++ | +++ |
| CFP7 | ++ | – |
| CFP17 | +++ | +++ |
| CFP21 | +++ | ++ |
| CFP22 | – | – |
| CFP25 | +++ | +++ |
| CFP29 | +++ | +++ |
| MPT51 | +++ | ++ |

+++ Strong immunogen/high protection (level of BCG)
++ Medium immunogen/medium protection
– No recognition/no protection In conclusion, we have identified a number of proteins inducing high levels of protection. Three of these CFP17, CFP25 and CFP29 giving rise to similar levels of protection as ST-CF and BCG while two proteins CFP21 and MPT51 induces protections around ⅔ the level of BCG and ST-CF. Two of the proteins CFP7 and CFP22 did not induce protection in the mouse model.

As is described for rCFP7, rCFP17, rCFP21, rCFP22, rCFP25, rCFP29 and rMPT51 the two antigens rCFP7A and rCFP30A were tested individually as subunit vaccines in mice. C57Bl/6j mice were immunized as described for rCFP7, rCFP17, rCFP21, rCFP22, rCFP25, rCFP29 and rMPT51 using either 10 μg rCFP7A or 10 μg rCFP30A. Controls were the same as in the experiment including rCFP7, rCFP17, rCFP21, rCFP22, rCFP25, rCFP29 and rMPT51.

Immunogenicity and protective efficacy in mice, of ST-CF and 2 subunit vaccines.

| Subunit vaccine | Immunogenicity | Protective efficacy |
|---|---|---|
| ST-CF | +++ | +++ |
| rCFP7A | +++ | +++ |
| rCFP30A | +++ | – |

+++ Strong immunogen/high protection (level of BCG)
++ Medium immunogen/medium protection
– No recognition/no protection In conclusion we have identified two strong immunogens of which one, rCFP7A, induces protection at the level of ST-CF.

Example 12

Species distribution of cfp7, cfp9, mpt51, rd1-orf2, rd1-orf3, rd1-orf4, rd1-orf5, rd1-orf8, rd1-orf9a and rd1-orf9b as well as of cfp7a, cfp7b, cfp10a, cfp17, cfp20, cfp21, cfp22, cfp22a, cfp23, cfp25 and cfp25a.

Presence of cfP7, cfp9, mpt51, rd1-orf2, rd1-orf3, rd1-orf4, rd1-orf5, rd1-orf8, rd1-orf9a and rd1-orf9b in Different Mycobacterial Species.

In order to determine the distribution of the cfp7, cfp9, mpt51, rd1-orf2, rd1-orf3, rd1-orf4, rd1-orf5, rd1-orf8, rd1-orf9a and rd1-orf9b genes in species belonging to the *M. tuberculosis*-complex and in other mycobacteria PCR and/or Southern blotting was used. The bacterial strains used are listed in TABLE 10. Genomic DNA was prepared from mycobacterial cells as described previously (Andersen et al. 1992).

PCR analyses were used in order to determine the distribution of the cfp7, cfp9 and mpt51 gene in species belonging to the tuberculosis-complex and in other mycobacteria. The bacterial strains used are listed in TABLE 10. PCR was performed on genomic DNA prepared from mycobacterial cells as described previously (Andersen et al., 1992).

The oligonucleotide primers used were synthesised automatically on a DNA synthesizer (Applied Biosystems, Forster City, Calif., ABI-391, PCR-mode), deblocked, and purified by ethanol precipitation. The primers used for the analyses are shown in TABLE 11.

The PCR amplification was carried out in a thermal reactor (Rapid cycler, Idaho Technology, Idaho) by mixing 20 ng chromosomal with the mastermix (contained 0.5 μM of each oligonucleotide primer, 0.25 μM BSA (Stratagene), low salt buffer (20 mM Tris-HCl, pH8.8, 10 mM KCl, 10 mM $(NH_4)_2SO_4$, 2 mM $MgSO_4$ and 0.1% Triton X-100) (Stratagene), 0.25 mM of each deoxynucleoside triphosphate and 0.5 U Taq Plus Long DNA polymerase (Stratagene)). Final volume was 10 μl (all concentrations given are concentrations in the final volume). Predenaturation was carried out at 94° C. for 30 s. 30 cycles of the following was performed: Denaturation at 94° C. for 30 s, annealing at 55° C. for 30 s and elongation at 72° C. for 1 min.

The following primer combinations were used (the length of the amplified products are given in parentheses):

mpt51: MPT51-3 and MPT51-2 (820 bp), MPT51-3 and MPT51-6 (108 bp), MPT51-5 and MPT51-4 (415 bp), MPT51-7 and MPT51-4 (325 bp).

cfp7: pVF1 and PVR1 (274 bp), pVF1 and PVR2 (197 bp), pVF3 and PVR1 (302 bp), pVF3 and PVR2 (125 bp).

cfp9: stR3 and stF1 (351 bp).

TABLE 10

Mycobacterial strains used in this Example.

| Species and strain(s) | | Source |
|---|---|---|
| 1. *M. tuberculosis* (ATCC 27294) | H37Rv | ATCC[a] |
| 2. (ATCC 25177) | H37Ra | ATCC |
| 3. | Erdman | Obtained from A. Lazlo, Ottawa, Canada |
| 4. *M. bovis* BCG substrain: | Danish 1331 | SSI[b] |
| 5. | Chinese | SSI[c] |
| 6. | Canadian | SSI[c] |
| 7. | Glaxo | SSI[c] |
| 8. | Russia | SSI[c] |
| 9. | Pasteur | SSI[c] |
| 10. | Japan | WHO[e] |
| 11. *M. bovis* MNC27 | | SSI[c] |
| 12. *M. africanum* | | Isolated from a Danish patient |
| 13. *M. leprae* (armadillo-derived) | | Obtained from J. M. Colston, London, UK |
| 14. *M. avium* (ATCC 15769) | | ATCC |
| 15. *M. kansasii* (ATCC 12478) | | ATCC |
| 16. *M. marinum* (ATCC 927) | | ATCC |
| 17. *M. scrofulaceum* (ATCC 19275) | | ATCC |
| 18. *M. intercellulare* (ATCC 15985) | | ATTC |
| 19. *M. fortuitum* (ATCC 6841) | | ATCC |
| 20. *M. xenopi* | | Isolated from a Danish patient |
| 21. *M. flavescens* | | Isolated from a Danish patient |
| 22. *M. szulgai* | | Isolated from a Danish patient |
| 23. *M. terrae* | | SSI[c] |
| 24. *E. coli* | | SSI[d] |
| 25. *S. aureus* | | SSI[d] |

[a]American Type Culture Collection, USA.
[b]Statens Serum Institut, Copenhagen, Denmark.
[c]Our collection Department of Mycobacteriology, Statens Serum Institut, Copenhagen, Denmark.
[d]Department of Clinical Microbiology, Statens Serum Institut, Denmark.
[e]WHO International Laboratory for Biological Standards, Statens Serum Institut, Copenhagen, Denmark.

TABLE 11

Sequences of the mpt51, cfp7 and cfp9 oligonucleotides.

| Orientation and oligonucleotide | Sequences (5' → 3')[a] | | Position[b] (nucleotides) | |
|---|---|---|---|---|
| Sense | | | | |
| MPT51-1 | CTCGAATTCGCCGGGTGCACACAG | (SEQ ID NO: 28) | 6–21 | (SEQ ID NO: 41) |
| MPT51-3 | CTCGAATTCGCCCCATACGAGAAC | (SEQ ID NO: 29) | 143–158 | (SEQ ID NO: 41) |
| MPT51-5 | GTGTATCTGCTGGAC | (SEQ ID NO: 30) | 228–242 | (SEQ ID NO: 41) |
| MPT51-7 | CCGACTGGCTGGCGG | (SEQ ID NO: 31) | 418–432 | (SEQ ID NO: 41) |
| pvR1 | GTACGAGAATTCATGTCGCAAATCATG | (SEQ ID NO: 35) | 91–105 | (SEQ ID NO: 1) |
| pvR2 | GTACGAGAATTCGAGCTTGGGGTGCCG | (SEQ ID NO: 36) | 168–181 | (SEQ ID NO: 1) |
| stR3 | CGATTCCAAGCTTGTGGCCGCCGACCCG | SEQ ID NO: 37) | 141–155 | (SEQ ID NO: 3) |
| Antisense | | | | |
| MPT51-2 | GAGGAATTCGCTTAGCGGATCGCA | (SEQ ID NO: 32) | 946–932 | (SEQ ID NO: 41) |
| MPT51-4 | CCCACATTCCGTTGG | (SEQ ID NO: 33) | 642–628 | (SEQ ID NO: 41) |
| MPT51-6 | GTCCAGCAGATACAC | (SEQ ID NO: 34) | 242–228 | (SEQ ID NO: 41) |
| pvF1 | CGTTAGGGATCCTCATCGCCATGGTGTTGG | (SEQ ID NO: 38) | 340–323 | (SEQ ID NO: 1) |

TABLE 11-continued

Sequences of the mpt51, cfp7 and cfp9 oligonucleotides.

| Orientation and oligonucleotide | Sequences (5' → 3')[a] | Position[b] (nucleotides) |
|---|---|---|
| pvF3 | <u>CGTTAGGGATCC</u>GGTTCCACTGTGCC (SEQ ID NO: 39) | 268–255 (SEQ ID NO: 1) |
| stE1 | <u>CGTTAGGGATCC</u>TCAGGTCTTTTCGATG (SEQ ID NO: 40) | 467–452 (SEQ ID NO: 3) |

[a]Nucleotides underlined are not contained in the nucleotide sequences of mpt51, cfp7, and cfp9.
[b]The positions referred to are of the non-underlined parts of the primers and correspond to the nucleotide sequence shown in SEQ ID NOs: 41, 1, and 3 for mpt51, cfp7, and cfp9, respectively.

The Southern blotting was carried out as described previously (Oettinger and Andersen, 1994) with the following modifications: 2 μg of genomic DNA was digested with PvuII, electrophoresed in an 0.8% agarose gel, and transferred onto a nylon membrane (Hybond N-plus; Amersham International plc, Little Chalfont, United Kingdom) with a vacuum transfer device (Milliblot, TM-v; Millipore Corp., Bedford, Mass.). The cfp7, cfp9, mpt51, rd1-orf2, rd1-orf3, rd1-orf4, rd1-orf5, rd1-orf8, rd1-orf9a and rd1-orf9b gene fragments were amplified by PCR from the plasmids pRVN01, pRVN02, pTO52, pTO87, pTO88, pTO89, pTO90, pTO91, pTO96 or pTO98 by using the primers shown in TABLE 11 and TABLE 2. The probes were labelled non-radioactively with an enhanced chemiluminescence kit (ECL; Amersham International plc, Little Chalfont, United Kingdom). Hybridization and detection was performed according to the instructions provided by the manufacturer. The results are summarized in TABLES 12 and 13.

TABLE 12

Interspecies analysis of the cfp7, cfp9 and mpt51 genes by PCR and/or Southern blotting and of MPT51 protein by Western blotting.

| Species and strain | PCR | | | Southern blot | | | Western blot |
|---|---|---|---|---|---|---|---|
| | cfp7 | cfp9 | mpt51 | cfp7 | cfp9 | mpt51 | MPT51 |
| 1. *M. tub.* H37Rv | + | + | + | + | + | + | + |
| 2. *M. tub.* H37Ra | + | + | + | N.D. | N.D. | + | + |
| 3. *M. tub.* Erdmann | + | + | + | + | + | + | + |
| 4. *M. bovis* | + | + | + | | | + | + |
| 5. *M. bovis* BCG Danish 1331 | + | + | + | + | + | + | + |
| 6. *M. bovis* BCG Japan | + | + | N.D. | + | + | + | N.D. |
| 7. *M. bovis* BCG Chinese | + | + | N.D. | + | + | N.D. | N.D. |
| 8. *M. bovis* BCG Canadian | + | + | N.D. | + | + | N.D. | N.D. |
| 9. *M. bovis* BCG Glaxo | + | + | N.D. | + | + | N.D. | N.D. |
| 10. *M. bovis* BCG Russia | + | + | N.D. | + | + | N.D. | N.D. |
| 11. *M. bovis* BCG Pasteur | + | + | N.D. | + | + | N.D. | N.D. |
| 12. *M. africanum* | + | + | + | + | + | + | + |
| 13. *M. leprae* | − | − | − | − | − | − | − |
| 14. *M. avium* | + | + | − | + | + | + | − |
| 15. *M. kansasii* | + | − | − | + | + | + | − |
| 16. *M. marinum* | − | (+) | − | + | + | + | − |
| 17. *M. scrofulaceum* | − | − | − | − | − | − | − |
| 18. *M. intercellulare* | + | (+) | − | + | + | + | − |
| 19. *M. fortuitum* | − | − | − | − | − | − | − |
| 20. *M. flavescens* | + | (+) | − | + | + | + | N.D. |
| 21. *M. xenopi* | − | − | − | N.D. | N.D. | + | − |
| 22. *M. szulgai* | (+) | (+) | − | − | + | − | − |
| 23. *M. terrae* | − | − | N.D. | N.D. | N.D. | N.D. | N.D. |

+, positive reaction;
−, no reaction,
N.D. not determined.
cfp7, cfp9 and mpt51 were found in the *M. tuberculosis* complex including BCG and the environmental mycobacteria; *M. avium*, *M. kansasii*, *M. marinum*, *M. intracellular* and *M. flavescens*. cfp9 was additionally found in *M. szulgai* and mpt51 in *M. xenopi*.

Furthermore the presence of native MPT51 in culture filtrates from different mycobacterial strains was investigated with western blots developed with Mab HBT4.

There is a strong band at around 26 kDa in *M. tuberculosis* H37Rv, Ra, Erdman, *M. bovis* AN5, *M. bovis* BCG substrain Danish 1331 and *M. africanum*. No band was seen in the region in any other tested mycobacterial strains.

Presence of cfp7a, cfp7b, cfp10a, cfp17, cfp20, cfp21, cfp22, cfp22a, cfp23, cfp25 and cpf25a in Different Mycobacterial Species.

Southern blotting was carried out as described for rd1-orf2, rd1-orf3, rd1-orf4, rd1-orf5, rd1-orf8, rd1-orf9a and rd1-orf9b. The cfp7a, cfp7b, cfp10a, cfp17, cfp20, cfp21, cfp22, cfp22a, cfp23, cfp25 and cfp25a gene fragments were amplified by PCR from the recombinant pMCT6 plasmids encoding the individual genes. The primers used (same as the primers used for cloning) are described in example 3, 3A and 3B. The results are summarized in Table 13b.

TABLE 13a

Interspecies analysis of the rd1-orf2, rd1-orf3, rd1-orf4, rd1-orf5, rd1-orf8, rd1-orf9a and rd1-orf9b genes by Southern blotting.

| Species and strain | rd1-orf2 | rd1-orf3 | rd1-orf4 | rd1-orf5 | rd1-orf8 | rd1-orf9a | rd1-orf9b |
|---|---|---|---|---|---|---|---|
| 1. *M. tub.* H37Rv | + | + | + | + | + | + | + |
| 2. *M. bovis* | + | + | + | + | N.D. | + | + |
| 3. *M. bovis* BCG Danish 1331 | + | − | − | − | N.D. | − | − |
| 4. *M. bovis* BCG Japan | + | − | − | − | N.D. | − | − |
| 5. *M. avium* | − | − | − | − | N.D. | − | − |
| 6. *M. kansasii* | − | − | − | − | N.D. | − | − |
| 7. *M. marinum* | + | − | + | − | N.D. | − | − |
| 8. *M. scrofulaceum* | + | − | − | − | N.D. | − | − |
| 9. *M. intercellulare* | − | − | − | − | N.D. | − | − |
| 10. *M. fortuitum* | − | − | − | − | N.D. | − | − |
| 11. *M. xenopi* | − | − | − | − | N.D. | − | − |
| 12. *M. szulgai* | + | − | − | − | N.D. | − | − |

+, positive reaction;
−, no reaction,
N.D. not determined.

Positive results for rd1-orf2, rd1-orf3, rd1-orf4, rd1-orf5, rd1-orf8, rd1-orf9a and rd1-orf9b were only obtained when using genomic DNA from *M. tuberculosis* and *M. bovis*, and not from *M. bovis* BCG or other mycobacteria analyzed except rd1-orf4 which also was found in *M. marinum*.

TABLE 13b

Interspecies analysis of the cfp7a, cfp7b, cfp10a, cfp17, cfp20, cfp21, cfp22, cfp22a, cfp23, cfp25, and cfp25a genes by Southern blotting.

| Species and strain | cfp7a | cfp7b | cfp10a | cfp17 | cfp20 | cfp21 | cfp22 | cfp22a | cfp23 | cfp25 | cfp25a |
|---|---|---|---|---|---|---|---|---|---|---|---|
| 1. *M. tub.* H37Rv | + | + | + | + | + | + | + | + | + | + | + |
| 2. *M. bovis* | + | + | + | + | + | + | + | + | + | + | + |
| 3. *M. bovis* BCG Danish 1331 | + | + | + | + | + | N.D. | + | + | + | + | + |
| 4. *M. bovis* BCG Japan | + | + | + | + | + | + | + | + | + | + | + |
| 5. *M. avium* | + | N.D. | − | + | − | + | + | + | + | + | − |
| 6. *M. kansasii* | − | N.D. | + | − | − | − | + | − | + | − | − |
| 7. *M. marinum* | + | + | − | + | + | + | + | + | + | + | + |
| 8. *M. scrofulaceum* | − | − | + | − | + | + | − | + | + | + | − |
| 9. *M. intercellulare* | + | + | − | + | − | + | + | − | + | + | − |
| 10. *M. fortuitum* | − | N.D. | − | − | − | − | − | − | + | − | − |
| 11. *M. xenopi* | + | + | + | + | + | + | + | + | + | + | + |
| 12. *M. szulgai* | + | + | − | + | + | + | + | + | + | + | + |

+, positive reaction;
−, no reaction,
N.D. not determined.

Example 13
Identification of the Immunogenic Portions of the Three Antigenic Molecules TB10.3 (Rv3019c), TB10.4 (Rv0288) and TB12.9 (Rv3017c).

The three immunologically active proteins, of which we are here identifying the immunogenic portions, were previously identified by the screening of a genomic library (TB10.4,—previously named CFP7) and due to homology to TB10.4 (TB10.3 and TB12.9) (WO98/44119, WO99/24577 and Skjøt et al, 2000). However, the immunogenic portions of these proteins have not previously been defined.

Synthetic overlapping peptides covering the complete amino acid sequence of the three proteins (FIGS. 13, 14 and 15) were synthesized either by standard solid-phase methods on an ABIMED peptide synthesizier (ABIMED, Langenfeld, Germany) at Dept. of infectious diseases and Immunohematology/Bloodbank C5-P, Leiden University Medical Centre, The Netherlands (TB10.4) or at Schafer-N, Copenhagen, Denmark on polyamide resins using Fmoc-strategy and purified by reverse phase HPLC on C18-columns in water/acetonitrile gradients containing 0.1% TFA (trifluoracetic acid) (TB10.3 and TB12.9). Purified peptides were lyophilized and stored dry until reconstitution in PBS.

The peptide sequences are as follows;
TB10.3:
TB10.3-P1 MSQIMYNYPAMMAHAGDMAG
TB10.3-P2 MMAHAGDMAGYAGTLQSLGA
TB10.3-P3 YAGTLQSLGADIASEQAVLS
TB10.3-P4 DIASEQAVLSSAWQGDTGIT
TB10.3-P5 SAWQGDTGITYQGWQTQWNQ
TB10.3-P6 YQGWQTQWNQALEDLVRAYQ
TB10.3-P7 ALEDLVRAYQSMSGTHESNT
TB10.3-P8 SMSGTHESNTMAMLARDGAE
TB10.3-P9 MAMLARDGAEAAKWGG
TB10.4:
TB10.4-P1 MSQIMYNYPAMLGHAGDM
TB10.4-P2 MLGHAGDMAGYAGTLQSL
TB10.4-P3 YAGTLQSLGAEIAVEQAA
TB10.4-P4 EIAVEQAALQSAWQGDTG
TB10.4-P5 SAWQGDTGITYQAWQAQW
TB10.4-P6 YQAWQAQWNQAMEDLVRA
TB10.4-P7 AMEDLVRAYHAMSSTHEA
TB10.4-P8 AMSSTHEANTMAMMARDT
TB10.4-P9 MAMMARDTAEAAKWGG
TB12.9:
TB12.9-P1 MSQSMYSYPAMTANVGDMAG
TB12.9-P2 MTANVGDMAGYTGTTQSLGA
TB12.9-P3 YTGTTQSLGADIASERTAPS
TB12.9-P4 DIASERTAPSRACQGDLGMS
TB12.9-P5 RACQGDLGMSHQDWQAQWNQ
TB12.9-P6 HQDWQAQWNQAMEALARAYR
TB12.9-P7 AMEALARAYRRCRRALRQIG
TB12.9-P8 RCRRALRQIGVLERPVGDSS
TB12.9-P9 VLERPVGDSSDCGTIRVGSF
TB12.9-P10 DCGTIRVGSFRGRWLDPRHA
TB12.9-P11 RGRWLDPRHAGPATAADAGD Peptides are encoded by the following DNA sequences:
tb10.3:
tb10.3-P1 atg tcg cag att atg tac aac tat ccg gcg atg atg gct cat gcc ggg gac atg gcc ggt
tb10.3-P2 atg atg gct cat gcc ggg gac atg gcc ggt tat gcg ggc acg ctg cag agc ttg ggg gcc
tb10.3-P3 tat gcg ggc acg ctg cag agc ttg ggg gcc gat atc gcc agt gag cag gcc gtg ctg tcc
tb10.3-P4 gat atc gcc agt gag cag gcc gtg ctg tcc agt gct tgg cag ggt gat acc ggg atc acg
tb10.3-P5 agt gct tgg cag ggt gat acc ggg atc acg tat cag ggc tgg cag acc cag tgg aac cag
tb10.3-P6 tat cag ggc tgg cag acc cag tgg aac cag gcc cta gag gat ctg gtg cgg gcc tat cag
tb10.3-P7 gcc cta gag gat ctg gtg cgg gcc tat cag tcg atg tct ggc acc cat gag tcc aac acc
tb10.3-P8 tcg atg tct ggc acc cat gag tcc aac acc atg gcg atg ttg gct cga gat ggg gcc gaa
tb10.3-P9 atg gcg atg ttg gct cga gat ggg gcc gaa gcc gcc aag tgg ggc ggc
tb10.4:
TB10.4-P1 atg tcg caa atc atg tac aac tac ccc gcg atg ttg ggt cac gcc ggg gat atg
TB10.4-P2 atg ttg ggt cac gcc ggg gat atg gcc gga tat gcc ggc acg ctg cag agc ttg
TB10.4-P3 tat gcc ggc acg ctg cag agc ttg ggt gcc gag atc gcc gtg gag cag gcc gcg
TB10.4-P4 gag atc gcc gtg gag cag gcc gcg ttg cag agt gcg tgg cag ggc gat acc ggg
TB10.4-P5 agt gcg tgg cag ggc gat acc ggg atc acg tat cag gcg tgg cag gca cag tgg
TB10.4-P6 tat cag gcg tgg cag gca cag tgg aac cag gcc atg gaa gat ttg gtg cgg
TB10.4-P7 gcc atg gaa gat ttg gtg cgg gcc tat cat gcg atg tcc agc acc cat gaa gcc
TB10.4-P8 gcg atg tcc agc acc cat gaa gcc aac acc atg atg atg gcc cgc gac acg
TB10.4-P9 atg gcg atg atg gcc cgc gac acc gcc gaa gcc gcc aaa tgg ggc ggc
tb12.9:
tb12.9-P1 gtg tcg cag agt atg tac agc tac ccg gcg atg acg gcc aat gtc gga gac atg gcc ggt
tb12.9-P2 atg acg gcc aat gtc gga gac atg gcc ggt tat acg ggc acg acg cag agc ttg ggg gcc
tb12.9-P3 tat acg ggc acg acg cag agc ttg ggg gcc gat atc gcc agt gag cgc acc gcg ccg tcg
tb12.9-P4 gat atc gcc agt gag cgc acc gcg ccg tcg tgc caa ggt gat ctc ggg atg agt
tb12.9-P5 cgt gct tgc caa ggt gat ctc ggg atg agt cat cag gac tgg cag gcc cag tgg aat cag
tb12.9-P6 cat cag gac tgg cag gcc cag tgg aat cag gcc atg gag gct ctc gcg cgg gcc tac cgt
tb12.9-P7 gcc atg gag gct ctc gcg cgg gcc tac cgt cgg tgc cgg cga gca cta cgc cag atc ggg
tb12.9-P8 cgg tgc cgg cga gca cta cgc cag atc ggg gtg ctg gaa agg ccg gta ggc gat tcg tca
tb12.9-P9 gtg ctg gaa agg ccg gta ggc gat tcg tca gao tgc gga acg att agg gtg ggg tcg ttc
tb12.9-P10 gac tgc gga acg att agg gtg ggg ttc cgg ggt cgg tgg ctg gac ccg cgc cat gcg
tb12.9-P11 cgg ggt cgg tgg ctg gac ccg cgc cat gcg ggt cca gcc acg gcc gcc gac gcc gga gac In tb12.9-P1, the start codon is indicated to be gtg, and the first amino acid in TB 12.9-P1 is indicated to be methionin. However, it is supposed that the first amino acid in TB 12.9 can be either methionin or valin. The invention therefore encompasses TB12.9-P1 and TB12.9 polypeptide sequences with amino acid sequences as indicated in this description and drawing, and sequences in which the first amino acid is replaced with valin. Accordingly, the invention encompasses tb12.9-P1 and tb12.9 DNA sequences as indicated in this description and drawing, and DNA sequences in which the gtg start codon is replaced with an atg start codon.

Example 14
Biological Activity of the Synthetic Peptides.

The above listed synthetic peptides, covering the protein sequences of TB10.3, TB10.4 and TB12.9, were screened for their ability to induce a T cell response measured as IFN-γ release. The screening involved testing of the IFN-γ induction in PBMC preparations obtained from TB patients and PPD positive donors.

Human donors: PBMC were obtained from healthy donors with a positive in vitro response to purified protein derivative (PPD) or non-vaccinated healthy donors with a negative in vitro response to PPD. PBMC were also obtained from TB patients with microscopy or culture proven infection. Blood samples were drawn from TB patients 0–6 months after diagnosis.

Lymphocyte preparations and cell culture: PBMC were freshly isolated by gradient centrifugation of heparinized blood on Lymphoprep (Nycomed, Oslo, Norway) and stored in liquid nitrogen until use. The cells were resuspended in complete RPMI 1640 medium (Gibco BRL, Life Technologies) supplemented with 1% penicillin/streptomycin (Gibco BRL, Life Technologies), 1% non-essential-amino acids (FLOW, ICN Biomedicals, CA, USA), and 10% heat-inactivated normal human AB serum (NHS). The viability and number of the cells were determined by Nigrosin staining. Cell cultures were established with $1.25 \times 10^5$ PBMCs in 100 µl in microtitre plates (Nunc, Roskilde, Denmark) and stimulated with 5 µg/ml PPD or single peptides in final concentrations of 10, 5 and 0.5 µg/ml or peptide pools corresponding to the full length proteins in which each peptide was included in concentrations of 0.5, 0.1 and 0.05 µg/ml (Table 1). "No antigen" was included as negative control and phytohaemagglutinin (PHA) was used as positive control. Moreover the response to the highly responsive recombinant TB10.4 was included for comparison. Supernatants for the analysis of secreted cytokines were harvested after 5 days of culture, pooled, and stored at −80° C. until use.

Cytokine Analysis:

In table 14 the maximal IFN-γ response of each peptide is shown. A response of >75 pg IFN-γ/ml (>background plus two standard deviations) is regarded positive (indicated in bold). In PPD negative healthy donors, the IFN-γ response to the peptides was at the same level as the buffer control (results not shown).

As shown in Table 14 the peptides TB10.3-P1, TB10.3-P2, TB10.3-P3, TB10.3-P4, TB10.3-P5, TB10.3-P6, TB10.3-P7, TB10.3-P8, TB10.3-P9, TB10.4-P1, TB10.4-P2, TB10.4-P3, TB10.4-P4, TB10.4-P5, TB10.4-P6, TB10.4-P7, TB10.4-P8, TB10.4-P9, TB12.9-P1, TB12.9-P2, TB12.9-P4, TB12.9-P5, TB12.9-P6, TB12.9-P7, TB12.9-P8, TB12.9-P9, TB12.9-P10 and TB12.9-P11 result in positive responses. As is expected, due to the genetical heterogeneity of the human population, some of the peptides are however recognized more frequently and to a higher extent than others.

The immunodominant peptides in the 8 donors tested herein are the peptides TB10.3-P1, TB10.4-P1, TB10.4-P3, TB10.4-P5, TB10.4-P6, and TB10.4-P9 which all give rise to IFN-γ responses >1000 pg/ml in at least one of the 8 donors tested herein. Of these peptides TB10.4-p1 and TB10.4-p3 give rise to responses at the level of the full protein in several donors and two donors (C and D in table 14) respond to TB10.4-p1 at a level comparable to PPD.

Other peptides that are highly responsive are TB10.3-P3, TB10.3-P6, TB10.3-P8, TB10.4-P4, TB12.9-P1, TB12.9-P8, TB12.9-P9, and TB12.9-P11 which give rise to IFN-γ responses >450 pg/ml (<1000 pg/ml) in at least one of the 8 donors tested herein.

The peptides; TB10.3-P2, TB10.3-P9, TB12.9-P2, TB12.9-P4 and TB12.9-P10 induce lower but still highly significant levels of IFN-γ >250 pg/ml (<450 pg/ml) in at least one of the 8 donors tested herein.

The surprisingly broad recognition pattern indicates the presence of multiple immunogenic portions scattered through out the protein sequences of TB10.3, TB10.4 and TB12.9. This makes these peptides attractive candidates for a TB vaccine or a therapeutic vaccine.

TABLE 14

Stimulation of PBMCs from 4 TB patients and 4 PPD positive healthy donors with synthetic peptides. Responses to PHA, PPD, no antigen and to rTB10.4 are shown for comparison. Results are given in pg IFN-γ/ml. TB10.4 p1–9, TB10.3 p1–9, TB12.9 p1–9 indicate peptide pools. Results indicated in bold are regarded positive.

| Peptide/ | TB patients | | | | PPD + healthy donors | | | |
|---|---|---|---|---|---|---|---|---|
| Antigen | 1 | 2 | 3 | 4 | A | B | C | D |
| No antigen | 7 | 0 | 21 | 3 | 5 | 3 | 0 | 0 |
| PHA | 16493 | 12187 | 13217 | 13458 | 14941 | 13051 | 10801 | 9112 |
| PPD | 5579 | 10164 | 8746 | 6697 | 16797 | 8963 | 6768 | 828 |
| rTB10.4 | 63 | 1766 | 610 | 3354 | 3295 | 2688 | 4296 | 1708 |
| TB10.4 p1 | 48 | 550 | 648 | 421 | 0 | 2149 | 7120 | 1007 |
| TB10.4 p2 | 132 | 125 | 103 | 113 | 51 | 2 | 3 | 0 |
| TB10.4 p3 | 306 | 1207 | 7 | 98 | 3121 | 7 | 0 | 638 |
| TB10.4 p4 | 248 | 7 | 102 | 226 | 79 | 5 | 0 | 593 |
| TB10.4 p5 | 136 | 0 | 0 | 1377 | 57 | 837 | 0 | 0 |
| TB10.4 p6 | 36 | 0 | 2183 | 180 | 24 | 13 | 0 | 0 |
| TB10.4 p7 | 74 | 27 | 0 | 164 | 184 | 5 | 0 | 0 |
| TB10.4 p8 | 67 | 27 | 117 | 46 | 128 | 7 | 0 | 0 |
| TB10.4 p9 | 14 | 0 | 1 | 1034 | 59 | 91 | 13 | 0 |
| TB10.4 p1–9 | 685 | 4495 | 3056 | 1435 | 2029 | 2981 | 3424 | 605 |
| TB12.9 p1 | 16 | 0 | 224 | 486 | 117 | 0 | 0 | 0 |
| TB12.9 p2 | 121 | 0 | 50 | 278 | 125 | 11 | 0 | 0 |
| TB12.9 p3 | 14 | 1 | 33 | 48 | 16 | 21 | 0 | 0 |
| TB12.9 p4 | 225 | 21 | 269 | 149 | 14 | 7 | 0 | 0 |
| TB12.9 p5 | 0 | 91 | 95 | 119 | 32 | 4 | 0 | 0 |
| TB12.9 p6 | 0 | 0 | 78 | 45 | 20 | 49 | 0 | 44 |
| TB12.9 p7 | 0 | 64 | 1 | 61 | 63 | 99 | 0 | 15 |
| TB12.9 p8 | 0 | 95 | 0 | 977 | 19 | 966 | 40 | 125 |

TABLE 14-continued

Stimulation of PBMCs from 4 TB patients and 4 PPD positive healthy donors with synthetic peptides. Responses to PHA, PPD, no antigen and to rTB10.4 are shown for comparison. Results are given in pg IFN-γ/ml. TB10.4 p1–9, TB10.3 p1–9, TB12.9 p1–9 indicate peptide pools. Results indicated in bold are regarded positive.

| Peptide/ | TB patients | | | | PPD + healthy donors | | | |
|---|---|---|---|---|---|---|---|---|
| Antigen | 1 | 2 | 3 | 4 | A | B | C | D |
| TB12.9 p9 | 0 | 0 | 505 | 67 | 15 | 2 | 0 | 29 |
| TB12.9 p10 | 54 | 0 | 206 | 369 | 17 | 1 | 0 | 6 |
| TB12.9 p11 | 54 | 0 | 118 | 484 | 13 | 0 | 0 | 9 |
| TB12.9 p1–11 | 256 | 0 | 0 | 204 | 11 | 217 | 0 | 13 |
| TB10.3 p1 | 88 | 449 | 30 | 76 | 196 | 1358 | 706 | 122 |
| TB10.3 p2 | 99 | 214 | 341 | 172 | 48 | 387 | 20 | 13 |
| TB10.3 p3 | 3 | 408 | 204 | 460 | 275 | 3 | 0 | 21 |
| TB10.3 p4 | 0 | 41 | 66 | 50 | 210 | 0 | 0 | 26 |
| TB10.3 p5 | 0 | 30 | 185 | 215 | 184 | 11 | 0 | 0 |
| TB10.3 p6 | 0 | 138 | 465 | 21 | 22 | 5 | 0 | 2 |
| TB10.3 p7 | 11 | 143 | 160 | 30 | 37 | 27 | 0 | 9 |
| TB10.3 p8 | 744 | 3 | 4 | 92 | 15 | 663 | 19 | 0 |
| TB10.3 p9 | 341 | 0 | 6 | 11 | 66 | 0 | 2 | 0 |
| TB10.3 p1–9 | 0 | 187 | 193 | 3 | 8 | 903 | 262 | 6 |

REFERENCES

Andersen P. et al., 1995, J. Immunol. 154: 3359–72

Andersen P., 1994, Infect. Immun. 62: 2536–44.

Andersen, P., and Heron, I. 1993 J. Immunol. Methods 161 29–39

Andersen, P., D. Askgaard, L. Ljungqvist, J. Bennedsen, I. Heron. 1991a. Infection and Immunity 59: 1558–1563.

Andersen, P., D. Askgaard, L. Ljungqvist, J. Bennedsen, I. Heron. 1991b. Infection and Immunity. 59: 1905–1910.

Andersen, Å. B. et al., 1992, Infect. Immun. 60: 2317–2323.

Barkholt, V. and Jensen, A. L., 1989, Anal. Biochem. 177: 318–322.

Borodovsky, M., and J. McIninch. 1993, Computers Chem. 17: 123–133.

Brandt, L., et al. 2000 Infect. Immun. 68:2; 791–795.

Cole, S. T et al 1998 Nature 393: 537–544

Cote-Sierra J, et al 1998, Gene October 9; 221(1):25–34

Flesch, I., and S. H. E. Kaufmann. 1987. J. Immunol. 138: 4408–4413

Gosselin et al 1992 J. Immunol. 149; 3477–3481

Harboe, M. et al., 1996, Infect. Immun. 64: 16–22.

Harboe, M., et al 1998 Infect. Immun. 66:2; 717–723

Hochstrasser, D. F. et al., 1988, Anal.Biochem. 173: 424–435

Kilgus J et al, J Immunol. 1991 Jan. 1; 146(1):307–15.

Köhler, G. and Milstein, C., 1975, Nature 256: 495–497.

Lefford, M. J., and D. D. McGregor. 1974. Cell. Immunol. 14: 417–428.

Li, H. et al., 1993, Infect. Immun. 61: 1730–1734.

Lindblad E. B. et al., 1997, Infect. Immun. 65: 623–629.

Lowry, D. B. et al 1999, Nature 400: 269–71

Mahairas, G. G. et al., 1996, J. Bacteriol 178: 1274–1282.

Maniatis T. et al., 1989, "Molecular cloning: a laboratory manual", 2nd ed., Cold Spring harbor Laboratory, Cold Spring Harbor, N.Y.

McCafferty et al., Nature, 348:552–554 (1990).

Nagai et al 1991 Infect. Immun 59:1; 372–382.

Oettinger, T. and Andersen, Å. B., 1994, Infect. Immun. 62: 2058–2064.

Ohara, N. et al., 1995, Scand. J. immunol. 41: 233–442.

Olsen A W et al Eur J Immunol. 2000 June; 30(6): 1724–32.

Orme, I. M. 1988. J. Immunol. 140: 3589–3593.

Pal P. G. and Horwitz M. A., 1992, Infect. Immun. 60: 4781–92.

Patent application WO 01/04151 entitled "Tuberculosis vaccine and diagnostic based on the *Mycobacterium tuberculosis* esat-6 gene family".

Patent application PA 2000 00666 entitled "Nucleic acid fragments and polypeptide fragments derived from *M. tuberculosis*"

Patent application U.S. Ser. No. 09/0505,739 "Nucleic acid fragments and polypeptide fragments derived from *M. tuberculosis*"

Pearson, W. R. and Lipman D. J., 1988. Proc. Natl. Acad. Sci. USA 85: 2444–2448.

Ploug, M. et al., 1989, Anal. Biochem. 181: 33–39.

Pollock. J., et al, 2000. The Veterinary record, 146:659–665

Porath, J. et al., 1985, FEBS Lett. 185: 306–310.

Ravn et al. 1999, Journal of infectious diseases 179:637–45

Roberts, A. D. et al., 1995, Immunol. 85: 502–508.

Rolph, M. S, and I. A. Ramshaw. 1997. Curr. Opin. Immunol. 9:517–24

Rook, G. A. W. 1990. Res. Microbiol. 141: 253–256.

Rosenkrands, I., et al 1998, Infect. Immun 66:6; 2728–2735

Sambrook et al (Molecular Cloning; A laboratory manual, Cold Spring Harbor Laboratories, NY, 1989

Sinigaglia F et al. Nature 1988 Dec. 22–29; 336(6201): 778–80

Skjøt, R. L. V., et al 2000, Infect. Immun 68:1; 214–220

Stryhn, A., et al 1996 Eur. J. Immunol. 26:1911–1918

Sørensen, A. L. et al., 1995, Infect. Immun. 63: 1710–1717.

Theisen, M. et al., 1995, Clinical and Diagnostic Laboratory Immunology, 2: 30–34.

Thompson J., et al Nucleic Acids Res 1994 22:4673–4680

Ulmer J. B et al 1993, Curr. Opin. Invest. Drugs 2(9): 983–989

Valdés-Stauber, N. and Scherer, S., 1994, Appl. Environ. Microbiol. 60: 3809–3814.

Valdés-Stauber, N. and Scherer, S., 1996, Appl. Environ. Microbiol. 62: 1283–1286.

van Dyke M. W. et al., 1992. Gene pp. 99–104.

von Heijne, G., 1984, J. Mol. Biol. 173: 243–251.

Williams, N., 1996, Science 272: 27.

Young, R. A. et al., 1985, Proc. Natl. Acad. Sci. USA 82: 2583–2587.

SEQUENCE LISTING

```
<160> NUMBER OF SEQ ID NOS: 257

<210> SEQ ID NO 1
<211> LENGTH: 381
<212> TYPE: DNA
<213> ORGANISM: Mycobacterium tuberculosis

<400> SEQUENCE: 1
ggccgccggt acctatgtgg ccgccgatgc tgcggacgcg tcgacctata ccggttctg     60 atcgaaccct gctgaccgag aggacttgtg atgtcgcaaa tcatgtacaa ctaccccgcg    120
atgttgggtc acgccgggga tatggccgga tatgccggca cgctgcagag cttgggtgcc    180
gagatcgccg tggagcaggc cgcgttgcag agtgcgtggc agggcgatac cgggatcacg    240
tatcaggcgt ggcaggcaca gtggaaccag gccatggaag atttggtgcg ggcctatcat    300
gcgatgtcca gcacccatga agccaacacc atggcgatga tggcccgcga caccgccgaa    360
gccgccaaat ggggcggcta g                                              381

<210> SEQ ID NO 2
<211> LENGTH: 96
<212> TYPE: PRT
<213> ORGANISM: Mycobacterium tuberculosis

<400> SEQUENCE: 2

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95

<210> SEQ ID NO 3
<211> LENGTH: 467
<212> TYPE: DNA
<213> ORGANISM: Mycobacterium tuberculosis

<400> SEQUENCE: 3
gggtagccgg accacggctg ggcaaagatg tgcaggccgc catcaaggcg gtcaaggccg     60
gcgacggcgt cataaacccg gacggcacct tgttggcggg ccccgcggtg ctgacgcccg    120
acgagtacaa ctcccggctg gtggccgccg accggagtc caccgcggcg ttgcccgacg    180
gcgccgggct ggtcgttctg gatggcaccg tcactgccga actcgaagcc gagggctggg    240
```

```
ccaaagatcg catccgcgaa ctgcaagagc tgcgtaagtc gaccgggctg gacgtttccg      300
accgcatccg ggtggtgatg tcggtgcctg cggaacgcga agactgggcg cgcacccatc      360
gcgacctcat tgccggagaa atcttggcta ccgacttcga attcgccgac ctcgccgatg      420
gtgtggccat cggcgacggc gtgcgggtaa gcatcgaaaa gacctga                    467
```

<210> SEQ ID NO 4
<211> LENGTH: 108
<212> TYPE: PRT
<213> ORGANISM: Mycobacterium tuberculosis

<400> SEQUENCE: 4

```
Met Ala Ala Asp Pro Glu Ser Thr Ala Ala Leu Pro Asp Gly Ala Gly
 1               5                  10                  15

Leu Val Val Leu Asp Gly Thr Val Thr Ala Glu Leu Glu Ala Glu Gly
                20                  25                  30

Trp Ala Lys Asp Arg Ile Arg Glu Leu Gln Glu Leu Arg Lys Ser Thr
            35                  40                  45

Gly Leu Asp Val Ser Asp Arg Ile Arg Val Val Met Ser Val Pro Ala
        50                  55                  60

Glu Arg Glu Asp Trp Ala Arg Thr His Arg Asp Leu Ile Ala Gly Glu
65                  70                  75                  80

Ile Leu Ala Thr Asp Phe Glu Phe Ala Asp Leu Ala Asp Gly Val Ala
                85                  90                  95

Ile Gly Asp Gly Val Arg Val Ser Ile Glu Lys Thr
            100                 105
```

<210> SEQ ID NO 5
<211> LENGTH: 889
<212> TYPE: DNA
<213> ORGANISM: Mycobacterium tuberculosis

<400> SEQUENCE: 5

```
cgggtctgca cggatccggg ccgggcaggg caatcgagcc tgggatccgc tggggtgcgc       60
acatcgcgga cccgtgcgcg gtacggtcga cacagcggca cgagaaagta gtaagggcga      120
taataggcgg taaagagtag cgggaagccg gccgaacgac tcggtcagac aacgccacag      180
cggccagtga ggagcagcgg gtgacggaca tgaacccgga tattgagaag gaccagacct      240
ccgatgaagt cacggtagag acgacctccg tcttccgcgc agacttcctc agcgagctgg      300
acgctcctgc gcaagcgggt acggagagcg cggtctccgg ggtggaaggg ctcccgccgg      360
gctcggcgtt gctggtagtc aaacgaggcc ccaacgccgg gtcccggttc ctactcgacc      420
aagccatcac gtcggctggt cggcatcccg acagcgacat atttctcgac gacgtgaccg      480
tgagccgtcg ccatgctgaa ttccggttgg aaaacaacga attcaatgtc gtcgatgtcg      540
ggagtctcaa cggcacctac gtcaaccgcg agcccgtgga ttcggcggtg ctggcgaacg      600
gcgacgaggt ccagatcggc aagttccggt tggtgttctt gaccggaccc aagcaaggcg      660
aggatgacgg gagtaccggg ggcccgtgag cgcacccgat agccccgcgc tggccgggat      720
gtcgatcggg gcggtcctcg acctgctacg accggatttt cctgatgtca ccatctccaa      780
gattcgattc ttggaggctg agggtctggt gacgccccgg cgggcctcat cggggtatcg      840
gcggttcacc gcatacgact gcgcacggct gcgattcatt ctcactgcc                  889
```

<210> SEQ ID NO 6
<211> LENGTH: 162
<212> TYPE: PRT

<210> SEQ ID NO 6 (continued)
<213> ORGANISM: Mycobacterium tuberculosis

<400> SEQUENCE: 6

```
Met Thr Asp Met Asn Pro Asp Ile Gly Leu Asp Gln Thr Ser Asp Glu
1               5                   10                  15

Val Thr Val Glu Thr Thr Ser Val Phe Arg Ala Asp Phe Leu Ser Glu
            20                  25                  30

Leu Asp Ala Pro Ala Gln Ala Gly Thr Glu Ser Ala Val Ser Gly Val
        35                  40                  45

Glu Gly Leu Pro Pro Gly Ser Ala Leu Leu Val Val Leu Arg Gly Pro
    50                  55                  60

Asn Ala Gly Ser Arg Pro Leu Leu Asp Gln Ala Ile Thr Ser Ala Gly
65                  70                  75                  80

Arg His Pro Asp Ser Asp Ile Pro Leu Asp Val Thr Val Ser Arg
                85                  90                  95

Arg His Ala Glu Phe Arg Leu Glu Asn Asn Glu Phe Asn Val Val Asp
            100                 105                 110

Val Gly Ser Leu Asn Gly Thr Thr Val Asn Arg Glu Pro Val Asp Ser
        115                 120                 125

Ala Val Leu Ala Asn Gly Asp Glu Val Gln Ile Gly Lys Phe Arg Leu
    130                 135                 140

Val Phe Leu Thr Gly Pro Leu Gln Gly Glu Asp Asp Gly Ser Thr Gly
145                 150                 155                 160

Gly Pro
```

<210> SEQ ID NO 7
<211> LENGTH: 898
<212> TYPE: DNA
<213> ORGANISM: Mycobacterium tuberculosis

<400> SEQUENCE: 7

```
tcgactccgg cgccaccggg caggatcacg gtgtcgacgg ggtcgccggg gaatcccacg      60
ataaccactc ttcgcgccat gaatgccagt gttggccagg cgctggcctg cgtccacgc     120
cacacaccgc acagattagg cacgccggc ggcgcagccc tgcccgaaag accgtgcacc     180
ggtcttggca gactgtgccc atggcacaga taaccctgcg aggaaacgcg atcaataccg     240
tcggtgagct acctgctgtc ggatccccgg ccccggcctt caccctgacc gggggcgatc     300
tgggggtgat cagcagcgac cagttccggg taagtccgt gttgctgaac atctttccat     360
ccgtggacac accggtgtgc gcgacgagtg tgcgaacctt cgacgagcgt gcggcggcaa     420
gtggcgctac cgtgctgtgt gtctcgaagg atctgccgtt cgcccagaag cgcttctgcg     480
gcgccgaggg caccgaaaac gtcatgcccg cgtcggcatt ccgggacagc ttcggcgagg     540
attacggcgt gaccatcgcc gacgggccga tggccgggct gctcgcccgc gcaatcgtgg     600
tgatcggcgc ggacggcaac gtcgcctaca cggaattggt gccggaaatc gcgcaagaac     660
ccaactacga agcggcgctg ccgcgctgg gcgcctaggc tttcacaagc ccgcgcgtt     720
cggcgagcag cgcacgattt cgagcgctgc tcccgaaaag cgcctcggtg gtcttggccc     780
ggcggtaata caggtgcagg tcgtgctccc acgtgaaggc gatggcaccg tggatctgaa     840
gagcggagcc ggcgcataac acaaaggttt ccgcggtctg cgccttcgcc agcggcgc       898
```

<210> SEQ ID NO 8
<211> LENGTH: 165
<212> TYPE: PRT
<213> ORGANISM: Mycobacterium tuberculosis

<400> SEQUENCE: 8

```
Met Ala Gln Ile Thr Leu Arg Gly Asn Ala Ile Asn Thr Val Gly Glu
1               5                   10                  15

Leu Pro Ala Val Gly Ser Pro Ala Pro Ala Phe Thr Leu Thr Gly Gly
            20                  25                  30

Asp Leu Gly Val Ile Ser Ser Asp Gln Phe Arg Gly Lys Ser Val Leu
        35                  40                  45

Leu Asn Ile Phe Pro Ser Val Asp Thr Pro Val Cys Ala Thr Ser Val
    50                  55                  60

Arg Thr Phe Asp Glu Arg Ala Ala Ser Gly Ser Thr Val Leu Cys
65                  70                  75                  80

Val Ser Leu Asp Leu Pro Phe Ala Gln Lys Arg Phe Cys Gly Ala Glu
                85                  90                  95

Gly Thr Glu Asn Val Met Pro Ala Ser Ala Phe Arg Asp Ser Phe Gly
            100                 105                 110

Glu Asp Tyr Gly Val Thr Ile Ala Asp Gly Pro Met Ala Gly Leu Leu
        115                 120                 125

Ala Arg Ala Ile Val Val Ile Gly Ala Asp Gly Asn Val Ala Tyr Thr
    130                 135                 140

Glu Leu Val Pro Glu Ile Ala Gln Glu Pro Asn Tyr Glu Ala Ala Leu
145                 150                 155                 160

Ala Ala Leu Gly Ala
            165
```

<210> SEQ ID NO 9
<211> LENGTH: 1054
<212> TYPE: DNA
<213> ORGANISM: Mycobacterium tuberculosis

<400> SEQUENCE: 9

```
ataatcagct caccgttggg accgacctcg accaggggtc ctttgtgact gccgggcttg      60
acgcggacga ccacagagtc ggtcatcgcc taaggctacc gttctgacct ggggctgcgt     120
gggcgccgac gacgtgaggc acgtcatgtc tcagcggccc accgccacct cggtcgccgg     180
cagtatgtca gcatgtgcag atgactccac gcagccttgt tcgcatcgtt ggtgtcgtgg     240
ttgcgacgac cttggcgctg gtgagcgcac ccgccggcgg tcgtgccgcg catgcggatc     300
cgtgttcgga catcgcggtc gttttcgctc gcggcacgca tcaggcttct ggtcttggcg     360
acgtcggtga ggcgttcgtc gactcgctta cctcgcaagt tggcgggcgg tcgattgggg     420
tctacgcggt gaactaccca gcaagcgacg actaccgcgc gagcgcgtca acggttccg      480
atgatgcgag cgcccacatc cagcgcaccg tcgccagctg cccgaacacc aggattgtgc     540
ttggtggcta ttcgcagggt gcgacggtca tcgatttgtc cacctcggcg atgccgcccg     600
cggtggcaga tcatgtcgcc gctgtcgccc ttttcggcga gccatccagt ggtttctcca     660
gcatgttgtg gggcggcggg tcgttgccga caatcggtcc gctgtatagc tctaagacca     720
taaacttgtg tgctcccgac gatccaatat gcaccggagg cggcaatatt atggcgcatg     780
tttcgtatgt tcagtcgggg atgacaagcc aggcggcgac attcgcggcg aacaggctcg     840
atcacgccgg atgatcaaag actgttgtcc ctataccgct ggggctgtag tcgatgtaca     900
ccggctggaa tctgaagggc aagaacccgg tattcatcag gccggatgaa atgacggtcg     960
ggcggtaatc gtttgtgttg aacgcgtaga gccgatcacc gccggggctg gtgtagacct    1020
caatgtttgt gttcgccggc agggttccgg atcc                                 1054
```

<210> SEQ ID NO 10
<211> LENGTH: 217
<212> TYPE: PRT
<213> ORGANISM: Mycobacterium tuberculosis

<400> SEQUENCE: 10

```
Met Thr Pro Arg Ser Leu Val Arg Ile Val Gly Val Val Ala Thr
1               5                  10                  15

Thr Leu Ala Leu Val Ser Ala Pro Ala Gly Gly Arg Ala Ala His Ala
            20                  25                  30

Asp Pro Cys Ser Asp Ile Ala Val Phe Ala Arg Gly Thr His Gln
            35                  40                  45

Ala Ser Gly Leu Gly Asp Val Gly Glu Ala Phe Val Asp Ser Leu Thr
        50                  55                  60

Ser Gln Val Gly Gly Arg Ser Ile Gly Val Tyr Ala Val Asn Tyr Pro
65                  70                  75                  80

Ala Ser Asp Asp Tyr Arg Ala Ser Ala Ser Asn Gly Ser Asp Asp Ala
                85                  90                  95

Ser Ala His Ile Gln Arg Thr Val Ala Ser Cys Pro Asn Thr Arg Ile
            100                 105                 110

Val Leu Gly Gly Tyr Ser Gln Gly Ala Thr Val Ile Asp Leu Ser Thr
        115                 120                 125

Ser Ala Met Pro Pro Ala Val Ala Asp His Val Ala Ala Val Ala Leu
    130                 135                 140

Phe Gly Glu Pro Ser Ser Gly Phe Ser Ser Met Leu Trp Gly Gly Gly
145                 150                 155                 160

Ser Leu Pro Thr Ile Gly Pro Leu Tyr Ser Ser Lys Thr Ile Asn Leu
                165                 170                 175

Cys Ala Pro Asp Asp Pro Ile Cys Thr Gly Gly Gly Asn Ile Met Ala
                180                 185                 190

His Val Ser Tyr Val Gln Ser Gly Met Thr Ser Gln Ala Ala Thr Phe
            195                 200                 205

Ala Ala Asn Arg Leu Asp His Ala Gly
    210                 215
```

<210> SEQ ID NO 11
<211> LENGTH: 949
<212> TYPE: DNA
<213> ORGANISM: Mycobacterium tuberculosis

<400> SEQUENCE: 11

```
agccgctcgc gtggggtcaa ccgggtttcc acctgctcac tcattttgcc gcctttctgt      60
gtccgggccg aggcttgcgc tcaataactc ggtcaagttc cttcacagac tgccatcact     120
ggcccgtcgg cgggctcgtt gcgggtgcgc cgcgtgcggg tttgtgttcc gggcaccggg     180
tgggggcccg cccggcgta atggcagact gtgattccgt gactaacagc cccttgcga      240
ccgctaccgc cacgctgcac actaaccgcg gcgacatcaa gatcgccctg ttcggaaacc     300
atgcgcccaa gaccgtcgcc aattttgtgg gccttgcgca gggcaccaag gactattcga     360
cccaaaacgc atcaggtggc ccgtccggcc cgttctacga cggcgcggtc tttcaccggg     420
tgatccaggg cttcatgatc cagggtggcg atccaaccgg gacgggtcgc ggcggacccg     480
gctacaagtt cgccgacgag ttccaccccg agctgcaatt cgacaagccc tatctgctcg     540
cgatggccaa cgccggtccg ggcaccaacg gctcacagtt tttcatcacc gtcggcaaga     600
```

```
ctccgcacct gaaccggcgc cacaccattt tcggtgaagt gatcgacgcg gagtcacagc     660
gggttgtgga ggcgatctcc aagacggcca ccgacggcaa cgatcggccg acggacccgg     720
tggtgatcga gtcgatcacc atctcctgac ccgaagctac gtcggctcgt cgctcgaata     780
caccttgtgg acccgccagg gcacgtggcg gtacaccgac acgccgttgg ggccgttcaa     840
ccggacgccc tcacgccaag tccgctcacc tttggccgcg accggcgtaa ccggcagcgg     900
taagcgcatc gagcacctcc actgggtcgg tgccgagatc ccagcggga              949
```

<210> SEQ ID NO 12
<211> LENGTH: 182
<212> TYPE: PRT
<213> ORGANISM: Mycobacterium tuberculosis

<400> SEQUENCE: 12

```
Met Ala Asp Cys Asp Ser Val Thr Asn Ser Pro Leu Ala Thr Ala Thr
1               5                   10                  15
Ala Thr Leu His Thr Asn Arg Gly Asp Ile Lys Ile Ala Leu Phe Gly
            20                  25                  30
Asn His Ala Pro Lys Thr Val Ala Asn Phe Val Gly Leu Ala Gln Gly
        35                  40                  45
Thr Lys Asp Tyr Ser Thr Gln Asn Ala Ser Gly Gly Pro Ser Gly Pro
    50                  55                  60
Phe Tyr Asp Gly Ala Val Phe His Arg Val Ile Gln Gly Phe Met Ile
65                  70                  75                  80
Gln Gly Gly Asp Pro Thr Gly Thr Gly Arg Gly Pro Gly Tyr Lys
                85                  90                  95
Phe Ala Asp Glu Phe His Pro Glu Leu Gln Phe Asp Lys Pro Tyr Leu
            100                 105                 110
Leu Ala Met Ala Asn Ala Gly Pro Gly Thr Asn Gly Ser Gln Phe Phe
        115                 120                 125
Ile Thr Val Gly Lys Thr Pro His Leu Asn Arg Arg His Thr Ile Phe
    130                 135                 140
Gly Glu Val Ile Asp Ala Glu Ser Gln Arg Val Val Glu Ala Ile Ser
145                 150                 155                 160
Lys Thr Ala Thr Asp Gly Asn Asp Arg Pro Thr Asp Pro Val Val Ile
                165                 170                 175
Glu Ser Ile Thr Ile Ser
            180
```

<210> SEQ ID NO 13
<211> LENGTH: 1060
<212> TYPE: DNA
<213> ORGANISM: Mycobacterium tuberculosis

<400> SEQUENCE: 13

```
tggaccttca ccggcggtcc cttcgcttcg ggggcgacac ctaacatact ggtcgtcaac      60
ctaccgcgac accgctggga ctttgtgcca ttgccggcca ctcggggccg ctgcggcctg     120
gaaaaattgg tcgggcacgg gcggccgcgg gtcgctacca tcccactgtg aatgatttac     180
tgacccgccg actgctcacc atgggcgcgg ccgccgcaat gctggccgcg gtgcttctgc     240
ttactcccat caccgttccc gccggctacc ccggtgccgt tgcacggcc actgcagcct     300 gccccgacgc cgaagtggtg ttcgcccgcg gccgcttcga accgcccggg attggcacgg     360
tcggcaacgc attcgtcagc gcgctgcgct cgaaggtcaa caagaatgtc ggggtctacg     420
cggtgaaata ccccgccgac aatcagatcg atgtgggcgc caacgacatg agcgcccaca     480
```

```
ttcagagcat ggccaacagc tgtccgaata cccgcctggt gcccggcggt tactcgctgg      540
gcgcggccgt caccgacgtg gtactcgcgg tgcccaccca gatgtggggc ttcaccaatc      600
ccctgcctcc cggcagtgat gagcacatcg ccgcggtcgc gctgttcggc aatggcagtc      660
agtgggtcgg ccccatcacc aacttcagcc ccgcctacaa cgatcggacc atcgagttgt      720
gtcacggcga cgaccccgtc tgccaccctg ccgaccccaa cacctgggag gccaactggc      780
cccagcacct cgccggggcc tatgtctcgt cgggcatggt caaccaggcg gctgacttcg      840
ttgccggaaa gctgcaatag ccacctagcc cgtgcgcgag tctttgcttc acgctttcgc      900
taaccgacca acgcgcgcac gatggagggg tccgtggtca tatcaagaca agaagggagt      960
aggcgatgca cgcaaaagtc ggcgactacc tcgtggtgaa gggcacaacc acggaacggc     1020
atgatcaaca tgctgagatc atcgaggtgc gctccgcaga                           1060
```

<210> SEQ ID NO 14
<211> LENGTH: 219
<212> TYPE: PRT
<213> ORGANISM: Mycobacterium tuberculosis

<400> SEQUENCE: 14

```
Met Gly Ala Ala Ala Met Leu Ala Ala Val Leu Leu Leu Thr Pro
 1               5                  10                  15

Ile Thr Val Pro Ala Gly Tyr Pro Gly Ala Val Ala Pro Thr Ala
                20                  25                  30

Ala Cys Pro Asp Ala Glu Val Val Phe Ala Arg Gly Arg Phe Glu Pro
         35                  40                      45

Pro Gly Ile Gly Thr Val Gly Asn Ala Phe Val Ser Ala Leu Arg Ser
 50                      55                      60

Lys Val Asn Lys Asn Val Gly Val Tyr Ala Val Lys Tyr Pro Ala Asp
 65                  70                      75                  80

Asn Gln Ile Asp Val Gly Ala Asn Asp Met Ser Ala His Ile Gln Ser
                 85                  90                      95

Met Ala Asn Ser Cys Pro Asn Thr Arg Leu Val Pro Gly Gly Tyr Ser
                100                 105                 110

Leu Gly Ala Ala Val Thr Asp Val Val Leu Ala Val Pro Thr Gln Met
            115                 120                 125

Trp Gly Phe Thr Asn Pro Leu Pro Pro Gly Ser Asp Glu His Ile Ala
130                 135                 140

Ala Val Ala Leu Phe Gly Asn Gly Ser Gln Trp Val Gly Pro Ile Thr
145                 150                 155                 160

Asn Phe Ser Pro Ala Tyr Asn Asp Arg Thr Ile Glu Leu Cys His Gly
                165                 170                 175

Asp Asp Pro Val Cys His Pro Ala Asp Pro Asn Thr Trp Glu Ala Asn
            180                 185                 190

Trp Pro Gln His Leu Ala Gly Ala Tyr Val Ser Ser Gly Met Val Asn
        195                 200                 205

Gln Ala Ala Asp Phe Val Ala Gly Lys Leu Gln
    210                 215
```

<210> SEQ ID NO 15
<211> LENGTH: 1198
<212> TYPE: DNA
<213> ORGANISM: Mycobacterium tuberculosis

<400> SEQUENCE: 15

-continued

```
cagatgctgc gcaacatgtt tctcggcgat ccggcaggca acaccgatcg agtgcttgac      60 tttccaccg cggtgaccgg cggactgttc ttctcaccca ccatcgactt tctcgaccat     120
ccaccgcccc taccgcaggc ggcgacgcca actctggcag ccgggtcgct atcgatcggc     180
agcttgaaag gaagcccccg atgaacaatc tctaccgcga tttggcaccg gtcaccgaag     240
ccgcttgggc ggaaatcgaa ttggaggcgc gcggacgtt caagcgacac atcgccgggc      300 gccggtggt cgatgtcagt gatcccgggg ggcccgtcac cgcggcggtc agcaccggcc      360
ggctgatcga tgttaaggca ccaaccaacg gcgtgatcgc ccacctgcgg gccagcaaac     420
cccttgtccg gctacgggtt ccgtttaccc tgtcgcgcaa cgagatcgac gacgtggaac     480
gtggctctaa ggactccgat tgggaaccgg taaaggaggc ggccaagaag ctggccttcg     540
tcgaggaccg cacaatattc gaaggctaca gcgccgcatc aatcgaaggg atccgcagcg     600
cgagttcgaa cccggcgctg acgttgcccg aggatccccg tgaaatccct gatgtcatct     660
cccaggcatt gtccgaactg cggttggccg gtgtggacgg accgtattcg gtgttgctct     720
ctgctgacgt ctacaccaag gttagcgaga cttccgatca cggctatccc atccgtgagc     780
atctgaaccg gctggtggac ggggacatca tttgggcccc ggccatcgac ggcgcgttcg     840
tgctgaccac tcgaggcggc gacttcgacc tacagctggg caccgacgtt gcaatcgggt     900
acgccagcca cgacacggac accgagcgcc tctacctgca ggagacgctg acgttcctt      960 gctacaccgc cgaggcgtcg gtcgcgctca gccactaagg cacgagcgcg agcaatagct    1020 cctatgcaa gcgccgcgg gttgggtgtg ttcggagctg ggctggtgga cggtgcgcag      1080
ggcctggaag acggtgcggg ctaggcggcg tttgaggcag cgtagtgctg cgcgtttggt    1140
ttccccggcg tcttgcagcc tttggtagta ggcctggccc cggctgtcgg tcatccgg      1198
```

<210> SEQ ID NO 16
<211> LENGTH: 265
<212> TYPE: PRT
<213> ORGANISM: Mycobacterium tuberculosis

<400> SEQUENCE: 16

```
Met Asn Asn Leu Tyr Arg Asp Leu Ala Pro Val Thr Glu Ala Ala Trp
1               5                   10                  15

Ala Glu Ile Glu Leu Glu Ala Ala Arg Thr Phe Lys Arg His Ile Ala
            20                  25                  30

Gly Arg Arg Val Val Asp Val Ser Asp Pro Gly Gly Pro Val Thr Ala
        35                  40                  45

Ala Val Ser Thr Gly Arg Leu Ile Asp Val Lys Ala Pro Thr Asn Gly
    50                  55                  60

Val Ile Ala His Leu Arg Ala Ser Lys Pro Leu Val Arg Leu Arg Val
65                  70                  75                  80

Pro Phe Thr Leu Ser Arg Asn Glu Ile Asp Asp Val Glu Arg Gly Ser
                85                  90                  95

Lys Asp Ser Asp Trp Glu Pro Val Lys Glu Ala Lys Lys Leu Ala
            100                 105                 110

Phe Val Glu Asp Arg Thr Ile Phe Glu Gly Tyr Ser Ala Ala Ser Ile
        115                 120                 125

Glu Gly Ile Arg Ser Ala Ser Ser Asn Pro Ala Leu Thr Leu Pro Glu
    130                 135                 140

Asp Pro Arg Glu Ile Pro Asp Val Ile Ser Gln Ala Leu Ser Glu Leu
145                 150                 155                 160

Arg Leu Ala Gly Val Asp Gly Pro Tyr Ser Val Leu Leu Ser Ala Asp
```

```
                   165                 170                 175
Val Tyr Thr Lys Val Ser Glu Thr Ser Asp His Gly Tyr Pro Ile Arg
            180                 185                 190

Glu His Leu Asn Arg Leu Val Asp Gly Asp Ile Ile Trp Ala Pro Ala
            195                 200                 205

Ile Asp Gly Ala Phe Val Leu Thr Thr Arg Gly Gly Asp Phe Asp Leu
            210                 215                 220

Gln Leu Gly Thr Asp Val Ala Ile Gly Tyr Ala Ser His Asp Thr Asp
225                 230                 235                 240

Thr Glu Arg Leu Tyr Leu Gln Glu Thr Leu Thr Phe Leu Cys Tyr Thr
                245                 250                 255

Ala Glu Ala Ser Val Ala Leu Ser His
            260                 265

<210> SEQ ID NO 17
<211> LENGTH: 15
<212> TYPE: PRT
<213> ORGANISM: Mycobacterium tuberculosis
<220> FEATURE:
<221> NAME/KEY: MISC_FEATURE
<222> LOCATION: (13)..(13)
<223> OTHER INFORMATION: "Xaa"  is unknown
<221> NAME/KEY: variant
<222> LOCATION: (1)..(1)
<223> OTHER INFORMATION: Ala is Ala or Ser

<400> SEQUENCE: 17

Ala Glu Leu Asp Ala Pro Ala Gln Ala Gly Thr Glu Xaa Ala Val
1               5                   10                  15

<210> SEQ ID NO 18
<211> LENGTH: 15
<212> TYPE: PRT
<213> ORGANISM: Mycobacterium tuberculosis

<400> SEQUENCE: 18

Ala Gln Ile Thr Leu Arg Gly Asn Ala Ile Asn Thr Val Gly Glu
1               5                   10                  15

<210> SEQ ID NO 19
<211> LENGTH: 15
<212> TYPE: PRT
<213> ORGANISM: Mycobacterium tuberculosis
<220> FEATURE:
<221> NAME/KEY: MISC_FEATURE
<222> LOCATION: (3)..(3)
<223> OTHER INFORMATION: "Xaa" is unknown

<400> SEQUENCE: 19

Asp Pro Xaa Ser Asp Ile Ala Val Val Phe Ala Arg Gly Thr His
1               5                   10                  15

<210> SEQ ID NO 20
<211> LENGTH: 15
<212> TYPE: PRT
<213> ORGANISM: Mycobacterium tuberculosis

<400> SEQUENCE: 20

Thr Asn Ser Pro Leu Ala Thr Ala Thr Ala Thr Leu His Thr Asn
1               5                   10                  15

<210> SEQ ID NO 21
<211> LENGTH: 15
<212> TYPE: PRT
```

<213> ORGANISM: Mycobacterium tuberculosis
<220> FEATURE:
<221> NAME/KEY: MISC_FEATURE
<222> LOCATION: (2)..(2)
<223> OTHER INFORMATION: "Xaa" is unknown

<400> SEQUENCE: 21

Ala Xaa Pro Asp Ala Glu Val Val Phe Ala Arg Gly Arg Phe Glu
1               5                   10                  15

<210> SEQ ID NO 22
<211> LENGTH: 15
<212> TYPE: PRT
<213> ORGANISM: Mycobacterium tuberculosis
<220> FEATURE:
<221> NAME/KEY: variant
<222> LOCATION: (14)..(14)
<223> OTHER INFORMATION: Asp is Asp or Gln
<221> NAME/KEY: variant
<222> LOCATION: (10)..(10)
<223> OTHER INFORMATION: Val is Val or Thr
<221> NAME/KEY: variant
<222> LOCATION: (2)..(2)
<223> OTHER INFORMATION: Ile is Ile or Val
<221> NAME/KEY: variant
<222> LOCATION: (11)..(11)
<223> OTHER INFORMATION: Val is Phe or Val
<221> NAME/KEY: MISC_FEATURE
<222> LOCATION: (1)..(1)
<223> OTHER INFORMATION: "Xaa" is unknown

<400> SEQUENCE: 22

Xaa Ile Gln Lys Ser Leu Glu Leu Ile Val Val Thr Ala Asp Glu
1               5                   10                  15

<210> SEQ ID NO 23
<211> LENGTH: 19
<212> TYPE: PRT
<213> ORGANISM: Mycobacterium tuberculosis

<400> SEQUENCE: 23

Met Asn Asn Leu Tyr Arg Asp Leu Ala Pro Val Thr Glu Ala Ala Trp
1               5                   10                  15

Ala Glu Ile

<210> SEQ ID NO 24
<211> LENGTH: 34
<212> TYPE: DNA
<213> ORGANISM: Mycobacterium tuberculosis

<400> SEQUENCE: 24
cccggctcga gaacctstac cgcgacctsg cscc                              34

<210> SEQ ID NO 25
<211> LENGTH: 37
<212> TYPE: DNA
<213> ORGANISM: Mycobacterium tuberculosis

<400> SEQUENCE: 25
gggccggatc cgasgcsgcg tccttsacsg gytgcca                           37

<210> SEQ ID NO 26
<211> LENGTH: 28
<212> TYPE: DNA
<213> ORGANISM: Mycobacterium tuberculosis

<400> SEQUENCE: 26

|  |  |
|---|---|
| ggaagcccca tatgaacaat ctctaccg | 28 |

<210> SEQ ID NO 27
<211> LENGTH: 32
<212> TYPE: DNA
<213> ORGANISM: Mycobacterium tuberculosis

<400> SEQUENCE: 27

|  |  |
|---|---|
| cgcgctcagc ccttagtgac tgagcgcgac cg | 32 |

<210> SEQ ID NO 28
<211> LENGTH: 24
<212> TYPE: DNA
<213> ORGANISM: Mycobacterium tuberculosis

<400> SEQUENCE: 28

|  |  |
|---|---|
| ctcgaattcg ccgggtgcac acag | 24 |

<210> SEQ ID NO 29
<211> LENGTH: 25
<212> TYPE: DNA
<213> ORGANISM: Mycobacterium tuberculosis

<400> SEQUENCE: 29

|  |  |
|---|---|
| ctcgaattcg cccccatacg agaac | 25 |

<210> SEQ ID NO 30
<211> LENGTH: 15
<212> TYPE: DNA
<213> ORGANISM: Mycobacterium tuberculosis

<400> SEQUENCE: 30

|  |  |
|---|---|
| gtgtatctgc tggac | 15 |

<210> SEQ ID NO 31
<211> LENGTH: 15
<212> TYPE: DNA
<213> ORGANISM: Mycobacterium tuberculosis

<400> SEQUENCE: 31

|  |  |
|---|---|
| ccgactggct ggccg | 15 |

<210> SEQ ID NO 32
<211> LENGTH: 24
<212> TYPE: DNA
<213> ORGANISM: Mycobacterium tuberculosis

<400> SEQUENCE: 32

|  |  |
|---|---|
| gaggaattcg cttagcggat cgca | 24 |

<210> SEQ ID NO 33
<211> LENGTH: 15
<212> TYPE: DNA
<213> ORGANISM: Mycobacterium tuberculosis

<400> SEQUENCE: 33

|  |  |
|---|---|
| cccacattcc gttgg | 15 |

<210> SEQ ID NO 34
<211> LENGTH: 15
<212> TYPE: DNA
<213> ORGANISM: Mycobacterium tuberculosis

<400> SEQUENCE: 34

```
gtccagcaga tacac                                                    15

<210> SEQ ID NO 35
<211> LENGTH: 27
<212> TYPE: DNA
<213> ORGANISM: Mycobacterium tuberculosis

<400> SEQUENCE: 35
gtacgagaat tcatgtcgca aatcatg                                       27

<210> SEQ ID NO 36
<211> LENGTH: 27
<212> TYPE: DNA
<213> ORGANISM: Mycobacterium tuberculosis

<400> SEQUENCE: 36
gtacgagaat tcgagcttgg ggtgccg                                       27

<210> SEQ ID NO 37
<211> LENGTH: 28
<212> TYPE: DNA
<213> ORGANISM: Mycobacterium tuberculosis

<400> SEQUENCE: 37
cgattccaag cttgtggccg ccgacccg                                      28

<210> SEQ ID NO 38
<211> LENGTH: 30
<212> TYPE: DNA
<213> ORGANISM: Mycobacterium tuberculosis

<400> SEQUENCE: 38
cgttagggat cctcatcgcc atggtgttgg                                    30

<210> SEQ ID NO 39
<211> LENGTH: 26
<212> TYPE: DNA
<213> ORGANISM: Mycobacterium tuberculosis

<400> SEQUENCE: 39
cgttagggat ccggttccac tgtgcc                                        26

<210> SEQ ID NO 40
<211> LENGTH: 28
<212> TYPE: DNA
<213> ORGANISM: Mycobacterium tuberculosis

<400> SEQUENCE: 40
cgttagggat cctcaggtct tttcgatg                                      28

<210> SEQ ID NO 41
<211> LENGTH: 952
<212> TYPE: DNA
<213> ORGANISM: Mycobacterium tuberculosis

<400> SEQUENCE: 41
gaattcgccg ggtgcacaca gccttacacg acggaggtgg acacatgaag ggtcggtcgg    60
cgctgctgcg ggcgctctgg attgccgcac tgtcattcgg gttgggcggt gtcgcggtag   120
ccgcggaacc caccgccaag gccgccccat acgagaacct gatggtgccg tcgccctcga   180
tgggccggga catcccggtg gccttcctag ccggtgggcc gcacgcggtg tatctgctgg   240
```

-continued

```
acgccttcaa cgccggcccg gatgtcagta actgggtcac cgcgggtaac gcgatgaaca      300
cgttggcggg caaggggatt tcggtggtgg caccggccgg tggtgcgtac agcatgtaca      360
ccaactggga gcaggatggc agcaagcagt gggacacctt cttgtccgct gagctgcccg      420
actggctggc cgctaaccgg ggcttggccc ccggtggcca tgcggccgtt ggcgccgctc      480
agggcggtta cggggcgatg gcgctggcgg ccttccaccc cgaccgcttc ggcttcgctg      540
gctcgatgtc gggcttttg tacccgtcga acaccaccac caacggtgcg atcgcggcgg      600
gcatgcagca attcggcggt gtggacacca acggaatgtg gggagcacca cagctgggtc      660
ggtggaagtg gcacgacccg tgggtgcatg ccagcctgct ggcgcaaaac aacacccggg      720
tgtgggtgtg gagcccgacc aacccgggag ccagcgatcc cgccgccatg atcggccaaa      780
ccgccgaggc gatgggtaac agccgcatgt tctacaacca gtatcgcagc gtcggcgggc      840
acaacggaca cttcgacttc ccagccagcg gtgacaacgg ctggggctcg tgggcgcccc      900
agctgggcgc tatgtcgggc gatatcgtcg gtgcgatccg ctaagcgaat tc             952
```

<210> SEQ ID NO 42
<211> LENGTH: 298
<212> TYPE: PRT
<213> ORGANISM: Mycobacterium tuberculosis

<400> SEQUENCE: 42

```
Met Lys Gly Arg Ser Ala Leu Leu Arg Ala Leu Trp Ile Ala Ala Leu
1               5                   10                  15

Ser Phe Gly Leu Gly Gly Val Ala Val Ala Ala Glu Pro Thr Ala Lys
            20                  25                  30

Ala Ala Pro Tyr Glu Asn Leu Met Val Pro Ser Pro Ser Met Gly Arg
        35                  40                  45

Ile Pro Val Ala Phe Leu Ala Gly Gly Pro His Ala Val Tyr Leu Leu
    50                  55                  60

Asp Ala Phe Asn Ala Gly Pro Asp Val Ser Asn Trp Val Thr Ala Gly
65                  70                  75                  80

Asn Ala Met Asn Thr Leu Ala Gly Lys Gly Ile Ser Val Val Ala Pro
                85                  90                  95

Ala Gly Gly Ala Tyr Ser Met Tyr Thr Asn Trp Glu Gln Asp Gly Ser
            100                 105                 110

Lys Gln Trp Asp Thr Phe Leu Ser Ala Glu Leu Pro Asp Trp Leu Ala
        115                 120                 125

Ala Asn Arg Gly Leu Ala Pro Gly Gly His Ala Ala Val Gly Ala Ala
    130                 135                 140

Gln Gly Gly Tyr Gly Ala Met Ala Leu Ala Ala Phe His Pro Asp Arg
145                 150                 155                 160

Phe Gly Phe Ala Gly Ser Met Ser Gly Phe Leu Tyr Pro Ser Asn Thr
                165                 170                 175

Thr Thr Asn Gly Ala Ile Ala Ala Gly Met Gln Gln Phe Gly Gly Val
            180                 185                 190

Asp Thr Asn Gly Met Trp Gly Ala Pro Gln Leu Gly Arg Trp Lys Trp
        195                 200                 205

His Asp Pro Trp Val His Ala Ser Leu Leu Ala Gln Asn Asn Thr Arg
    210                 215                 220

Val Trp Val Trp Ser Pro Thr Asn Pro Gly Ala Ser Asp Pro Ala Ala
225                 230                 235                 240

Met Ile Gly Gln Thr Ala Glu Ala Met Gly Asn Ser Arg Met Phe Tyr
                245                 250                 255
```

```
Asn Gln Tyr Arg Ser Val Gly Gly His Asn Gly His Phe Asp Phe Pro
            260                 265                 270

Ala Ser Gly Asp Asn Gly Trp Gly Ser Trp Ala Pro Gln Leu Gly Ala
        275                 280                 285

Met Ser Gly Asp Ile Val Gly Ala Ile Arg
    290                 295

<210> SEQ ID NO 43
<211> LENGTH: 27
<212> TYPE: DNA
<213> ORGANISM: Mycobacterium tuberculosis

<400> SEQUENCE: 43
gcaacacccg ggatgtcgca aatcatg                                            27

<210> SEQ ID NO 44
<211> LENGTH: 27
<212> TYPE: DNA
<213> ORGANISM: Mycobacterium tuberculosis

<400> SEQUENCE: 44
gtaacacccg gggtggccgc cgacccg                                            27

<210> SEQ ID NO 45
<211> LENGTH: 37
<212> TYPE: DNA
<213> ORGANISM: Mycobacterium tuberculosis

<400> SEQUENCE: 45
ctactaagct tggatcccta gccgccccat ttggcgg                                 37

<210> SEQ ID NO 46
<211> LENGTH: 38
<212> TYPE: DNA
<213> ORGANISM: Mycobacterium tuberculosis

<400> SEQUENCE: 46
ctactaagct tccatggtca ggtcttttcg atgcttac                                38

<210> SEQ ID NO 47
<211> LENGTH: 450
<212> TYPE: DNA
<213> ORGANISM: Mycobacterium tuberculosis

<400> SEQUENCE: 47
gtgccgcgct ccccaggggtt cttatggttc gatatacctg agtttgatgg aagtccgatg       60
accagcagtc agcatacggc atggccgaaa agagtggggt gatgatggcc gaggatgttc      120
gcgccgagat cgtggccagc gttctcgaag tcgttgtcaa cgaaggcgat cagatcgaca      180
agggcgacgt cgtggtgctg ctggagtcga tgaagatgga gatccccgtc ctggccgaag      240
ctgccggaac ggtcagcaag gtggcggtat cggtgggcga tgtcattcag gccggcgacc      300
ttatcgcggt gatcagctag tcgttgatag tcactcatgt ccacactcgg tgatctgctc      360
gccgaacaca cggtgctgcc gggcagcgcg gtggaccacc tgcatgcggt ggtcggggag      420
tggcagctcc ttgccgactt gtcgtttgcc                                       450

<210> SEQ ID NO 48
<211> LENGTH: 71
<212> TYPE: PRT
<213> ORGANISM: Mycobacterium tuberculosis
```

-continued

<400> SEQUENCE: 48

Met Ala Glu Asp Val Arg Ala Glu Ile Val Ala Ser Val Leu Glu Val
1               5                   10                  15

Val Val Asn Glu Gly Asp Gln Ile Asp Lys Gly Asp Val Val Leu
            20                  25                  30

Leu Glu Ser Met Lys Met Glu Ile Pro Val Leu Ala Glu Ala Ala Gly
        35                  40                  45

Thr Val Ser Lys Val Ala Val Ser Val Gly Asp Val Ile Gln Ala Gly
    50                  55                  60

Asp Leu Ile Ala Val Ile Ser
65                  70

<210> SEQ ID NO 49
<211> LENGTH: 749
<212> TYPE: DNA
<213> ORGANISM: Mycobacterium tuberculosis

<400> SEQUENCE: 49
gggtacccat cgatgggttg cggttcggca ccgaggtgct aacgcacttg ctgacacact      60
gctagtcgaa aacgaggcta gtcgcaacgt cgatcacacg agaggactga ccatgacaac    120
ttcacccgac ccgtatgccg cgctgcccaa gctgccgtcc ttcagcctga cgtcaacctc    180
gatcaccgat gggcagccgc tggctacacc ccaggtcagc gggatcatgg gtgcgggcgg    240
ggcggatgcc agtccgcagc tgaggtggtc gggatttccc agcgagaccc gcagcttcgc    300
ggtaaccgtc tacgaccctg atgcccccac cctgtccggg ttctggcact gggcggtggc    360
caacctgcct gccaacgtca ccgagttgcc cgagggtgtc ggcgatggcc gcgaactgcc    420
gggcggggca ctgacattgg tcaacgacgc cggtatgcgc cggtatgtgg gtgcggcgcc    480
gcctcccggt catggggtgc atcgctacta cgtcgcggta cacgcggtga aggtcgaaaa    540
gctcgacctc cccgaggacg cgagtcctgc atatctggga ttcaacctgt ccagcacgc    600
gattgcacga gcggtcatct tcggcaccta cgagcagcgt tagcgcttta gctgggttgc    660
cgacgtcttg ccgagccgac cgcttcgtgc agcgagccga acccgccgtc atgcagcctg    720
gggcaatgcc ttcatggatg tccttggcc                                     749

<210> SEQ ID NO 50
<211> LENGTH: 176
<212> TYPE: PRT
<213> ORGANISM: Mycobacterium tuberculosis

<400> SEQUENCE: 50

Met Thr Thr Ser Pro Asp Pro Tyr Ala Ala Leu Pro Lys Leu Pro Ser
1               5                   10                  15

Phe Ser Leu Thr Ser Thr Ser Ile Thr Asp Gly Gln Pro Leu Ala Thr
            20                  25                  30

Pro Gln Val Ser Gly Ile Met Gly Ala Gly Gly Ala Asp Ala Ser Pro
        35                  40                  45

Gln Leu Arg Trp Ser Gly Phe Pro Ser Glu Thr Arg Ser Phe Ala Val
    50                  55                  60

Thr Val Tyr Asp Pro Asp Ala Pro Thr Leu Ser Gly Phe Trp His Trp
65                  70                  75                  80

Ala Val Ala Asn Leu Pro Ala Asn Val Thr Glu Leu Pro Glu Gly Val
                85                  90                  95

Gly Asp Gly Arg Glu Leu Pro Gly Gly Ala Leu Thr Leu Val Asn Asp

```
                 100                 105                 110
Ala Gly Met Arg Arg Tyr Val Gly Ala Ala Pro Pro Gly His Gly
        115                 120                 125

Val His Arg Tyr Tyr Val Ala Val His Ala Val Lys Val Glu Lys Leu
        130                 135                 140

Asp Leu Pro Glu Asp Ala Ser Pro Ala Tyr Leu Gly Phe Asn Leu Phe
145                 150                 155                 160

Gln His Ala Ile Ala Arg Ala Val Ile Phe Gly Thr Tyr Glu Gln Arg
                165                 170                 175

<210> SEQ ID NO 51
<211> LENGTH: 800
<212> TYPE: DNA
<213> ORGANISM: Mycobacterium tuberculosis

<400> SEQUENCE: 51
tcatgaggtt catcggggtg atcccacgcc cgcagccgca ttcgggccgc tggcgagccg     60
gtgccgcacg ccgcctcacc agcctggtgg ccgccgcctt tgcggcggcc acactgttgc    120 ttaccccgc gctggcacca ccggcatcgg cgggctgccc ggatgccgag gtggtgttcg    180
cccgcggaac cggcgaacca cctggcctcg gtcgggtagg ccaagctttc gtcagttcat    240
tgcgccagca gaccaacaag agcatcggga catacggagt caactacccg gccaacggtg    300
atttcttggc cgccgctgac ggcgcgaacg acgccagcga ccacattcag cagatggcca    360
gcgcgtgccg ggccacgagg ttggtgctcg gcggctactc ccagggtgcg gccgtgatcg    420
acatcgtcac cgccgcacca ctgcccggcc tcgggttcac gcagccgttg ccgcccgcag    480
cggacgatca catcgccgcg atcgccctgt tcgggaatcc ctcgggccgc gctggcgggc    540
tgatgagcgc cctgacccct caattcgggt ccaagaccat caacctctgc aacaacggcg    600
acccgatttg ttcggacggc aaccggtggc gagcgcacct aggctacgtg cccgggatga    660
ccaaccaggc ggcgcgtttc gtcgcgagca ggatctaacg cgagccgccc catagattcc    720
ggctaagcaa cggctgcgcc gccgcccggc cacgagtgac cgccgccgac tggcacaccg    780
cttaccacgg ccttatgctg                                               800

<210> SEQ ID NO 52
<211> LENGTH: 226
<212> TYPE: PRT
<213> ORGANISM: Mycobacterium tuberculosis

<400> SEQUENCE: 52

Met Ile Pro Arg Pro Gln Pro His Ser Gly Arg Trp Arg Ala Gly Ala
1               5                   10                  15

Ala Arg Arg Leu Thr Ser Leu Val Ala Ala Phe Ala Ala Ala Thr
            20                  25                  30

Leu Leu Leu Thr Pro Ala Leu Ala Pro Ala Ser Ala Gly Cys Pro
        35                  40                  45

Asp Ala Glu Val Val Phe Ala Arg Gly Thr Gly Glu Pro Pro Gly Leu
    50                  55                  60

Gly Arg Val Gly Gln Ala Phe Val Ser Ser Leu Arg Gln Gln Thr Asn
65                  70                  75                  80

Lys Ser Ile Gly Thr Tyr Gly Val Asn Tyr Pro Ala Asn Gly Asp Phe
                85                  90                  95

Leu Ala Ala Ala Asp Gly Ala Asn Asp Ala Ser Asp His Ile Gln Gln
            100                 105                 110
```

-continued

```
Met Ala Ser Ala Cys Arg Ala Thr Arg Leu Val Leu Gly Gly Tyr Ser
        115                 120                 125
Gln Gly Ala Ala Val Ile Asp Ile Val Thr Ala Ala Pro Leu Pro Gly
    130                 135                 140
Leu Gly Phe Thr Gln Pro Leu Pro Pro Ala Ala Asp Asp His Ile Ala
145                 150                 155                 160
Ala Ile Ala Leu Phe Gly Asn Pro Ser Gly Arg Ala Gly Gly Leu Met
                165                 170                 175
Ser Ala Leu Thr Pro Gln Phe Gly Ser Lys Thr Ile Asn Leu Cys Asn
            180                 185                 190
Asn Gly Asp Pro Ile Cys Ser Asp Gly Asn Arg Trp Arg Ala His Leu
        195                 200                 205
Gly Tyr Val Pro Gly Met Thr Asn Gln Ala Ala Arg Phe Val Ala Ser
    210                 215                 220
Arg Ile
225
```

<210> SEQ ID NO 53
<211> LENGTH: 700
<212> TYPE: DNA
<213> ORGANISM: Mycobacterium tuberculosis

<400> SEQUENCE: 53

| | | |
|---|---|---|
| ctaggaaagc ctttcctgag taagtattgc cttcgttgca taccgccctt tacctgcgtt | 60 |
| aatctgcatt ttatgacaga atacgaaggg cctaagacaa aattccacgc gttaatgcag | 120 |
| gaacagattc ataacgaatt cacagcggca caacaatatg tcgcgatcgc ggtttatttc | 180 |
| gacagcgaag acctgccgca gttggcgaag cattttttaca gccaagcggt cgaggaacga | 240 |
| aaccatgcaa tgatgctcgt gcaacacctg ctcgaccgcg accttcgtgt cgaaattccc | 300 |
| ggcgtagaca cggtgcgaaa ccagttcgac agaccccgcg aggcactggc gctggcgctc | 360 |
| gatcaggaac gcacagtcac cgaccaggtc ggtcggctga cagcggtggc ccgcgacgag | 420 |
| ggcgatttcc tcggcgagca gttcatgcag tggttcttgc aggaacagat cgaagaggtg | 480 |
| gccttgatgg caaccctggt gcgggttgcc gatcgggccg gggccaacct gttcgagcta | 540 |
| gagaacttcg tcgcacgtga agtggatgtg gcgccggccg catcaggcgc cccgcacgct | 600 |
| gccggggcc gcctctagat ccctggcggg gatcagcgag tggtcccgtt cgcccgcccg | 660 |
| tcttccagcc aggccttggt gcggccgggg tggtgagtac | 700 |

<210> SEQ ID NO 54
<211> LENGTH: 181
<212> TYPE: PRT
<213> ORGANISM: Mycobacterium tuberculosis

<400> SEQUENCE: 54

```
Met Thr Glu Tyr Glu Gly Pro Lys Thr Lys Phe His Ala Leu Met Gln
1               5                   10                  15
Glu Gln Ile His Asn Glu Phe Thr Ala Ala Gln Gln Tyr Val Ala Ile
            20                  25                  30
Ala Val Tyr Phe Asp Ser Glu Asp Leu Pro Gln Leu Ala Lys His Phe
        35                  40                  45
Tyr Ser Gln Ala Val Glu Glu Arg Asn His Ala Met Met Leu Val Gln
    50                  55                  60
His Leu Leu Asp Arg Asp Leu Arg Val Glu Ile Pro Gly Val Asp Thr
65                  70                  75                  80
```

```
Val Arg Asn Gln Phe Asp Arg Pro Arg Glu Ala Leu Ala Leu Ala Leu
                 85                  90                  95
Asp Gln Glu Arg Thr Val Thr Asp Gln Val Gly Arg Leu Thr Ala Val
            100                 105                 110
Ala Arg Asp Glu Gly Asp Phe Leu Gly Glu Gln Phe Met Gln Trp Phe
        115                 120                 125
Leu Gln Glu Gln Ile Glu Glu Val Ala Leu Met Ala Thr Leu Val Arg
    130                 135                 140
Val Ala Asp Arg Ala Gly Ala Asn Leu Phe Glu Leu Glu Asn Phe Val
145                 150                 155                 160
Ala Arg Glu Val Asp Val Ala Pro Ala Ser Gly Ala Pro His Ala
                165                 170                 175
Ala Gly Gly Arg Leu
            180

<210> SEQ ID NO 55
<211> LENGTH: 950
<212> TYPE: DNA
<213> ORGANISM: Mycobacterium tuberculosis

<400> SEQUENCE: 55
tgggctcggc actggctctc ccacggtggc gcgctgattt ctccccacgg taggcgttgc     60
gacgcatgtt cttcaccgtc tatccacagc taccgacatt tgctccggct ggatcgcggg    120
taaaattccg tcgtgaacaa tcgacccatc cgcctgctga catccggcag ggctggtttg    180
ggtgcgggcg cattgatcac cgccgtcgtc ctgctcatcg ccttgggcgc tgtttggacc    240
ccggttgcct tcgccgatgg atgcccggac gccgaagtca cgttcgcccg cggcaccggc    300
gagccgcccg gaatcgggcg cgttggccag gcgttcgtcg actcgctgcg ccagcagact    360
ggcatggaga tcggagtata cccggtgaat tacgccgcca ccgcctaca gctgcacggg     420 ggagacggcg ccaacgacgc catatcgcac attaagtcca tggcctcgtc atgcccgaac    480
accaagctgg tcttgggcgg ctattcgcag gcgcaaccg tgatcgatat cgtggccggg     540
gttccgttgg gcagcatcag ctttggcagt ccgctacctg cggcatacgc agacaacgtc    600
gcagcggtcg cggtcttcgg caatccgtcc aaccgcgccg gcggatcgct gtcgagcctg    660
agcccgctat tcggttccaa ggcgattgac ctgtgcaatc ccaccgatcc gatctgccat    720
gtgggccccg gcaacgaatt cagcggacac atcgacggct acatacccac ctacaccacc    780
caggcggcta gtttcgtcgt gcagaggctc cgcgccgggt cggtgccaca tctgcctgga    840
tccgtcccgc agctgcccgg gtctgtcctt cagatgcccg gcactgccgc accggctccc    900
gaatcgctgc acggtcgctg acgctttgtc agtaagccca taaatcgcg               950

<210> SEQ ID NO 56
<211> LENGTH: 262
<212> TYPE: PRT
<213> ORGANISM: Mycobacterium tuberculosis

<400> SEQUENCE: 56

Met Asn Asn Arg Pro Ile Arg Leu Leu Thr Ser Gly Arg Ala Gly Leu
1               5                   10                  15

Gly Ala Gly Ala Leu Ile Thr Ala Val Val Leu Leu Ile Ala Leu Gly
            20                  25                  30

Ala Val Trp Thr Pro Val Ala Phe Ala Asp Gly Cys Pro Asp Ala Glu
        35                  40                  45

Val Thr Phe Ala Arg Gly Thr Gly Glu Pro Pro Gly Ile Gly Arg Val
```

```
                    50                  55                  60
Gly Gln Ala Phe Val Asp Ser Leu Arg Gln Gln Thr Gly Met Glu Ile
 65                  70                  75                  80

Gly Val Tyr Pro Val Asn Tyr Ala Ala Ser Arg Leu Gln Leu His Gly
                 85                  90                  95

Gly Asp Gly Ala Asn Asp Ala Ile Ser His Ile Lys Ser Met Ala Ser
            100                 105                 110

Ser Cys Pro Asn Thr Lys Leu Val Leu Gly Gly Tyr Ser Gln Gly Ala
            115                 120                 125

Thr Val Ile Asp Ile Val Ala Gly Val Pro Leu Gly Ser Ile Ser Phe
        130                 135                 140

Gly Ser Pro Leu Pro Ala Ala Tyr Ala Asp Asn Val Ala Ala Val Ala
145                 150                 155                 160

Val Phe Gly Asn Pro Ser Asn Arg Ala Gly Gly Ser Leu Ser Ser Leu
                165                 170                 175

Ser Pro Leu Phe Gly Ser Lys Ala Ile Asp Leu Cys Asn Pro Thr Asp
            180                 185                 190

Pro Ile Cys His Val Gly Pro Gly Asn Glu Phe Ser Gly His Ile Asp
        195                 200                 205

Gly Tyr Ile Pro Thr Tyr Thr Thr Gln Ala Ala Ser Phe Val Val Gln
        210                 215                 220

Arg Leu Arg Ala Gly Ser Val Pro His Leu Pro Gly Ser Val Pro Gln
225                 230                 235                 240

Leu Pro Gly Ser Val Leu Gln Met Pro Gly Thr Ala Ala Pro Ala Pro
                245                 250                 255

Glu Ser Leu His Gly Arg
            260

<210> SEQ ID NO 57
<211> LENGTH: 1000
<212> TYPE: DNA
<213> ORGANISM: Mycobacterium tuberculosis

<400> SEQUENCE: 57
cgaggagacc gacgatctgc tcgacgaaat cgacgacgtc ctcgaggaga acgccgagga      60
cttcgtccgc gcatacgtcc aaaagggcgg acagtgacct ggccgttgcc cgatcgcctg     120
tccattaatt cactctctgg aacacccgct gtagacctat cttctttcac tgacttcctg     180
cgccgccagg cgccggagtt gctgccggca agcatcagcg gcggtgcgcc actcgcaggc     240
ggcgatgcgc aactgccgca cggcaccacc attgtcgcgc tgaaataccc cggcggtgtt     300
gtcatggcgg gtgaccggcg ttcgacgcag ggcaacatga tttctgggcg tgatgtgcgc     360
aaggtgtata tcaccgatga ctacaccgct accggcatcg ctggcacggc tgcggtcgcg     420
gttgagtttg cccggctgta tgccgtggaa cttgagcact acgagaagct cgagggtgtg     480
ccgctgacgt ttgccggcaa aatcaaccgg ctggcgatta tggtgcgtgg caatctggcg     540
gccgcgatgc agggtctgct ggcgttgccg ttgctggcgg gctacgacat tcatgcgtct     600
gacccgcaga gcgcgggtcg tatcgtttcg ttcgacgccg ccggcggttg aacatcgag      660 gaagagggct atcaggcggt gggctcgggt tcgctgttcg cgaagtcgtc gatgaagaag     720
ttgtattcgc aggttaccga cggtgattcg gggctgcggg tggcggtcga ggcgctctac     780
gacgccgccg acgacgactc cgccaccggc ggtccggacc tggtgcgggg catctttccg     840
acggcggtga tcatcgacgc cgacggggcg gttgacgtgc cggagagccg gattgccgaa     900
```

```
ttggcccgcg cgatcatcga aagccgttcg ggtgcggata ctttcggctc cgatggcggt      960
gagaagtgag ttttccgtat tcatctcgc ctgagcaggc                            1000
```

<210> SEQ ID NO 58
<211> LENGTH: 291
<212> TYPE: PRT
<213> ORGANISM: Mycobacterium tuberculosis

<400> SEQUENCE: 58

```
Met Thr Trp Pro Leu Pro Asp Arg Leu Ser Ile Asn Ser Leu Ser Gly
1               5                   10                  15

Thr Pro Ala Val Asp Leu Ser Ser Phe Thr Asp Phe Leu Arg Arg Gln
            20                  25                  30

Ala Pro Glu Leu Leu Pro Ala Ser Ile Ser Gly Gly Ala Pro Leu Ala
        35                  40                  45

Gly Gly Asp Ala Gln Leu Pro His Gly Thr Thr Ile Val Ala Leu Lys
    50                  55                  60

Tyr Pro Gly Gly Val Val Met Ala Gly Asp Arg Arg Ser Thr Gln Gly
65                  70                  75                  80

Asn Met Ile Ser Gly Arg Asp Val Arg Lys Val Tyr Ile Thr Asp Asp
                85                  90                  95

Tyr Thr Ala Thr Gly Ile Ala Gly Thr Ala Ala Val Ala Val Glu Phe
            100                 105                 110

Ala Arg Leu Tyr Ala Val Glu Leu Glu His Tyr Glu Lys Leu Glu Gly
        115                 120                 125

Val Pro Leu Thr Phe Ala Gly Lys Ile Asn Arg Leu Ala Ile Met Val
    130                 135                 140

Arg Gly Asn Leu Ala Ala Ala Met Gln Gly Leu Leu Ala Leu Pro Leu
145                 150                 155                 160

Leu Ala Gly Tyr Asp Ile His Ala Ser Asp Pro Gln Ser Ala Gly Arg
                165                 170                 175

Ile Val Ser Phe Asp Ala Ala Gly Gly Trp Asn Ile Glu Glu Glu Gly
            180                 185                 190

Tyr Gln Ala Val Gly Ser Gly Ser Leu Phe Ala Lys Ser Ser Met Lys
        195                 200                 205

Lys Leu Tyr Ser Gln Val Thr Asp Gly Asp Ser Gly Leu Arg Val Ala
    210                 215                 220

Val Glu Ala Leu Tyr Asp Ala Asp Asp Ser Ala Thr Gly Gly
225                 230                 235                 240

Pro Asp Leu Val Arg Gly Ile Phe Pro Thr Ala Val Ile Ile Asp Ala
                245                 250                 255

Asp Gly Ala Val Asp Val Pro Glu Ser Arg Ile Ala Glu Leu Ala Arg
            260                 265                 270

Ala Ile Ile Glu Ser Arg Ser Gly Ala Asp Thr Phe Gly Ser Asp Gly
        275                 280                 285

Gly Glu Lys
    290
```

<210> SEQ ID NO 59
<211> LENGTH: 899
<212> TYPE: DNA
<213> ORGANISM: Mycobacterium tuberculosis

<400> SEQUENCE: 59

```
ttggcccgcg cgatcatcga aagccgttcg ggtgcggata ctttcggctc cgatggcggt       60
```

-continued

```
gagaagtgag ttttccgtat tcatctcgc ctgagcaggc gatgcgcgag cgcagcgagt      120
tggcgcgtaa gggcattgcg cgggccaaaa gcgtggtggc gctggcctat gccggtggtg      180
tgctgttcgt cgcggagaat ccgtcgcggt cgctgcagaa gatcagtgag ctctacgatc      240
gggtgggttt tgcggctgcg gcaagttcaa cgagttcgac aatttgcgcc gcggcgggat      300
ccagttcgcc gacacccgcg gttacgccta tgaccgtcgt gacgtcacgg gtcggcagtt      360
ggccaatgtc tacgcgcaga ctctaggcac catcttcacc gaacaggcca agccctacga      420
ggttgagttg tgtgtggccg aggtggcgca ttacggcgag acgaaacgcc ctgagttgta      480
tcgtattacc tacgacgggt cgatcgccga cgagccgcat ttcgtggtga tgggcggcac      540
cacggagccg atcgccaacg cgctcaaaga gtcgtatgcc gagaacgcca gcctgaccga      600
cgccctgcgt atcgcggtcg ctgcattgcg ggccggcagt gccgacacct cgggtggtga      660
tcaacccacc cttggcgtgg ccagcttaga ggtggccgtt ctcgatgcca accggccacg      720
gcgcgcgttc cggcgcatca ccggctccgc cctgcaagcg ttgctggtag accaggaaag      780
cccgcagtct gacggcgaat cgtcgggctg agtccgaaag tccgacgcgt gtctgggacc      840
ccgctgcgac gttaactgcg cctaaccccg gctcgacgcg tcgccggccg tcctgactt       899
```

<210> SEQ ID NO 60
<211> LENGTH: 248
<212> TYPE: PRT
<213> ORGANISM: Mycobacterium tuberculosis

<400> SEQUENCE: 60

```
Met Ser Phe Pro Tyr Phe Ile Ser Pro Glu Gln Ala Met Arg Glu Arg
1               5                   10                  15

Ser Glu Leu Ala Arg Lys Gly Ile Ala Arg Ala Lys Ser Val Val Ala
            20                  25                  30

Leu Ala Tyr Ala Gly Gly Val Leu Phe Val Ala Glu Asn Pro Ser Arg
        35                  40                  45

Ser Leu Gln Lys Ile Ser Glu Leu Tyr Asp Arg Val Gly Phe Ala Ala
    50                  55                  60

Ala Gly Lys Phe Asn Glu Phe Asp Asn Leu Arg Arg Gly Gly Ile Gln
65                  70                  75                  80

Phe Ala Asp Thr Arg Gly Tyr Ala Tyr Asp Arg Arg Asp Val Thr Gly
                85                  90                  95

Arg Gln Leu Ala Asn Val Tyr Ala Gln Thr Leu Gly Thr Ile Phe Thr
            100                 105                 110

Glu Gln Ala Lys Pro Tyr Glu Val Glu Leu Cys Val Ala Glu Val Ala
        115                 120                 125

His Tyr Gly Glu Thr Lys Arg Pro Glu Leu Tyr Arg Ile Thr Tyr Asp
    130                 135                 140

Gly Ser Ile Ala Asp Glu Pro His Phe Val Val Met Gly Gly Thr Thr
145                 150                 155                 160

Glu Pro Ile Ala Asn Ala Leu Lys Glu Ser Tyr Ala Glu Asn Ala Ser
                165                 170                 175

Leu Thr Asp Ala Leu Arg Ile Ala Val Ala Ala Leu Arg Ala Gly Ser
            180                 185                 190

Ala Asp Thr Ser Gly Gly Asp Gln Pro Thr Leu Gly Val Ala Ser Leu
        195                 200                 205

Glu Val Ala Val Leu Asp Ala Asn Arg Pro Arg Arg Ala Phe Arg Arg
    210                 215                 220

Ile Thr Gly Ser Ala Leu Gln Ala Leu Leu Val Asp Gln Glu Ser Pro
```

Gln Ser Asp Gly Glu Ser Ser Gly
225                 230                 235                 240
            245

<210> SEQ ID NO 61
<211> LENGTH: 1560
<212> TYPE: DNA
<213> ORGANISM: Mycobacterium tuberculosis

<400> SEQUENCE: 61

| | | |
|---|---|---|
| gagtcattgc ctggtcggcg tcattccgta ctagtcggtt gtcggacttg acctactggg | 60 |
| tcaggccgac gagcactcga ccattagggt aggggccgtg acccactatg acgtcgtcgt | 120 |
| tctcggagcc ggtcccggcg ggtatgtcgc ggcgattcgc gccgcacagc tcggcctgag | 180 |
| cactgcaatc gtcgaaccca agtactgggg cggagtatgc ctcaatgtcg gctgtatccc | 240 |
| atccaaggcg ctgttgcgca acgccgaact ggtccacatc ttcaccaagg acgccaaagc | 300 |
| atttggcatc agcggcgagg tgaccttcga ctacggcatc gcctatgacc gcagccgaaa | 360 |
| ggtagccgag ggcagggtgg ccggtgtgca cttcctgatg aagaagaaca agatcaccga | 420 |
| gatccacggg tacggcacat tgccgacgc caacacgttg ttggttgatc tcaacgacgg | 480 |
| cggtacagaa tcggtcacgt tcgacaacgc catcatcgcg accggcagta gcacccggct | 540 |
| ggttcccggc acctcactgt cggccaacgt agtcacctac gaggaacaga tcctgtcccg | 600 |
| agagctgccg aaatcgatca ttattgccgg agctggtgcc attggcatgg agttcggcta | 660 |
| cgtgctgaag aactacggcg ttgacgtgac catcgtggaa ttccttccgc gggcgctgcc | 720 |
| caacgaggac gccgatgtgt ccaaggagat cgagaagcag ttcaaaaagc tgggtgtcac | 780 |
| gatcctgacc gccacgaagg tcgagtccat cgccgatggg gggtcgcagg tcaccgtgac | 840 |
| cgtcaccaag gacggcgtgg cgcaagagct taaggcggaa aaggtgttgc aggccatcgg | 900 |
| atttgcgccc aacgtcgaag ggtacgggct ggacaaggcg ggcgtcgcgc tgaccgaccg | 960 |
| caaggctatc ggtgtcgacg actacatgcg taccaacgtg ggccacatct acgctatcgg | 1020 |
| cgatgtcaat ggattactgc agctggcgca cgtcgccgag gcacaaggcg tggtagccgc | 1080 |
| cgaaaccatt gccggtgcag agactttgac gctgggcgac catcggatgt gccgcgcgc | 1140 |
| gacgttctgt cagccaaacg ttgccagctt cgggctcacc gagcagcaag cccgcaacga | 1200 |
| aggttacgac gtggtggtgg ccaagttccc gttcacggcc aacgccaagg cgcacggcgt | 1260 |
| gggtgacccc agtgggttcg tcaagctggt ggccgacgcc aagcacggcg agctactggg | 1320 |
| tgggcacctg gtcggccacg acgtggccga gctgctgccg gagctcacgc tggcgcagag | 1380 |
| gtgggacctg accgccagcg agctggctcg caacgtccac acccacccaa cgatgtctga | 1440 |
| ggcgctgcag gagtgcttcc acggcctggt tggccacatg atcaatttct gagcggctca | 1500 |
| tgacgaggcg cgcgagcact gacaccccccc agatcatcat gggtgccatc ggtggtgtgg | 1560 |

<210> SEQ ID NO 62
<211> LENGTH: 464
<212> TYPE: PRT
<213> ORGANISM: Mycobacterium tuberculosis

<400> SEQUENCE: 62

Met Thr His Tyr Asp Val Val Leu Gly Ala Gly Pro Gly Gly Tyr
1               5                   10                  15

Val Ala Ala Ile Arg Ala Ala Gln Leu Gly Leu Ser Thr Ala Ile Val
            20                  25                  30

-continued

```
Glu Pro Lys Tyr Trp Gly Gly Val Cys Leu Asn Val Gly Cys Ile Pro
         35                  40                  45
Ser Lys Ala Leu Leu Arg Asn Ala Glu Leu Val His Ile Phe Thr Lys
         50                  55                  60
Asp Ala Lys Ala Phe Gly Ile Ser Gly Glu Val Thr Phe Asp Tyr Gly
 65                  70                  75                  80
Ile Ala Tyr Asp Arg Ser Arg Lys Val Ala Glu Gly Arg Val Ala Gly
                     85                  90                  95
Val His Phe Leu Met Lys Lys Asn Lys Ile Thr Glu Ile His Gly Tyr
                 100                 105                 110
Gly Thr Phe Ala Asp Ala Asn Thr Leu Leu Val Asp Leu Asn Asp Gly
             115                 120                 125
Gly Thr Glu Ser Val Thr Phe Asp Asn Ala Ile Ile Ala Thr Gly Ser
         130                 135                 140
Ser Thr Arg Leu Val Pro Gly Thr Ser Leu Ser Ala Asn Val Val Thr
145                 150                 155                 160
Tyr Glu Glu Gln Ile Leu Ser Arg Glu Leu Pro Lys Ser Ile Ile Ile
                 165                 170                 175
Ala Gly Ala Gly Ala Ile Gly Met Glu Phe Gly Tyr Val Leu Lys Asn
             180                 185                 190
Tyr Gly Val Asp Val Thr Ile Val Glu Phe Leu Pro Arg Ala Leu Pro
         195                 200                 205
Asn Glu Asp Ala Asp Val Ser Lys Glu Ile Glu Lys Gln Phe Lys Lys
     210                 215                 220
Leu Gly Val Thr Ile Leu Thr Ala Thr Lys Val Glu Ser Ile Ala Asp
225                 230                 235                 240
Gly Gly Ser Gln Val Thr Val Thr Val Thr Lys Asp Gly Val Ala Gln
                 245                 250                 255
Glu Leu Lys Ala Glu Lys Val Leu Gln Ala Ile Gly Phe Ala Pro Asn
             260                 265                 270
Val Glu Gly Tyr Gly Leu Asp Lys Ala Gly Val Ala Leu Thr Asp Arg
         275                 280                 285
Lys Ala Ile Gly Val Asp Asp Tyr Met Arg Thr Asn Val Gly His Ile
290                 295                 300
Tyr Ala Ile Gly Asp Val Asn Gly Leu Leu Gln Leu Ala His Val Ala
305                 310                 315                 320
Glu Ala Gln Gly Val Val Ala Ala Glu Thr Ile Ala Gly Ala Glu Thr
                 325                 330                 335
Leu Thr Leu Gly Asp His Arg Met Leu Pro Arg Ala Thr Phe Cys Gln
             340                 345                 350
Pro Asn Val Ala Ser Phe Gly Leu Thr Glu Gln Gln Ala Arg Asn Glu
         355                 360                 365
Gly Tyr Asp Val Val Ala Lys Phe Pro Phe Thr Ala Asn Ala Lys
     370                 375                 380
Ala His Gly Val Gly Asp Pro Ser Gly Phe Val Lys Leu Val Ala Asp
385                 390                 395                 400
Ala Lys His Gly Glu Leu Leu Gly Gly His Leu Val Gly His Asp Val
                 405                 410                 415
Ala Glu Leu Leu Pro Glu Leu Thr Leu Ala Gln Arg Trp Asp Leu Thr
             420                 425                 430
Ala Ser Glu Leu Ala Arg Asn Val His Thr His Pro Thr Met Ser Glu
         435                 440                 445
Ala Leu Gln Glu Cys Phe His Gly Leu Val Gly His Met Ile Asn Phe
```

```
                    450       455       460

<210> SEQ ID NO 63
<211> LENGTH: 550
<212> TYPE: DNA
<213> ORGANISM: Mycobacterium tuberculosis

<400> SEQUENCE: 63
ggcccggctc gcggccgccc tgcaggaaaa gaaggcctgc ccaggcccag actcagccga      60
gtagtcaccc agtacccac accaggaagg accgcccatc atggcaaagc tctccaccga     120
cgaactgctg gacgcgttca aggaaatgac cctgttggag ctctccgact cgtcaagaa     180 gttcgaggag accttcgagg tcaccgccgc cgctccagtc gccgtcgccg ccgccggtgc     240
cgccccggcc ggtgccgccg tcgaggctgc gaggagcag tccgagttcg acgtgatcct     300
tgaggccgcc ggcgacaaga agatcggcgt catcaaggtg gtccgggaga tcgtttccgg     360
cctgggcctc aaggaggcca aggacctggt cgacggcgcg cccaagccgc tgctggagaa     420
ggtcgccaag gaggccgccg acgaggccaa ggccaagctg gaggccgccg gcgccaccgt     480
caccgtcaag tagctctgcc cagcgtgttc ttttgcgtct gctcggcccg tagcgaacac     540
tgcgcccgct                                                            550

<210> SEQ ID NO 64
<211> LENGTH: 130
<212> TYPE: PRT
<213> ORGANISM: Mycobacterium tuberculosis

<400> SEQUENCE: 64

Met Ala Lys Leu Ser Thr Asp Glu Leu Leu Asp Ala Phe Lys Glu Met
1               5                   10                  15

Thr Leu Leu Glu Leu Ser Asp Phe Val Lys Lys Phe Glu Glu Thr Phe
                20                  25                  30

Glu Val Thr Ala Ala Ala Pro Val Ala Val Ala Ala Gly Ala Ala
            35                  40                  45

Pro Ala Gly Ala Ala Val Glu Ala Ala Glu Gln Ser Glu Phe Asp
    50                  55                  60

Val Ile Leu Glu Ala Ala Gly Asp Lys Lys Ile Gly Val Ile Lys Val
65                  70                  75                  80

Val Arg Glu Ile Val Ser Gly Leu Gly Leu Lys Glu Ala Lys Asp Leu
                85                  90                  95

Val Asp Gly Ala Pro Lys Pro Leu Leu Glu Lys Val Ala Lys Glu Ala
                100                 105                 110

Ala Asp Glu Ala Lys Ala Lys Leu Glu Ala Ala Gly Ala Thr Val Thr
            115                 120                 125

Val Lys
    130

<210> SEQ ID NO 65
<211> LENGTH: 900
<212> TYPE: DNA
<213> ORGANISM: Mycobacterium tuberculosis

<400> SEQUENCE: 65
tgaacgccat cgggtccaac gaacgcagcg ctacctgatc accaccgggt ctgttagggc      60
tcttccccag gtcgtacagt cgggccatgg ccattgaggt ttcggtgttg cgggttttca    120
ccgattcaga cgggaatttc ggtaatccgc tgggggtgat caacgccagc aaggtcgaac    180
```

```
accgcgacag gcagcagctg gcagcccaat cgggctacag cgaaaccata ttcgtcgatc      240
ttcccagccc cggctcaacc accgcacacg ccaccatcca tactcccgc accgaaattc       300 cgttcgccgg acacccgacc gtgggagcgt cctggtggct gcgcgagagg gggacgccaa     360
ttaacacgct gcaggtgccg gccggcatcg tccaggtgag ctaccacggt gatctcaccg     420
ccatcagcgc ccgctcggaa tgggcacccg agttcgccat ccacgacctg gattcacttg     480
atgcgcttgc cgccgccgac cccgccgact tccggacga catcgcgcac tacctctgga      540
cctggaccga ccgctccgct ggctcgctgc gcgcccgcat gtttgccgcc aacttgggcg     600
tcaccgaaga cgaagcgacc ggtgccgcgg ccatccggat taccgattac ctcagccgtg     660
acctcaccat cacccagggc aaaggatcgt tgatccacac cacctggagt cccgagggct     720
gggttcgggt agccggccga gttgtcagcg acggtgtggc acaactcgac tgacgtagag     780
ctcagcgctg ccgatgcaac acggcggcaa ggtgatcctg caggggttgc ccgaccgcgc     840
gcatctgcaa cgagtacgaa agctcgtcgc cgtcgatgcg gtaggaacgg tcaagggcgg     900
```

<210> SEQ ID NO 66
<211> LENGTH: 228
<212> TYPE: PRT
<213> ORGANISM: Mycobacterium tuberculosis

<400> SEQUENCE: 66

```
Met Ala Ile Glu Val Ser Val Leu Arg Val Phe Thr Asp Ser Asp Gly
 1               5                  10                  15

Asn Phe Gly Asn Pro Leu Gly Val Ile Asn Ala Ser Lys Val Glu His
            20                  25                  30

Arg Asp Arg Gln Gln Leu Ala Ala Gln Ser Gly Tyr Ser Glu Thr Ile
        35                  40                  45

Phe Val Asp Leu Pro Ser Pro Gly Ser Thr Thr Ala His Ala Thr Ile
    50                  55                  60

His Thr Pro Arg Thr Glu Ile Pro Phe Ala Gly His Pro Thr Val Gly
65                  70                  75                  80

Ala Ser Trp Trp Leu Arg Glu Arg Gly Thr Pro Ile Asn Thr Leu Gln
                85                  90                  95

Val Pro Ala Gly Ile Val Gln Val Ser Tyr His Gly Asp Leu Thr Ala
            100                 105                 110

Ile Ser Ala Arg Ser Glu Trp Ala Pro Glu Phe Ala Ile His Asp Leu
        115                 120                 125

Asp Ser Leu Asp Ala Leu Ala Ala Asp Pro Ala Asp Phe Pro Asp
    130                 135                 140

Asp Ile Ala His Tyr Leu Trp Thr Trp Thr Asp Arg Ser Ala Gly Ser
145                 150                 155                 160

Leu Arg Ala Arg Met Phe Ala Ala Asn Leu Gly Val Thr Glu Asp Glu
                165                 170                 175

Ala Thr Gly Ala Ala Ala Ile Arg Ile Thr Asp Tyr Leu Ser Arg Asp
            180                 185                 190

Leu Thr Ile Thr Gln Gly Lys Gly Ser Leu Ile His Thr Thr Trp Ser
        195                 200                 205

Pro Glu Gly Trp Val Arg Val Ala Gly Arg Val Val Ser Asp Gly Val
    210                 215                 220

Ala Gln Leu Asp
225
```

<210> SEQ ID NO 67

-continued

<211> LENGTH: 500
<212> TYPE: DNA
<213> ORGANISM: Mycobacterium tuberculosis

<400> SEQUENCE: 67

```
gtttgtggtg tcggtggtct gggggcgcc aactgggatt cggttggggt gggtgcaggt 60
ccggcgatgg gcatcggagg tgtgggtggt ttgggtgggg ccggttcggg tccggcgatg 120
ggcatggggg gtgtgggtgg tttgggtggg gccggttcgg gtccggcgat gggcatgggg 180
ggtgtgggtg gtttagatgc ggccggttcc ggcgagggcg gctctcctgc ggcgatcggc 240
atcggagttg gcggaggcgg aggtgggggt gggggtggcg gcggcggggc cgacacgaac 300
cgctccgaca ggtcgtcgga cgtcgggggc ggagtctggc cgttgggctt cggtaggttt 360
gccgatgcgg gcgccggcgg aaacgaagca ctggggtcga agaacggctg cgctgccata 420
tcgtccggag cttccatacc ttcgtgcggc cggaagagct tgtcgtagtc ggccgccatg 480
acaacctctc agagtgcgct 500

<210> SEQ ID NO 68
<211> LENGTH: 139
<212> TYPE: PRT
<213> ORGANISM: Mycobacterium tuberculosis

<400> SEQUENCE: 68

Met Gly Ala Gly Pro Ala Met Gly Ile Gly Gly Val Gly Gly Leu Gly
1 5 10 15

Gly Ala Gly Ser Gly Pro Ala Met Gly Met Gly Gly Val Gly Gly Leu
20 25 30

Gly Gly Ala Gly Ser Gly Pro Ala Met Gly Met Gly Gly Val Gly Gly
35 40 45

Leu Asp Ala Ala Gly Ser Gly Glu Gly Gly Ser Pro Ala Ala Ile Gly
50 55 60

Ile Gly Val Gly Gly Gly Gly Gly Gly Gly Gly Gly Gly Gly Gly Gly
65 70 75 80

Ala Asp Thr Asn Arg Ser Asp Arg Ser Ser Asp Val Gly Gly Gly Val
85 90 95

Trp Pro Leu Gly Phe Gly Arg Phe Ala Asp Ala Gly Ala Gly Gly Asn
100 105 110

Glu Ala Leu Gly Ser Lys Asn Gly Cys Ala Ala Ile Ser Ser Gly Ala
115 120 125

Ser Ile Pro Ser Cys Gly Arg Lys Ser Leu Ser
130 135

<210> SEQ ID NO 69
<211> LENGTH: 2050
<212> TYPE: DNA
<213> ORGANISM: Mycobacterium tuberculosis
<400> SEQUENCE: 69
agcgcactct gagaggttgt catggcggcc gactacgaca agctcttccg gccgcacgaa 60
ggtatggaag ctccggacga tatggcagcg cagccgttct tcgaccccag tgcttcgttt 120
ccgccggcgc ccgcatcggc aaacctaccg aagcccaacg gccagactcc gcccccgacg 180
tccgacgacc tgtcggagcg gttcgtgtcg gccccgccgc cgccaccccc acccccacct 240
ccgcctccgc caactccgat gccgatcgcc gcaggagagc cgccctcgcc ggaaccggcc 300
gcatctaaac cacccacacc ccccatgccc atcgccggac ccgaaccggc cccacccaaa 360

-continued

```
ccacccacac ccccccatgcc catcgccgga cccgaaccgg ccccacccaa accacccaca      420
cctccgatgc ccatcgccgg acctgcaccc accccaaccc aatcccagtt ggcgcccccc      480
agaccaccga caccacaaac gccaaccgga gcgccgcagc aaccggaatc accggcgccc      540 cacgtacccct cgcacgggcc acatcaaccc cggcgcaccg caccagcacc gccctgggca     600
aagatgccaa tcggcgaacc cccgcccgct ccgtccagac cgtctgcgtc cccggccgaa     660
ccaccgaccc ggcctgcccc ccaacactcc cgacgtgcgc gccggggtca ccgctatcgc     720
acagacaccg aacgaaacgt cgggaaggta gcaactggtc catccatcca ggcgcggctg     780
cgggcagagg aagcatccgg cgcgcagctc gcccccggaa cggagccctc gccagcgccg     840
ttgggccaac cgagatcgta tctggctccg cccacccgcc ccgcgccgac agaacctccc     900
cccagcccct cgccgcagcg caactccggt cggcgtgccg agcgacgcgt ccaccccgat     960
ttagccgccc aacatgccgc ggcgcaacct gattcaatta cggccgcaac cactggcggt     1020
cgtcgccgca agcgtgcagc gccggatctc gacgcgcaca agaaatcctt aaggccggcg    1080
gccaaggggc cgaaggtgaa gaaggtgaag ccccagaaac cgaaggccac gaagccgccc    1140
aaagtggtgt cgcagcgcgg ctggcgacat tgggtgcatg cgttgacgcg aatcaacctg    1200
ggcctgtcac ccgacgagaa gtacgagctg gacctgcacg ctcgagtccg ccgcaatccc    1260
cgcgggtcgt atcagatcgc cgtcgtcggt ctcaaaggtg gggctggcaa aaccacgctg    1320
acagcagcgt tggggtcgac gttggctcag gtgcgggccg accggatcct ggctctagac    1380
gcggatccag cgcgccggaaa cctcgccgat cgggtagggc gacaatcggg cgcgaccatc    1440
gctgatgtgc ttgcagaaaa agagctgtcg cactacaacg acatccgcgc acacactagc    1500
gtcaatgcgg tcaatctgga agtgctgccg gcaccggaat acagctcggc gcagcgcgcg    1560
ctcagcgacg ccgactggca tttcatcgcc gatcctgcgt cgaggtttta caacctcgtc    1620
ttggctgatt gtggggccgg cttcttcgac ccgctgaccc gcggcgtgct gtccacggtg    1680
tccggtgtcg tggtcgtggc aagtgtctca atcgacggcg cacaacaggc gtcggtcgcg    1740
ttggactggt tgcgcaacaa cggttaccaa gatttggcga gccgcgcatg cgtggtcatc    1800
aatcacatca tgccgggaga acccaatgtc gcagttaaag acctggtgcg gcatttcgaa    1860
cagcaagttc aacccggccg ggtcgtggtc atgccgtggg acaggcacat tgcgccgga     1920 accgagattt cactcgactt gctcgaccct atctacaagc gcaaggtcct cgaattggcc    1980
gcagcgctat ccgacgattt cgagagggct ggacgtcgtt gagcgcacct gctgttgctg    2040
ctggtcctac                                                           2050
```

<210> SEQ ID NO 70
<211> LENGTH: 666
<212> TYPE: PRT
<213> ORGANISM: Mycobacterium tuberculosis

<400> SEQUENCE: 70

```
Met Ala Ala Asp Tyr Asp Lys Leu Phe Arg Pro His Glu Gly Met Glu
1               5                   10                  15

Ala Pro Asp Asp Met Ala Ala Gln Pro Phe Phe Asp Pro Ser Ala Ser
            20                  25                  30

Phe Pro Pro Ala Pro Ala Ser Ala Asn Leu Pro Lys Pro Asn Gly Gln
        35                  40                  45

Thr Pro Pro Thr Ser Asp Asp Leu Ser Glu Arg Phe Val Ser Ala
    50                  55                  60

Pro Pro Pro Pro Pro Pro Pro Pro Pro Pro Pro Pro Thr Pro Met
```

-continued

```
                65                  70                  75                  80
        Pro Ile Ala Ala Gly Glu Pro Pro Ser Pro Glu Pro Ala Ala Ser Lys
                        85                  90                  95
        Pro Pro Thr Pro Pro Met Pro Ile Ala Gly Pro Glu Pro Ala Pro Pro
                        100                 105                 110
        Lys Pro Pro Thr Pro Pro Met Pro Ile Ala Gly Pro Glu Pro Ala Pro
                        115                 120                 125
        Pro Lys Pro Pro Thr Pro Pro Met Pro Ile Ala Gly Pro Ala Pro Thr
                        130                 135                 140
        Pro Thr Glu Ser Gln Leu Ala Pro Pro Arg Pro Pro Thr Pro Gln Thr
        145                 150                 155                 160
        Pro Thr Gly Ala Pro Gln Gln Pro Glu Ser Pro Ala Pro His Val Pro
                        165                 170                 175
        Ser His Gly Pro His Gln Pro Arg Arg Thr Ala Pro Ala Pro Pro Trp
                        180                 185                 190
        Ala Lys Met Pro Ile Gly Glu Pro Pro Ala Pro Ser Arg Pro Ser
                        195                 200                 205
        Ala Ser Pro Ala Glu Pro Pro Thr Arg Pro Ala Pro Gln His Ser Arg
        210                 215                 220
        Arg Ala Arg Arg Gly His Arg Tyr Arg Thr Asp Thr Glu Arg Asn Val
        225                 230                 235                 240
        Gly Lys Val Ala Thr Gly Pro Ser Ile Gln Ala Arg Leu Arg Ala Glu
                        245                 250                 255
        Glu Ala Ser Gly Ala Gln Leu Ala Pro Gly Thr Glu Pro Ser Pro Ala
                        260                 265                 270
        Pro Leu Gly Gln Pro Arg Ser Tyr Leu Ala Pro Pro Thr Arg Pro Ala
                        275                 280                 285
        Pro Thr Glu Pro Pro Pro Ser Pro Ser Pro Gln Arg Asn Ser Gly Arg
                        290                 295                 300
        Arg Ala Glu Arg Arg Val His Pro Asp Leu Ala Ala Gln His Ala Ala
        305                 310                 315                 320
        Ala Gln Pro Asp Ser Ile Thr Ala Ala Thr Thr Gly Gly Arg Arg Arg
                        325                 330                 335
        Lys Arg Ala Ala Pro Asp Leu Asp Ala Thr Gln Lys Ser Leu Arg Pro
                        340                 345                 350
        Ala Ala Lys Gly Pro Lys Val Lys Val Lys Pro Gln Lys Pro Lys
                        355                 360                 365
        Ala Thr Lys Pro Pro Lys Val Val Ser Gln Arg Gly Trp Arg His Trp
                        370                 375                 380
        Val His Ala Leu Thr Arg Ile Asn Leu Gly Leu Ser Pro Asp Glu Lys
        385                 390                 395                 400
        Tyr Glu Leu Asp Leu His Ala Arg Val Arg Arg Asn Pro Arg Gly Ser
                        405                 410                 415
        Tyr Gln Ile Ala Val Val Gly Leu Lys Gly Gly Ala Gly Lys Thr Thr
                        420                 425                 430
        Leu Thr Ala Ala Leu Gly Ser Thr Leu Ala Gln Val Arg Ala Asp Arg
                        435                 440                 445
        Ile Leu Ala Leu Asp Ala Asp Pro Gly Ala Gly Asn Leu Ala Asp Arg
                        450                 455                 460
        Val Gly Arg Gln Ser Gly Ala Thr Ile Ala Asp Val Leu Ala Glu Lys
        465                 470                 475                 480
        Glu Leu Ser His Tyr Asn Asp Ile Arg Ala His Thr Ser Val Asn Ala
                        485                 490                 495
```

-continued

```
Val Asn Leu Glu Val Leu Pro Ala Pro Glu Tyr Ser Ser Ala Gln Arg
            500                 505                 510

Ala Leu Ser Asp Ala Asp Trp His Phe Ile Ala Asp Pro Ala Ser Arg
        515                 520                 525

Phe Tyr Asn Leu Val Leu Ala Asp Cys Gly Ala Gly Phe Phe Asp Pro
    530                 535                 540

Leu Thr Arg Gly Val Leu Ser Thr Val Ser Gly Val Val Val Val Ala
545                 550                 555                 560

Ser Val Ser Ile Asp Gly Ala Gln Gln Ala Ser Val Ala Leu Asp Trp
                565                 570                 575

Leu Arg Asn Asn Gly Tyr Gln Asp Leu Ala Ser Arg Ala Cys Val Val
            580                 585                 590

Ile Asn His Ile Met Pro Gly Glu Pro Asn Val Ala Val Lys Asp Leu
        595                 600                 605

Val Arg His Phe Glu Gln Gln Val Gln Pro Gly Arg Val Val Val Met
    610                 615                 620

Pro Trp Asp Arg His Ile Ala Ala Gly Thr Glu Ile Ser Leu Asp Leu
625                 630                 635                 640

Leu Asp Pro Ile Tyr Lys Arg Lys Val Leu Glu Leu Ala Ala Ala Leu
                645                 650                 655

Ser Asp Asp Phe Glu Arg Ala Gly Arg Arg
            660                 665

<210> SEQ ID NO 71
<211> LENGTH: 1890
<212> TYPE: DNA
<213> ORGANISM: Mycobacterium tuberculosis

<400> SEQUENCE: 71
gcagcgatga ggaggagcgg cgccaacggc ccgcgccggc gacgatgcaa agcgcagcga      60
tgaggaggag cggcgcgcat gactgctgaa ccggaagtac ggacgctgcg cgaggttgtg     120
ctggaccagc tcggcactgc tgaatcgcgt gcgtacaaga gtggctgcc gccgttgacc     180 aatccggtcc cgctcaacga gctcatcgcc cgtgatcggc gacaacccct gcgatttgcc     240
ctggggatca tggatgaacc cgccgccat ctacaggatg tgtggggcgt agacgttccc     300
ggggccggcg caacatcgg tattgggggc gcacctcaaa ccgggaagtc gacgctactg     360
cagacgatgg tgatgtcggc cgccgccaca cactcaccgc gcaacgttca gttctattgc     420
atcgacctag gtggcggcgg gctgatctat ctcgaaaacc ttccacacgt cggtggggta     480
gccaatcggt ccgagcccga caaggtcaac cgggtggtcg cagagatgca agccgtcatg     540
cggcaacggg aaaccacctt caaggaacac cgagtgggct cgatcgggat gtaccggcag     600
ctgcgtgacg atccaagtca acccgttgcg tccgatccat acggcgacgt ctttctgatc     660
atcgacggat ggcccggttt tgtcggcgag ttccccgacc ttgaggggca ggttcaagat     720
ctggccgccc aggggctggg gttcggcgtc cacgtcatca tctccacgcc acgctggaca     780
gagctgaagt cgcgtgttcg cgactacctc ggcaccaaga tcgagttccg gcttggtgac     840
gtcaatgaaa cccagatcga ccggattacc cgcgagatcc ggcgaatcg tccgggtcgg     900 gcagtgtcga tggaaaagca ccatctgatg atcggcgtgc caggttcga cggcgtgcac     960 agcgccgata acctggtgga ggcgatcacc gcggggtga cgcagatcgc ttcccagcac    1020
accgaacagg cacctccggt gcgggtcctg ccggagcgta tccacctgca cgaactcgac    1080
ccgaacccgc cgggaccaga gtccgactac cgcactcgct gggagattcc gatcggcttg    1140
```

-continued

```
cgcgagacgg acctgacgcc ggctcactgc cacatgcaca cgaacccgca cctactgatc   1200
ttcggtgcgg ccaaatcggg caagacgacc attgcccacg cgatcgcgcg cgccatttgt   1260
gcccgaaaca gtccccagca ggtgcggttc atgctcgcgg actaccgctc gggcctgctg   1320
gacgcggtgc cggacaccca tctgctgggc gccggcgcga tcaaccgcaa cagcgcgtcg   1380
ctagacgagg ccgctcaagc actggcggtc aacctgaaga agcggttgcc gccgaccgac   1440
ctgacgacgg cgcagctacg ctcgcgttcg tggtggagcg gatttgacgt cgtgcttctg   1500
gtcgacgatt ggcacatgat cgtgggtgcc gccgggggga tgccgccgat ggcaccgctg   1560
gccccgttat tgccggcggc ggcagatatc gggttgcaca tcattgtcac ctgtcagatg   1620
agccaggctt acaaggcaac catggacaag ttcgtcggcg ccgcattcgg gtcgggcgct   1680
ccgacaatgt tcctttcggg cgagaagcag gaattcccat ccagtgagtt caaggtcaag   1740
cggcgccccc ctggccaggc atttctcgtc tcgccagacg gcaaagaggt catccaggcc   1800
ccctacatcg agcctccaga agaagtgttc gcagcacccc caagcgccgg ttaagattat   1860
ttcattgccg gtgtagcagg acccgagctc                                    1890
```

<210> SEQ ID NO 72
<211> LENGTH: 591
<212> TYPE: PRT
<213> ORGANISM: Mycobacterium tuberculosis

<400> SEQUENCE: 72

```
Met Thr Ala Glu Pro Glu Val Arg Thr Leu Arg Glu Val Val Leu Asp
1               5                   10                  15

Gln Leu Gly Thr Ala Glu Ser Arg Ala Tyr Lys Met Trp Leu Pro Pro
            20                  25                  30

Leu Thr Asn Pro Val Pro Leu Asn Glu Leu Ile Ala Arg Asp Arg Arg
        35                  40                  45

Gln Pro Leu Arg Phe Ala Leu Gly Ile Met Asp Glu Pro Arg Arg His
    50                  55                  60

Leu Gln Asp Val Trp Gly Val Asp Val Ser Gly Ala Gly Gly Asn Ile
65                  70                  75                  80

Gly Ile Gly Gly Ala Pro Gln Thr Gly Lys Ser Thr Leu Leu Gln Thr
                85                  90                  95

Met Val Met Ser Ala Ala Ala Thr His Ser Pro Arg Asn Val Gln Phe
            100                 105                 110

Tyr Cys Ile Asp Leu Gly Gly Gly Gly Leu Ile Tyr Leu Glu Asn Leu
        115                 120                 125

Pro His Val Gly Gly Val Ala Asn Arg Ser Glu Pro Asp Lys Val Asn
    130                 135                 140

Arg Val Val Ala Glu Met Gln Ala Val Met Arg Gln Arg Glu Thr Thr
145                 150                 155                 160

Phe Lys Glu His Arg Val Gly Ser Ile Gly Met Tyr Arg Gln Leu Arg
                165                 170                 175

Asp Asp Pro Ser Gln Pro Val Ala Ser Asp Pro Tyr Gly Asp Val Phe
            180                 185                 190

Leu Ile Ile Asp Gly Trp Pro Gly Phe Val Gly Glu Phe Pro Asp Leu
        195                 200                 205

Glu Gly Gln Val Gln Asp Leu Ala Ala Gln Gly Leu Gly Phe Gly Val
    210                 215                 220

His Val Ile Ile Ser Thr Pro Arg Trp Thr Glu Leu Lys Ser Arg Val
225                 230                 235                 240
```

```
Arg Asp Tyr Leu Gly Thr Lys Ile Glu Phe Arg Leu Gly Asp Val Asn
            245                 250                 255

Glu Thr Gln Ile Asp Arg Ile Thr Arg Glu Ile Pro Ala Asn Arg Pro
            260                 265                 270

Gly Arg Ala Val Ser Met Glu Lys His His Leu Met Ile Gly Val Pro
            275                 280                 285

Arg Phe Asp Gly Val His Ser Ala Asp Asn Leu Val Glu Ala Ile Thr
            290                 295                 300

Ala Gly Val Thr Gln Ile Ala Ser Gln His Thr Glu Gln Ala Pro Pro
305                 310                 315                 320

Val Arg Val Leu Pro Glu Arg Ile His Leu His Glu Leu Asp Pro Asn
            325                 330                 335

Pro Pro Gly Pro Glu Ser Asp Tyr Arg Thr Arg Trp Glu Ile Pro Ile
            340                 345                 350

Gly Leu Arg Glu Thr Asp Leu Thr Pro Ala His Cys His Met His Thr
            355                 360                 365

Asn Pro His Leu Leu Ile Phe Gly Ala Ala Lys Ser Gly Lys Thr Thr
            370                 375                 380

Ile Ala His Ala Ile Ala Arg Ala Ile Cys Ala Arg Asn Ser Pro Gln
385                 390                 395                 400

Gln Val Arg Phe Met Leu Ala Asp Tyr Arg Ser Gly Leu Leu Asp Ala
            405                 410                 415

Val Pro Asp Thr His Leu Leu Gly Ala Gly Ala Ile Asn Arg Asn Ser
            420                 425                 430

Ala Ser Leu Asp Glu Ala Ala Gln Ala Leu Ala Val Asn Leu Lys Lys
            435                 440                 445

Arg Leu Pro Pro Thr Asp Leu Thr Thr Ala Gln Leu Arg Ser Arg Ser
            450                 455                 460

Trp Trp Ser Gly Phe Asp Val Val Leu Leu Val Asp Asp Trp His Met
465                 470                 475                 480

Ile Val Gly Ala Ala Gly Gly Met Pro Pro Met Ala Pro Leu Ala Pro
            485                 490                 495

Leu Leu Pro Ala Ala Asp Ile Gly Leu His Ile Ile Val Thr Cys
            500                 505                 510

Gln Met Ser Gln Ala Tyr Lys Ala Thr Met Asp Lys Phe Val Gly Ala
            515                 520                 525

Ala Phe Gly Ser Gly Ala Pro Thr Met Phe Leu Ser Gly Glu Lys Gln
            530                 535                 540

Glu Phe Pro Ser Ser Glu Phe Lys Val Lys Arg Arg Pro Pro Gly Gln
545                 550                 555                 560

Ala Phe Leu Val Ser Pro Asp Gly Lys Glu Val Ile Gln Ala Pro Tyr
            565                 570                 575

Ile Glu Pro Pro Glu Glu Val Phe Ala Ala Pro Pro Ser Ala Gly
            580                 585                 590

<210> SEQ ID NO 73
<211> LENGTH: 15
<212> TYPE: PRT
<213> ORGANISM: Mycobacterium tuberculosis

<400> SEQUENCE: 73

Asp Pro Val Asp Asp Ala Phe Ile Ala Lys Leu Asn Thr Ala Gly
1               5                   10                  15
```

<210> SEQ ID NO 74
<211> LENGTH: 14
<212> TYPE: PRT
<213> ORGANISM: Mycobacterium tuberculosis
<220> FEATURE:
<221> NAME/KEY: MISC_FEATURE
<222> LOCATION: (14)..(14)
<223> OTHER INFORMATION: "Xaa" is unknown

<400> SEQUENCE: 74

Asp Pro Val Asp Ala Ile Ile Asn Leu Asp Asn Tyr Gly Xaa
1               5                   10

<210> SEQ ID NO 75
<211> LENGTH: 15
<212> TYPE: PRT
<213> ORGANISM: Mycobacterium tuberculosis
<220> FEATURE:
<221> NAME/KEY: MISC_FEATURE
<222> LOCATION: (5)..(5)
<223> OTHER INFORMATION: "Xaa" is unknown

<400> SEQUENCE: 75

Ala Glu Met Lys Xaa Phe Lys Asn Ala Ile Val Gln Glu Ile Asp
1               5                   10                  15

<210> SEQ ID NO 76
<211> LENGTH: 14
<212> TYPE: PRT
<213> ORGANISM: Mycobacterium tuberculosis
<220> FEATURE:
<221> NAME/KEY: variant
<222> LOCATION: (3)..(3)
<223> OTHER INFORMATION: Ala is Ala or Gln
<221> NAME/KEY: variant
<222> LOCATION: (7)..(7)
<223> OTHER INFORMATION: Thr is Gly or Thr
<221> NAME/KEY: MISC_FEATURE
<222> LOCATION: (11)..(11)
<223> OTHER INFORMATION: "Xaa" is unknown

<400> SEQUENCE: 76

Val Ile Ala Gly Met Val Thr His Ile His Xaa Val Ala Gly
1               5                   10

<210> SEQ ID NO 77
<211> LENGTH: 15
<212> TYPE: PRT
<213> ORGANISM: Mycobacterium tuberculosis

<400> SEQUENCE: 77

Thr Asn Ile Val Val Leu Ile Lys Gln Val Pro Asp Thr Trp Ser
1               5                   10                  15

<210> SEQ ID NO 78
<211> LENGTH: 15
<212> TYPE: PRT
<213> ORGANISM: Mycobacterium tuberculosis

<400> SEQUENCE: 78

Ala Ile Glu Val Ser Val Leu Arg Val Phe Thr Asp Ser Asp Gly
1               5                   10                  15

<210> SEQ ID NO 79
<211> LENGTH: 15
<212> TYPE: PRT
<213> ORGANISM: Mycobacterium tuberculosis

<400> SEQUENCE: 79

```
Ala Lys Leu Ser Thr Asp Glu Leu Leu Asp Ala Phe Lys Glu Met
1               5                   10                  15

<210> SEQ ID NO 80
<211> LENGTH: 15
<212> TYPE: PRT
<213> ORGANISM: Mycobacterium tuberculosis
<220> FEATURE:
<221> NAME/KEY: variant
<222> LOCATION: (4)..(4)
<223> OTHER INFORMATION: Asp is Asp or Glu

<400> SEQUENCE: 80

Asp Pro Ala Asp Ala Pro Asp Val Pro Thr Ala Ala Gln Leu Thr
1               5                   10                  15

<210> SEQ ID NO 81
<211> LENGTH: 50
<212> TYPE: PRT
<213> ORGANISM: Mycobacterium tuberculosis

<400> SEQUENCE: 81

Ala Glu Asp Val Arg Ala Glu Ile Val Ala Ser Val Leu Glu Val Val
1               5                   10                  15

Val Asn Glu Gly Asp Gln Ile Asp Lys Gly Asp Val Val Leu Leu
            20                  25                  30

Glu Ser Met Tyr Met Glu Ile Pro Val Leu Ala Glu Ala Ala Gly Thr
        35                  40                  45

Val Ser
    50

<210> SEQ ID NO 82
<211> LENGTH: 15
<212> TYPE: PRT
<213> ORGANISM: Mycobacterium tuberculosis

<400> SEQUENCE: 82

Thr Thr Ser Pro Asp Pro Tyr Ala Ala Leu Pro Lys Leu Pro Ser
1               5                   10                  15

<210> SEQ ID NO 83
<211> LENGTH: 15
<212> TYPE: PRT
<213> ORGANISM: Mycobacterium tuberculosis

<400> SEQUENCE: 83

Thr Glu Tyr Glu Gly Pro Lys Thr Lys Phe His Ala Leu Met Gln
1               5                   10                  15

<210> SEQ ID NO 84
<211> LENGTH: 15
<212> TYPE: PRT
<213> ORGANISM: Mycobacterium tuberculosis

<400> SEQUENCE: 84

Thr Thr Ile Val Ala Leu Lys Tyr Pro Gly Gly Val Val Met Ala
1               5                   10                  15

<210> SEQ ID NO 85
<211> LENGTH: 15
<212> TYPE: PRT
<213> ORGANISM: Mycobacterium tuberculosis
<220> FEATURE:
<221> NAME/KEY: MISC_FEATURE
```

```
<222> LOCATION: (10)..(10)
<223> OTHER INFORMATION: "Xaa" is unknown
<221> NAME/KEY: MISC_FEATURE
<222> LOCATION: (15)..(15)
<223> OTHER INFORMATION: "Xaa" is unknown

<400> SEQUENCE: 85

Ser Phe Pro Tyr Phe Ile Ser Pro Glu Xaa Ala Met Arg Glu Xaa
1               5                   10                  15

<210> SEQ ID NO 86
<211> LENGTH: 15
<212> TYPE: PRT
<213> ORGANISM: Mycobacterium tuberculosis

<400> SEQUENCE: 86

Thr His Tyr Asp Val Val Val Leu Gly Ala Gly Pro Gly Gly Tyr
1               5                   10                  15

<210> SEQ ID NO 87
<211> LENGTH: 450
<212> TYPE: DNA
<213> ORGANISM: Mycobacterium tuberculosis

<400> SEQUENCE: 87
agcccggtaa tcgagttcgg gcaatgctga ccatcgggtt tgtttccggc tataaccgaa      60
cggtttgtgt acgggataca aatacaggga gggaagaagt aggcaaatgg aaaaaatgtc     120
acatgatccg atcgctgccg acattggcac gcaagtgagc gacaacgctc tgcacggcgt     180
gacggccggc tcgacggcgc tgacgtcggt gaccgggctg gttccgcgg gggccgatga      240 ggtctccgcc caagcggcga cggcgttcac atcggagggc atccaattgc tggcttccaa     300
tgcatcggcc caagaccagc tccaccgtgc gggcgaagcg gtccaggacg tcgcccgcac     360
ctattcgcaa atcgacgacg cgccgccgg cgtcttcgcc taataggccc ccaacacatc      420
ggagggagtg atcaccatgc tgtggcacgc                                      450

<210> SEQ ID NO 88
<211> LENGTH: 98
<212> TYPE: PRT
<213> ORGANISM: Mycobacterium tuberculosis

<400> SEQUENCE: 88

Met Glu Lys Met Ser His Asp Pro Ile Ala Ala Asp Ile Gly Thr Gln
1               5                   10                  15

Val Ser Asp Asn Ala Leu His Gly Val Thr Ala Gly Ser Thr Ala Leu
                20                  25                  30

Thr Ser Val Thr Gly Leu Val Pro Ala Gly Ala Asp Glu Val Ser Ala
            35                  40                  45

Gln Ala Ala Thr Ala Phe Thr Ser Glu Gly Ile Gln Leu Leu Ala Ser
        50                  55                  60

Asn Ala Ser Ala Gln Asp Gln Leu His Arg Ala Gly Glu Ala Val Gln
65                  70                  75                  80

Asp Val Ala Arg Thr Tyr Ser Gln Ile Asp Asp Gly Ala Ala Gly Val
                85                  90                  95

Phe Ala

<210> SEQ ID NO 89
<211> LENGTH: 460
<212> TYPE: DNA
<213> ORGANISM: Mycobacterium tuberculosis
```

<400> SEQUENCE: 89

```
gcaaccggct tttcgatcag ctgagacatc agcggcgtgc gggtcaacga cccacctgcg      60
ccaggtagcg actccgcgcg cagcaggccc gcgcccgcgc tggggcctga tccaccagcc     120
agcggatggt tcgacagcgg actggtgccg agcaggccca tctgcgcggc ttcctcgtcg     180
gctgggttgc cgccgccggt gccgcccacc tggctgaaca acgacgtcac ctgctgcagc     240
ggctgggtca gctgctgcat cgggccgctc atctcaccca gttggccgag ggtctgggta     300
gccgccggcg gcaactggcc aaccggtgtt gagctgccag ggagggcat  tccgaagatc     360
gggttcgtcg tgctctggct cgcgccggga tcaaggatcg acgccatcgg ctcgagcttc     420
tcgaaaagcg tgttaaccgc ggtctcggcc tggtagacct                           460
```

<210> SEQ ID NO 90
<211> LENGTH: 139
<212> TYPE: PRT
<213> ORGANISM: Mycobacterium tuberculosis

<400> SEQUENCE: 90

```
Met Arg Val Asn Asp Pro Pro Ala Pro Gly Ser Asp Ser Ala Arg Ser
  1               5                  10                  15
Arg Pro Ala Pro Ala Leu Gly Pro Asp Pro Ala Ser Gly Trp Phe
             20                  25                  30
Asp Ser Gly Leu Val Pro Ser Arg Pro Ile Cys Ala Ala Ser Ser Ser
         35                  40                  45
Ala Gly Leu Pro Pro Pro Val Pro Pro Thr Trp Leu Asn Asn Asp Val
     50                  55                  60
Thr Cys Cys Ser Gly Trp Val Ser Cys Cys Ile Gly Pro Leu Ile Ser
 65                  70                  75                  80
Pro Ser Trp Pro Arg Val Trp Val Ala Ala Gly Gly Asn Trp Pro Thr
                 85                  90                  95
Gly Val Glu Leu Pro Gly Glu Gly Ile Pro Lys Ile Gly Phe Val Val
            100                 105                 110
Leu Trp Leu Ala Pro Gly Ser Arg Ile Asp Ala Ile Gly Ser Ser Phe
        115                 120                 125
Ser Lys Ser Val Leu Thr Ala Val Ser Ala Trp
    130                 135
```

<210> SEQ ID NO 91
<211> LENGTH: 1200
<212> TYPE: DNA
<213> ORGANISM: Mycobacterium tuberculosis

<400> SEQUENCE: 91

```
taataggccc ccaacacatc ggagggagtg atcaccatgc tgtggcacgc aatgccaccg      60
gagctaaata ccgcacggct gatggccggc gcgggtccgg ctccaatgct tgcggcggcc     120
gcgggatggc agacgctttc ggcggctctg gacgctcagg ccgtcgagtt gaccgcgcgc     180
ctgaactctc tgggagaagc ctggactgga ggtggcagcg acaaggcgct tgcggctgca     240
acgccgatgg tggtctggct acaaaccgcg tcaacacagg ccaagacccg tgcgatgcag     300
gcgacggcgc aagccgcggc atacccccag gccatggcca cgacgccgtc gctgccggag     360
atcgccgcca accacatcac ccaggccgtc cttacggcca ccaacttctt cggtatcaac     420
acgatcccga tcgcgttgac cgagatggat tatttcatcc gtatgtggaa ccaggcagcc     480
ctggcaatgg aggtctacca ggccgagacc gcggttaaca cgcttttcga aagctcgag      540
```

-continued

```
ccgatggcgt cgatccttga tcccggcgcg agccagagca cgacgaaccc gatcttcgga    600
atgccctccc ctggcagctc aacaccggtt ggccagttgc cgccggcggc tacccagacc    660
ctcggccaac tgggtgagat gagcggcccg atgcagcagc tgacccagcc gctgcagcag    720
gtgacgtcgt tgttcagcca ggtgggcggc accggcggcg gcaacccagc cgacgaggaa    780
gccgcgcaga tgggcctgct cggcaccagt ccgctgtcga accatccgct ggctggtgga    840
tcaggcccca gcgcgggcgc gggcctgctg cgcgcggagt cgctacctgg cgcaggtggg    900
tcgttgaccc gcacgccgct gatgtctcag ctgatcgaaa agccggttgc ccctcggtg     960 atgccggcgg ctgctgccgg atcgtcggcg acgggtggcg ccgctccggt gggtgcggga   1020
gcgatgggcc aggtgcgcca atccggcggc tccaccaggc cgggtctggt cgcgccggca   1080
ccgctcgcgc aggagcgtga agaagacgac gaggacgact gggacgaaga ggacgactgg   1140
tgagctcccg taatgacaac agacttcccg gccacccggg ccggaagact tgccaacatt   1200
```

<210> SEQ ID NO 92
<211> LENGTH: 371
<212> TYPE: PRT
<213> ORGANISM: Mycobacterium tuberculosis

<400> SEQUENCE: 92

```
Met Ile Thr Met Leu Trp His Ala Met Pro Pro Glu Leu Asn Thr Ala
1               5                   10                  15

Arg Leu Met Ala Gly Ala Gly Pro Ala Pro Met Leu Ala Ala Ala Ala
                20                  25                  30

Gly Trp Gln Thr Leu Ser Ala Ala Leu Asp Ala Gln Ala Val Glu Leu
            35                  40                  45

Thr Ala Arg Leu Asn Ser Leu Gly Glu Ala Trp Thr Gly Gly Gly Ser
        50                  55                  60

Asp Lys Ala Leu Ala Ala Ala Thr Pro Met Val Val Trp Leu Gln Thr
65                  70                  75                  80

Ala Ser Thr Gln Ala Lys Thr Arg Ala Met Gln Ala Thr Ala Gln Ala
                85                  90                  95

Ala Ala Tyr Thr Gln Ala Met Ala Thr Thr Pro Ser Leu Pro Glu Ile
            100                 105                 110

Ala Ala Asn His Ile Thr Gln Ala Val Leu Thr Ala Thr Asn Phe Phe
        115                 120                 125

Gly Ile Asn Thr Ile Pro Ile Ala Leu Thr Glu Met Asp Tyr Phe Ile
    130                 135                 140

Arg Met Trp Asn Gln Ala Ala Leu Ala Met Glu Val Tyr Gln Ala Glu
145                 150                 155                 160

Thr Ala Val Asn Thr Leu Phe Glu Lys Leu Glu Pro Met Ala Ser Ile
                165                 170                 175

Leu Asp Pro Gly Ala Ser Gln Ser Thr Thr Asn Pro Ile Phe Gly Met
            180                 185                 190

Pro Ser Pro Gly Ser Ser Thr Pro Val Gly Gln Leu Pro Pro Ala Ala
        195                 200                 205

Thr Gln Thr Leu Gly Gln Leu Gly Glu Met Ser Gly Pro Met Gln Gln
    210                 215                 220

Leu Thr Gln Pro Leu Gln Val Thr Ser Leu Phe Ser Gln Val Gly
225                 230                 235                 240

Gly Thr Gly Gly Gly Asn Pro Ala Asp Glu Glu Ala Ala Gln Met Gly
                245                 250                 255
```

-continued

Leu Leu Gly Thr Ser Pro Leu Ser Asn His Pro Leu Ala Gly Gly Ser
            260                 265                 270

Gly Pro Ser Ala Gly Ala Gly Leu Leu Arg Ala Glu Ser Leu Pro Gly
        275                 280                 285

Ala Gly Gly Ser Leu Thr Arg Thr Pro Leu Met Ser Gln Leu Ile Glu
    290                 295                 300

Lys Pro Val Ala Pro Ser Val Met Pro Ala Ala Ala Gly Ser Ser
305                 310                 315                 320

Ala Thr Gly Gly Ala Ala Pro Val Gly Ala Gly Ala Met Gly Gln Gly
                325                 330                 335

Ala Gln Ser Gly Gly Ser Thr Arg Pro Gly Leu Val Ala Pro Ala Pro
            340                 345                 350

Leu Ala Gln Glu Arg Glu Glu Asp Asp Glu Asp Asp Trp Asp Glu Glu
            355                 360                 365

Asp Asp Trp
    370

<210> SEQ ID NO 93
<211> LENGTH: 1000
<212> TYPE: DNA
<213> ORGANISM: Mycobacterium tuberculosis

<400> SEQUENCE: 93
gacgcgacac agaaatcctt aaggccggcg gccaagggc cgaaggtgaa gaaggtgaag    60
ccccagaaac cgaaggccac gaagccgccc aaagtggtgt cgcagcgcgg ctggcgacat   120
tgggtgcatg cgttgacgcg aatcaacctg gcctgtcac ccgacgagaa gtacgagctg   180
gacctgcacg ctcgagtccg ccgcaatccc cgcgggtcgt atcagatcgc cgtcgtcggt   240
ctcaaaggtg gggctggcaa aaccacgctg acagcagcgt tgggtcgac gttggctcag   300
gtgcgggccg accggatcct ggctctagac gcggatccag gcgccggaaa cctcgccgat   360
cgggtagggc gacaatcggg cgcgaccatc gctgatgtgc ttgcagaaaa agagctgtcg   420
cactacaacg acatccgcgc acacactagc gtcaatgcgg tcaatctgga agtgctgccg   480
gcaccggaat acagctcggc gcagcgcgcg ctcagcgacg ccgactggca tttcatcgcc   540
gatcctgcgt cgaggtttta caacctcgtc ttggctgatt gtggggccgg cttcttcgac   600
ccgctgaccc gcggcgtgct gtccacggtg tccggtgtcg tggtcgtggc aagtgtctca   660
atcgacggcg cacaacaggc gtcggtcgcg ttggactggt tgcgcaacaa cggttaccaa   720
gatttggcga gccgcgcatg cgtggtcatc aatcacatca tgccgggaga acccaatgtc   780
gcagttaaag acctggtgcg gcatttcgaa cagcaagttc aacccggccg ggtcgtggtc   840
atgccgtggg acaggcacat tgcggccgga accgagattt cactcgactt gctcgaccct   900
atctacaagc gcaaggtcct cgaattggcc gcagcgctat ccgacgattt cgagagggct   960
ggacgtcgtt gagcgcacct gctgttgctg ctggtcctac                        1000

<210> SEQ ID NO 94
<211> LENGTH: 308
<212> TYPE: PRT
<213> ORGANISM: Mycobacterium tuberculosis

<400> SEQUENCE: 94

Met Lys Lys Val Lys Pro Gln Lys Pro Lys Ala Thr Lys Pro Pro Lys
1               5                   10                  15

Val Val Ser Gln Arg Gly Trp Arg His Trp Val His Ala Leu Thr Arg
            20                  25                  30

Ile Asn Leu Gly Leu Ser Pro Asp Glu Lys Tyr Glu Leu Asp Leu His
            35                  40                  45
Ala Arg Val Arg Arg Asn Pro Arg Gly Ser Tyr Gln Ile Ala Val Val
    50                  55                  60
Gly Leu Lys Gly Gly Ala Gly Lys Thr Thr Leu Thr Ala Ala Leu Gly
65                  70                  75                  80
Ser Thr Leu Ala Gln Val Arg Ala Asp Arg Ile Leu Ala Leu Asp Ala
                85                  90                  95
Asp Pro Gly Ala Gly Asn Leu Ala Asp Arg Val Gly Arg Gln Ser Gly
            100                 105                 110
Ala Thr Ile Ala Asp Val Leu Ala Glu Lys Glu Leu Ser His Tyr Asn
            115                 120                 125
Asp Ile Arg Ala His Thr Ser Val Asn Ala Val Asn Leu Glu Val Leu
            130                 135                 140
Pro Ala Pro Glu Tyr Ser Ser Ala Gln Arg Ala Leu Ser Asp Ala Asp
145                 150                 155                 160
Trp His Phe Ile Ala Asp Pro Ala Ser Arg Phe Tyr Asn Leu Val Leu
                165                 170                 175
Ala Asp Cys Gly Ala Gly Phe Phe Asp Pro Leu Thr Arg Gly Val Leu
            180                 185                 190
Ser Thr Val Ser Gly Val Val Val Ala Ser Val Ser Ile Asp Gly
            195                 200                 205
Ala Gln Gln Ala Ser Val Ala Leu Asp Trp Leu Arg Asn Asn Gly Tyr
            210                 215                 220
Gln Asp Leu Ala Ser Arg Ala Cys Val Val Ile Asn His Ile Met Pro
225                 230                 235                 240
Gly Glu Pro Asn Val Ala Val Lys Asp Leu Val Arg His Phe Glu Gln
                245                 250                 255
Gln Val Gln Pro Gly Arg Val Val Met Pro Trp Asp Arg His Ile
            260                 265                 270
Ala Ala Gly Thr Glu Ile Ser Leu Asp Leu Asp Pro Ile Tyr Lys
            275                 280                 285
Arg Lys Val Leu Glu Leu Ala Ala Ala Leu Ser Asp Asp Phe Glu Arg
    290                 295                 300
Ala Gly Arg Arg
305

<210> SEQ ID NO 95
<211> LENGTH: 34
<212> TYPE: DNA
<213> ORGANISM: Mycobacterium tuberculosis

<400> SEQUENCE: 95
aagagtagat ctatgatggc cgaggatgtt cgcg                                    34

<210> SEQ ID NO 96
<211> LENGTH: 27
<212> TYPE: DNA
<213> ORGANISM: Mycobacterium tuberculosis

<400> SEQUENCE: 96
cggcgacgac ggatcctacc gcgtcgg                                            27

<210> SEQ ID NO 97
<211> LENGTH: 28
<212> TYPE: DNA

-continued

<213> ORGANISM: Mycobacterium tuberculosis

<400> SEQUENCE: 97
ccttgggaga tctttggacc ccggttgc                                    28

<210> SEQ ID NO 98
<211> LENGTH: 25
<212> TYPE: DNA
<213> ORGANISM: Mycobacterium tuberculosis

<400> SEQUENCE: 98
gacgagatct tatgggctta ctgac                                       25

<210> SEQ ID NO 99
<211> LENGTH: 33
<212> TYPE: DNA
<213> ORGANISM: Mycobacterium tuberculosis

<400> SEQUENCE: 99 cccccccagat ctgcaccacc ggcatcggcg ggc                             33

<210> SEQ ID NO 100
<211> LENGTH: 24
<212> TYPE: DNA
<213> ORGANISM: Mycobacterium tuberculosis

<400> SEQUENCE: 100
gcggcggatc cgttgcttag ccgg                                        24

<210> SEQ ID NO 101
<211> LENGTH: 32
<212> TYPE: DNA
<213> ORGANISM: Mycobacterium tuberculosis

<400> SEQUENCE: 101
ccggctgaga tctatgacag aatacgaagg gc                               32

<210> SEQ ID NO 102
<211> LENGTH: 24
<212> TYPE: DNA
<213> ORGANISM: Mycobacterium tuberculosis

<400> SEQUENCE: 102
ccccgccagg gaactagagg cggc                                        24

<210> SEQ ID NO 103
<211> LENGTH: 38
<212> TYPE: DNA
<213> ORGANISM: Mycobacterium tuberculosis

<400> SEQUENCE: 103
ctgccgagat ctaccaccat tgtcgcgctg aaataccc                         38

<210> SEQ ID NO 104
<211> LENGTH: 25
<212> TYPE: DNA
<213> ORGANISM: Mycobacterium tuberculosis

<400> SEQUENCE: 104
cgccatggcc ttacgcgcca actcg                                       25

<210> SEQ ID NO 105
<211> LENGTH: 32

-continued

```
<212> TYPE: DNA
<213> ORGANISM: Mycobacterium tuberculosis

<400> SEQUENCE: 105
ggcggagatc tgtgagtttt ccgtatttca tc                                32

<210> SEQ ID NO 106
<211> LENGTH: 25
<212> TYPE: DNA
<213> ORGANISM: Mycobacterium tuberculosis

<400> SEQUENCE: 106
cgcgtcgagc catggttagg cgcag                                        25

<210> SEQ ID NO 107
<211> LENGTH: 32
<212> TYPE: DNA
<213> ORGANISM: Mycobacterium tuberculosis

<400> SEQUENCE: 107
gaggaagatc tatgacaact tcacccgacc cg                                32

<210> SEQ ID NO 108
<211> LENGTH: 28
<212> TYPE: DNA
<213> ORGANISM: Mycobacterium tuberculosis

<400> SEQUENCE: 108
catgaagcca tggcccgcag gctgcatg                                     28

<210> SEQ ID NO 109
<211> LENGTH: 33
<212> TYPE: DNA
<213> ORGANISM: Mycobacterium tuberculosis

<400> SEQUENCE: 109
ggccgagatc tgtgacccac tatgacgtcg tcg                               33

<210> SEQ ID NO 110
<211> LENGTH: 36
<212> TYPE: DNA
<213> ORGANISM: Mycobacterium tuberculosis

<400> SEQUENCE: 110
ggcgcccatg gtcagaaatt gatcatgtgg ccaacc                            36

<210> SEQ ID NO 111
<211> LENGTH: 33
<212> TYPE: DNA
<213> ORGANISM: Mycobacterium tuberculosis

<400> SEQUENCE: 111
ccgggagatc tatggcaaag ctctccaccg acg                               33

<210> SEQ ID NO 112
<211> LENGTH: 32
<212> TYPE: DNA
<213> ORGANISM: Mycobacterium tuberculosis

<400> SEQUENCE: 112
cgctgggcag agctacttga cggtgacggt gg                                32

<210> SEQ ID NO 113
```

```
<211> LENGTH: 36
<212> TYPE: DNA
<213> ORGANISM: Mycobacterium tuberculosis

<400> SEQUENCE: 113
ggcccagatc tatggccatt gaggtttcgg tgttgc                              36

<210> SEQ ID NO 114
<211> LENGTH: 26
<212> TYPE: DNA
<213> ORGANISM: Mycobacterium tuberculosis

<400> SEQUENCE: 114
cgccgtgttg catggcagcg ctgagc                                          26

<210> SEQ ID NO 115
<211> LENGTH: 24
<212> TYPE: DNA
<213> ORGANISM: Mycobacterium tuberculosis

<400> SEQUENCE: 115
ggacgttcaa gcgacacatc gccg                                            24

<210> SEQ ID NO 116
<211> LENGTH: 24
<212> TYPE: DNA
<213> ORGANISM: Mycobacterium tuberculosis

<400> SEQUENCE: 116
cagcacgaac gcgccgtcga tggc                                            24

<210> SEQ ID NO 117
<211> LENGTH: 26
<212> TYPE: DNA
<213> ORGANISM: Mycobacterium tuberculosis

<400> SEQUENCE: 117
acagatctgt gacggacatg aacccg                                          26

<210> SEQ ID NO 118
<211> LENGTH: 28
<212> TYPE: DNA
<213> ORGANISM: Mycobacterium tuberculosis

<400> SEQUENCE: 118
ttttccatgg tcacgggccc ccggtact                                        28

<210> SEQ ID NO 119
<211> LENGTH: 26
<212> TYPE: DNA
<213> ORGANISM: Mycobacterium tuberculosis

<400> SEQUENCE: 119
acagatctgt gcccatggca cagata                                          26

<210> SEQ ID NO 120
<211> LENGTH: 27
<212> TYPE: DNA
<213> ORGANISM: Mycobacterium tuberculosis

<400> SEQUENCE: 120
tttaagcttc taggcgccca gcgcggc                                         27
```

-continued

```
<210> SEQ ID NO 121
<211> LENGTH: 26
<212> TYPE: DNA
<213> ORGANISM: Mycobacterium tuberculosis

<400> SEQUENCE: 121
acagatctgc gcatgcggat ccgtgt                                              26

<210> SEQ ID NO 122
<211> LENGTH: 28
<212> TYPE: DNA
<213> ORGANISM: Mycobacterium tuberculosis

<400> SEQUENCE: 122
ttttccatgg tcatccggcg tgatcgag                                            28

<210> SEQ ID NO 123
<211> LENGTH: 26
<212> TYPE: DNA
<213> ORGANISM: Mycobacterium tuberculosis

<400> SEQUENCE: 123
acagatctgt aatggcagac tgtgat                                              26

<210> SEQ ID NO 124
<211> LENGTH: 28
<212> TYPE: DNA
<213> ORGANISM: Mycobacterium tuberculosis

<400> SEQUENCE: 124
ttttccatgg tcaggagatg gtgatcga                                            28

<210> SEQ ID NO 125
<211> LENGTH: 26
<212> TYPE: DNA
<213> ORGANISM: Mycobacterium tuberculosis

<400> SEQUENCE: 125
acagatctgc cggctacccc ggtgcc                                              26

<210> SEQ ID NO 126
<211> LENGTH: 28
<212> TYPE: DNA
<213> ORGANISM: Mycobacterium tuberculosis

<400> SEQUENCE: 126
ttttccatgg ctattgcagc tttccggc                                            28

<210> SEQ ID NO 127
<211> LENGTH: 50
<212> TYPE: PRT
<213> ORGANISM: Mycobacterium tuberculosis

<400> SEQUENCE: 127

Ala Glu Asp Val Arg Ala Glu Ile Val Ala Ser Val Leu Glu Val Val
 1               5                  10                  15

Val Asn Glu Gly Asp Gln Ile Asp Lys Gly Asp Val Val Val Leu Leu
            20                  25                  30

Glu Ser Met Tyr Met Glu Ile Pro Val Leu Ala Glu Ala Ala Gly Thr
        35                  40                  45

Val Ser
    50
```

```
<210> SEQ ID NO 128
<211> LENGTH: 49
<212> TYPE: PRT
<213> ORGANISM: Mycobacterium tuberculosis

<400> SEQUENCE: 128

Ala Glu Asp Val Arg Ala Glu Ile Val Ala Ser Val Leu Glu Val Val
 1               5                  10                  15
Val Asn Glu Gly Asp Gln Ile Asp Lys Gly Asp Val Val Leu Leu
            20                  25                  30
Glu Ser Met Met Glu Ile Pro Val Leu Ala Glu Ala Ala Gly Thr Val
        35                  40                  45
Ser

<210> SEQ ID NO 129
<211> LENGTH: 50
<212> TYPE: PRT
<213> ORGANISM: Mycobacterium tuberculosis

<400> SEQUENCE: 129

Ala Glu Asp Val Arg Ala Glu Ile Val Ala Ser Val Leu Glu Val Val
 1               5                  10                  15
Val Asn Glu Gly Asp Gln Ile Asp Lys Gly Asp Val Val Leu Leu
            20                  25                  30
Glu Ser Met Lys Met Glu Ile Pro Val Leu Ala Glu Ala Ala Gly Thr
        35                  40                  45
Val Ser
    50

<210> SEQ ID NO 130
<211> LENGTH: 33
<212> TYPE: DNA
<213> ORGANISM: Mycobacterium tuberculosis

<400> SEQUENCE: 130
ccgggagatc tatggcaaag ctctccaccg acg                               33

<210> SEQ ID NO 131
<211> LENGTH: 32
<212> TYPE: DNA
<213> ORGANISM: Mycobacterium tuberculosis

<400> SEQUENCE: 131
cgctgggcag agctacttga cggtgacggt gg                                32

<210> SEQ ID NO 132
<211> LENGTH: 36
<212> TYPE: DNA
<213> ORGANISM: Mycobacterium tuberculosis

<400> SEQUENCE: 132
ggcgccggca agcttgccat gacagagcag cagtgg                            36

<210> SEQ ID NO 133
<211> LENGTH: 26
<212> TYPE: DNA
<213> ORGANISM: Mycobacterium tuberculosis

<400> SEQUENCE: 133
cgaactcgcc ggatcccgtg tttcgc                                       26
```

-continued

```
<210> SEQ ID NO 134
<211> LENGTH: 32
<212> TYPE: DNA
<213> ORGANISM: Mycobacterium tuberculosis

<400> SEQUENCE: 134
ggcaaccgcg agatctttct cccggccggg gc                              32

<210> SEQ ID NO 135
<211> LENGTH: 27
<212> TYPE: DNA
<213> ORGANISM: Mycobacterium tuberculosis

<400> SEQUENCE: 135
ggcaagcttg ccggcgccta acgaact                                    27

<210> SEQ ID NO 136
<211> LENGTH: 30
<212> TYPE: DNA
<213> ORGANISM: Mycobacterium tuberculosis

<400> SEQUENCE: 136
ggacccagat ctatgacaga gcagcagtgg                                 30

<210> SEQ ID NO 137
<211> LENGTH: 47
<212> TYPE: DNA
<213> ORGANISM: Mycobacterium tuberculosis

<400> SEQUENCE: 137
ccggcagccc cggccgggag aaaagctttg cgaacatccc agtgacg              47

<210> SEQ ID NO 138
<211> LENGTH: 44
<212> TYPE: DNA
<213> ORGANISM: Mycobacterium tuberculosis

<400> SEQUENCE: 138
gttcgcaaag cttttctccc ggccggggct gccggtcgag tacc                 44

<210> SEQ ID NO 139
<211> LENGTH: 20
<212> TYPE: DNA
<213> ORGANISM: Mycobacterium tuberculosis

<400> SEQUENCE: 139
ccttcggtgg atcccgtcag                                            20

<210> SEQ ID NO 140
<211> LENGTH: 450
<212> TYPE: DNA
<213> ORGANISM: Mycobacterium tuberculosis

<400> SEQUENCE: 140
tggcgctgtc accgaggaac ctgtcaatgt cgtcgagcag tactgaaccg ttccgagaaa    60
ggccagcatg aacgtcaccg tatccattcc gaccatcctg cggccccaca ccggcggcca   120
gaagagtgtc tcggcagcg gcgatacctt gggtgccgtc atcagcgacc tggaggccaa   180
ctattcgggc atttccgagc gcctgatgga cccgtcttcc ccaggtaagt tgcaccgctt   240
cgtgaacatc tacgtcaacg acgaggacgt gcggttctcc ggcggcttgg ccaccgcgat   300
cgctgacggt gactcggtca ccatcctccc cgccgtggcc ggtgggtgag cggagcacat   360
```

```
gacacgatac gactcgctgt tgcaggcctt gggcaacacg ccgctggttg gcctgcagcg    420
attgtcgcca cgctgggatg acgggcgaga                                     450
```

```
<210> SEQ ID NO 141
<211> LENGTH: 93
<212> TYPE: PRT
<213> ORGANISM: Mycobacterium tuberculosis

<400> SEQUENCE: 141
```

Met Asn Val Thr Val Ser Ile Pro Thr Ile Leu Arg Pro His Thr Gly
1               5                   10                  15

Gly Gln Lys Ser Val Ser Ala Ser Gly Asp Thr Leu Gly Ala Val Ile
            20                  25                  30

Ser Asp Leu Glu Ala Asn Tyr Ser Gly Ile Ser Glu Arg Leu Met Asp
        35                  40                  45

Pro Ser Ser Pro Gly Lys Leu His Arg Phe Val Asn Ile Tyr Val Asn
    50                  55                  60

Asp Glu Asp Val Arg Phe Ser Gly Gly Leu Ala Thr Ala Ile Ala Asp
65                  70                  75                  80

Gly Asp Ser Val Thr Ile Leu Pro Ala Val Ala Gly Gly
                85                  90

```
<210> SEQ ID NO 142
<211> LENGTH: 480
<212> TYPE: DNA
<213> ORGANISM: Mycobacterium tuberculosis
<400> SEQUENCE: 142
ggtgttcccg cggccggcta tgacaacagt caatgtgcat gacaagttac aggtattagg     60
tccaggttca acaaggagac aggcaacatg gcaacacgtt ttatgacgga tccgcacgcg   120
atgcgggaca tggcgggccg ttttgaggtg cacgcccaga cggtggagga cgaggctcgc   180
cggatgtggg cgtccgcgca aacatctcg ggcgcgggct ggagtggcat ggccgaggcg    240
acctcgctag acaccatggc ccagatgaat caggcgtttc gcaacatcgt gaacatgctg   300
cacggggtgc gtgacgggct ggttcgcgac gccaacaact acgagcagca agagcaggcc   360
tcccagcaga tcctcagcag ctaacgtcag ccgctgcagc acaatacttt tacaagcgaa   420
ggagaacagg ttcgatgacc atcaactatc agttcggtga tgtcgacgct catggcgcca   480
```

```
<210> SEQ ID NO 143
<211> LENGTH: 98
<212> TYPE: PRT
<213> ORGANISM: Mycobacterium tuberculosis

<400> SEQUENCE: 143
```

Met Ala Thr Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Ala Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu

-continued

```
                      85                  90                  95
Ser Ser

<210> SEQ ID NO 144
<211> LENGTH: 940
<212> TYPE: DNA
<213> ORGANISM: Mycobacterium tuberculosis

<400> SEQUENCE: 144
gccccagtcc tcgatcgcct catcgccttc accggccgcc agccgaccgc aggccacgtg      60
tccgccacct aacgaaagga tgatcatgcc aagagaagc gaatacaggc aaggcacgcc     120
gaactgggtc gaccttcaga ccaccgatca gtccgccgcc aaaaagttct acacatcgtt     180
gttcggctgg ggttacgacg acaacccggt ccccggaggc ggtggggtct attccatggc     240
cacgctgaac ggcgaagccg tggccgccat cgcaccgatg cccccgggtg caccggaggg     300
gatgccgccg atctggaaca cctatatcgc ggtggacgac gtcgatgcgg tggtggacaa     360
ggtggtgccc gggggcgggc aggtgatgat gccggccttc gacatcggcg atgccggccg     420
gatgtcgttc atcaccgatc cgaccggcgc tgccgtgggc ctatggcagg ccaatcggca     480
catcggagcg acgttggtca acgagacggg cacgctcatc tggaacgaac tgctcacgga     540
caagccggat ttggcgctag cgttctacga ggctgtggtt ggcctcaccc actcgagcat     600
ggagatagct gcgggccaga actatcgggt gctcaaggcc ggcgacgcgg aagtcggcgg     660
ctgtatggaa ccgccgatgc ccggcgtgcc gaatcattgg cacgtctact ttgcggtgga     720
tgacgccgac gccacggcgg ccaaagccgc cgcagcgggc ggccaggtca ttgcggaacc     780
ggctgacatt ccgtcggtgg gccggttcgc cgtgttgtcc gatccgcagg gcgcgatctt     840
cagtgtgttg aagcccgcac cgcagcaata gggagcatcc cgggcaggcc cgccggccgg     900
cagattcgga gaatgctaga agctgccgcc ggcgccgccg                           940

<210> SEQ ID NO 145
<211> LENGTH: 261
<212> TYPE: PRT
<213> ORGANISM: Mycobacterium tuberculosis

<400> SEQUENCE: 145

Met Pro Lys Arg Ser Glu Tyr Arg Gln Gly Thr Pro Asn Trp Val Asp
1               5                   10                  15

Leu Gln Thr Thr Asp Gln Ser Ala Ala Lys Lys Phe Tyr Thr Ser Leu
            20                  25                  30

Phe Gly Trp Gly Tyr Asp Asp Asn Pro Val Pro Gly Gly Gly Val
        35                  40                  45

Tyr Ser Met Ala Thr Leu Asn Gly Glu Ala Val Ala Ala Ile Ala Pro
    50                  55                  60

Met Pro Pro Gly Ala Pro Glu Gly Met Pro Pro Ile Trp Asn Thr Tyr
65                  70                  75                  80

Ile Ala Val Asp Asp Val Asp Ala Val Val Asp Lys Val Val Pro Gly
                85                  90                  95

Gly Gly Gln Val Met Met Pro Ala Phe Asp Ile Gly Asp Ala Gly Arg
            100                 105                 110

Met Ser Phe Ile Thr Asp Pro Thr Gly Ala Ala Val Gly Leu Trp Gln
        115                 120                 125

Ala Asn Arg His Ile Gly Ala Thr Leu Val Asn Glu Thr Gly Thr Leu
    130                 135                 140
```

```
Ile Trp Asn Glu Leu Leu Thr Asp Lys Pro Asp Leu Ala Leu Ala Phe
145                 150                 155                 160

Tyr Glu Ala Val Val Gly Leu Thr His Ser Ser Met Glu Ile Ala Ala
            165                 170                 175

Gly Gln Asn Tyr Arg Val Leu Lys Ala Gly Asp Ala Glu Val Gly Gly
        180                 185                 190

Cys Met Glu Pro Pro Met Pro Gly Val Pro Asn His Trp His Val Tyr
    195                 200                 205

Phe Ala Val Asp Asp Ala Asp Ala Thr Ala Lys Ala Ala Ala Ala
    210                 215                 220

Gly Gly Gln Val Ile Ala Glu Pro Ala Asp Ile Pro Ser Val Gly Arg
225                 230                 235                 240

Phe Ala Val Leu Ser Asp Pro Gln Gly Ala Ile Phe Ser Val Leu Lys
                245                 250                 255

Pro Ala Pro Gln Gln
            260
```

<210> SEQ ID NO 146
<211> LENGTH: 280
<212> TYPE: DNA
<213> ORGANISM: Mycobacterium tuberculosis

<400> SEQUENCE: 146

```
ccgaaaggcg gtgcaccgca cccagaagaa aaggaaagat cgagaaatgc acagggaac      60
tgtgaagtgg ttcaacgcgg agaaggggtt cggctttatc gcccccgaag acggttccgc     120
ggatgtattt gtccactaca cggagatcca gggaacgggc ttccgcaccc ttgaagaaaa    180
ccagaaggtc gagttcgaga tcggccacag ccctaagggc ccccaggcca ccggagtccg    240
ctcgctctga gttaccccc g cgagcagacg caaaaagccc                          280
```

<210> SEQ ID NO 147
<211> LENGTH: 67
<212> TYPE: PRT
<213> ORGANISM: Mycobacterium tuberculosis

<400> SEQUENCE: 147

```
Met Pro Gln Gly Thr Val Lys Trp Phe Asn Ala Glu Lys Gly Phe Gly
1               5                   10                  15

Phe Ile Ala Pro Glu Asp Gly Ser Ala Asp Val Phe Val His Tyr Thr
            20                  25                  30

Glu Ile Gln Gly Thr Gly Phe Arg Thr Leu Glu Glu Asn Gln Lys Val
        35                  40                  45

Glu Phe Glu Ile Gly His Ser Pro Lys Gly Pro Gln Ala Thr Gly Val
    50                  55                  60

Arg Ser Leu
65
```

<210> SEQ ID NO 148
<211> LENGTH: 540
<212> TYPE: DNA
<213> ORGANISM: Mycobacterium tuberculosis

<400> SEQUENCE: 148

```
atcgtgtcgt atcgagaacc ccggccggta tcagaacgcg ccagagcgca aacctttata     60
acttcgtgtc ccaaatgtga cgaccatgga ccaaggttcc tgagatgaac ctacggcgcc    120
atcagaccct gacgctgcga ctgctggcgg catccgcggg cattctcagc gccgcggcct    180
```

```
tcgccgcgcc agcacaggca aaccccgtcg acgacgcgtt catcgccgcg ctgaacaatg    240
ccggcgtcaa ctacggcgat ccggtcgacg ccaaagcgct gggtcagtcc gtctgcccga    300
tcctggccga gccggcgggt cgtttaaca ccgcggtagc cagcgttgtg gcgcgcgccc    360
aaggcatgtc ccaggacatg gcgcaaacct tcaccagtat cgcgatttcg atgtactgcc    420
cctcggtgat ggcagacgtc gccagcggca acctgccggc cctgccagac atgccggggc    480
tgcccgggtc ctaggcgtgc gcggctccta gccggtccct aacggatcga tcgtggatgc    540
```

<210> SEQ ID NO 149
<211> LENGTH: 129
<212> TYPE: PRT
<213> ORGANISM: Mycobacterium tuberculosis

<400> SEQUENCE: 149

```
Met Asn Leu Arg Arg His Gln Thr Leu Thr Leu Arg Leu Leu Ala Ala
1               5                   10                  15

Ser Ala Gly Ile Leu Ser Ala Ala Phe Ala Ala Pro Ala Gln Ala
            20                  25                  30

Asn Pro Val Asp Asp Ala Phe Ile Ala Ala Leu Asn Asn Ala Gly Val
        35                  40                  45

Asn Tyr Gly Asp Pro Val Asp Ala Lys Ala Leu Gly Gln Ser Val Cys
    50                  55                  60

Pro Ile Leu Ala Glu Pro Gly Gly Ser Phe Asn Thr Ala Val Ala Ser
65                  70                  75                  80

Val Val Ala Arg Ala Gln Gly Met Ser Gln Asp Met Ala Gln Thr Phe
                85                  90                  95

Thr Ser Ile Ala Ile Ser Met Tyr Cys Pro Ser Val Met Ala Asp Val
            100                 105                 110

Ala Ser Gly Asn Leu Pro Ala Leu Pro Asp Met Pro Gly Leu Pro Gly
        115                 120                 125

Ser
```

<210> SEQ ID NO 150
<211> LENGTH: 400
<212> TYPE: DNA
<213> ORGANISM: Mycobacterium tuberculosis

<400> SEQUENCE: 150

```
atagtttggg gaaggtgtcc ataaatgagg ctgtcgttga ccgcattgag cgccggtgta    60
ggcgccgtgg caatgtcgtt gaccgtcggg gccgggtcg cctccgcaga tcccgtggac    120
gcggtcatta acaccacctg caattacggg caggtagtag ctgcgctcaa cgcgacggat    180
ccgggggctg ccgcacagtt caacgcctca ccggtggcgc agtcctattt gcgcaatttc    240
ctcgccgcac cgccacctca gcgcgctgcc atggccgcgc aattgcaagc tgtgccgggg    300
gcggcacagt acatcggcct tgtcgagtcg gttgccggct cctgcaacaa ctattaagcc    360
catgcgggcc ccatcccgcg acccggcatc gtcgccgggg                          400
```

<210> SEQ ID NO 151
<211> LENGTH: 110
<212> TYPE: PRT
<213> ORGANISM: Mycobacterium tuberculosis

<400> SEQUENCE: 151

```
Met Arg Leu Ser Leu Thr Ala Leu Ser Ala Gly Val Gly Ala Val Ala
1               5                   10                  15
```

```
Met Ser Leu Thr Val Gly Ala Gly Val Ala Ser Ala Asp Pro Val Asp
            20                  25                  30

Ala Val Ile Asn Thr Thr Cys Asn Tyr Gly Gln Val Val Ala Ala Leu
        35                  40                  45

Asn Ala Thr Asp Pro Gly Ala Ala Gln Phe Asn Ala Ser Pro Val
    50                  55                  60

Ala Gln Ser Tyr Leu Arg Asn Phe Leu Ala Pro Pro Pro Gln Arg
65              70                  75                  80

Ala Ala Met Ala Ala Gln Leu Gln Ala Val Pro Gly Ala Ala Gln Tyr
                85                  90                  95

Ile Gly Leu Val Glu Ser Val Ala Gly Ser Cys Asn Asn Tyr
            100                 105                 110

<210> SEQ ID NO 152
<211> LENGTH: 990
<212> TYPE: DNA
<213> ORGANISM: Mycobacterium tuberculosis

<400> SEQUENCE: 152
aatagtaata tcgctgtgcg gttgcaaaac gtgtgaccga ggttccgcag tcgagcgctg      60
cgggccgcct tcgaggagga cgaaccacag tcatgacgaa catcgtggtc ctgatcaagc     120
aggtcccaga tacctggtcg gagcgcaagc tgaccgacgg cgatttcacg ctggaccgcg     180
aggccgccga cgcggtgctg gacgagatca acgagcgcgc cgtggaggaa gcgctacaga     240
ttcgggagaa agaggccgcc gacggcatcg aaggtcggt aaccgtgctg acggcgggcc     300
ccgagcgcgc caccgaggcg atccgcaagg cgctgtcgat gggtgccgac aaggccgtcc     360
acctaaagga cgacggcatg cacggctcgg acgtcatcca aaccgggtgg gctttggcgc     420
gcgcgttggg caccatcgag ggcaccgagc tggtgatcgc aggcaacgaa tcgaccgacg     480
gggtgggcgg tgcggtgccg gccatcatcg ccgagtacct gggcctgccg cagctcaccc     540
acctgcgcaa agtgtcgatc gagggcggca agatcaccgg cgagcgtgag accgatgagg     600
gcgtattcac cctcgaggcc acgctgcccg cggtgatcag cgtgaacgag aagatcaacg     660
agccgcgctt cccgtccttc aaaggcatca tggccgccaa gaagaaggaa gttaccgtgc     720
tgaccctggc cgagatcggt gtcgagagcg acgaggtggg gctggccaac gccggatcca     780
ccgtgctggc gtcgacgccc aaaccggcca agactgccgg ggagaaggtc accgacgagg     840
gtgaaggcgg caaccagatc gtgcagtacc tggttgccca gaaaatcatc taagacatac     900
gcacctccca aagacgagag cgatataacc catggctgaa gtactggtgc tcgttgagca     960
cgctgaaggc gcgttaaaga aggtcagcgc                                       990

<210> SEQ ID NO 153
<211> LENGTH: 266
<212> TYPE: PRT
<213> ORGANISM: Mycobacterium tuberculosis

<400> SEQUENCE: 153

Met Thr Asn Ile Val Val Leu Ile Lys Gln Val Pro Asp Thr Trp Ser
1               5                   10                  15

Glu Arg Lys Leu Thr Asp Gly Asp Phe Thr Leu Asp Arg Glu Ala Ala
            20                  25                  30

Asp Ala Val Leu Asp Glu Ile Asn Glu Arg Ala Val Glu Glu Ala Leu
        35                  40                  45

Gln Ile Arg Glu Lys Glu Ala Ala Asp Gly Ile Glu Gly Ser Val Thr
    50                  55                  60
```

```
Val Leu Thr Ala Gly Pro Glu Arg Ala Thr Glu Ala Ile Arg Lys Ala
 65                  70                  75                  80

Leu Ser Met Gly Ala Asp Lys Ala Val His Leu Lys Asp Asp Gly Met
                 85                  90                  95

His Gly Ser Asp Val Ile Gln Thr Gly Trp Ala Leu Ala Arg Ala Leu
            100                 105                 110

Gly Thr Ile Glu Gly Thr Glu Leu Val Ile Ala Gly Asn Glu Ser Thr
        115                 120                 125

Asp Gly Val Gly Gly Ala Val Pro Ala Ile Ile Ala Glu Tyr Leu Gly
130                 135                 140

Leu Pro Gln Leu Thr His Leu Arg Lys Val Ser Ile Glu Gly Gly Lys
145                 150                 155                 160

Ile Thr Gly Glu Arg Glu Thr Asp Glu Gly Val Phe Thr Leu Glu Ala
                165                 170                 175

Thr Leu Pro Ala Val Ile Ser Val Asn Glu Lys Ile Asn Glu Pro Arg
            180                 185                 190

Phe Pro Ser Phe Lys Gly Ile Met Ala Ala Lys Lys Glu Val Thr
        195                 200                 205

Val Leu Thr Leu Ala Glu Ile Gly Val Glu Ser Asp Glu Val Gly Leu
210                 215                 220

Ala Asn Ala Gly Ser Thr Val Leu Ala Ser Thr Pro Lys Pro Ala Lys
225                 230                 235                 240

Thr Ala Gly Glu Lys Val Thr Asp Glu Gly Gly Asn Gln Ile
                245                 250                 255

Val Gln Tyr Leu Val Ala Gln Lys Ile Ile
            260                 265

<210> SEQ ID NO 154
<211> LENGTH: 25
<212> TYPE: DNA
<213> ORGANISM: Mycobacterium tuberculosis

<400> SEQUENCE: 154
ctgagatcta tgaacctacg gcgcc                                        25

<210> SEQ ID NO 155
<211> LENGTH: 35
<212> TYPE: DNA
<213> ORGANISM: Mycobacterium tuberculosis

<400> SEQUENCE: 155
ctcccatggt accctaggac ccgggcagcc ccggc                             35

<210> SEQ ID NO 156
<211> LENGTH: 29
<212> TYPE: DNA
<213> ORGANISM: Mycobacterium tuberculosis

<400> SEQUENCE: 156
ctgagatcta tgaggctgtc gttgaccgc                                    29

<210> SEQ ID NO 157
<211> LENGTH: 30
<212> TYPE: DNA
<213> ORGANISM: Mycobacterium tuberculosis

<400> SEQUENCE: 157
ctccccgggc ttaatagttg ttgcaggagc                                   30
```

<210> SEQ ID NO 158
<211> LENGTH: 33
<212> TYPE: DNA
<213> ORGANISM: Mycobacterium tuberculosis

<400> SEQUENCE: 158
gcttagatct atgattttct gggcaaccag gta                33

<210> SEQ ID NO 159
<211> LENGTH: 30
<212> TYPE: DNA
<213> ORGANISM: Mycobacterium tuberculosis

<400> SEQUENCE: 159
gcttccatgg gcgaggcaca ggcgtgggaa                30

<210> SEQ ID NO 160
<211> LENGTH: 30
<212> TYPE: DNA
<213> ORGANISM: Mycobacterium tuberculosis

<400> SEQUENCE: 160
ctgagatcta gaatgccaca gggaactgtg                30

<210> SEQ ID NO 161
<211> LENGTH: 30
<212> TYPE: DNA
<213> ORGANISM: Mycobacterium tuberculosis

<400> SEQUENCE: 161
tctcccgggg gtaactcaga gcgagcggac                30

<210> SEQ ID NO 162
<211> LENGTH: 27
<212> TYPE: DNA
<213> ORGANISM: Mycobacterium tuberculosis

<400> SEQUENCE: 162
ctgagatcta tgaacgtcac cgtatcc                27

<210> SEQ ID NO 163
<211> LENGTH: 27
<212> TYPE: DNA
<213> ORGANISM: Mycobacterium tuberculosis

<400> SEQUENCE: 163
tctcccgggg ctcacccacc ggccacg                27

<210> SEQ ID NO 164
<211> LENGTH: 30
<212> TYPE: DNA
<213> ORGANISM: Mycobacterium tuberculosis

<400> SEQUENCE: 164
ctgagatcta tggcaacacg ttttatgacg                30

<210> SEQ ID NO 165
<211> LENGTH: 30
<212> TYPE: DNA
<213> ORGANISM: Mycobacterium tuberculosis

<400> SEQUENCE: 165

-continued

```
ctccccgggt tagctgctga ggatctgcth                                              30
```

<210> SEQ ID NO 166
<211> LENGTH: 31
<212> TYPE: DNA
<213> ORGANISM: Mycobacterium tuberculosis

<400> SEQUENCE: 166

```
ctgaagatct atgcccaaga gaagcgaata c                                            31
```

<210> SEQ ID NO 167
<211> LENGTH: 31
<212> TYPE: DNA
<213> ORGANISM: Mycobacterium tuberculosis

<400> SEQUENCE: 167

```
cggcagctgc tagcattctc cgaatctgcc g                                            31
```

<210> SEQ ID NO 168
<211> LENGTH: 15
<212> TYPE: PRT
<213> ORGANISM: Mycobacterium tuberculosis

<400> SEQUENCE: 168

```
Pro Gln Gly Thr Val Lys Trp Phe Asn Ala Glu Lys Gly Phe Gly
1               5                   10                  15
```

<210> SEQ ID NO 169
<211> LENGTH: 15
<212> TYPE: PRT
<213> ORGANISM: Mycobacterium tuberculosis
<220> FEATURE:
<221> NAME/KEY: misc_feature
<222> LOCATION: (15)..(15)
<223> OTHER INFORMATION: "Xaa" is unknown
<221> NAME/KEY: misc_feature
<222> LOCATION: (13)..(13)
<223> OTHER INFORMATION: "Xaa" is unknown
<221> NAME/KEY: misc_feature
<222> LOCATION: (14)..(14)
<223> OTHER INFORMATION: "Xaa" is unknown

<400> SEQUENCE: 169

```
Asn Val Thr Val Ser Ile Pro Thr Ile Leu Arg Pro Xaa Xaa Xaa
1               5                   10                  15
```

<210> SEQ ID NO 170
<211> LENGTH: 15
<212> TYPE: PRT
<213> ORGANISM: Mycobacterium tuberculosis
<220> FEATURE:
<221> NAME/KEY: variant
<222> LOCATION: (1)..(1)
<223> OTHER INFORMATION: Thr can be Thr or Ala

<400> SEQUENCE: 170

```
Thr Arg Phe Met Thr Asp Pro His Ala Met Arg Asp Met Ala Gly
1               5                   10                  15
```

<210> SEQ ID NO 171
<211> LENGTH: 15
<212> TYPE: PRT
<213> ORGANISM: Mycobacterium tuberculosis

<400> SEQUENCE: 171

```
Pro Lys Arg Ser Glu Tyr Arg Gln Gly Thr Pro Asn Trp Val Asp
1               5                   10                  15
```

<210> SEQ ID NO 172
<211> LENGTH: 404
<212> TYPE: PRT
<213> ORGANISM: Mycobacterium tuberculosis

<400> SEQUENCE: 172

Met Ala Thr Val Asn Arg Ser Arg His His His His His His
1               5                   10                  15

Ile Glu Gly Arg Ser Phe Ser Arg Pro Gly Leu Pro Val Glu Tyr Leu
            20                  25                  30

Gln Val Pro Ser Pro Ser Met Gly Arg Asp Ile Lys Val Gln Phe Gln
        35                  40                  45

Ser Gly Gly Asn Asn Ser Pro Ala Val Tyr Leu Leu Asp Gly Leu Arg
    50                  55                  60

Ala Gln Asp Asp Tyr Asn Gly Trp Asp Ile Asn Thr Pro Ala Phe Glu
65                  70                  75                  80

Trp Tyr Tyr Gln Ser Gly Leu Ser Ile Val Met Pro Val Gly Gly Gln
                85                  90                  95

Ser Ser Phe Tyr Ser Asp Trp Tyr Ser Pro Ala Cys Gly Lys Ala Gly
            100                 105                 110

Cys Gln Thr Tyr Lys Trp Glu Thr Phe Leu Thr Ser Glu Leu Pro Gln
        115                 120                 125

Trp Leu Ser Ala Asn Arg Ala Val Lys Pro Thr Gly Ser Ala Ala Ile
    130                 135                 140

Gly Leu Ser Met Ala Gly Ser Ser Ala Met Ile Leu Ala Ala Tyr His
145                 150                 155                 160

Pro Gln Gln Phe Ile Tyr Ala Gly Ser Leu Ser Ala Leu Leu Asp Pro
                165                 170                 175

Ser Gln Gly Met Gly Pro Ser Leu Ile Gly Leu Ala Met Gly Asp Ala
            180                 185                 190

Gly Gly Tyr Lys Ala Ala Asp Met Trp Gly Pro Ser Ser Asp Pro Ala
        195                 200                 205

Trp Glu Arg Asn Asp Pro Thr Gln Gln Ile Pro Lys Leu Val Ala Asn
    210                 215                 220

Asn Thr Arg Leu Trp Val Tyr Cys Gly Asn Gly Thr Pro Asn Glu Leu
225                 230                 235                 240

Gly Gly Ala Asn Ile Pro Ala Glu Phe Leu Glu Asn Phe Val Arg Ser
                245                 250                 255

Ser Asn Leu Lys Phe Gln Asp Ala Tyr Asn Ala Ala Gly Gly His Asn
            260                 265                 270

Ala Val Phe Asn Phe Pro Pro Asn Gly Thr His Ser Trp Glu Tyr Trp
        275                 280                 285

Gly Ala Gln Leu Asn Ala Met Lys Gly Asp Leu Gln Ser Ser Leu Gly
    290                 295                 300

Ala Gly Lys Leu Ala Met Thr Glu Gln Gln Trp Asn Phe Ala Gly Ile
305                 310                 315                 320

Glu Ala Ala Ala Ser Ala Ile Gln Gly Asn Val Thr Ser Ile His Ser
                325                 330                 335

Leu Leu Asp Glu Gly Lys Gln Ser Leu Thr Lys Leu Ala Ala Ala Trp
            340                 345                 350

Gly Gly Ser Gly Ser Glu Ala Tyr Gln Gly Val Gln Gln Lys Trp Asp
        355                 360                 365

Ala Thr Ala Thr Glu Leu Asn Asn Ala Leu Gln Asn Leu Ala Arg Thr

```
            370                 375                 380
Ile Ser Glu Ala Gly Gln Ala Met Ala Ser Thr Glu Gly Asn Val Thr
385                 390                 395                 400

Gly Met Phe Ala

<210> SEQ ID NO 173
<211> LENGTH: 403
<212> TYPE: PRT
<213> ORGANISM: Mycobacterium tuberculosis

<400> SEQUENCE: 173

Met Ala Thr Val Asn Arg Ser Arg His His His His His His
1               5                   10                  15

Ile Glu Gly Arg Ser Met Thr Glu Gln Gln Trp Asn Phe Ala Gly Ile
                20                  25                  30

Glu Ala Ala Ala Ser Ala Ile Gln Gly Asn Val Thr Ser Ile His Ser
            35                  40                  45

Leu Leu Asp Glu Gly Lys Gln Ser Leu Thr Lys Leu Ala Ala Ala Trp
        50                  55                  60

Gly Gly Ser Gly Ser Glu Ala Tyr Gln Gly Val Gln Gln Lys Trp Asp
65                  70                  75                  80

Ala Thr Ala Thr Glu Leu Asn Asn Ala Leu Gln Asn Leu Ala Arg Thr
                85                  90                  95

Ile Ser Glu Ala Gly Gln Ala Met Ala Ser Thr Glu Gly Asn Val Thr
            100                 105                 110

Gly Met Phe Ala Lys Leu Phe Ser Arg Pro Gly Leu Pro Val Glu Tyr
        115                 120                 125

Leu Gln Val Pro Ser Pro Ser Met Gly Arg Asp Ile Lys Val Gln Phe
130                 135                 140

Gln Ser Gly Gly Asn Asn Ser Pro Ala Val Tyr Leu Leu Asp Gly Leu
145                 150                 155                 160

Arg Ala Gln Asp Asp Tyr Asn Gly Trp Asp Ile Asn Thr Pro Ala Phe
                165                 170                 175

Glu Trp Tyr Tyr Gln Ser Gly Leu Ser Ile Val Met Pro Val Gly Gly
            180                 185                 190

Gln Ser Ser Phe Tyr Ser Asp Trp Tyr Ser Pro Ala Cys Gly Lys Ala
        195                 200                 205

Gly Cys Gln Thr Tyr Lys Trp Glu Thr Phe Leu Thr Ser Glu Leu Pro
210                 215                 220

Gln Trp Leu Ser Ala Asn Arg Ala Val Lys Pro Thr Gly Ser Ala Ala
225                 230                 235                 240

Ile Gly Leu Ser Met Ala Gly Ser Ser Ala Met Ile Leu Ala Ala Tyr
                245                 250                 255

His Pro Gln Gln Phe Ile Tyr Ala Gly Ser Leu Ser Ala Leu Leu Asp
            260                 265                 270

Pro Ser Gln Gly Met Gly Pro Ser Leu Ile Gly Leu Ala Met Gly Asp
        275                 280                 285

Ala Gly Gly Tyr Lys Ala Ala Asp Met Trp Gly Pro Ser Ser Asp Pro
    290                 295                 300

Ala Trp Glu Arg Asn Asp Pro Thr Gln Gln Ile Pro Lys Leu Val Ala
305                 310                 315                 320

Asn Asn Thr Arg Leu Trp Val Tyr Cys Gly Asn Gly Thr Pro Asn Glu
                325                 330                 335

Leu Gly Gly Ala Asn Ile Pro Ala Glu Phe Leu Glu Asn Phe Val Arg
```

```
                    340                 345                 350
Ser Ser Asn Leu Lys Phe Gln Asp Ala Tyr Asn Ala Ala Gly Gly His
                355                 360                 365

Asn Ala Val Phe Asn Phe Pro Pro Asn Gly Thr His Ser Trp Glu Tyr
            370                 375                 380

Trp Gly Ala Gln Leu Asn Ala Met Lys Gly Asp Leu Gln Ser Ser Leu
385                 390                 395                 400

Gly Ala Gly

<210> SEQ ID NO 174
<211> LENGTH: 291
<212> TYPE: DNA
<213> ORGANISM: Mycobacterium tuberculosis

<400> SEQUENCE: 174
atgtcgcaga ttatgtacaa ctatccggcg atgatggctc atgccgggga catggccggt      60
tatgcgggca cgctgcagag cttgggggcc gatatcgcca gtgagcaggc cgtgctgtcc     120
agtgcttggc aggtgatac cgggatcacg tatcagggct ggcagaccca gtggaaccag      180
gccctagagg atctggtgcg ggcctatcag tcgatgtctg gcacccatga gtccaacacc     240
atggcgatgt tggctcgaga tggggccgaa gccgccaagt ggggcggcta g              291

<210> SEQ ID NO 175
<211> LENGTH: 96
<212> TYPE: PRT
<213> ORGANISM: Mycobacterium tuberculosis

<400> SEQUENCE: 175

Met Ser Gln Ile Met Tyr Asn Tyr Pro Ala Met Met Ala His Ala Gly
1               5                   10                  15

Asp Met Ala Gly Tyr Ala Gly Thr Leu Gln Ser Leu Gly Ala Asp Ile
            20                  25                  30

Ala Ser Glu Gln Ala Val Leu Ser Ser Ala Trp Gln Gly Asp Thr Gly
        35                  40                  45

Ile Thr Tyr Gln Gly Trp Gln Thr Gln Trp Asn Gln Ala Leu Glu Asp
    50                  55                  60

Leu Val Arg Ala Tyr Gln Ser Met Ser Gly Thr His Glu Ser Asn Thr
65                  70                  75                  80

Met Ala Met Leu Ala Arg Asp Gly Ala Glu Ala Ala Lys Trp Gly Gly
                85                  90                  95

<210> SEQ ID NO 176
<211> LENGTH: 363
<212> TYPE: DNA
<213> ORGANISM: Mycobacterium tuberculosis

<400> SEQUENCE: 176
gtgtcgcaga gtatgtacag ctacccggcg atgacggcca atgtcggaga catggccggt      60
tatacgggca cgacgcagag cttgggggcc gatatcgcca gtgagcgcac cgcgccgtcg     120
cgtgcttgcc aaggtgatct cgggatgagt catcaggact ggcaggccca gtggaatcag     180
gccatggagg ctctcgcgcg ggcctaccgt cggtgccggc gagcactacg ccagatcggg     240
gtgctggaaa ggccggtagg cgattcgtca gactgcggaa cgattagggt ggggtcgttc     300
cggggtcggt ggctggaccc gcgccatgcg ggtccagcca cggccgccga cgccggagac     360
taa                                                                  363
```

<210> SEQ ID NO 177
<211> LENGTH: 120
<212> TYPE: PRT
<213> ORGANISM: Mycobacterium tuberculosis

<400> SEQUENCE: 177

Met Ser Gln Ser Met Tyr Ser Tyr Pro Ala Met Thr Ala Asn Val Gly
1               5                   10                  15

Asp Met Ala Gly Tyr Thr Gly Thr Thr Gln Ser Leu Gly Ala Asp Ile
            20                  25                  30

Ala Ser Glu Arg Thr Ala Pro Ser Arg Ala Cys Gln Gly Asp Leu Gly
        35                  40                  45

Met Ser His Gln Asp Trp Gln Ala Gln Trp Asn Gln Ala Met Glu Ala
    50                  55                  60

Leu Ala Arg Ala Tyr Arg Arg Cys Arg Arg Ala Leu Arg Gln Ile Gly
65                  70                  75                  80

Val Leu Glu Arg Pro Val Gly Asp Ser Ser Asp Cys Gly Thr Ile Arg
                85                  90                  95

Val Gly Ser Phe Arg Gly Arg Trp Leu Asp Pro Arg His Ala Gly Pro
            100                 105                 110

Ala Thr Ala Ala Asp Ala Gly Asp
        115                 120

<210> SEQ ID NO 178
<211> LENGTH: 297
<212> TYPE: DNA
<213> ORGANISM: Mycobacterium tuberculosis

<400> SEQUENCE: 178
atggcctcgc gttttatgac ggatccgcac gcgatgcggg acatggcggg ccgttttgag      60
gtgcacgccc agacggtgga ggacgaggct cgccggatgt gggcgtccgc gcaaaacatc     120
tcgggcgcgg gctggagtgg catggccgag gcgacctcgc tagacaccat gacccagatg     180
aatcaggcgt tcgcaacat cgtgaacatg ctgcacgggg tgcgtgacgg gctggttcgc      240
gacgccaaca actacgaaca gcaagagcag gcctcccagc agatcctcag cagctga        297

<210> SEQ ID NO 179
<211> LENGTH: 98
<212> TYPE: PRT
<213> ORGANISM: Mycobacterium tuberculosis

<400> SEQUENCE: 179

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser Ser

```
<210> SEQ ID NO 180
<211> LENGTH: 297
<212> TYPE: DNA
<213> ORGANISM: Mycobacterium tuberculosis

<400> SEQUENCE: 180
atggcctcac gttttatgac ggatccgcac gcgatgcggg acatggcggg ccgttttgag      60
gtgcacgccc agacggtgga ggacgaggct cgccggatgt gggcgtccgc gcaaaacatt     120
tccggtgcgg gctggagtgg catggccgag gcgacctcgc tagacaccat ggcccagatg     180
aatcaggcgt tcgcaacat cgtgaacatg ctgcacgggg tgcgtgacgg gctggttcgc      240
gacgccaaca actacgagca gcaagagcag gcctcccagc agatcctcag cagctaa       297

<210> SEQ ID NO 181
<211> LENGTH: 98
<212> TYPE: PRT
<213> ORGANISM: Mycobacterium tuberculosis

<400> SEQUENCE: 181

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Ala Gln Met Asn Gln Ala Phe
    50                  55                  60

Arg Asn Ile Val Asn Met Leu His Gly Val Arg Asp Gly Leu Val Arg
65                  70                  75                  80

Asp Ala Asn Asn Tyr Glu Gln Gln Glu Gln Ala Ser Gln Gln Ile Leu
                85                  90                  95

Ser Ser

<210> SEQ ID NO 182
<211> LENGTH: 297
<212> TYPE: DNA
<213> ORGANISM: Mycobacterium tuberculosis

<400> SEQUENCE: 182
atggcctcac gttttatgac ggatccgcat gcgatgcggg acatggcggg ccgttttgag      60
gtgcacgccc agacggtgga ggacgaggct cgccggatgt gggcgtccgc gcaaaacatt     120
tccggtgcgg gctggagtgg catggccgag gcgacctcgc tagacaccat gacctagatg     180
aatcaggcgt tcgcaacat cgtgaacatg ctgcacgggg tgcgtgacgg gctggttcgc      240
gacgccaaca actacgaaca gcaagagcag gcctcccagc agatcctgag cagctag       297

<210> SEQ ID NO 183
<211> LENGTH: 98
<212> TYPE: PRT
<213> ORGANISM: Mycobacterium tuberculosis

<400> SEQUENCE: 183

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45
```

```
Ala Glu Ala Thr Ser Leu Asp Thr Met Thr Gln Met Asn Gln Ala Phe
         50                  55                  60

Arg Asn Ile Val Asn Met Leu His Gly Val Arg Asp Gly Leu Val Arg
 65                  70                  75                  80

Asp Ala Asn Asn Tyr Glu Gln Gln Glu Gln Ala Ser Gln Gln Ile Leu
                 85                  90                  95

Ser Ser

<210> SEQ ID NO 184
<211> LENGTH: 297
<212> TYPE: DNA
<213> ORGANISM: Mycobacterium tuberculosis

<400> SEQUENCE: 184
atgacctcgc gttttatgac ggatccgcac gcgatgcggg acatggcggg ccgttttgag      60
gtgcacgccc agacggtgga ggacgaggct cgccggatgt gggcgtccgc gcaaaacatt     120
tccggcgcgg gctggagtgg catggccgag gcgacctcgc tagacaccat gacccagatg     180
aatcaggcgt tcgcaacat cgtgaacatg ctgcacgggg tgcgtgacgg gctggttcgc     240
gacgccaaca actacgaaca gcaagagcag gcctcccagc agatcctcag cagctga       297

<210> SEQ ID NO 185
<211> LENGTH: 98
<212> TYPE: PRT
<213> ORGANISM: Mycobacterium tuberculosis

<400> SEQUENCE: 185

Met Thr Ser Arg Phe Met Thr Asp Pro His Ala Met Arg Asp Met Ala
 1               5                  10                  15

Gly Arg Phe Glu Val His Ala Gln Thr Val Glu Asp Glu Ala Arg Arg
                 20                  25                  30

Met Trp Ala Ser Ala Gln Asn Ile Ser Gly Ala Gly Trp Ser Gly Met
             35                  40                  45

Ala Glu Ala Thr Ser Leu Asp Thr Met Thr Gln Met Asn Gln Ala Phe
         50                  55                  60

Arg Asn Ile Val Asn Met Leu His Gly Val Arg Asp Gly Leu Val Arg
 65                  70                  75                  80

Asp Ala Asn Asn Tyr Glu Gln Gln Glu Gln Ala Ser Gln Gln Ile Leu
                 85                  90                  95

Ser Ser

<210> SEQ ID NO 186
<211> LENGTH: 20
<212> TYPE: DNA
<213> ORGANISM: Mycobacterium tuberculosis

<400> SEQUENCE: 186
ggaatgaaaa ggggtttgtg                                                  20

<210> SEQ ID NO 187
<211> LENGTH: 20
<212> TYPE: DNA
<213> ORGANISM: Mycobacterium tuberculosis

<400> SEQUENCE: 187
gaccacgccc gcgccgtgtg                                                  20
```

```
<210> SEQ ID NO 188
<211> LENGTH: 27
<212> TYPE: DNA
<213> ORGANISM: Mycobacterium tuberculosis

<400> SEQUENCE: 188
gcaacacccg ggatgtcgca gattatg                                         27

<210> SEQ ID NO 189
<211> LENGTH: 30
<212> TYPE: DNA
<213> ORGANISM: Mycobacterium tuberculosis

<400> SEQUENCE: 189
ctaagcttgg atccctagcc gccccacttg                                      30

<210> SEQ ID NO 190
<211> LENGTH: 22
<212> TYPE: DNA
<213> ORGANISM: Mycobacterium tuberculosis

<400> SEQUENCE: 190
gaatatttga aagggattcg tg                                              22

<210> SEQ ID NO 191
<211> LENGTH: 30
<212> TYPE: DNA
<213> ORGANISM: Mycobacterium tuberculosis

<400> SEQUENCE: 191
ctactaagct tggatcctta gtctccggcg                                      30

<210> SEQ ID NO 192
<211> LENGTH: 27
<212> TYPE: DNA
<213> ORGANISM: Mycobacterium tuberculosis

<400> SEQUENCE: 192
gcaacacccg gggtgtcgca gagtatg                                         27

<210> SEQ ID NO 193
<211> LENGTH: 30
<212> TYPE: DNA
<213> ORGANISM: Mycobacterium tuberculosis

<400> SEQUENCE: 193
ctactaagct tggatcctta gtctccggcg                                      30

<210> SEQ ID NO 194
<211> LENGTH: 381
<212> TYPE: DNA
<213> ORGANISM: Mycobacterium tuberculosis
<220> FEATURE:
<221> NAME/KEY: CDS
<222> LOCATION: (91)..(378)

<400> SEQUENCE: 194
ggccgccggt acctatgtgg ccgccgatgc tgcggacgcg tcgacctata ccgggttctg     60
atcgaaccct gctgaccgag aggacttgtg atg tcg caa atc atg tac aac tac    114
                                  Met Ser Gln Ile Met Tyr Asn Tyr
                                    1               5 ccc gcg atg ttg ggt cac gcc ggg gat atg gcc gga tat gcc ggc acg      162
Pro Ala Met Leu Gly His Ala Gly Asp Met Ala Gly Tyr Ala Gly Thr
         10                  15                  20
```

```
ctg cag agc ttg ggt gcc gag atc gcc gtg gag cag gcc gcg ttg cag        210
Leu Gln Ser Leu Gly Ala Glu Ile Ala Val Glu Gln Ala Ala Leu Gln
 25                  30                  35                  40 agt gcg tgg cag ggc gat acc ggg atc acg tat cag gcg tgg cag gca        258
Ser Ala Trp Gln Gly Asp Thr Gly Ile Thr Tyr Gln Ala Trp Gln Ala
                     45                  50                  55 cag tgg aac cag gcc atg gaa gat ttg gtg cgg gcc tat cat gcg atg        306
Gln Trp Asn Gln Ala Met Glu Asp Leu Val Arg Ala Tyr His Ala Met
             60                  65                  70 tcc agc acc cat gaa gcc aac acc atg gcg atg atg gcc cgc gac acc        354
Ser Ser Thr His Glu Ala Asn Thr Met Ala Met Met Ala Arg Asp Thr
         75                  80                  85 gcc gaa gcc gcc aaa tgg ggc ggc tag                                    381
Ala Glu Ala Ala Lys Trp Gly Gly
 90                  95

<210> SEQ ID NO 195
<211> LENGTH: 96
<212> TYPE: PRT
<213> ORGANISM: Mycobacterium tuberculosis

<400> SEQUENCE: 195

Met Ser Gln Ile Met Tyr Asn Tyr Pro Ala Met Leu Gly His Ala Gly
 1               5                   10                  15

Asp Met Ala Gly Tyr Ala Gly Thr Leu Gln Ser Leu Gly Ala Glu Ile
                 20                  25                  30

Ala Val Glu Gln Ala Ala Leu Gln Ser Ala Trp Gln Gly Asp Thr Gly
             35                  40                  45

Ile Thr Tyr Gln Ala Trp Gln Ala Gln Trp Asn Gln Ala Met Glu Asp
         50                  55                  60

Leu Val Arg Ala Tyr His Ala Met Ser Ser Thr His Glu Ala Asn Thr
 65                  70                  75                  80

Met Ala Met Met Ala Arg Asp Thr Ala Glu Ala Ala Lys Trp Gly Gly
                 85                  90                  95

<210> SEQ ID NO 196
<211> LENGTH: 363
<212> TYPE: DNA
<213> ORGANISM: Mycobacterium tuberculosis
<220> FEATURE:
<221> NAME/KEY: CDS
<222> LOCATION: (1)..(360)

<400> SEQUENCE: 196 gtg tcg cag agt atg tac agc tac ccg gcg atg acg gcc aat gtc gga        48
Val Ser Gln Ser Met Tyr Ser Tyr Pro Ala Met Thr Ala Asn Val Gly
 1               5                   10                  15 gac atg gcc ggt tat acg ggc acg acg cag agc ttg ggg gcc gat atc        96
Asp Met Ala Gly Tyr Thr Gly Thr Thr Gln Ser Leu Gly Ala Asp Ile
                 20                  25                  30 gcc agt gag cgc acc gcg ccg tcg cgt gct tgc caa ggt gat ctc ggg        144
Ala Ser Glu Arg Thr Ala Pro Ser Arg Ala Cys Gln Gly Asp Leu Gly
             35                  40                  45 atg agt cat cag gac tgg cag gcc cag tgg aat cag gcc atg gag gct        192
Met Ser His Gln Asp Trp Gln Ala Gln Trp Asn Gln Ala Met Glu Ala
         50                  55                  60 ctc gcg cgg gcc tac cgt cgg tgc cgg cga gca cta cgc cag atc ggg        240
Leu Ala Arg Ala Tyr Arg Arg Cys Arg Arg Ala Leu Arg Gln Ile Gly
 65                  70                  75                  80 gtg ctg gaa agg ccg gta ggc gat tcg tca gac tgc gga acg att agg        288
```

```
Val Leu Glu Arg Pro Val Gly Asp Ser Ser Asp Cys Gly Thr Ile Arg
                85                  90                  95 gtg ggg tcg ttc cgg ggt cgg tgg ctg gac ccg cgc cat gcg ggt cca        336
Val Gly Ser Phe Arg Gly Arg Trp Leu Asp Pro Arg His Ala Gly Pro
            100                 105                 110 gcc acg gcc gcc gac gcc gga gac taa                                    363
Ala Thr Ala Ala Asp Ala Gly Asp
        115                 120

<210> SEQ ID NO 197
<211> LENGTH: 120
<212> TYPE: PRT
<213> ORGANISM: Mycobacterium tuberculosis

<400> SEQUENCE: 197

Val Ser Gln Ser Met Tyr Ser Tyr Pro Ala Met Thr Ala Asn Val Gly
1               5                   10                  15

Asp Met Ala Gly Tyr Thr Gly Thr Thr Gln Ser Leu Gly Ala Asp Ile
            20                  25                  30

Ala Ser Glu Arg Thr Ala Pro Ser Arg Ala Cys Gln Gly Asp Leu Gly
        35                  40                  45

Met Ser His Gln Asp Trp Gln Ala Gln Trp Asn Gln Ala Met Glu Ala
    50                  55                  60

Leu Ala Arg Ala Tyr Arg Arg Cys Arg Arg Ala Leu Arg Gln Ile Gly
65                  70                  75                  80

Val Leu Glu Arg Pro Val Gly Asp Ser Ser Asp Cys Gly Thr Ile Arg
                85                  90                  95

Val Gly Ser Phe Arg Gly Arg Trp Leu Asp Pro Arg His Ala Gly Pro
            100                 105                 110

Ala Thr Ala Ala Asp Ala Gly Asp
        115                 120

<210> SEQ ID NO 198
<211> LENGTH: 291
<212> TYPE: DNA
<213> ORGANISM: Mycobacterium tuberculosis
<220> FEATURE:
<221> NAME/KEY: CDS
<222> LOCATION: (1)..(288)

<400> SEQUENCE: 198 atg tcg cag att atg tac aac tat ccg gcg atg atg gct cat gcc ggg         48
Met Ser Gln Ile Met Tyr Asn Tyr Pro Ala Met Met Ala His Ala Gly
1               5                   10                  15 gac atg gcc ggt tat gcg ggc acg ctg cag agc ttg ggg gcc gat atc         96
Asp Met Ala Gly Tyr Ala Gly Thr Leu Gln Ser Leu Gly Ala Asp Ile
            20                  25                  30 gcc agt gag cag gcc gtg ctg tcc agt gct tgg cag ggt gat acc ggg        144
Ala Ser Glu Gln Ala Val Leu Ser Ser Ala Trp Gln Gly Asp Thr Gly
        35                  40                  45 atc acg tat cag ggc tgg cag acc cag tgg aac cag gcc cta gag gat        192
Ile Thr Tyr Gln Gly Trp Gln Thr Gln Trp Asn Gln Ala Leu Glu Asp
    50                  55                  60 ctg gtg cgg gcc tat cag tcg atg tct ggc acc cat gag tcc aac acc        240
Leu Val Arg Ala Tyr Gln Ser Met Ser Gly Thr His Glu Ser Asn Thr
65                  70                  75                  80 atg gcg atg ttg gct cga gat ggg gcc gaa gcc gcc aag tgg ggc ggc        288
Met Ala Met Leu Ala Arg Asp Gly Ala Glu Ala Ala Lys Trp Gly Gly
                85                  90                  95 tag                                                                    291
```

```
<210> SEQ ID NO 199
<211> LENGTH: 96
<212> TYPE: PRT
<213> ORGANISM: Mycobacterium tuberculosis

<400> SEQUENCE: 199

Met Ser Gln Ile Met Tyr Asn Tyr Pro Ala Met Met Ala His Ala Gly
1               5                   10                  15

Asp Met Ala Gly Tyr Ala Gly Thr Leu Gln Ser Leu Gly Ala Asp Ile
            20                  25                  30

Ala Ser Glu Gln Ala Val Leu Ser Ala Trp Gln Gly Asp Thr Gly
        35                  40                  45

Ile Thr Tyr Gln Gly Trp Gln Thr Gln Trp Asn Gln Ala Leu Glu Asp
    50                  55                  60

Leu Val Arg Ala Tyr Gln Ser Met Ser Gly Thr His Glu Ser Asn Thr
65                  70                  75                  80

Met Ala Met Leu Ala Arg Asp Gly Ala Glu Ala Ala Lys Trp Gly Gly
                85                  90                  95

<210> SEQ ID NO 200
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 200 atg tcg cag att atg tac aac tat ccg gcg atg atg gct cat gcc ggg    48
Met Ser Gln Ile Met Tyr Asn Tyr Pro Ala Met Met Ala His Ala Gly
1               5                   10                  15 gac atg gcc ggt                                                    60
Asp Met Ala Gly
            20

<210> SEQ ID NO 201
<211> LENGTH: 20
<212> TYPE: PRT
<213> ORGANISM: Mycobacterium tuberculosis

<400> SEQUENCE: 201

Met Ser Gln Ile Met Tyr Asn Tyr Pro Ala Met Met Ala His Ala Gly
1               5                   10                  15

Asp Met Ala Gly
            20

<210> SEQ ID NO 202
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 202 atg atg gct cat gcc ggg gac atg gcc ggt tat gcg ggc acg ctg cag    48
Met Met Ala His Ala Gly Asp Met Ala Gly Tyr Ala Gly Thr Leu Gln
1               5                   10                  15 agc ttg ggg gcc                                                    60
Ser Leu Gly Ala
            20
```

```
<210> SEQ ID NO 203
<211> LENGTH: 20
<212> TYPE: PRT
<213> ORGANISM: Mycobacterium tuberculosis

<400> SEQUENCE: 203

Met Met Ala His Ala Gly Asp Met Ala Gly Tyr Ala Gly Thr Leu Gln
1               5                   10                  15

Ser Leu Gly Ala
            20

<210> SEQ ID NO 204
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 204 tat gcg ggc acg ctg cag agc ttg ggg gcc gat atc gcc agt gag cag      48
Tyr Ala Gly Thr Leu Gln Ser Leu Gly Ala Asp Ile Ala Ser Glu Gln
1               5                   10                  15 gcc gtg ctg tcc                                                       60
Ala Val Leu Ser
            20

<210> SEQ ID NO 205
<211> LENGTH: 20
<212> TYPE: PRT
<213> ORGANISM: Mycobacterium tuberculosis

<400> SEQUENCE: 205

Tyr Ala Gly Thr Leu Gln Ser Leu Gly Ala Asp Ile Ala Ser Glu Gln
1               5                   10                  15

Ala Val Leu Ser
            20

<210> SEQ ID NO 206
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 206 gat atc gcc agt gag cag gcc gtg ctg tcc agt gct tgg cag ggt gat      48
Asp Ile Ala Ser Glu Gln Ala Val Leu Ser Ser Ala Trp Gln Gly Asp
1               5                   10                  15 acc ggg atc acg                                                       60
Thr Gly Ile Thr
            20

<210> SEQ ID NO 207
<211> LENGTH: 20
<212> TYPE: PRT
<213> ORGANISM: Mycobacterium tuberculosis

<400> SEQUENCE: 207

Asp Ile Ala Ser Glu Gln Ala Val Leu Ser Ser Ala Trp Gln Gly Asp
1               5                   10                  15

Thr Gly Ile Thr
            20
```

<210> SEQ ID NO 208
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 208 agt gct tgg cag ggt gat acc ggg atc acg tat cag ggc tgg cag acc    48
Ser Ala Trp Gln Gly Asp Thr Gly Ile Thr Tyr Gln Gly Trp Gln Thr
1               5                   10                  15 cag tgg aac cag                                                    60
Gln Trp Asn Gln
            20

<210> SEQ ID NO 209
<211> LENGTH: 20
<212> TYPE: PRT
<213> ORGANISM: Mycobacterium tuberculosis

<400> SEQUENCE: 209

Ser Ala Trp Gln Gly Asp Thr Gly Ile Thr Tyr Gln Gly Trp Gln Thr
1               5                   10                  15

Gln Trp Asn Gln
            20

<210> SEQ ID NO 210
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 210 tat cag ggc tgg cag acc cag tgg aac cag gcc cta gag gat ctg gtg    48
Tyr Gln Gly Trp Gln Thr Gln Trp Asn Gln Ala Leu Glu Asp Leu Val
1               5                   10                  15 cgg gcc tat cag                                                    60
Arg Ala Tyr Gln
            20

<210> SEQ ID NO 211
<211> LENGTH: 20
<212> TYPE: PRT
<213> ORGANISM: Mycobacterium tuberculosis

<400> SEQUENCE: 211

Tyr Gln Gly Trp Gln Thr Gln Trp Asn Gln Ala Leu Glu Asp Leu Val
1               5                   10                  15

Arg Ala Tyr Gln
            20

<210> SEQ ID NO 212
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 212 gcc cta gag gat ctg gtg cgg gcc tat cag tcg atg tct ggc acc cat    48

```
Ala Leu Glu Asp Leu Val Arg Ala Tyr Gln Ser Met Ser Gly Thr His
1               5                   10                  15 gag tcc aac acc                                                     60
Glu Ser Asn Thr
            20

<210> SEQ ID NO 213
<211> LENGTH: 20
<212> TYPE: PRT
<213> ORGANISM: Mycobacterium tuberculosis

<400> SEQUENCE: 213

Ala Leu Glu Asp Leu Val Arg Ala Tyr Gln Ser Met Ser Gly Thr His
1               5                   10                  15

Glu Ser Asn Thr
            20

<210> SEQ ID NO 214
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 214 tcg atg tct ggc acc cat gag tcc aac acc atg gcg atg ttg gct cga   48
Ser Met Ser Gly Thr His Glu Ser Asn Thr Met Ala Met Leu Ala Arg
1               5                   10                  15 gat ggg gcc gaa                                                     60
Asp Gly Ala Glu
            20

<210> SEQ ID NO 215
<211> LENGTH: 20
<212> TYPE: PRT
<213> ORGANISM: Mycobacterium tuberculosis

<400> SEQUENCE: 215

Ser Met Ser Gly Thr His Glu Ser Asn Thr Met Ala Met Leu Ala Arg
1               5                   10                  15

Asp Gly Ala Glu
            20

<210> SEQ ID NO 216
<211> LENGTH: 48
<212> TYPE: DNA
<213> ORGANISM: Mycobacterium tuberculosis
<220> FEATURE:
<221> NAME/KEY: CDS
<222> LOCATION: (1)..(48)

<400> SEQUENCE: 216 atg gcg atg ttg gct cga gat ggg gcc gaa gcc gcc aag tgg ggc ggc   48
Met Ala Met Leu Ala Arg Asp Gly Ala Glu Ala Ala Lys Trp Gly Gly
1               5                   10                  15

<210> SEQ ID NO 217
<211> LENGTH: 16
<212> TYPE: PRT
<213> ORGANISM: Mycobacterium tuberculosis

<400> SEQUENCE: 217

Met Ala Met Leu Ala Arg Asp Gly Ala Glu Ala Ala Lys Trp Gly Gly
1               5                   10                  15
```

<210> SEQ ID NO 218
<211> LENGTH: 54
<212> TYPE: DNA
<213> ORGANISM: Mycobacterium tuberculosis
<220> FEATURE:
<221> NAME/KEY: CDS
<222> LOCATION: (1)..(54)

<400> SEQUENCE: 218

```
atg tcg caa atc atg tac aac tac ccc gcg atg ttg ggt cac gcc ggg      48
Met Ser Gln Ile Met Tyr Asn Tyr Pro Ala Met Leu Gly His Ala Gly
1               5                   10                  15 gat atg                                                               54
Asp Met
```

<210> SEQ ID NO 219
<211> LENGTH: 18
<212> TYPE: PRT
<213> ORGANISM: Mycobacterium tuberculosis

<400> SEQUENCE: 219

```
Met Ser Gln Ile Met Tyr Asn Tyr Pro Ala Met Leu Gly His Ala Gly
1               5                   10                  15

Asp Met
```

<210> SEQ ID NO 220
<211> LENGTH: 54
<212> TYPE: DNA
<213> ORGANISM: Mycobacterium tuberculosis
<220> FEATURE:
<221> NAME/KEY: CDS
<222> LOCATION: (1)..(54)

<400> SEQUENCE: 220

```
atg ttg ggt cac gcc ggg gat atg gcc gga tat gcc ggc acg ctg cag      48
Met Leu Gly His Ala Gly Asp Met Ala Gly Tyr Ala Gly Thr Leu Gln
1               5                   10                  15 agc ttg                                                               54
Ser Leu
```

<210> SEQ ID NO 221
<211> LENGTH: 18
<212> TYPE: PRT
<213> ORGANISM: Mycobacterium tuberculosis

<400> SEQUENCE: 221

```
Met Leu Gly His Ala Gly Asp Met Ala Gly Tyr Ala Gly Thr Leu Gln
1               5                   10                  15

Ser Leu
```

<210> SEQ ID NO 222
<211> LENGTH: 54
<212> TYPE: DNA
<213> ORGANISM: Mycobacterium tuberculosis
<220> FEATURE:
<221> NAME/KEY: CDS
<222> LOCATION: (1)..(54)

<400> SEQUENCE: 222

```
tat gcc ggc acg ctg cag agc ttg ggt gcc gag atc gcc gtg gag cag      48
Tyr Ala Gly Thr Leu Gln Ser Leu Gly Ala Glu Ile Ala Val Glu Gln
1               5                   10                  15 gcc gcg                                                               54
```

Ala Ala

<210> SEQ ID NO 223
<211> LENGTH: 18
<212> TYPE: PRT
<213> ORGANISM: Mycobacterium tuberculosis

<400> SEQUENCE: 223

Tyr Ala Gly Thr Leu Gln Ser Leu Gly Ala Glu Ile Ala Val Glu Gln
1               5                   10                  15

Ala Ala

<210> SEQ ID NO 224
<211> LENGTH: 54
<212> TYPE: DNA
<213> ORGANISM: Mycobacterium tuberculosis
<220> FEATURE:
<221> NAME/KEY: CDS
<222> LOCATION: (1)..(54)

<400> SEQUENCE: 224 gag atc gcc gtg gag cag gcc gcg ttg cag agt gcg tgg cag ggc gat     48
Glu Ile Ala Val Glu Gln Ala Ala Leu Gln Ser Ala Trp Gln Gly Asp
1               5                   10                  15 acc ggg                                                              54
Thr Gly

<210> SEQ ID NO 225
<211> LENGTH: 18
<212> TYPE: PRT
<213> ORGANISM: Mycobacterium tuberculosis

<400> SEQUENCE: 225

Glu Ile Ala Val Glu Gln Ala Ala Leu Gln Ser Ala Trp Gln Gly Asp
1               5                   10                  15

Thr Gly

<210> SEQ ID NO 226
<211> LENGTH: 54
<212> TYPE: DNA
<213> ORGANISM: Mycobacterium tuberculosis
<220> FEATURE:
<221> NAME/KEY: CDS
<222> LOCATION: (1)..(54)

<400> SEQUENCE: 226 agt gcg tgg cag ggc gat acc ggg atc acg tat cag gcg tgg cag gca     48
Ser Ala Trp Gln Gly Asp Thr Gly Ile Thr Tyr Gln Ala Trp Gln Ala
1               5                   10                  15 cag tgg                                                              54
Gln Trp

<210> SEQ ID NO 227
<211> LENGTH: 18
<212> TYPE: PRT
<213> ORGANISM: Mycobacterium tuberculosis

<400> SEQUENCE: 227

Ser Ala Trp Gln Gly Asp Thr Gly Ile Thr Tyr Gln Ala Trp Gln Ala
1               5                   10                  15

Gln Trp

<210> SEQ ID NO 228

-continued

```
<211> LENGTH: 51
<212> TYPE: DNA
<213> ORGANISM: Mycobacterium tuberculosis
<220> FEATURE:
<221> NAME/KEY: CDS
<222> LOCATION: (1)..(51)

<400> SEQUENCE: 228 tat cag gcg tgg cag gca cag tgg aac cag gcc atg gaa gat ttg gtg    48
Tyr Gln Ala Trp Gln Ala Gln Trp Asn Gln Ala Met Glu Asp Leu Val
1               5                   10                  15 cgg                                                                51
Arg

<210> SEQ ID NO 229
<211> LENGTH: 17
<212> TYPE: PRT
<213> ORGANISM: Mycobacterium tuberculosis

<400> SEQUENCE: 229

Tyr Gln Ala Trp Gln Ala Gln Trp Asn Gln Ala Met Glu Asp Leu Val
1               5                   10                  15

Arg

<210> SEQ ID NO 230
<211> LENGTH: 54
<212> TYPE: DNA
<213> ORGANISM: Mycobacterium tuberculosis
<220> FEATURE:
<221> NAME/KEY: CDS
<222> LOCATION: (1)..(54)

<400> SEQUENCE: 230 gcc atg gaa gat ttg gtg cgg gcc tat cat gcg atg tcc agc acc cat    48
Ala Met Glu Asp Leu Val Arg Ala Tyr His Ala Met Ser Ser Thr His
1               5                   10                  15 gaa gcc                                                            54
Glu Ala

<210> SEQ ID NO 231
<211> LENGTH: 18
<212> TYPE: PRT
<213> ORGANISM: Mycobacterium tuberculosis

<400> SEQUENCE: 231

Ala Met Glu Asp Leu Val Arg Ala Tyr His Ala Met Ser Ser Thr His
1               5                   10                  15

Glu Ala

<210> SEQ ID NO 232
<211> LENGTH: 54
<212> TYPE: DNA
<213> ORGANISM: Mycobacterium tuberculosis
<220> FEATURE:
<221> NAME/KEY: CDS
<222> LOCATION: (1)..(54)

<400> SEQUENCE: 232 gcg atg tcc agc acc cat gaa gcc aac acc atg gcg atg atg gcc cgc    48
Ala Met Ser Ser Thr His Glu Ala Asn Thr Met Ala Met Met Ala Arg
1               5                   10                  15 gac acg                                                            54
Asp Thr
```

-continued

<210> SEQ ID NO 233
<211> LENGTH: 18
<212> TYPE: PRT
<213> ORGANISM: Mycobacterium tuberculosis

<400> SEQUENCE: 233

Ala Met Ser Ser Thr His Glu Ala Asn Thr Met Ala Met Met Ala Arg
1               5                   10                  15

Asp Thr

<210> SEQ ID NO 234
<211> LENGTH: 48
<212> TYPE: DNA
<213> ORGANISM: Mycobacterium tuberculosis
<220> FEATURE:
<221> NAME/KEY: CDS
<222> LOCATION: (1)..(48)

<400> SEQUENCE: 234 atg gcg atg atg gcc cgc gac acc gcc gaa gcc gcc aaa tgg ggc ggc      48
Met Ala Met Met Ala Arg Asp Thr Ala Glu Ala Ala Lys Trp Gly Gly
1               5                   10                  15

<210> SEQ ID NO 235
<211> LENGTH: 16
<212> TYPE: PRT
<213> ORGANISM: Mycobacterium tuberculosis

<400> SEQUENCE: 235

Met Ala Met Met Ala Arg Asp Thr Ala Glu Ala Ala Lys Trp Gly Gly
1               5                   10                  15

<210> SEQ ID NO 236
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 236 gtg tcg cag agt atg tac agc tac ccg gcg atg acg gcc aat gtc gga      48
Val Ser Gln Ser Met Tyr Ser Tyr Pro Ala Met Thr Ala Asn Val Gly
1               5                   10                  15 gac atg gcc ggt                                                       60
Asp Met Ala Gly
            20

<210> SEQ ID NO 237
<211> LENGTH: 20
<212> TYPE: PRT
<213> ORGANISM: Mycobacterium tuberculosis

<400> SEQUENCE: 237

Val Ser Gln Ser Met Tyr Ser Tyr Pro Ala Met Thr Ala Asn Val Gly
1               5                   10                  15

Asp Met Ala Gly
            20

<210> SEQ ID NO 238
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

```
<400> SEQUENCE: 238 atg acg gcc aat gtc gga gac atg gcc ggt tat acg ggc acg acg cag      48
Met Thr Ala Asn Val Gly Asp Met Ala Gly Tyr Thr Gly Thr Thr Gln
1               5                   10                  15 agc ttg ggg gcc                                                      60
Ser Leu Gly Ala
        20

<210> SEQ ID NO 239
<211> LENGTH: 20
<212> TYPE: PRT
<213> ORGANISM: Mycobacterium tuberculosis

<400> SEQUENCE: 239

Met Thr Ala Asn Val Gly Asp Met Ala Gly Tyr Thr Gly Thr Thr Gln
1               5                   10                  15

Ser Leu Gly Ala
        20

<210> SEQ ID NO 240
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 240 tat acg ggc acg acg cag agc ttg ggg gcc gat atc gcc agt gag cgc      48
Tyr Thr Gly Thr Thr Gln Ser Leu Gly Ala Asp Ile Ala Ser Glu Arg
1               5                   10                  15 acc gcg ccg tcg                                                      60
Thr Ala Pro Ser
        20

<210> SEQ ID NO 241
<211> LENGTH: 20
<212> TYPE: PRT
<213> ORGANISM: Mycobacterium tuberculosis

<400> SEQUENCE: 241

Tyr Thr Gly Thr Thr Gln Ser Leu Gly Ala Asp Ile Ala Ser Glu Arg
1               5                   10                  15

Thr Ala Pro Ser
        20

<210> SEQ ID NO 242
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 242 gat atc gcc agt gag cgc acc gcg ccg tcg cgt gct tgc caa ggt gat      48
Asp Ile Ala Ser Glu Arg Thr Ala Pro Ser Arg Ala Cys Gln Gly Asp
1               5                   10                  15 ctc ggg atg agt                                                      60
Leu Gly Met Ser
        20

<210> SEQ ID NO 243
```

```
<211> LENGTH: 20
<212> TYPE: PRT
<213> ORGANISM: Mycobacterium tuberculosis

<400> SEQUENCE: 243

Asp Ile Ala Ser Glu Arg Thr Ala Pro Ser Arg Ala Cys Gln Gly Asp
1               5                   10                  15

Leu Gly Met Ser
            20

<210> SEQ ID NO 244
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 244 cgt gct tgc caa ggt gat ctc ggg atg agt cat cag gac tgg cag gcc      48
Arg Ala Cys Gln Gly Asp Leu Gly Met Ser His Gln Asp Trp Gln Ala
1               5                   10                  15 cag tgg aat cag                                                      60
Gln Trp Asn Gln
            20

<210> SEQ ID NO 245
<211> LENGTH: 20
<212> TYPE: PRT
<213> ORGANISM: Mycobacterium tuberculosis

<400> SEQUENCE: 245

Arg Ala Cys Gln Gly Asp Leu Gly Met Ser His Gln Asp Trp Gln Ala
1               5                   10                  15

Gln Trp Asn Gln
            20

<210> SEQ ID NO 246
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 246 cat cag gac tgg cag gcc cag tgg aat cag gcc atg gag gct ctc gcg      48
His Gln Asp Trp Gln Ala Gln Trp Asn Gln Ala Met Glu Ala Leu Ala
1               5                   10                  15 cgg gcc tac cgt                                                      60
Arg Ala Tyr Arg
            20

<210> SEQ ID NO 247
<211> LENGTH: 20
<212> TYPE: PRT
<213> ORGANISM: Mycobacterium tuberculosis

<400> SEQUENCE: 247

His Gln Asp Trp Gln Ala Gln Trp Asn Gln Ala Met Glu Ala Leu Ala
1               5                   10                  15

Arg Ala Tyr Arg
            20
```

<210> SEQ ID NO 248
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 248

```
gcc atg gag gct ctc gcg cgg gcc tac cgt cgg tgc cgg cga gca cta      48
Ala Met Glu Ala Leu Ala Arg Ala Tyr Arg Arg Cys Arg Arg Ala Leu
1               5                   10                  15 cgc cag atc ggg                                                      60
Arg Gln Ile Gly
            20
```

<210> SEQ ID NO 249
<211> LENGTH: 20
<212> TYPE: PRT
<213> ORGANISM: Mycobacterium tuberculosis

<400> SEQUENCE: 249

```
Ala Met Glu Ala Leu Ala Arg Ala Tyr Arg Arg Cys Arg Arg Ala Leu
1               5                   10                  15

Arg Gln Ile Gly
            20
```

<210> SEQ ID NO 250
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 250

```
cgg tgc cgg cga gca cta cgc cag atc ggg gtg ctg gaa agg ccg gta      48
Arg Cys Arg Arg Ala Leu Arg Gln Ile Gly Val Leu Glu Arg Pro Val
1               5                   10                  15 ggc gat tcg tca                                                      60
Gly Asp Ser Ser
            20
```

<210> SEQ ID NO 251
<211> LENGTH: 20
<212> TYPE: PRT
<213> ORGANISM: Mycobacterium tuberculosis

<400> SEQUENCE: 251

```
Arg Cys Arg Arg Ala Leu Arg Gln Ile Gly Val Leu Glu Arg Pro Val
1               5                   10                  15

Gly Asp Ser Ser
            20
```

<210> SEQ ID NO 252
<211> LENGTH: 60
<212> TYPE: DNA
<213> ORGANISM: Mycobacterium tuberculosis
<220> FEATURE:
<221> NAME/KEY: CDS
<222> LOCATION: (1)..(60)

<400> SEQUENCE: 252

```
gtg ctg gaa agg ccg gta ggc gat tcg tca gac tgc gga acg att agg      48
Val Leu Glu Arg Pro Val Gly Asp Ser Ser Asp Cys Gly Thr Ile Arg
1               5                   10                  15
```

```
-continued gtg ggg tcg ttc                                              60
Val Gly Ser Phe
            20

<210> SEQ ID NO 253
<211> LENGTH: 20
<212> TYPE: PRT
<213> ORGANISM: Mycobacterium tuberculosis

<400> SEQUENCE: 253

Val Leu Glu Arg Pro Val Gly Asp Ser Ser Asp Cys Gly Thr Ile Arg
1               5                   10                  15

Val Gly Ser Phe
            20

<210> SEQ ID NO 254
<211> LENGTH: 60
<212> TYPE: DNA
<213> ORGANISM: Mycobacterium tuberculosis

<400> SEQUENCE: 254
gactgcggaa cgattagggt ggggtcgttc cggggtcggt ggctggaccc gcgccatgcg    60

<210> SEQ ID NO 255
<211> LENGTH: 20
<212> TYPE: PRT
<213> ORGANISM: Mycobacterium tuberculosis

<400> SEQUENCE: 255

Asp Cys Gly Thr Ile Arg Val Gly Ser Phe Arg Gly Arg Trp Leu Asp
1               5                   10                  15

Pro Arg His Ala
            20

<210> SEQ ID NO 256
<211> LENGTH: 60
<212> TYPE: DNA
<213> ORGANISM: Mycobacterium tuberculosis

<400> SEQUENCE: 256
cggggtcggt ggctggaccc gcgccatgcg ggtccagcca cggccgccga cgccggagac    60

<210> SEQ ID NO 257
<211> LENGTH: 20
<212> TYPE: PRT
<213> ORGANISM: Mycobacterium tuberculosis

<400> SEQUENCE: 257

Arg Gly Arg Trp Leu Asp Pro Arg His Ala Gly Pro Ala Thr Ala Ala
1               5                   10                  15

Asp Ala Gly Asp
            20
```

What is claimed is:

1. A substantially pure polypeptide, which comprises an amino acid sequence selected from (a) the group consisting of Rv0288 (SEQ ID NO: 2) and its homologues Rv3019c (SEQ ID NO: 199) and Rv3017c (SEQ ID NO: 197);

(b) an immunogenic portion, e.g. a T-cell epitope, of any one of the sequences in (a); and/or (c) an amino acid sequence analogue having at least 70% sequence identity to any one of the sequences in (a) or (b) and at the same time being immunogenic.

2. A substantially pure polypeptide according to claim 1, wherein the amino acid sequence analogue has at least 80% sequence identity to a sequence in (a) or (b).

3. A fusion polypeptide which comprises an amino acid sequence selected from
   (a) the group consisting of Rv0288 (SEQ ID NO: 2) and its homologues Rv3019c (SEQ ID NO: 199) and Rv3017c (SEQ ID NO: 197);
   (b) an immunogenic portion, e.g. a T-cell epitope, of any one of the sequences in (a); and/or
   (c) an amino acid sequence analogue having at least 70% sequence identity to any one of the sequences in (a) or (b) and at the same time being immunogenic;
and at least one fusion partner.

4. A fusion polypeptide according to claim 3, wherein the fusion partner comprises a polypeptide fragment selected from
   (a) a polypeptide fragment from a virulent *mycobacterium*, such as ESAT-6, MPB64, MPT64, TB10.4, CFP10, RD1-ORF5, RD1-ORF2, Rv1036, Ag85A, Ag85B, Ag85C, 19 kDa lipoprotein, MPT32, MPB59 and alpha-crystallin;
   (b) a polypeptide according to claim 1 and/or
   (c) at least one immunogenic portion, e.g. a T-cell epitope, of any of the polypeptides in (a) or (b).

5. A polypeptide which comprises an amino acid sequence selected from
   (a) the group consisting of Rv0288 (SEQ ID NO: 2) and its homologues Rv3019c (SEQ ID NO: 199) and Rv3017c (SEQ ID NO: 197);
   (b) an immunogenic portion, e.g. a T-cell epitope, of any one of the sequences in (a); and/or
   (c) an amino acid sequence analogue having at least 70% sequence identity to any one of the sequences in (a) or (b) and at the same time being immunogenic;
which is lipidated so as to allow a self-adjuvating effect of the polypeptide.

6. A substantially pure polypeptide according to any of the claims 1–5 for use as a vaccine, as a pharmaceutical or as a diagnostic reagent.

7. An immunogenic composition comprising a polypeptide according to any of the preceding claims.

8. An immunogenic composition according to claim 7, which is in the form of a vaccine.

9. An immunogenic composition according to claim 7, which is in the form of a skin test reagent.

10. A pharmaceutical composition which comprises an immunologically responsive amount of at least one member selected from the group consisting of:
    (a) a polypeptide selected from the group consisting of Rv0288 (SEQ ID NO: 2), Rv3019c (SEQ ID NO: 199), Rv3017c (SEQ ID NO: 197) and an immunogenic portion of any of these polypeptides;
    (b) an amino acid sequence which has a sequence identity of at least 70% to any one of said polypeptides in (a) and is immunogenic;
    (c) a fusion polypeptide comprising at least one polypeptide or amino acid sequence according to (a) or (b) and at least one fusion partner;
    (d) a nucleic acid sequence which encodes a polypeptide or amino acid sequence according to (a), (b) or (c);
    (e) a nucleic acid sequence which is complementary to a sequence according to (d);
    (f) a nucleic acid sequence which has a length of at least 10 nucleotides and which hybridizes under stringent conditions with a nucleic acid sequence according to (d) or (e); and
    (g) a non-pathogenic micro-organism which has incorporated (e.g. placed on a plasmid or in the genome) therein a nucleic acid sequence according to (d), (e) or (f) in a manner to permit expression of a polypeptide encoded thereby.

11. Immunogenic composition according to claim 8 or pharmaceutical composition according to claim 10, wherein said immunogenic composition/pharmaceutical composition can be used prophylactically in a subject not infected with a virulent *mycobacterium*; or therapeutically in a subject already infected with a virulent *mycobacterium*.

12. A pharmaceutical composition which comprises an immunologically responsive amount of at least one member selected from the group consisting of:
    (a) a polypeptide selected from the group consisting of Rv0288 (SEQ ID NO: 2), Rv3019c (SEQ ID NO: 199), Rv3017c (SEQ ID NO: 197) and an immunogenic portion of any of these polypeptides;
    (b) an amino acid sequence which has a sequence identity of at least 70% to any one of said polypeptides in (a) and is immunogenic; and
    (c) a fusion polypeptide comprising at least one polypeptide or amino acid sequence according to (a) or (b) and at least one fusion partner.

13. A pharmaceutical composition according to claim 10, characterized in that said pharmaceutical composition can be used prophylactically in a subject not infected with a virulent *mycobacterium*; or therapeutically in a subject already infected with a virulent *mycobacterium*.

* * * * *